US012773571B2

(12) United States Patent
Richelieu

(10) Patent No.: US 12,773,571 B2
(45) Date of Patent: Oct. 27, 2026

(54) SAFETY ENHANCED APPARATUS AND METHODS FOR CANCER TREATMENT UTILIZING HIGH INTENSITY UV-C LEDS AND LONG LENGTH HIGH UV-C TRANSMISSION FIBER OPTIC CABLE

(71) Applicant: American UVC Science Inc, Reno, NV (US)

(72) Inventor: Jozef Richelieu, Reno, NV (US)

(73) Assignee: AMERICAN UVC SCIENCE INC, Reno, NV (US)

( * ) Notice: Subject to any disclaimer, the term of this patent is extended or adjusted under 35 U.S.C. 154(b) by 0 days.

(21) Appl. No.: 19/174,743

(22) Filed: Apr. 9, 2025

(65) Prior Publication Data

US 2025/0319323 A1 Oct. 16, 2025

Related U.S. Application Data

(60) Provisional application No. 63/740,681, filed on Dec. 31, 2024, provisional application No. 63/632,424, filed on Apr. 10, 2024.

(51) Int. Cl.
*A61N 5/06* (2006.01)
*G02B 23/24* (2006.01)

(52) U.S. Cl.
CPC ....... *A61N 5/0603* (2013.01); *G02B 23/2469* (2013.01); *A61N 2005/063* (2013.01);
(Continued)

(58) Field of Classification Search
CPC ............ A61N 5/0603; A61N 2005/063; A61N 2005/0652; A61N 2005/0661; A61N 5/06–2005/073; G02B 23/2469
See application file for complete search history.

(56) References Cited

U.S. PATENT DOCUMENTS 7,422,599 B2 9/2008 Perez
7,988,715 B2 8/2011 Johansson et al.
(Continued)

FOREIGN PATENT DOCUMENTS

WO WO 2019/83920 5/2019
WO WO 2024/155634 7/2024

OTHER PUBLICATIONS

Xie, et al., Ultraviolet light-emitting diode irradiation-induced cell death in HL-60 human leukemia calls in vitro, Molecular Medicine Reports 13: 2506-2510, 2016, Mar. 5, 2015.
(Continued)

*Primary Examiner* — Jonathan T Kuo
(74) *Attorney, Agent, or Firm* — Knobbe, Martens, Olson & Bear, LLP

(57) ABSTRACT

A UV-C projection unit comprises at least one solid-state UV-C light emitter, e.g., an array of UV-C LEDs, emitting UV-C radiation and projection optics such as a lens comprising high purity fused silica configured to transmit UV-C light to form a beam such as a collimated beam, the unit useable for projecting UV-C radiation onto, for example, cancerous tissue to potentially inactivate cancer cells. The UV-C radiation from the solid state UV-C light emitter, e.g., the array, may additionally or alternatively be coupled into and transmitted along an optical fiber to facilitate delivery of the light to the cancerous tissue. Various features are described herein for increasing the safety of such a UV-C projection unit and/or for applying such unit to the treatment of cancer.

20 Claims, 63 Drawing Sheets

(52) U.S. Cl.
CPC ................ *A61N 2005/0652* (2013.01); *A61N 2005/0661* (2013.01)

(56) References Cited

U.S. PATENT DOCUMENTS

| | | | |
|---|---|---|---|
| 8,109,981 B2 | 2/2012 | Gertner et al. | |
| 8,282,631 B2 | 10/2012 | Davalos et al. | |
| 8,435,276 B2 | 5/2013 | Perez | |
| 8,445,864 B2 * | 5/2013 | Thoren | C02F 1/325 210/764 |
| 8,770,203 B2 | 7/2014 | Bourke, Jr. et al. | |
| 9,333,037 B2 * | 5/2016 | Loeb | A61B 18/20 |
| 9,414,887 B2 | 8/2016 | Alfano et al. | |
| 9,474,811 B2 | 10/2016 | Sharma | |
| 9,486,640 B2 | 11/2016 | Thompson et al. | |
| 9,550,005 B2 | 1/2017 | Lin et al. | |
| 9,561,077 B2 | 2/2017 | Alfano et al. | |
| 9,827,438 B2 | 11/2017 | Johnson et al. | |
| 9,833,634 B2 | 12/2017 | Bourke, Jr. et al. | |
| 10,179,247 B2 | 1/2019 | Tomasello et al. | |
| 10,261,277 B2 | 4/2019 | Johnson et al. | |
| 10,293,965 B2 | 5/2019 | Victor et al. | |
| 10,512,788 B2 | 12/2019 | Johnson et al. | |
| 10,624,697 B2 | 4/2020 | Dickhans | |
| 10,765,768 B2 | 9/2020 | Victor et al. | |
| 10,835,756 B2 | 11/2020 | Bourke, Jr. et al. | |
| 11,173,321 B2 | 11/2021 | Basiony | |
| 11,179,530 B1 | 11/2021 | Corey | |
| 11,351,393 B2 | 6/2022 | Feldreich | |
| 11,439,839 B2 | 9/2022 | Harlan et al. | |
| 11,439,840 B2 | 9/2022 | McQuirter, Sr. | |
| 11,554,187 B2 * | 1/2023 | Nissenbaum | A61B 1/00126 |
| 11,590,358 B2 | 2/2023 | Osypka et al. | |
| 11,766,285 B2 | 9/2023 | Tegg et al. | |
| 11,806,549 B2 | 11/2023 | Eltorai | |
| 11,813,369 B2 | 11/2023 | Dinc | |
| 11,819,644 B2 | 11/2023 | Kalorin et al. | |
| 11,850,314 B2 * | 12/2023 | Klubben, III | A61L 2/084 |
| 11,852,884 B2 | 12/2023 | Utz et al. | |
| 11,870,013 B2 | 1/2024 | Gindele et al. | |
| 11,957,804 B2 * | 4/2024 | Chan | A61L 2/10 |
| 12,029,826 B2 | 7/2024 | Westerhoff et al. | |
| 12,059,576 B2 | 8/2024 | Morio et al. | |
| 2003/0017073 A1 | 1/2003 | Eckhardt et al. | |
| 2003/0018373 A1 | 1/2003 | Eckhardt et al. | |
| 2005/0090722 A1 | 4/2005 | Perez | |
| 2005/0261621 A1 | 11/2005 | Perez | |
| 2005/0261622 A1 | 11/2005 | Perez | |
| 2006/0009821 A1 | 1/2006 | Perez | |
| 2006/0189965 A1 | 8/2006 | Litvak et al. | |
| 2006/0259101 A1 | 11/2006 | Perez | |
| 2007/0135874 A1 | 6/2007 | Bala | |
| 2007/0203550 A1 | 8/2007 | Perez | |
| 2008/0177357 A1 | 7/2008 | Perez | |
| 2009/0143842 A1 | 6/2009 | Cumbie et al. | |
| 2010/0185099 A1 | 7/2010 | Johansson et al. | |
| 2011/0178510 A1 | 7/2011 | Cumbie et al. | |
| 2011/0288465 A1 | 11/2011 | Ming et al. | |
| 2011/0288617 A1 | 11/2011 | Sharma | |
| 2012/0171745 A1 | 7/2012 | Itoh | |
| 2012/0271296 A1 | 10/2012 | Young et al. | |
| 2013/0046364 A1 | 2/2013 | Itoh | |
| 2013/0048877 A1 * | 2/2013 | Thoren | B08B 17/02 250/492.1 |
| 2013/0131423 A1 | 5/2013 | Wang et al. | |
| 2014/0088488 A1 * | 3/2014 | Loeb | A61B 18/20 606/14 |
| 2014/0128943 A1 | 5/2014 | Rogers et al. | |
| 2015/0283318 A1 | 10/2015 | Wang et al. | |
| 2016/0008624 A1 | 1/2016 | Grossman | |
| 2016/0067520 A1 | 3/2016 | McNeill | |
| 2016/0114185 A1 | 4/2016 | Mankin | |
| 2019/0099610 A1 | 4/2019 | Garrett | |
| 2019/0328916 A1 | 10/2019 | Koponen et al. | |
| 2020/0018914 A1 | 1/2020 | Johnson et al. | |
| 2020/0069962 A1 | 3/2020 | Johnson et al. | |
| 2020/0230435 A1 | 7/2020 | Bae et al. | |
| 2020/0324135 A1 | 10/2020 | Greenbaum | |
| 2020/0360548 A1 * | 11/2020 | Klubben, III | A61L 2/0052 |
| 2020/0397369 A1 | 12/2020 | Greenbaum | |
| 2021/0113819 A1 | 4/2021 | Kalorin et al. | |
| 2021/0122667 A1 | 4/2021 | Westerhoff et al. | |
| 2021/0338854 A1 * | 11/2021 | Nissenbaum | A61L 2/0047 |
| 2021/0387016 A1 | 12/2021 | Scordos | |
| 2022/0016439 A1 * | 1/2022 | Shah | A61L 2/025 |
| 2022/0096677 A1 * | 3/2022 | Chan | A61L 2/10 |
| 2022/0125964 A1 * | 4/2022 | Swaney | A61L 2/084 |
| 2022/0226669 A1 | 7/2022 | McQuirter, Sr. | |
| 2022/0249719 A1 * | 8/2022 | Westerhoff | C03C 25/305 |
| 2022/0355127 A1 | 11/2022 | Harlan | |
| 2023/0045570 A1 | 2/2023 | Bae et al. | |
| 2023/0310882 A1 | 10/2023 | Nissenbaum et al. | |
| 2023/0398245 A1 | 12/2023 | Duffner et al. | |
| 2024/0024698 A1 | 1/2024 | Eltorai | |
| 2024/0042180 A1 | 2/2024 | Kalorin et al. | |
| 2024/0366960 A1 | 11/2024 | Rezaie et al. | |
| 2024/0399168 A1 | 12/2024 | Morio et al. | |

OTHER PUBLICATIONS

Zou, et al., Flexible fiberoptic laser scalpels: Material and fabrication challenges, Matter 7, 758-771, Mar. 6, 2024.

International Search Report and Written Opinion for PCT/US2025/023953, dated Jun. 20, 2025.

Adachi, et al., Ultraviolet Irradiation can Induce Evasion of Colon Cancer Cells from Stimulation of Epidermal Growth Factor, Journal of Biological Chemistry, vol. 286, No. 29, Jul. 22, 2011.

American Air & Water, Pulsed UVC irradiation selectively kills cancer cells, UV News 2012, https:/www.americanairandwater.com/UV-news/UV-news.12.htm (10 pages).

Arciga et al., Pulsed electric field ablation as a candidate to enhance the anti-tumor immune response to immune checkpoint inhibitors, Cancer Letters 609 (2025) 217361 (9 pages). https://doi.org/10.1016/j.canlet.2024.217361.

Asia Research News, New cancer therapy using ultra-violet C (Uvc) pulse flash irradiation, Aug. 2012, https://www.asiaresearchnews.com/html/article.php/aid/7383/cid/2/research/medicine/tokai_univeristy_school_of_medicine/new_cancer_therapy_using_ultra-violet_c_%28uvc%29_pulse_flash_irradiation.html (8 pages).

Benencia, et al., Whole tumor antigen vaccination using dendritic cells: Comparison of RNA electroporation and pulsing with UV-irradiated tumor cells, *Journal of Translational Medicine* 2008, 6:21 (14 pages). doi:10.1186/1479-5876-6-21.

Corning, et al., The Healing Power of Light: From UV Disinfection to Photodynamic Cancer Treatments, Konica Minolta web site—*The Healing Power of Light: From UV Disinfection to Photodynamic Cancer Treatments | Radiant Vision Systems* (radiantvisionsystems.com ), Jun. 29, 2020 (5 pages).

Dai, et al., Ultraviolet C irradiation: an alternative antimicrobial approach to localized infections? Expert Rev Anti Infect Ther. Feb. 2012; 10(2): 185-195. doi:10.1586/eri.11.166.

Dong, et al., Role of pulsed-xenon ultraviolet light in reducing healthcare-associated infections: a systematic review and meta-analysis (2020) Epidemiology and Infection 148, e165, 1-10. https://doi.org/10.1017/S095026882000148X.

Bernhard Franz, Fused Silica: A Transparent Look at a Complex Material, BioPHotonics, Nov. 2022 https:/www.photonics.com/Article.aspx?AID=68477.

Gerchman, et al., UV-LED disinfection of Coronavirus: Wavelength effect, Journal of Photochemistry & Photobiology, B: Biology 212 (2020) 112044 (8 pages). https://doi.org/10.1016/j.jphotobiol.2020.112044.

GMY Lighting Technology Co., Ltd website, 222 mm-Far-UVC Solution, The Wayback Machine—https://web.archive.org/web/20241210013017/https://en.gmylight.com/222nm-Far-UVC-Solution.html, Dec. 10, 2024.

Hayashi, et al., UV light-emitting diode (UV-LED) at 265 nm as a potential light source for disinfecting human platelet concentrates, Plos One | https://doi.org/10.1371/journal.pone.0251650 May 20, 2021 (21 pages).

(56) References Cited

OTHER PUBLICATIONS

Itoh, et al., A New Drug-Free Cancer Therapy Using Ultraviolet Pulsed Irradiation. PDT (PhotoDynamic Therapy) to PPT (Pulsed Photon Therapy), Front. Biosci (Schol Ed) 2022, 14(4) 27, Jun. 10, 2022 21 pages). https://doi.org/10.31083/j.fbs1404027.

Kimura, et al., UV Light Killing Efficacy of Fluorescent Protein-Expressing Cancer Cells In Vitro and In Vivo, Journal of Cellular Biochemistry 110:1439-1446 (2010) pp. 1439-1446.

Lai, et al., A new UVC-LED system for disinfection of pathogens generated by toilet flushing, Indoor Air. 2021;31:324-334. DOI: 10.1111/ina. 12752.

Laser Components website, *Transmission of UV Light with Optical Fiber*, dated Dec. 8, 2014 from Wayback Machine, archived Jan. 16, 2025.

Laser Components, molex®, Polymicro SILICA/SILICA optical Fiber DUV Solarization Resistant, 09/21/V06/FT-IF/polymicro/duv, Sep. 2021.

Laser Components, molex®, Slica/Silica optical Fiber FV-High-OH 1 09/21/V08/FT-IF/polymicro/fv-high-oh, Sep. 2021.

Laser Focus World, Cancer therapy method uses UVC pulse flash irradiation to destroy neoplastic cells, Aug. 21, 2012, https://www.laserfocusworld.com/biooptics/biomedicine/article/14193513/cancer-therapy-method-uses-uvc-pulse-flash-irradiation-to-destroy-neoplastic-cells (8 pages).

Model, et al., Fiber Optics in Medicine, Encyclopedia of Medical Devices and Instrumentation, Second Edition, edited by John G. Webster © 2006 John Wiley & Sons, Inc pp. 301-315.

Nishikawa, et al., Far-Ultraviolet Light at 222 nm Affects Membrane Integrity in Monolayered DLD1 Colon Cancer Cells. *Int. J. Mol. Sci.* 2024, 25, 7051. https://doi.org/10.3390/ijms25137051.

A.G. Richards, Threshold Limit Values for Ultraviolet Radiation Measured for Sources Used in Research Equipment and Some Cases of Overexposure to UV Radiation, v. 1. pp. 775-778 1992.

Sasanpour, et al., Novel Method for Cancer Cell Apoptosis by Localized UV Light with Gold Nanostructures: A Theoretical Investigation, Nano., vol. 5, No. 6, pp. 325-332 (2010). https://doi.org/10.1142/S1793292010=002232.

Sciencedaily, New cancer therapy using ultra-violet C (UVC) pulse flash irradiation, Aug. 21, 2012 https:/www.sciencedaily.com/releases/2012/08/120821143221.htm (7 pages).

Simmons, et al., Deactivation of SARS-COV-2 with pulsed-xenon ultraviolet light: Implications for environmental COVID-19 control, Infection Control & Hospital Epidemiology (2020), 1-4. doi:10.1017/ice.2020.399.

Stanley Electric Co., LTD Data Sheet, Part No. ZUEDE265-TR, Apr. 26, 2022, 7 pages.

SunTechLed web page Far UVC Led Light 207-220nm-222nm Far UV Led Chip—Buy China, manufacturers, factory Product on Shenzhen Suntech Company Limited, Wayback Machine Archived, Mar. 10, 2021.

Thor Labs, 0.22 NA Silica Core, Glass Clad Multimode Optical Fiber, Step Index, at least as early as Sep. 25, 2024.

Thor Labs, λ=405 nm FC/PC Collimation Package, NA=0.60 f=4.02mm, Oct. 27, 2016.

Yasoubi, et al., Evaluation of pulsed xenon UV irradiation on inactivation of Listeria monocytogenes on stainless-steel surfaces, LWT—Food Science and Technology 184 (2023) 115068 (8 pages).

Yamauchi, et al., Ultra-violet irradiation induces apoptosis via mitochondrial pathway in pancreatic cancer cells, Int'l Journal of Oncology 39: 1375-1380, 2011. DOI: 10.3892/ijo.2011.1188.

Yu et al., Ultraviolet (UV) radiation: a double-edged sword in cancer development and therapy, Molecular Biomedicine (2024) 5:49 (24 pages). https://doi.org/10.1186/s43556-024-00209-8.

* cited by examiner

CHART 1

| 265 nm LED PULSE RATES, TIME PERIOD ($T_{on}$ or $T_{high}$) OR EXPOSURE TIMES | | |
|---|---|---|
| Microseconds $10^{-6}$ | Milliseconds $10^{-3}$ | Seconds $10^{0}$ |
| 100 | 100 | 1 |
| 200 | 200 | 2 |
| 300 | 300 | 3 |
| 400 | 400 | 4 |
| 500 | 500 | 5 |
| 600 | 600 | 6 |
| 700 | 700 | 7 |
| 800 | 800 | 8 |
| 900 | 900 | 9 |
| 1000 | 1000 | 10 |

FIG. 9

| Test # | Duty Cycle | Voltage | Frequency | Fiber Optic | Temp. | Benchmark Exposure | mW/cm2 | Exposure | Maximum |
|---|---|---|---|---|---|---|---|---|---|
| 1 | 100% | 29.07v | 60 Hz | 157.4" Length | 84° F | 29.0 Sec | **3.5498** | 28.1 Sec | 100 mJ/cm2 |
| 2 | 90% | 28.06v | 60 Hz | 157.4" Length | 84° F | 29.0 Sec | **3.1680** | 31.5 Sec | 100 mJ/cm2 |
| 3 | 80% | 26.93v | 60 Hz | 157.4" Length | 84° F | 29.0 Sec | **2.7873** | 35.8 Sec | 100 mJ/cm2 |
| 4 | 70% | 25.75v | 60 Hz | 157.4" Length | 84° F | 29.0 Sec | **2.4180** | 41.3 Sec | 100 mJ/cm2 |
| 5 | 60% | 24.52v | 60 Hz | 157.4" Length | 84° F | 29.0 Sec | **2.0705** | 48.2 Sec | 100 mJ/cm2 |
| 6 | 50% | 23.28v | 60 Hz | 157.4" Length | 84° F | 29.0 Sec | **1.6970** | 58.9 Sec | 100 mJ/cm2 |
| 7 | 40% | 21.95v | 60 Hz | 157.4" Length | 84° F | 29.0 Sec | **1.3334** | 74.9 Sec | 100 mJ/cm2 |
| 8 | 30% | 20.65v | 60 Hz | 157.4" Length | 84° F | 29.0 Sec | **0.9871** | 101.3 Sec | 100 mJ/cm2 |
| 9 | 20% | 19.32v | 60 Hz | 157.4" Length | 84° F | 29.0 Sec | **0.6459** | 154.8 Sec | 100 mJ/cm2 |
| 10 | 10% | 17.92v | 60 Hz | 157.4" Length | 84° F | 29.0 Sec | **0.3137** | 317 Sec | 100 mJ/cm2 |

FIG. 25

FIG. 30A

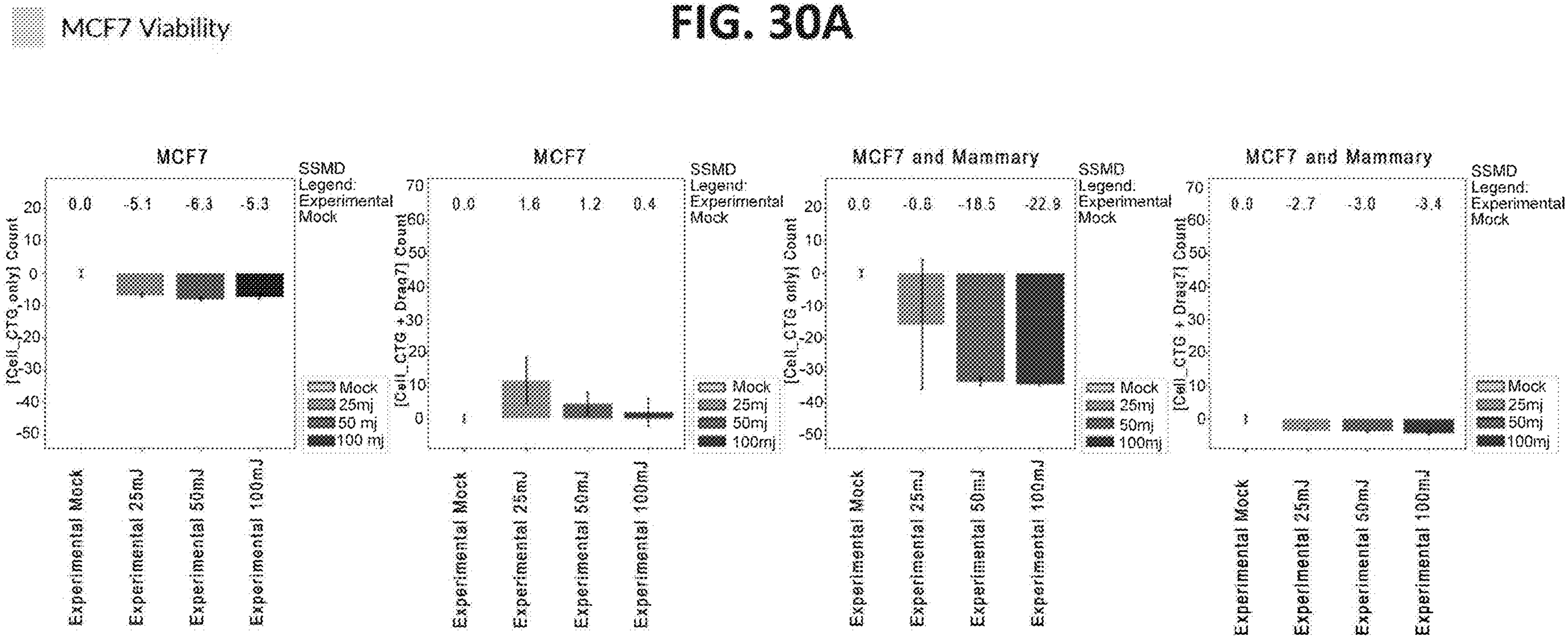

[Cell_CTG only] Count: The average number of CellTracker Green-positive cells within the ROI. This number indicates the number of viable CTG-labelled cells remaining in the population.

- In both monoculture and coculture, the number of viable MCF7 cells is significantly reduced in response to treatment
- The reduction in more pronounced when cocultured with primary mammary cells.

[Cell_CTG + Draq7] Count: The average number of CellTracker Green / Draq7 double positive cells within the ROI. This number measures the number of dead CTG-labelled cells in the population.

- The number of dead MCF7 cells does not change in monoculture and decreases in coculture. Taken together the cell count data, this indicates that most dead cells detach from the slide surface and are no longer present at the time of image capture.

FIG. 30B

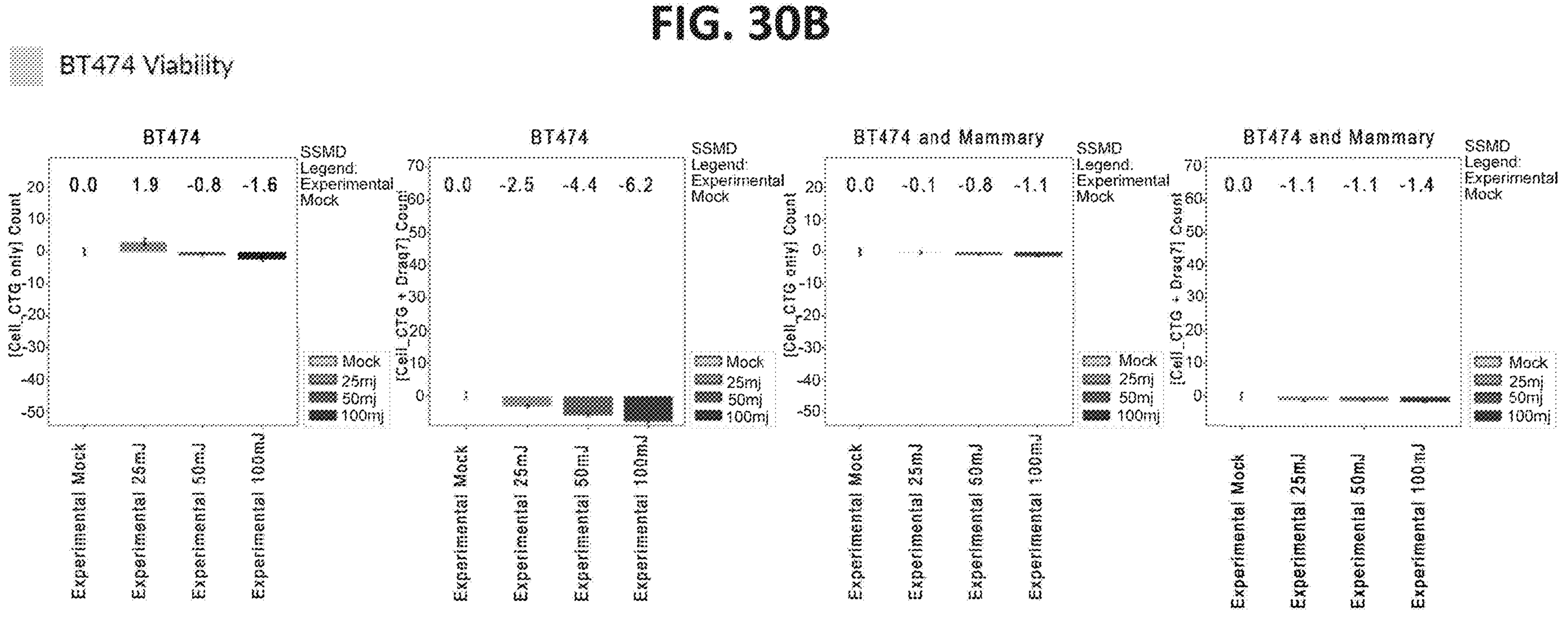

[Cell_CTG only] Count: The average number of CellTracker Green-positive cells within the ROI. This number indicates the number of viable CTG-labelled cells remaining in the population.

- The number of viable BT474 cells is reduced in a dose-dependent manner but does not reach the level of statistical-significance.

[Cell_CTG + Draq7] Count: The average number of CellTracker Green / Draq7 double positive cells within the ROI. This number measures the number of dead CTG-labelled cells in the population.

- The number of dead BT474 cells present at the time of image capture is reduced in monoculture by not in coculture.

FIG. 30C

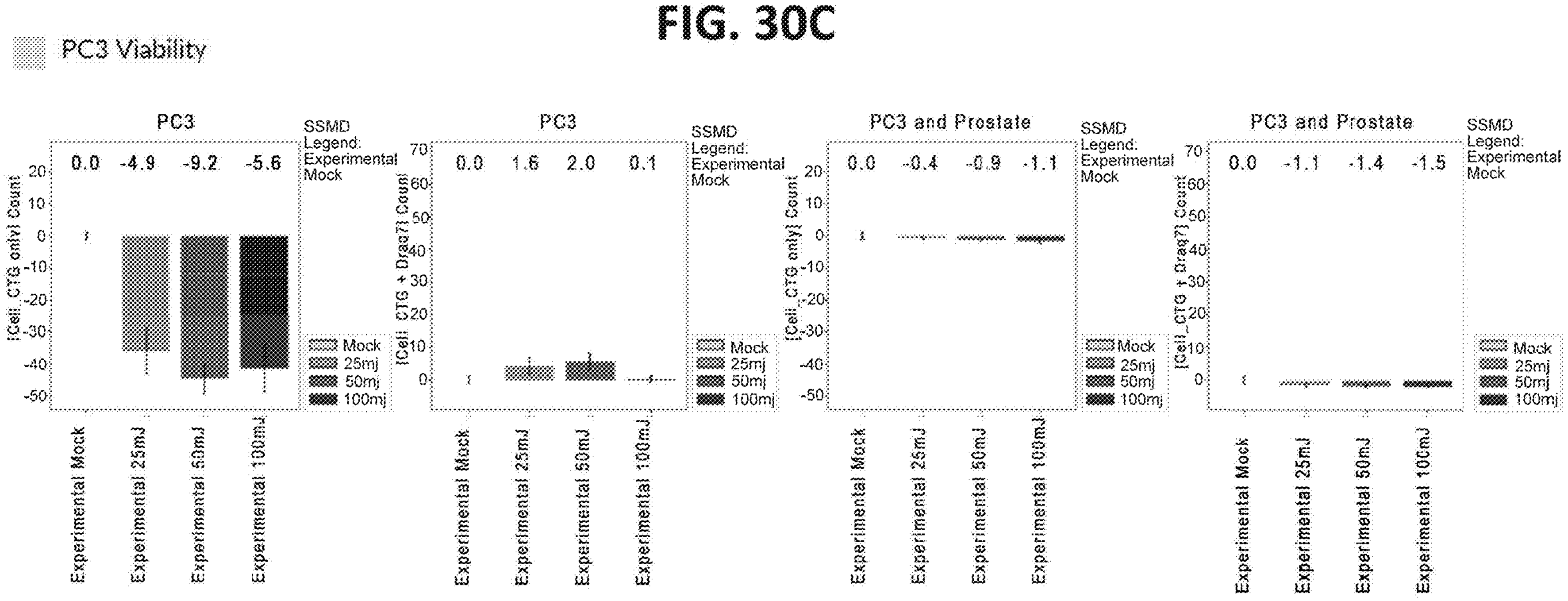

[Cell_CTG only] Count: The average number of CellTracker Green-positive cells within the ROI. This number indicates the number of viable CTG-labelled cells remaining in the population.

- The number of viable PC3 cells is significantly reduced in monoculture in response to treatment. In coculture, the viable PC3 count also decreases but does not reach the level of statistical significance.

[Cell_CTG + Draq7] Count: The average number of CellTracker Green / Draq7 double positive cells within the ROI. This number measures the number of dead CTG-labelled cells in the population.

- The number of dead PC3 present at image capture is increased in response to 50mj exposure in monoculture.
- In coculture, the number of dead PC3 cells remaining does not change.

FIG. 30D

LNCAP Viability

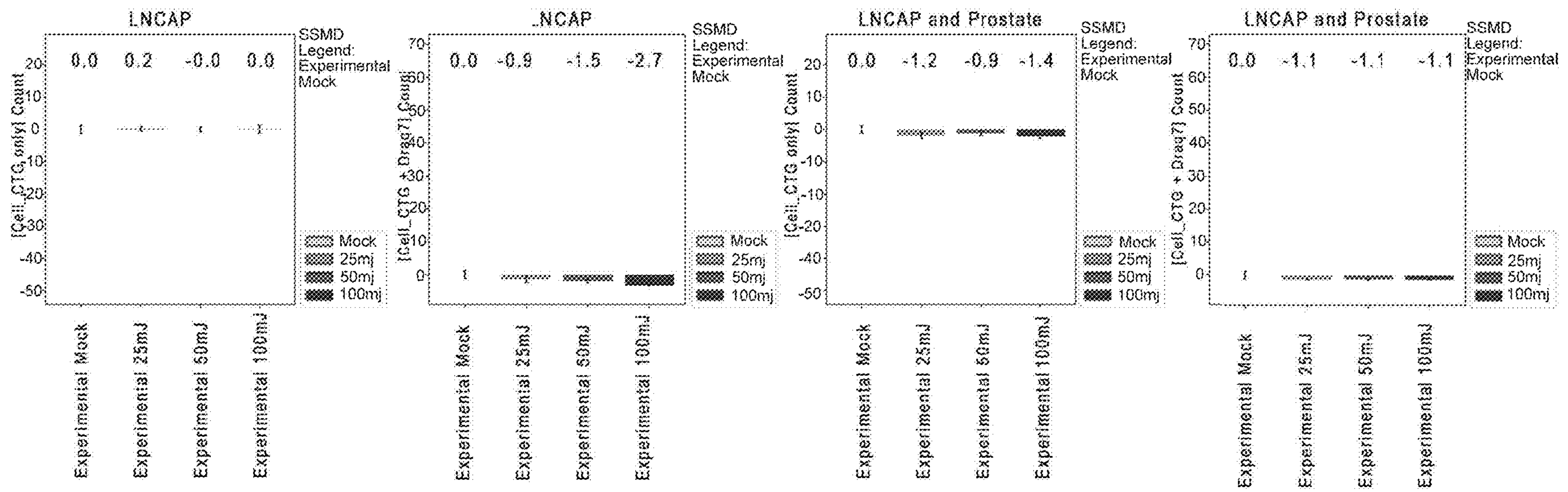

[Cell_CTG only] Count: The average number of CellTracker Green-positive cells within the ROI. This number indicates the number of viable CTG-labelled cells remaining in the population.

- LNCAP viability is minimally impacted by treatment.

[Cell_CTG + Draq7] Count: The average number of CellTracker Green / Draq7 double positive cells within the ROI. This number measures the number of dead CTG-labelled cells in the population.

- LNCAP viability is minimally impacted by treatment.

FIG. 30E

Primary Mammary Viability with MCF7 Co-culture

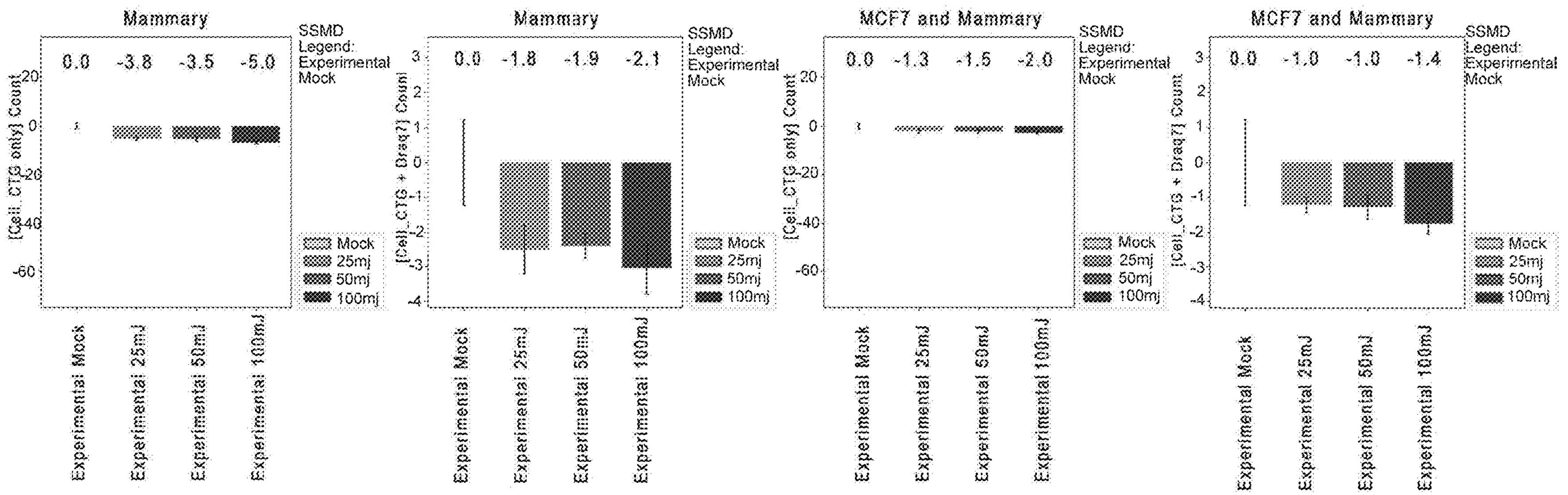

[Cell_CTR only] Count: The average number of CellTracker Red-positive cells within the ROI. This number indicates the number of viable CTR-labelled cells remaining in the population.

- In both monoculture and coculture, the number of viable primary mammary cells is significantly reduced in response to treatment
- The reduction in less pronounced when cocultured with cancer cells.

[Cell_CTR + Draq7] Count: The average number of CellTracker Red / Draq7 double positive cells within the ROI. This number measures the number of dead CTR-labelled cells in the population at the time of imaging.

FIG. 30F

Primary Mammary Viability with BT474 Co-culture

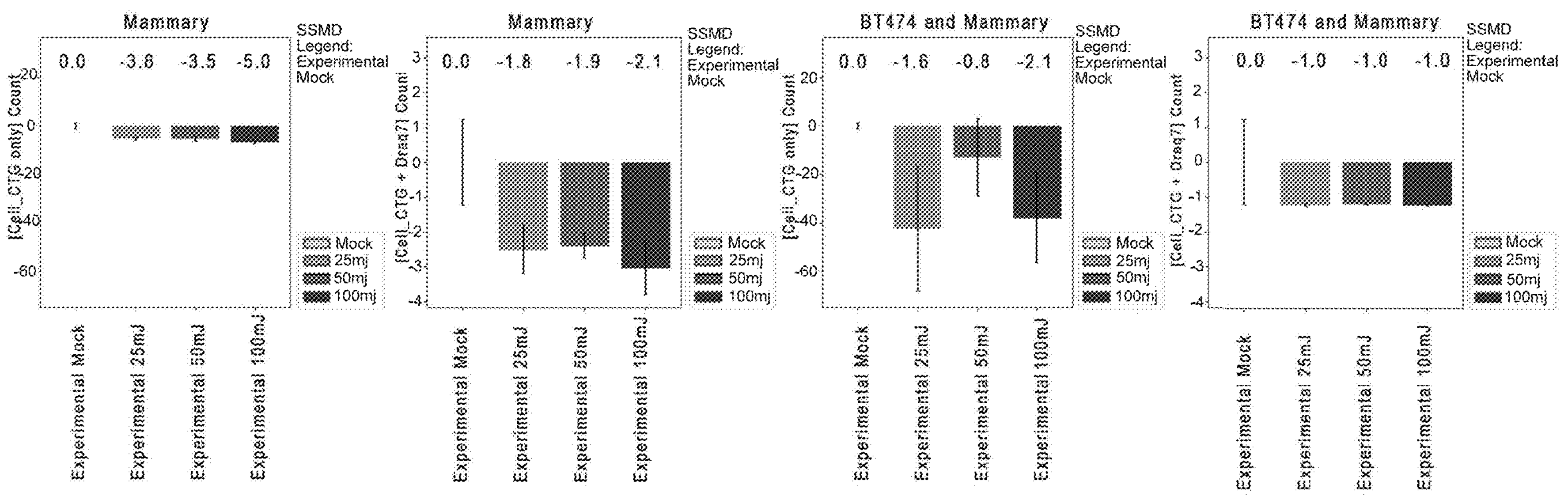

[Cell_CTR only] Count: The average number of CellTracker Red-positive cells within the ROI. This number indicates the number of viable CTR-labelled cells remaining in the population.

- In both monoculture and coculture, the number of viable primary mammary cells is significantly reduced in response to treatment
- The reduction in less pronounced when cocultured with cancer cells.

[Cell_CTR + Draq7] Count: The average number of CellTracker Red / Draq7 double positive cells within the ROI. This number measures the number of dead CTR-labelled cells in the population at the time of imaging.

FIG. 30G

Primary Prostate Viability with LNCAP Co-culture

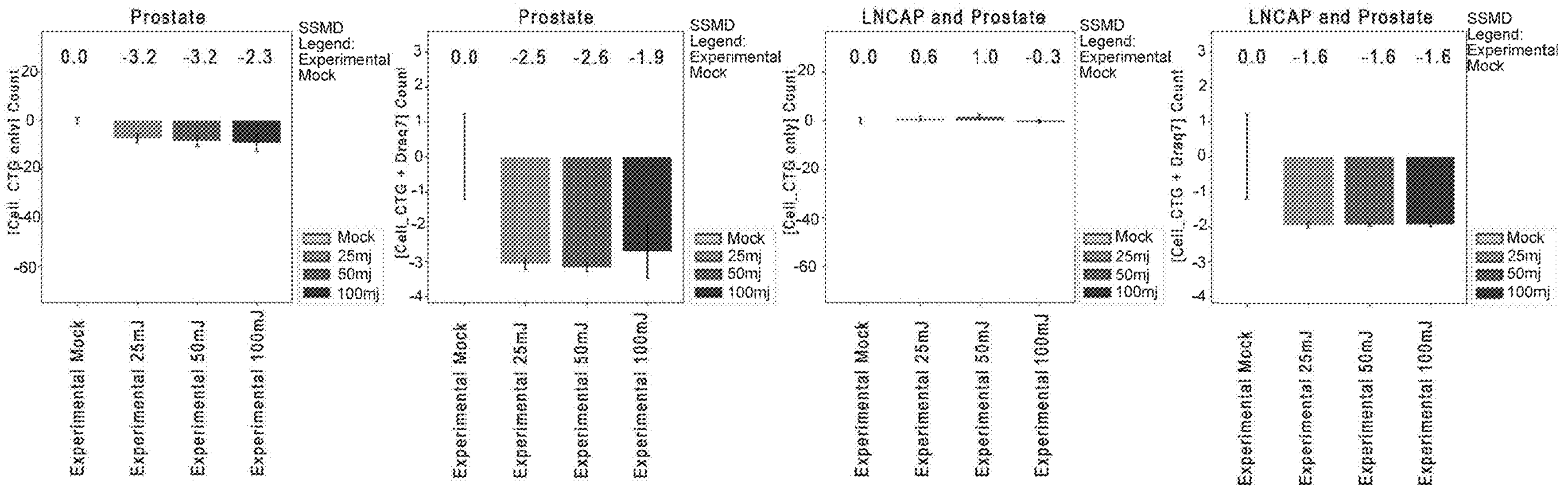

[Cell_CTR only] Count: The average number of CellTracker Red-positive cells within the ROI. This number indicates the number of viable CTR-labelled cells remaining in the population.

- In both monoculture and coculture, the number of viable primary mammary cells is significantly reduced in response to treatment
- The reduction in less pronounced when cocultured with cancer cells.

[Cell_CTR + Draq7] Count: The average number of CellTracker Red / Draq7 double positive cells within the ROI. This number measures the number of dead CTR-labelled cells in the population at the time of imaging.

FIG. 30H

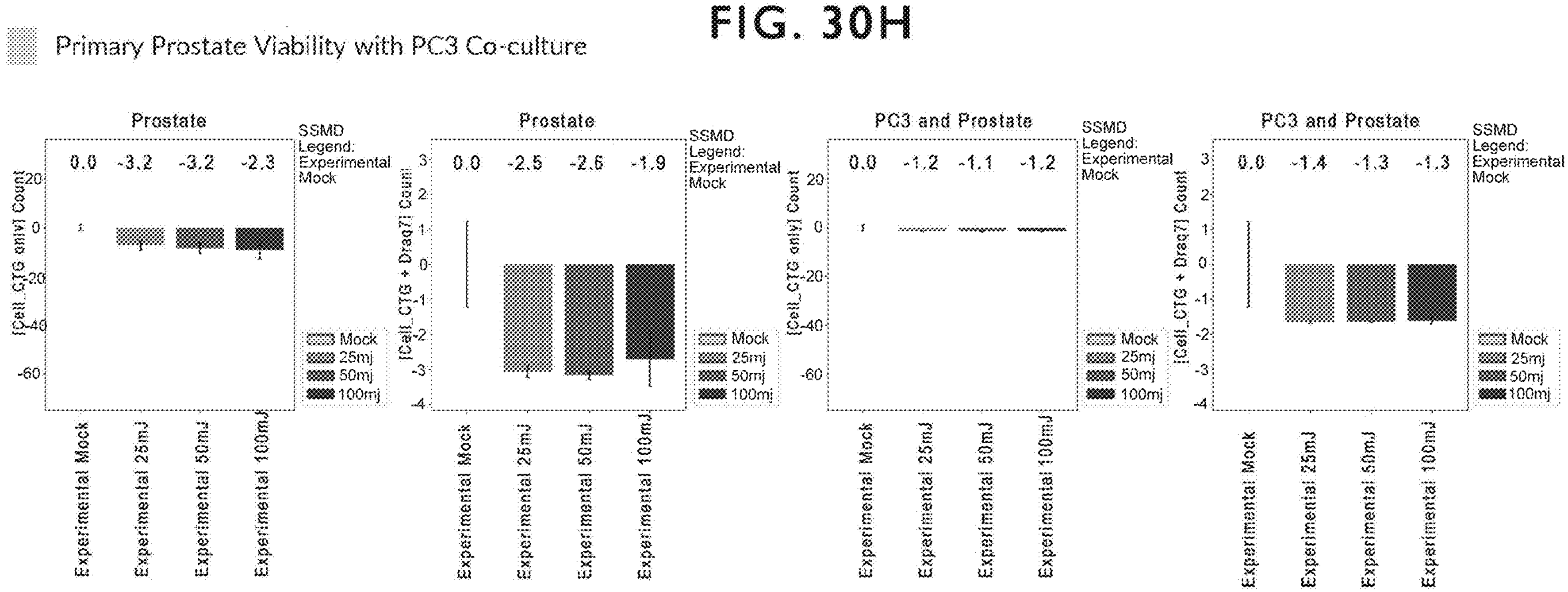

[Cell_CTR only] Count: The average number of CellTracker Red-positive cells within the ROI. This number indicates the number of viable CTR-labelled cells remaining in the population.

- In both monoculture and coculture, the number of viable primary mammary cells is significantly reduced in response to treatment
- The reduction in less pronounced when cocultured with cancer cells.

[Cell_CTR + Draq7] Count: The average number of CellTracker Red / Draq7 double positive cells within the ROI. This number measures the number of dead CTR-labelled cells in the population at the time of imaging.

SAFETY ENHANCED APPARATUS AND METHODS FOR CANCER TREATMENT UTILIZING HIGH INTENSITY UV-C LEDS AND LONG LENGTH HIGH UV-C TRANSMISSION FIBER OPTIC CABLE

INCORPORATION BY REFERENCE TO RELATED APPLICATION

This application is related to U.S. Provisional Application No. 63/632,424 titled "A PLURALITY OF PULSED LED DIODES EMITTING 265 nm WAVELENGTH LIGHT INTO A SINGLE BEAM USING UV-C LED PROJECTION OPTICS", which was filed on Apr. 10, 2024, as well as U.S. Provisional Application No. 63/740,681 titled "APPARATUS AND METHODS UTILIZING LIGHT SOURCES THAT EMIT ULTRAVIOLET-C (UV-C) WAVELENGTH LIGHT", which was filed on Dec. 31, 2024. The entire disclosure of each of the applications listed in this paragraph is expressly incorporated herein by reference.

FIELD OF THE INVENTION

Various embodiments of this application relate to systems that output ultraviolet (UV) light such as UV-C light (e.g., 100 to 280 nm), and more particularly systems that output UV, e.g., UV-C, light for therapy and/or treatment of ailments or diseases such as cancer.

BACKGROUND

Cancer is the second highest cause of death in the United States. Cancer can be devastating on a person's life and their family. Cancer imposes cost on the economy as well. Although significant advances have been made on the treatment of cancer and survivability has thus improved, continued progress is desirable. Thus, what is needed are more ways of successfully treating cancer.

SUMMARY

A wide variety of example systems, structures, devices, designs, methods, and implementations described herein have several features, no single one of which is indispensable or solely responsible for their desirable attributes. For example, a variety of example systems and methods are provided below.

UV-C light can destroy, disable and/or inactivate cancer cells. Accordingly, various systems, devices and methods are described herein for outputting and/or using UV-C light potentially to treat cancer. The UV-C light may be in the range of from 200 nm to 280 nm in various implementations. One UV-C light projection unit described herein, for example, comprises an array of UV-C light emitters and UV-C collecting optics. The UV-C light emitters comprise solid state emitters such as UV-C light emitting diodes (LEDs) configured to emit light having a wavelength in the range of 250 to 280 nanometers (nm). The UV-C collecting optics are disposed with respect to the array of UV-C light emitters to receive light emitted by the array of UV-C light emitters and to transmit the light.

Another example UV-C light projection unit described herein comprises at least one UV-C light emitter configured to emit light having a wavelength in the range of 250 to 280 nm and an optical fiber or optical fiber line or fiber optic cable configured to receive light from said at least one UV-C light emitter in the wavelength range of 250 to 280 nm and transmit and output a portion of said light in the wavelength range of 250 to 280.

A method of exposing cancerous tissue to UV-C light is also described herein. The method comprises producing UV-C light from an array of UV-C light emitters, collecting light emitted by the array of UV-C light emitters with UV-C collecting optics, and directing UV-C light collected by the UV-C collecting optics onto the cancerous tissue. The light that is emitted from this array of UV-C light emitters has a wavelength in the range of 250 to 280 nm. This light may comprise a wavelength of 265 nanometer (nm). The UV-C light emitters may comprise solid state emitters such as UV-C light emitting diodes (LEDs). The light collected by the UV-C collecting optics may be coupled into an optical fiber/optical fiber line/fiber optic cable, which can be used to direct UV-C light onto the cancerous tissue. In some such designs, this optical fiber is part of an endoscope and/or is optical coupled to an endoscope that can be used by a physician to direct UV-C light onto cancerous tissue.

Similarly, another method of exposing cancerous tissue or cells to UV-C light comprises producing UV-C light, coupling the UV-C light into an optical fiber line or optical fiber or fiber optic cable; and directing UV-C light onto said cancerous tissue or cells using the optical fiber line, optical fiber or fiber optic cable. Most of the UV-C light directed onto the cancerous cells has a wavelength in the range of 250 to 280 nm.

Various systems and methods described herein are configured to reduce the hazards associated with the production and application of UV-C light in sufficient amounts to damage, destroy, deactivate, or inhibit the growth of cancer cells. Such safety enhanced systems and methods include features and/or measures that may reduce the health risks to the operator and/or bystanders such as physicians, nurses, technicians and other health care providers present during the treatment of the patient.

Various systems and methods are also described herein that are configured to increase the efficiency of transmission of UV light through the system such that sufficient amounts of UV light can be delivered to the cancerous tissue. The systems may include, for example, lenses and/or optical fibers comprising materials that provide for reduced UV (e.g., UV-C) absorption.

Various systems and methods are also described herein that include features that enable the treatment to be more practically administered. Examples include systems and methods configured to provide for variable beam sizes as well as systems and methods configured to customize the parameters of pulsed UV light delivered to the cancerous tissue based on the type of cancer, the cell line and possibly based on a biopsy taken from the patient. Features for reducing obstructions that limit output of UV light to be directed to the tumor(s) or cancerous tissue are also provided.

Other systems, devices and methods are also disclosed herein.

Also, as used herein, the optical fiber may be referred to as an optical fiber line or optical fiber cable (or fiber optic cable). The terms fiber, optical fiber, optical fiber line, optical fiber cable, fiber optic, fiber optic line, fiber optic cable are used interchangeably herein. The optical fiber need not be a single strand of optical fiber and may be comprised of separate parts (e.g., separate strands), for example, stringed, optically connected, optically coupled or concatenated together. The separate portions or strands of optical fiber may be strung together in the longitudinal direction to provide for an elongated waveguide through which light can propagate from the proximal end to the distal end thereof. The separate strands of optical fiber may be optically connected or optically coupled together, e.g., via optical connectors and may be butt coupled in some cases. In some implementations, optics may be used to connect the strands or portions of optical fiber together. Other ways of stringing, optically coupling or concatenating the portions of optical fiber or strands of optical fiber together are possible. In some implementations, however, the optical fiber comprises a single (e.g., continuous) strand of optical fiber as opposed to discrete or separate parts coupled, e.g., butt coupled together or otherwise optically coupled together.

For purposes of this summary, certain aspects, advantages, and novel features of the invention are described herein. It is to be understood that not necessarily all such aspects, advantages, and features may be employed and/or achieved in accordance with any particular implementation of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF DRAWINGS

The foregoing and other features, aspects and advantages of the present invention are described in detail below with reference to the drawings of various embodiments, which are intended to illustrate and not to limit the invention.

FIG. 3B shows the distal portion of the optical fiber/fiber optic line and output optics positioned at the distal end of the optical fiber to receive UV-C light therefrom and to reduce divergence, collimate and/or focus UV-C light onto the target, e.g., target tissue and/or target cells.

Figure 8A:
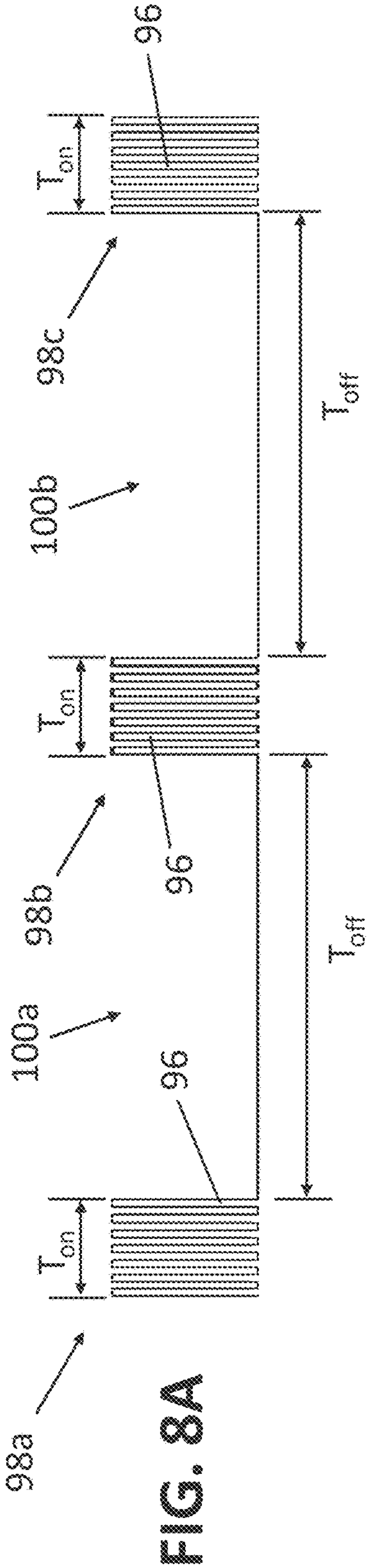
FIGS. 8A and 8B are plots of electrical signal versus time illustrating the electrical signal provided by the power supply, e.g., pulsed power source, to drive the UV-C light emitters (e.g., UV-C LEDs). The pulsed power source can turn on and off the pulses of UV-C light applied for periods of time, $T_{on}$ and $T_{off}$, respectively. The duration, $T_{on}$ or $T_{high}$, over which the pulses of UV-C light are applied (or are above a threshold level) is twice as large in the example driving signal shown in FIG. 8B as the example driving signal shown in FIG. 8A. However, the duration over which the UV-C pulses are not applied (or are below a threshold level), as in $T_{off}$, is the same in both FIG. 8A and FIG. 8A.
Figure 8B:
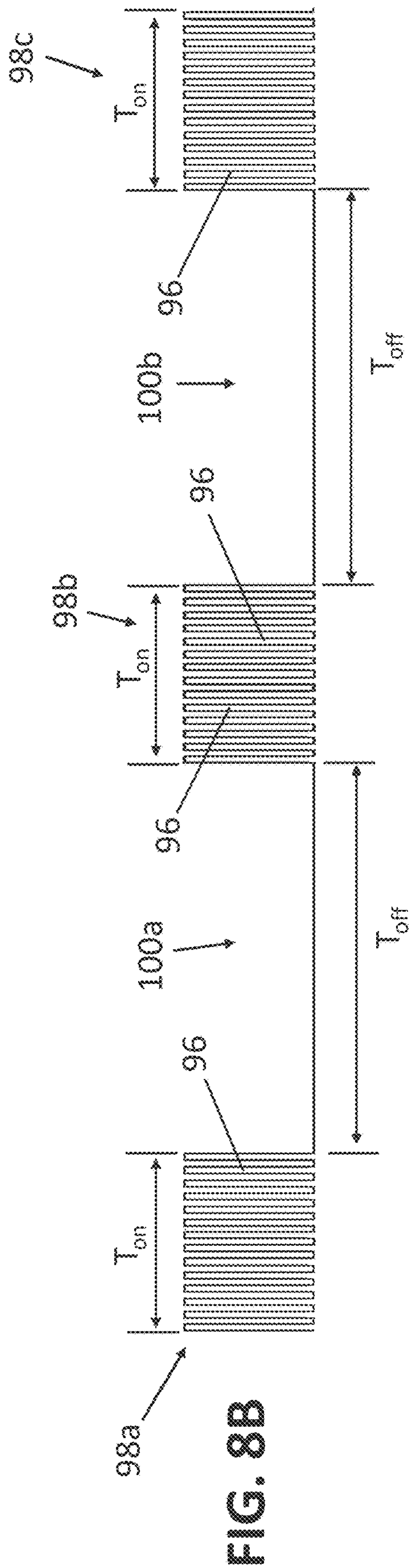

Thus, the total fluence and thus exposure and/or dosage is twice as much in the example shown in FIG. 8B as in 8A. These plots in FIGS. 8A and 8B also correspond to the intensity, radiant exposure, radiant fluence, and/or luminance of light output by the array of light emitters and/or that are directed at the target (e.g., cancer cells).

FIG. 9 is a chart that includes example durations, $T_{on}$, or exposure times over which the UV-C light or UV-C pulses may be applied. The UV-C emitters may be driven such that the UV-C emitters emit UV-C light and/or UV-C pulses, or emit above a threshold amount, for a duration, $T_{on}$, that may, for example, be from 100 microseconds to 10 seconds.

Figure 10:
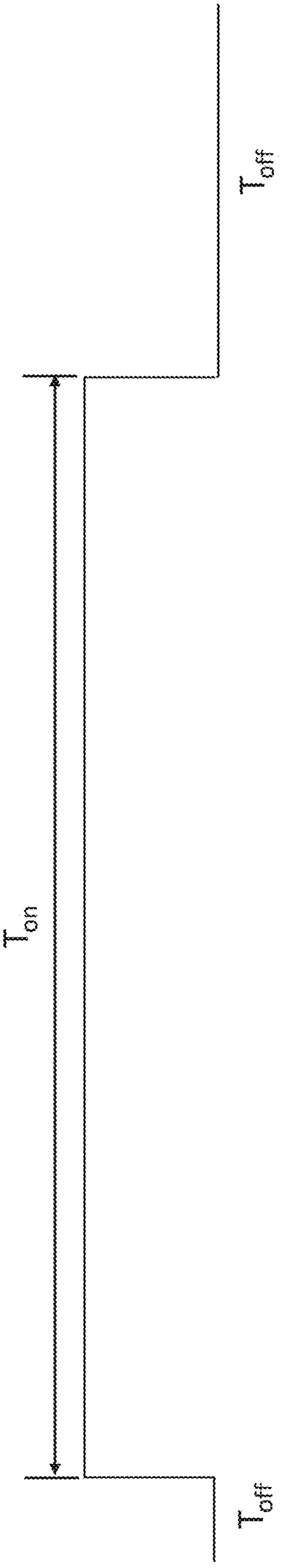

FIG. 10 is a plot of electrical signal versus time illustrating the electrical signal provided by the power supply (e.g., pulsed power source) to drive the UV-C light emitters (e.g., UV-C LEDs). The power supply can turn on and off the UV-C light applied for periods of time, $T_{on}$ and $T_{off}$, respectively. This plot in FIG. 10 also corresponds to the intensity, radiant exposure, radiant fluence and/or luminance of light output by the array of light emitters and/or that are directed at the target (e.g., cancer cells).

Figure 11:
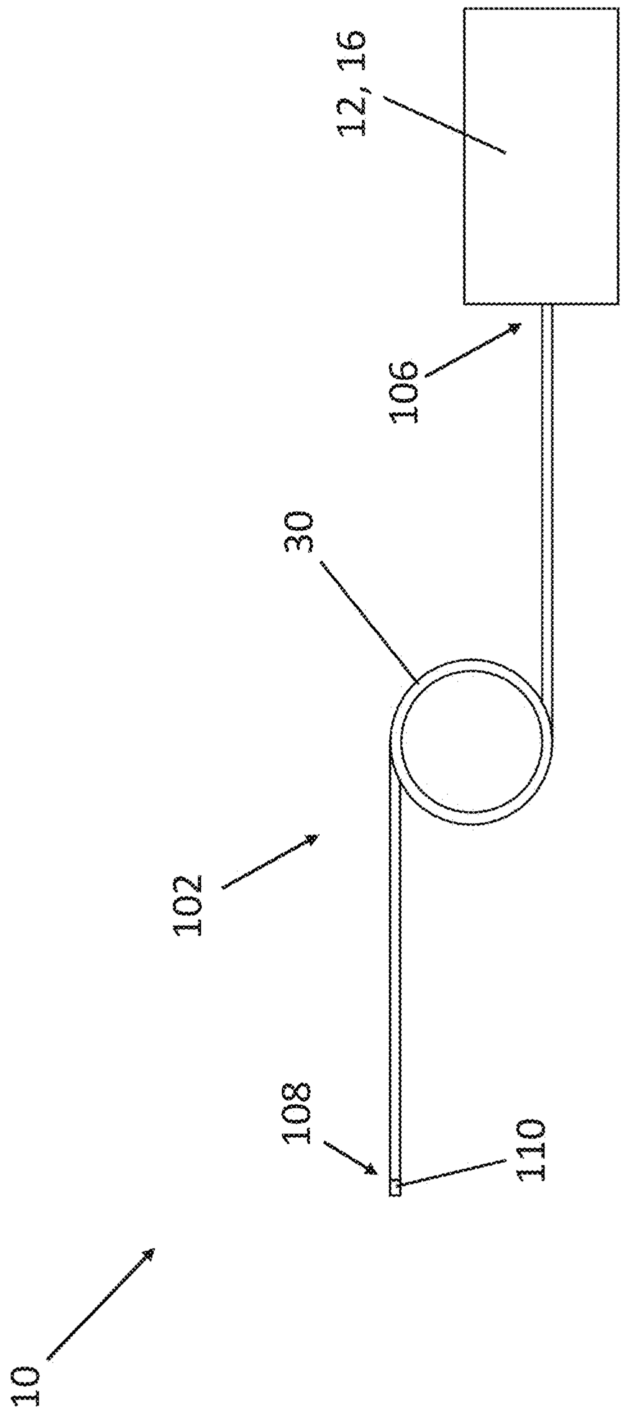

FIG. 11 is a schematic illustration of an endoscope comprising an optical fiber or fiber optic cable or optical fiber line and a UV-C light source configured to deliver UV-C light to tissue (e.g., cancerous tissue or cells) within the body.

Figure 12A:
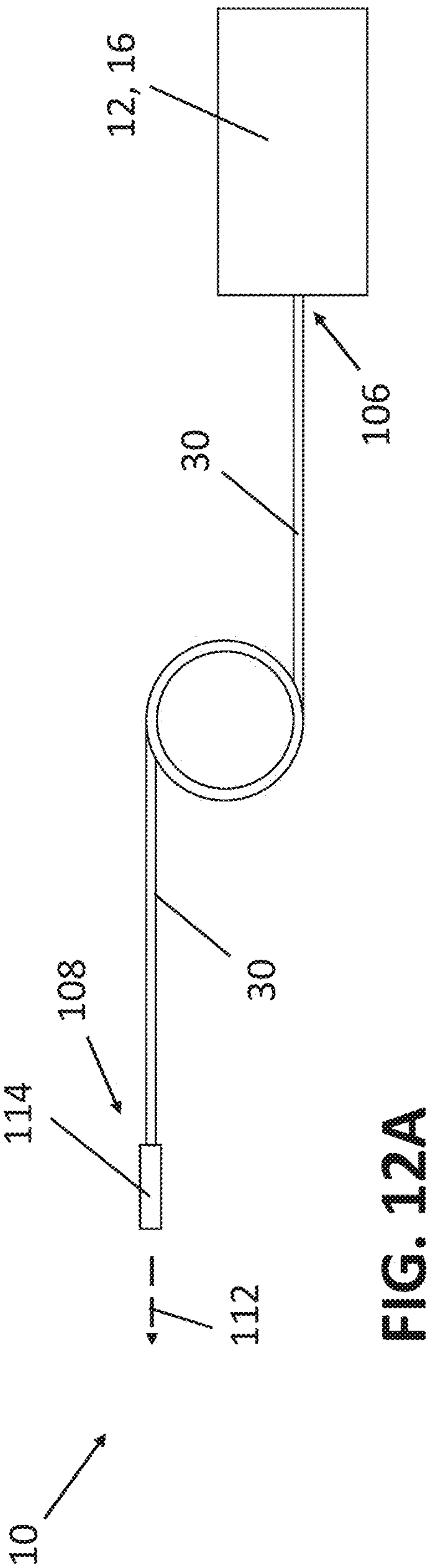

FIG. 12A is schematic illustration of a system comprising an optical fiber/fiber optic cable/optical fiber line and a UV-C light source configured to deliver UV-C light to exposed tissue (e.g., cancerous tissue or cells) such as on the skin or during open surgery. The system may include a handpiece at the distal end of the optical fiber/fiber optic cable/fiber optic line that can be manipulated by the physician or other medical professional to deliver the UV-C light to the target site.

Figure 12B:
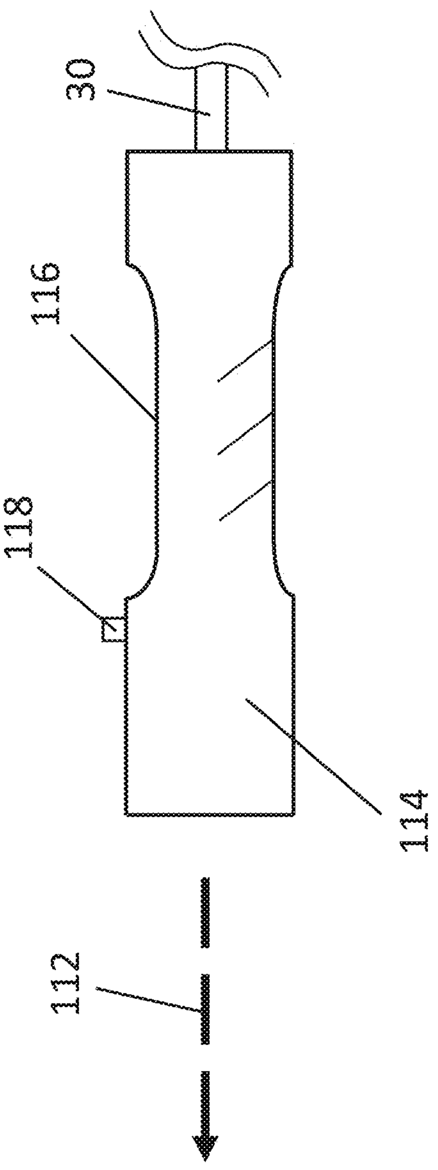

FIG. 12B is schematic drawing of an example handheld output tool, delivery device or handpiece configured to be held, for example, by a physician or surgeon, to manually apply UV-C light to the cancerous tissue or cells.

Figure 13A:
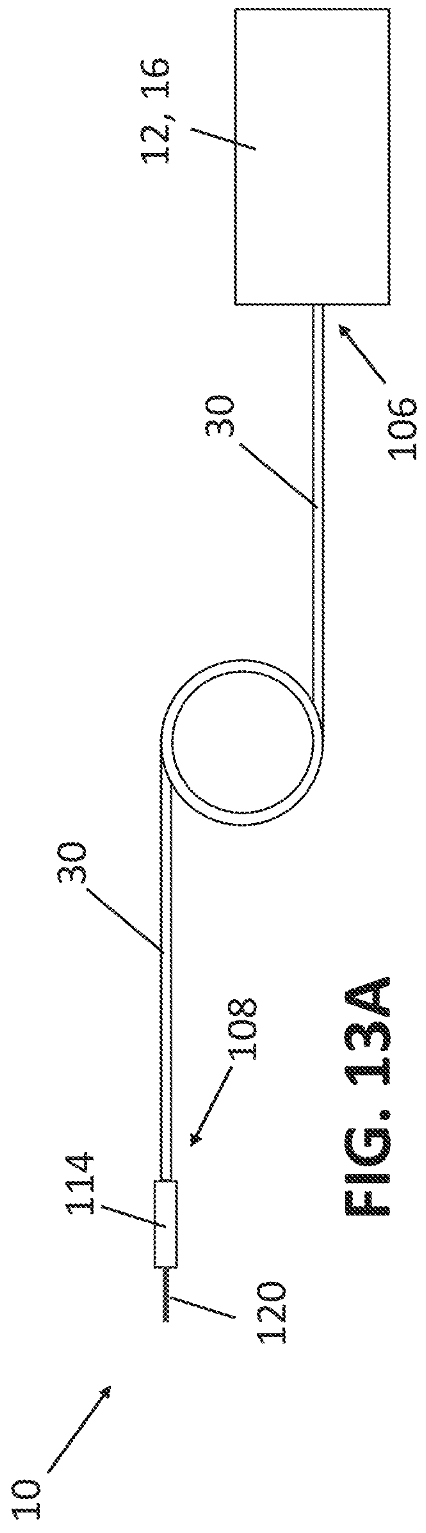

FIG. 13A is a schematic illustration of a system comprising an optical fiber/optical fiber line/fiber optic cable and a UV-C light source configured to deliver UV-C light to tissue (e.g., cancerous tissue or cells) using a handheld output tool, delivery device or handpiece having a tube, lumen, catheter, such as for a laparoscope at the distal end thereof for directing the UV-C light to the target area.

Figure 13B:
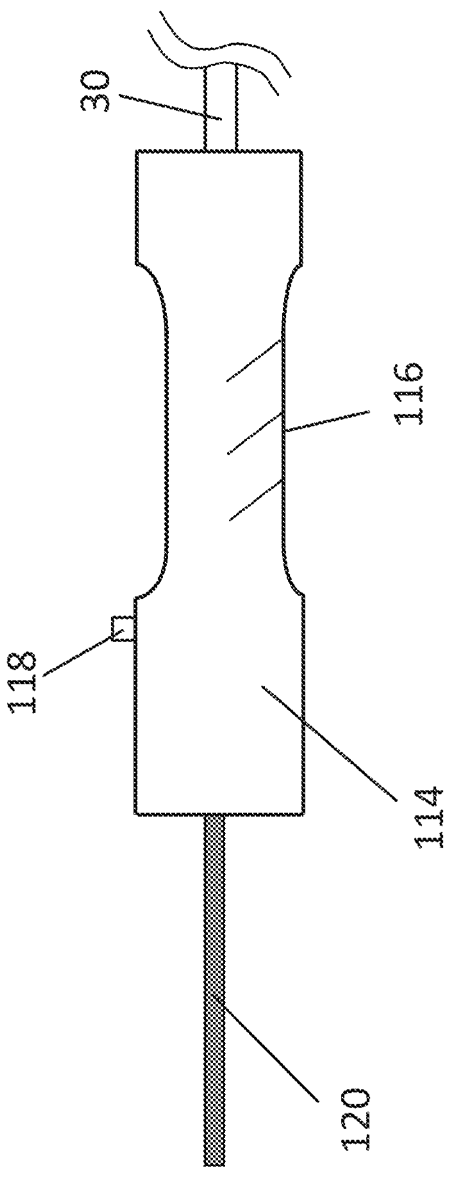

FIG. 13B is a schematic drawing of the handheld output tool, delivery device or handpiece of FIG. 13A having a rigid or flexible tube at the distal end thereof for directing the UV-C light to the target area.

Figures 14A, 14B:
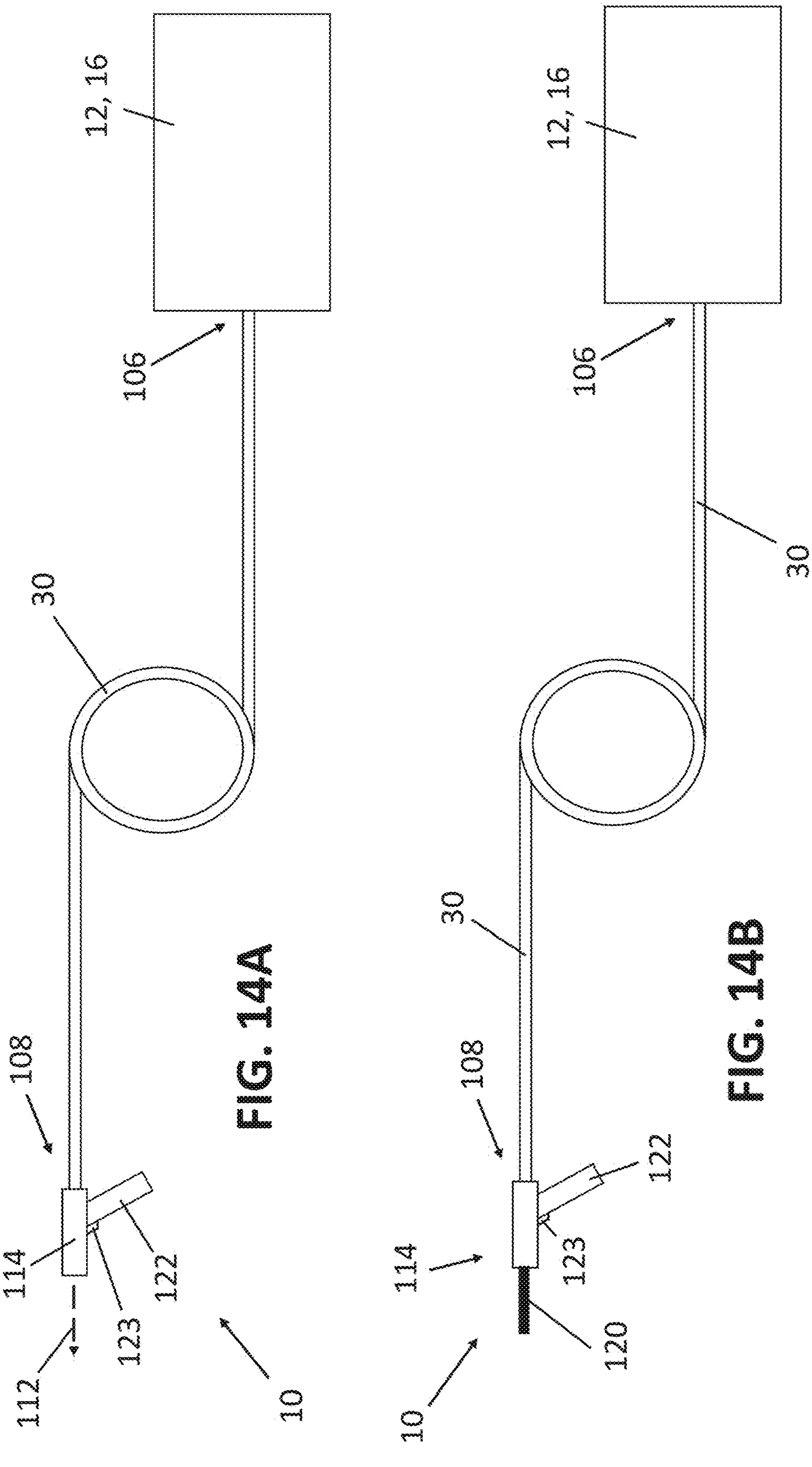

FIG. 14A is a schematic illustration of a system comprising an optical fiber and a UV-C light source configured to deliver UV-C light to expose tissue (e.g., cancerous tissue or cells) such as on the skin or during open surgery to UV light. This system includes a handheld output tool, delivery device or handpiece with a pistol grip for enhance control.

FIG. 14B is a schematic illustration of a system comprising an optical fiber and a UV-C light source configured to deliver UV-C light to tissue (e.g., cancerous tissue or cells) using a handheld output tool, delivery device or handpiece having a tube at the distal end thereof for directing the UV-C light to the target area. This system includes a handheld output tool, delivery device or handpiece with a pistol grip for enhanced control. In various implementations, the optical fiber/fiber optic cable/optical fiber line can approach the end of the tube where an output lens receives the light from the optical fiber/fiber optic cable/fiber optic line such that the light, possibly collimated or focused by the lens, can be directed onto the target (e.g., tumor or cancerous tissue).

Figure 15A:
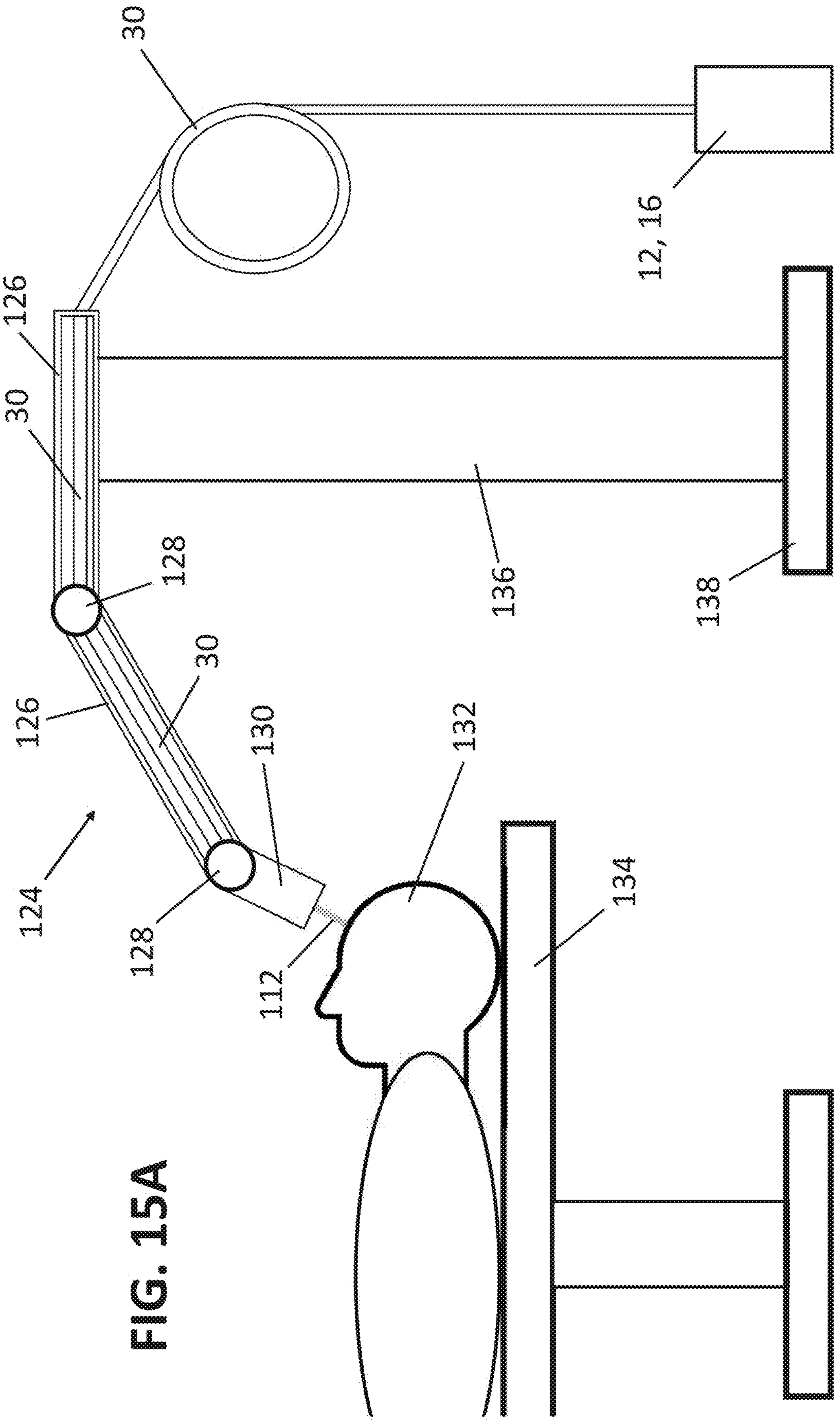

FIG. 15A is a schematic illustration of a system comprising an articulated arm, an optical fiber or fiber optic line or fiber optic cable and a UV-C light source that is configured to deliver UV-C light to tissue (e.g., cancerous tissue or cells) via the optical fiber/optical fiber line/fiber optic cable that extends along the articulated arm. This system may comprise a robotic system such as a robotic surgical system that can be operated by the surgeon or medical profession using controls or that can potentially be autonomous or partially automatic or autonomous.

Figure 15B:
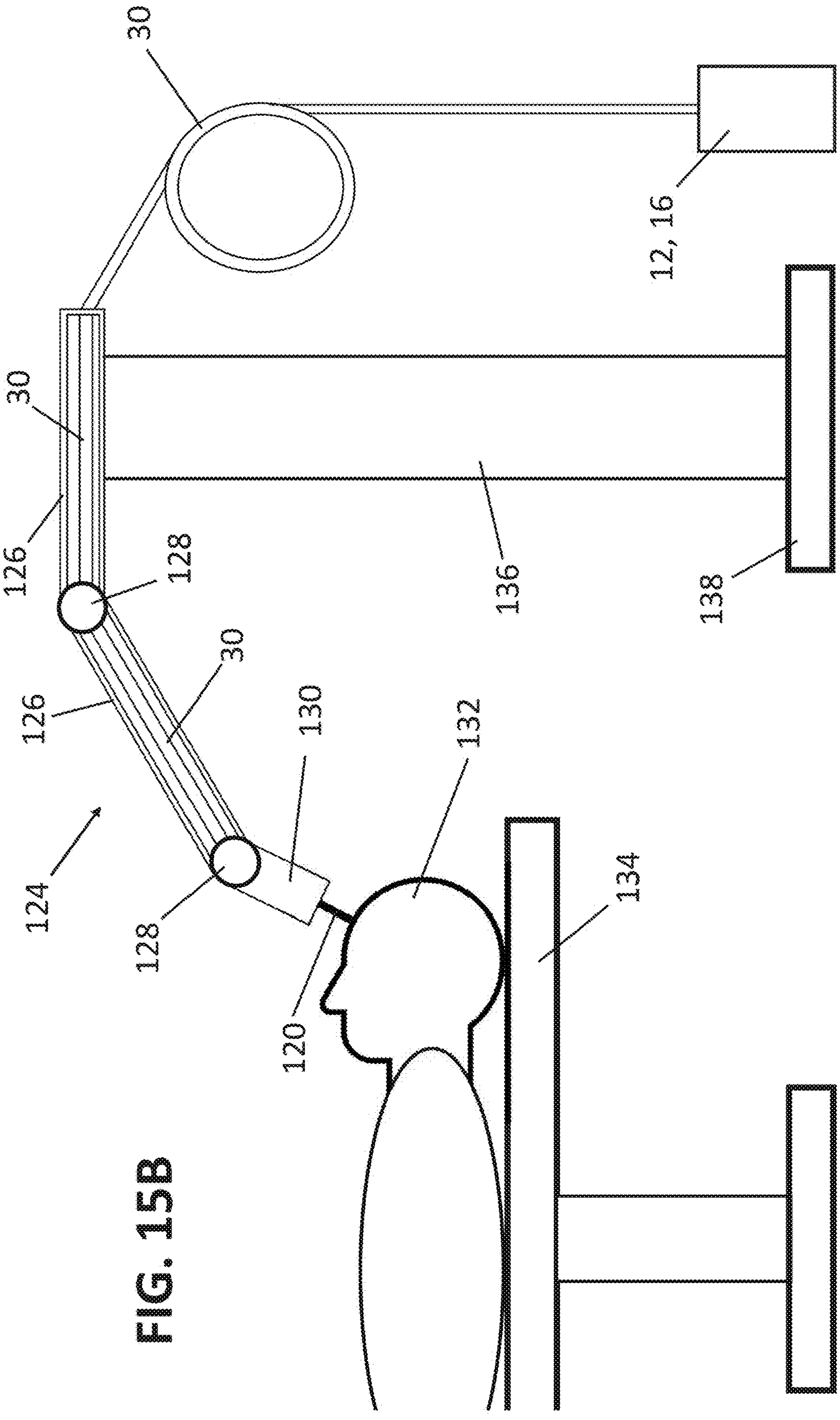

FIG. 15B is a schematic illustration of a system similar to that shown in FIG. 15A comprising an articulated arm, an optical fiber or fiber optic line or fiber optic cable and a UV-C light source that is configured to deliver UV-C light to tissue (e.g., cancerous tissue or cells) via the optical fiber/optical fiber line/fiber optic cable that extends along the articulated arm. The system further comprises a tube at the distal end of the articulated arm for directing the UV-C light to the target area. In various implementations, the optical fiber/optical fiber line/fiber optic cable can approach the end of the tube where an output lens receives the light from the optical fiber/optical fiber line/fiber optic cable such that the light, possibly collimated or focused by the lens, can be directed onto the target (e.g., tumor or cancerous tissue).

Figure 16A:
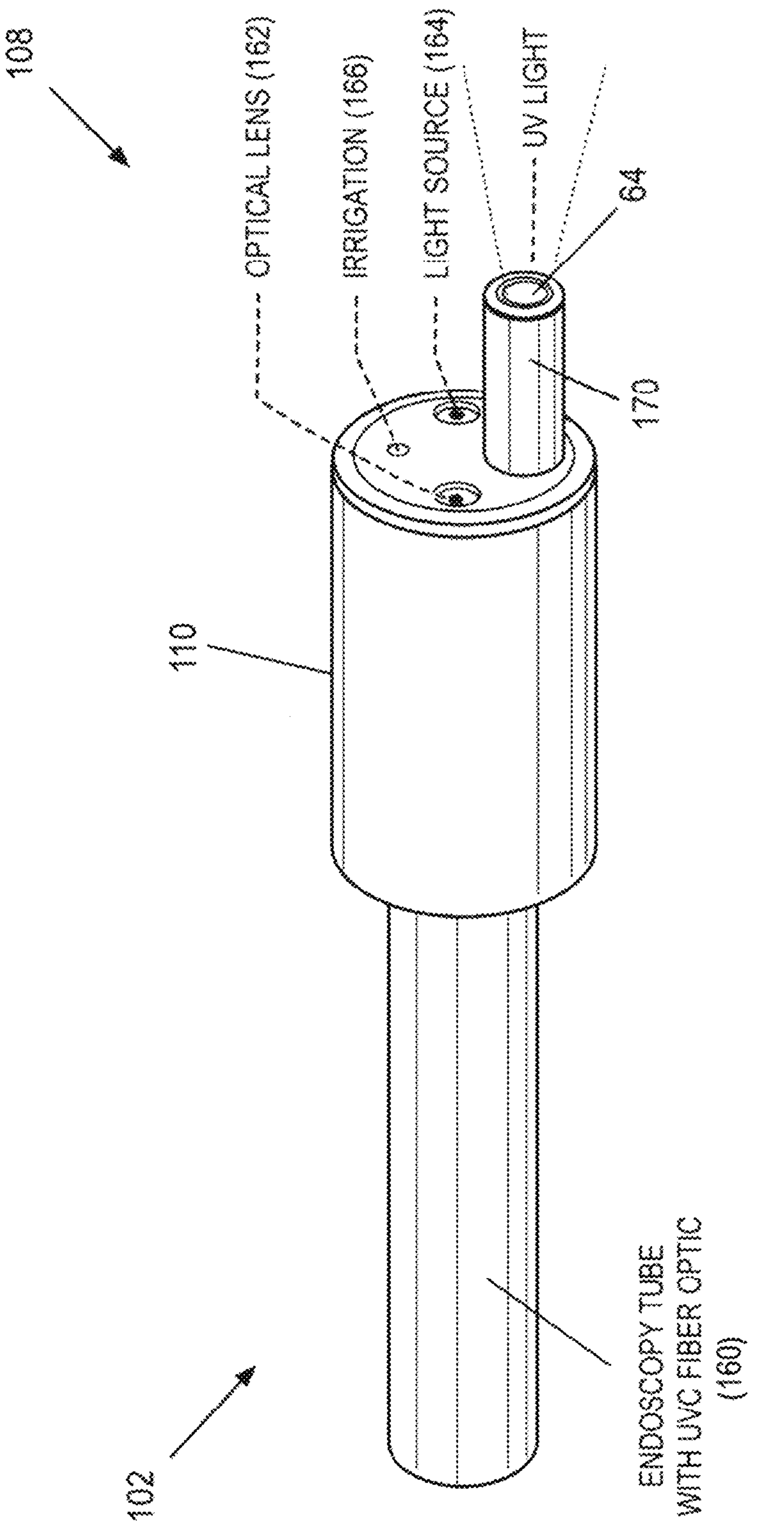

FIG. 16A is a schematic drawing of an endpiece at the distal end of an endoscope including an output for UV (e.g., UV-C) light, imaging optics for capturing an image of inside the body as well as a visible illumination source and an irrigation channel.

Figure 16B:
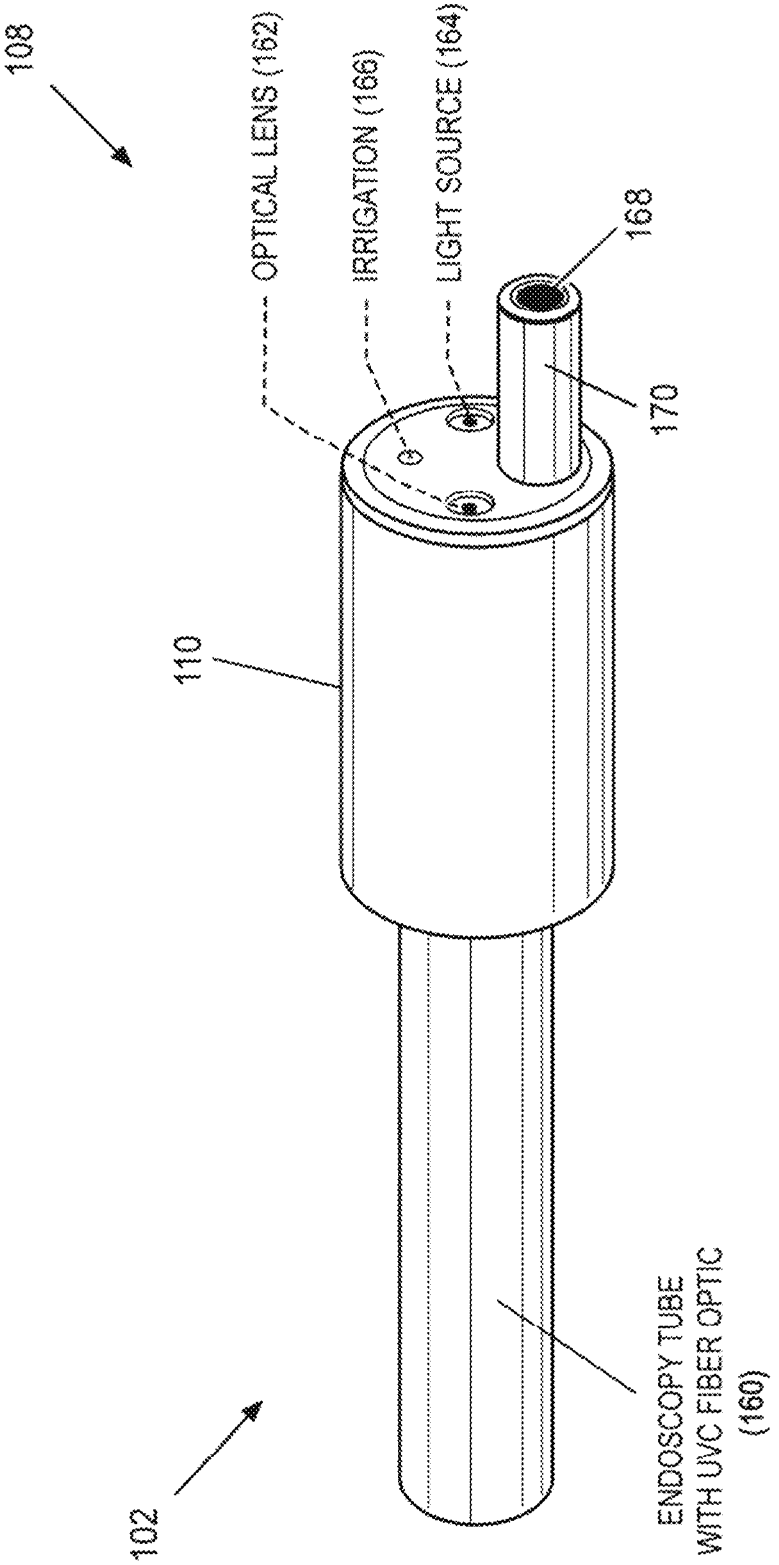

FIG. 16B is a schematic drawing of an endpiece at the distal end of an endoscope similar to that shown in FIG. 16A further comprising a movable or switchable cover in front of the output for UV (e.g., UV-C) light.

FIGS. 17A-17E schematically illustrate examples of the endoscope being inserted into the human body in different scenarios to treat different ailments such as different forms of cancer.

Figure 17A:
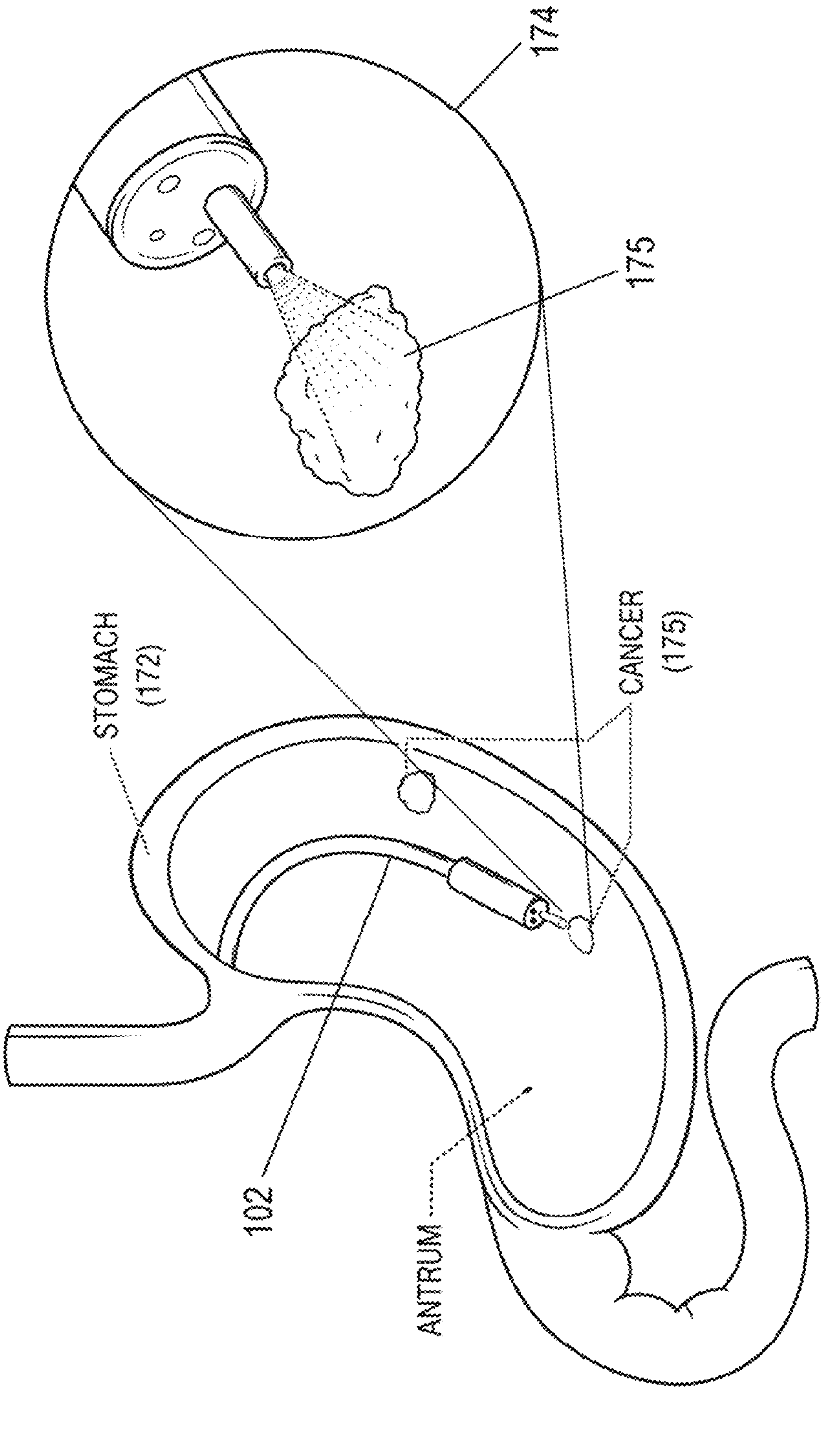
Figure 17B:
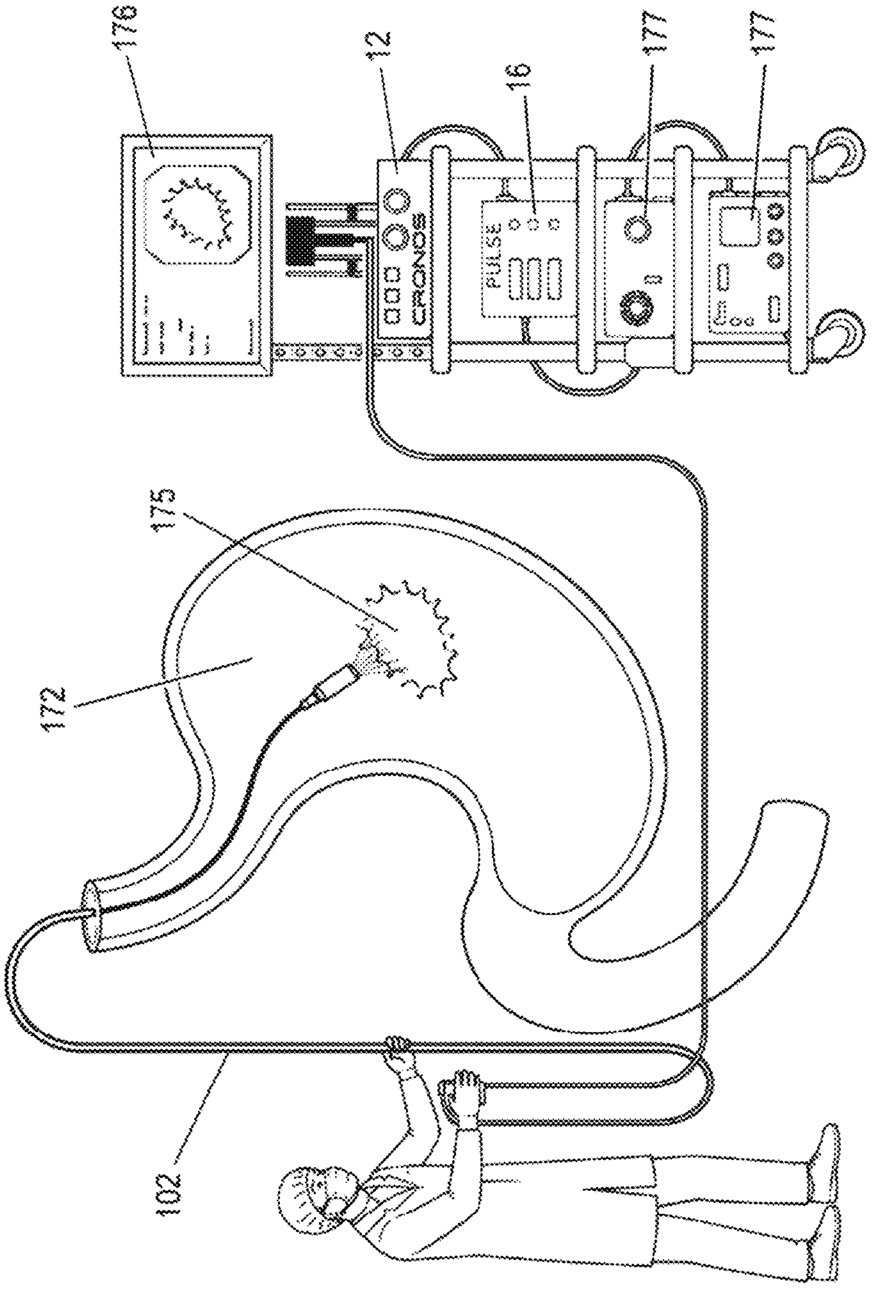
Figure 17C:
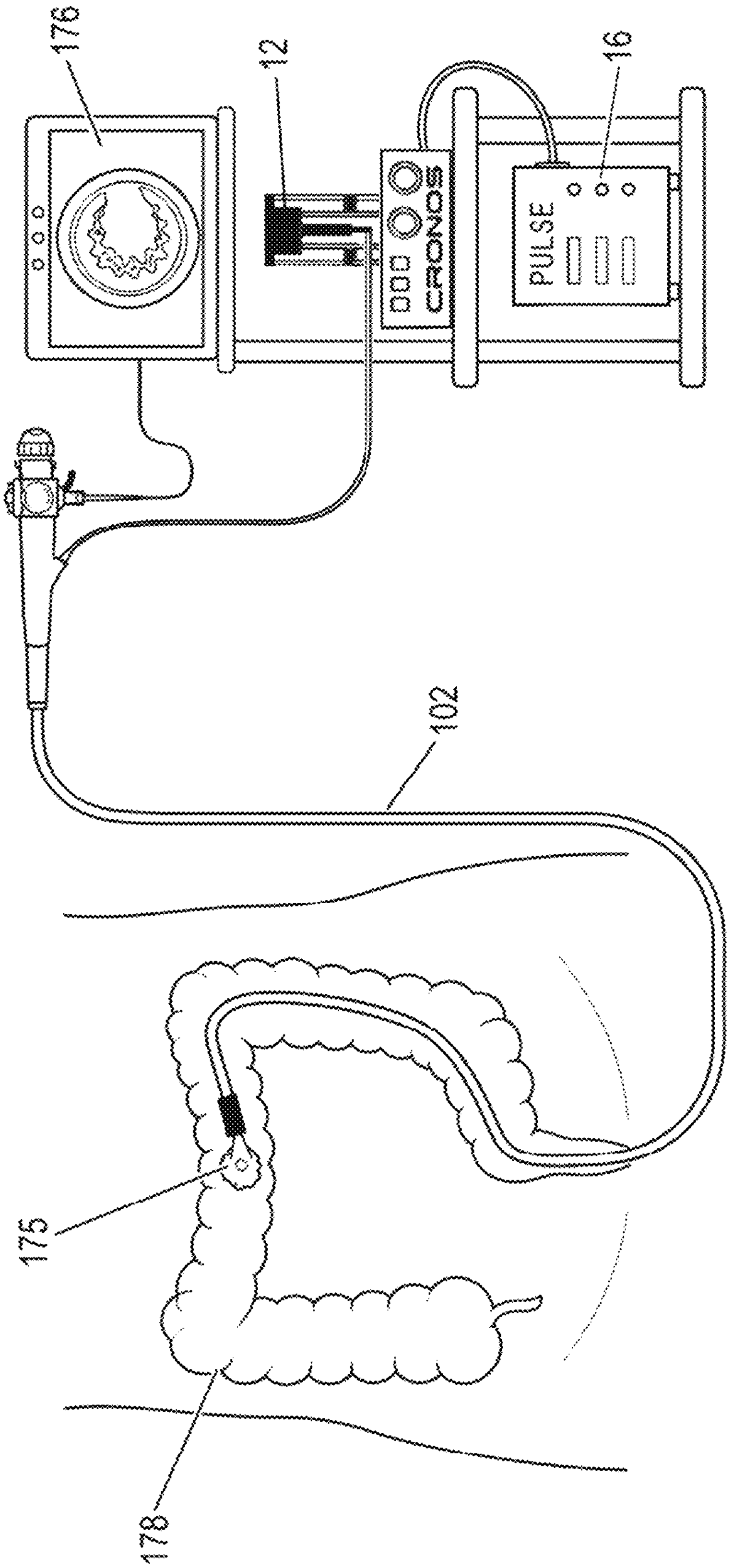
Figure 17D:
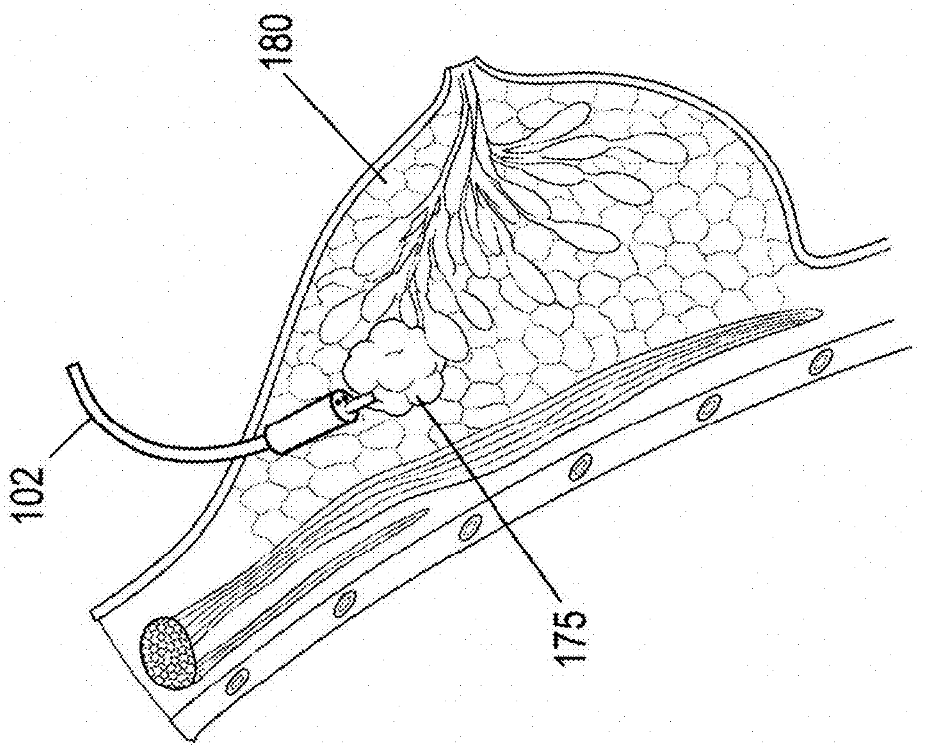
Figure 17E:
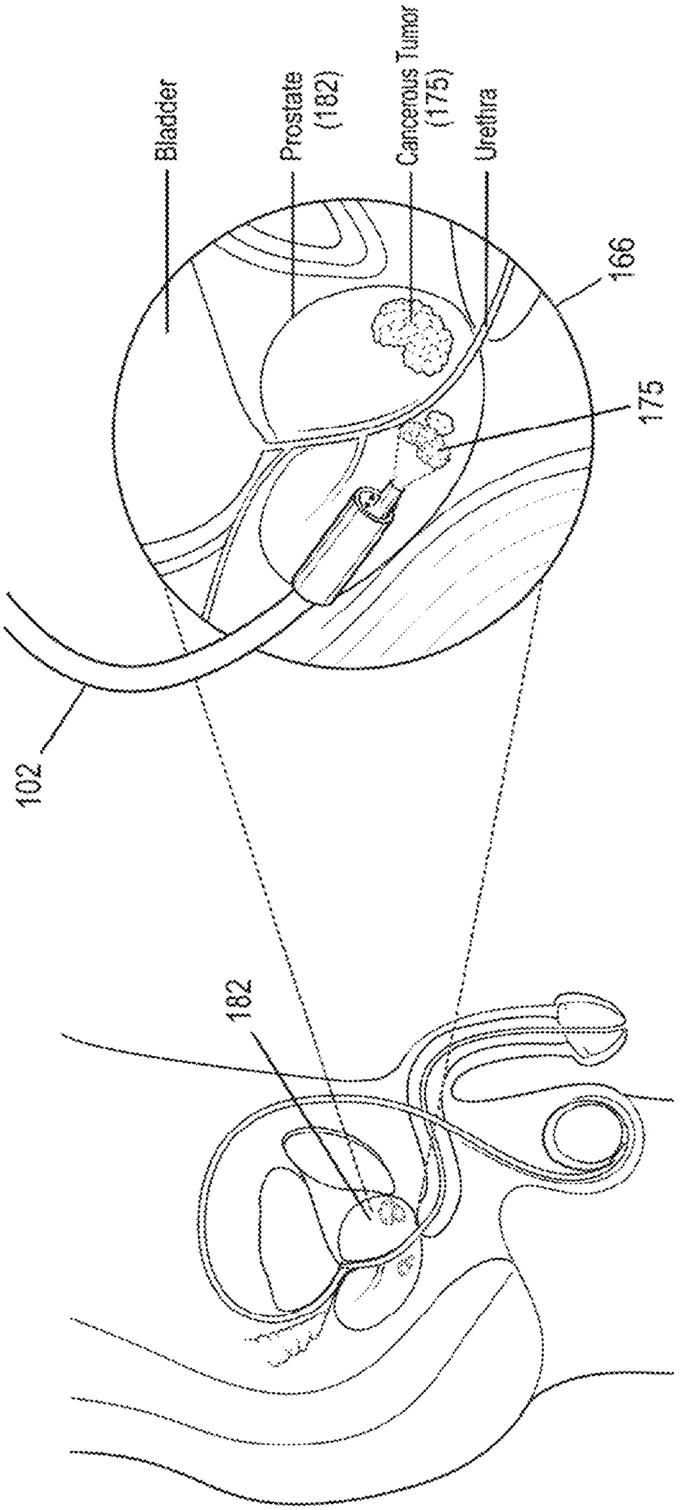
Figure 17F:
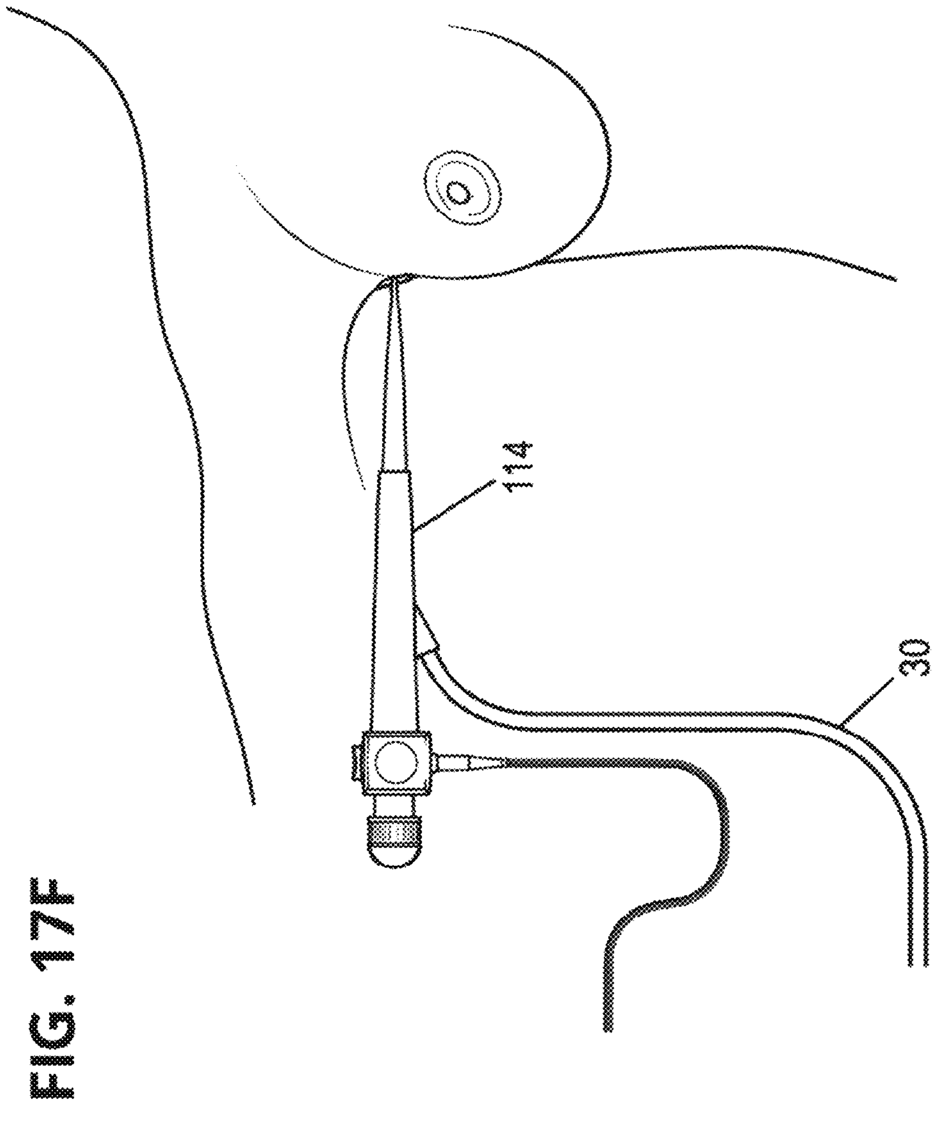

FIG. 17F is a schematic drawing of a handheld output tool, delivery device or handpiece inserted through an incision to administer UV or UV-C light within the body.

Figure 18:
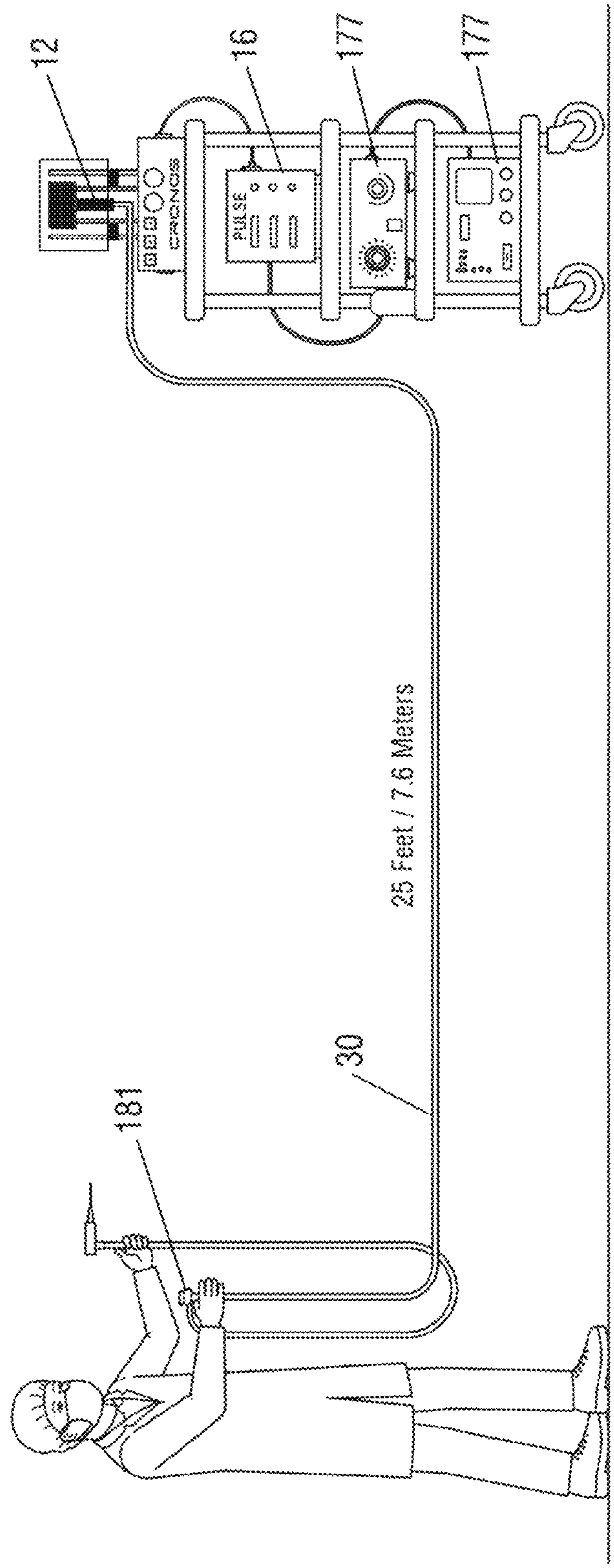

FIG. 18 is a schematic drawing of a system that includes an optical fiber or optical fiber line or fiber optic cable having an increased length such as a length of 25 feet.

Figure 19A:
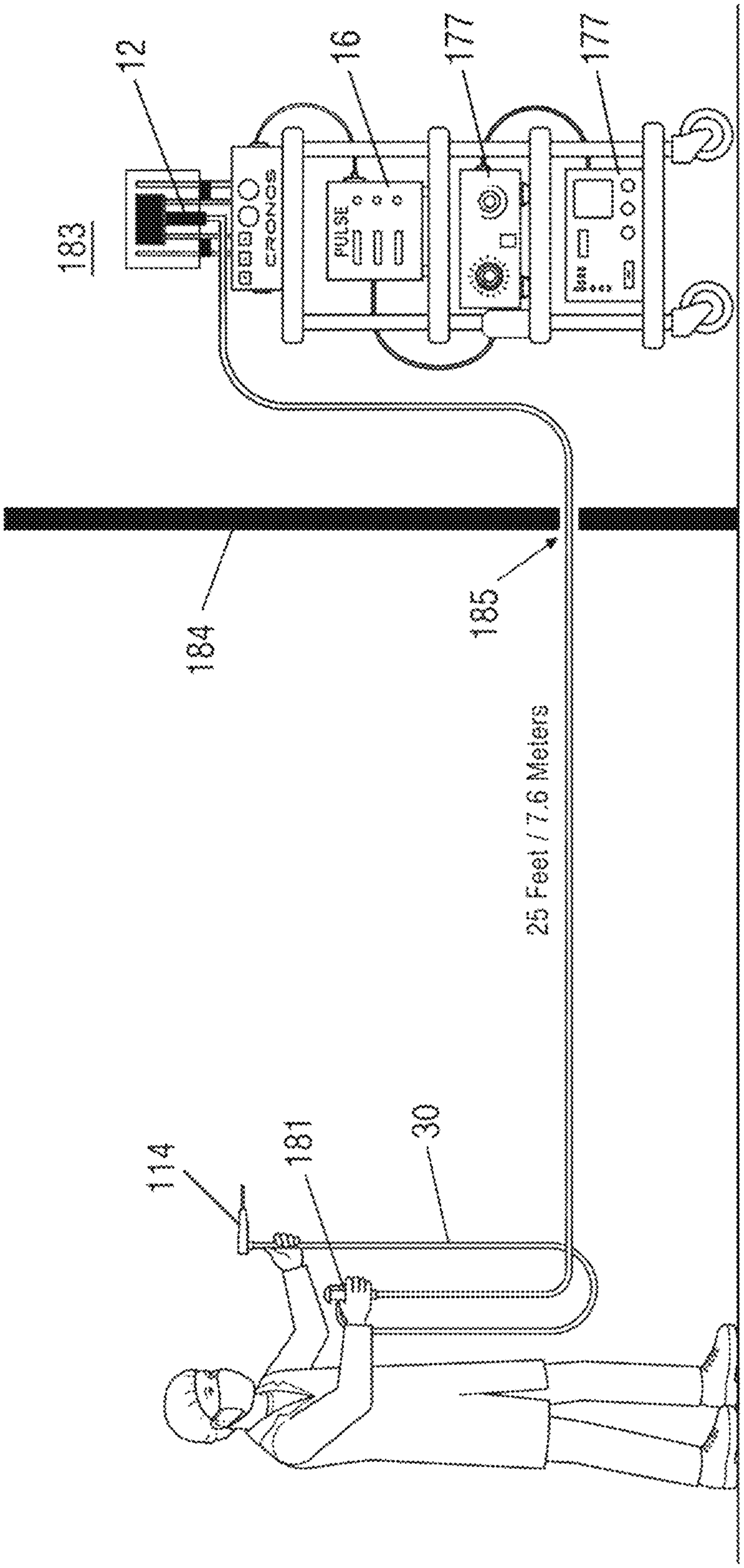

FIG. 19A is a schematic drawing of a system with the light source in a separate room as the distal end of the optical fiber or optical fiber line or fiber optic cable where the patient will undergo treatment.

Figure 19B:
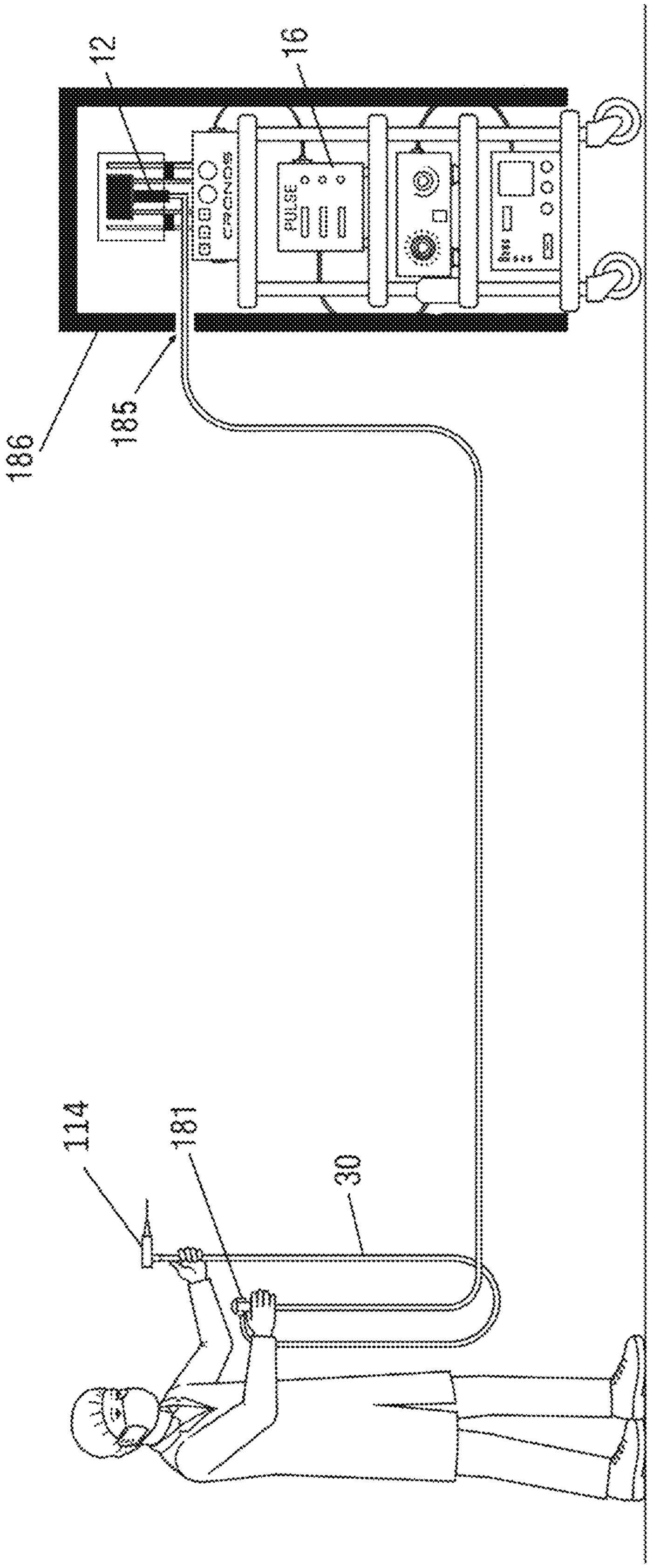

FIG. 19B is a schematic drawing showing shielding disposed about the light source as well as the proximal end of the optical fiber/optical fiber line/fiber optic cable.

Figure 20A:
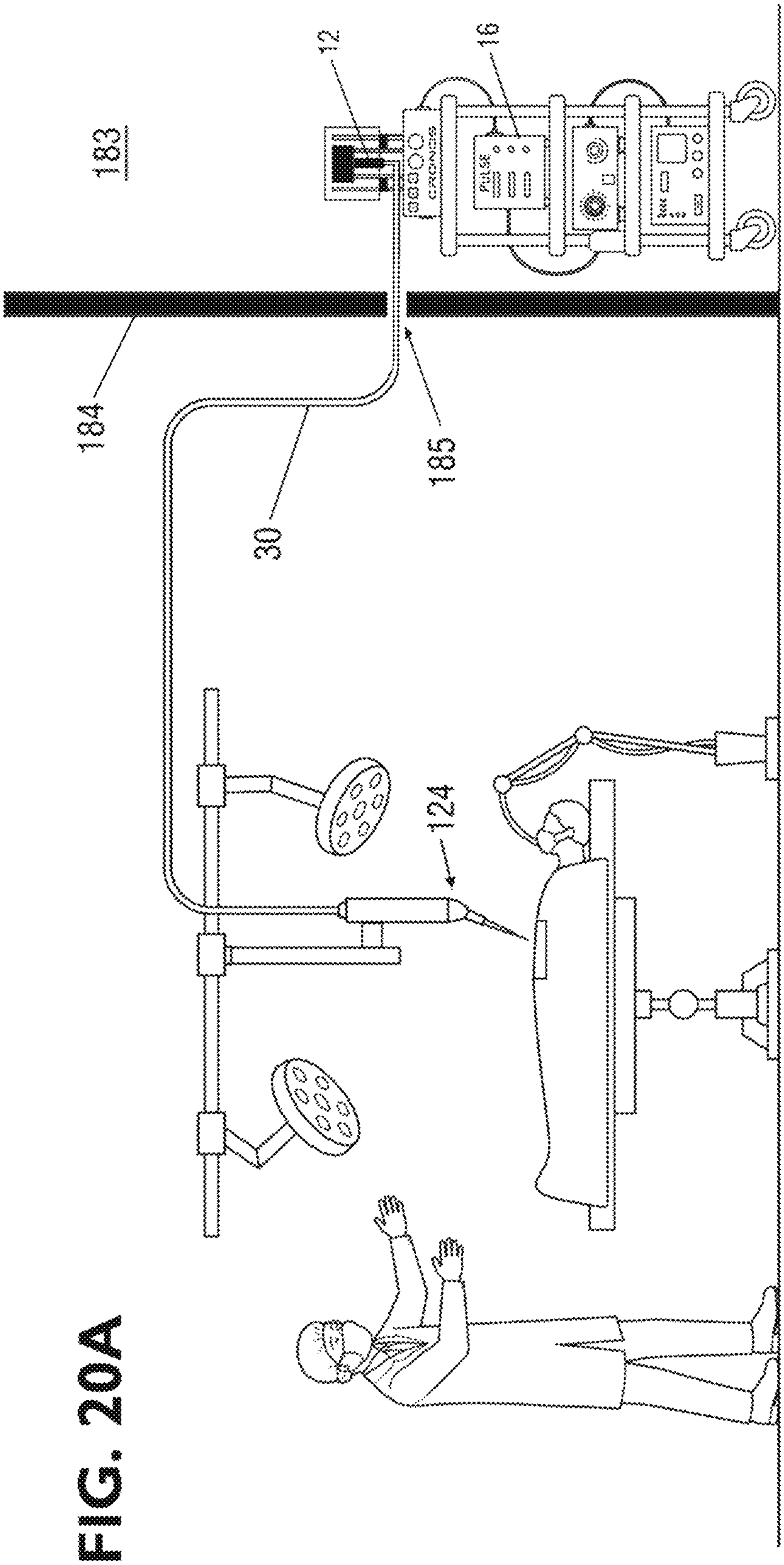
Figure 20B:
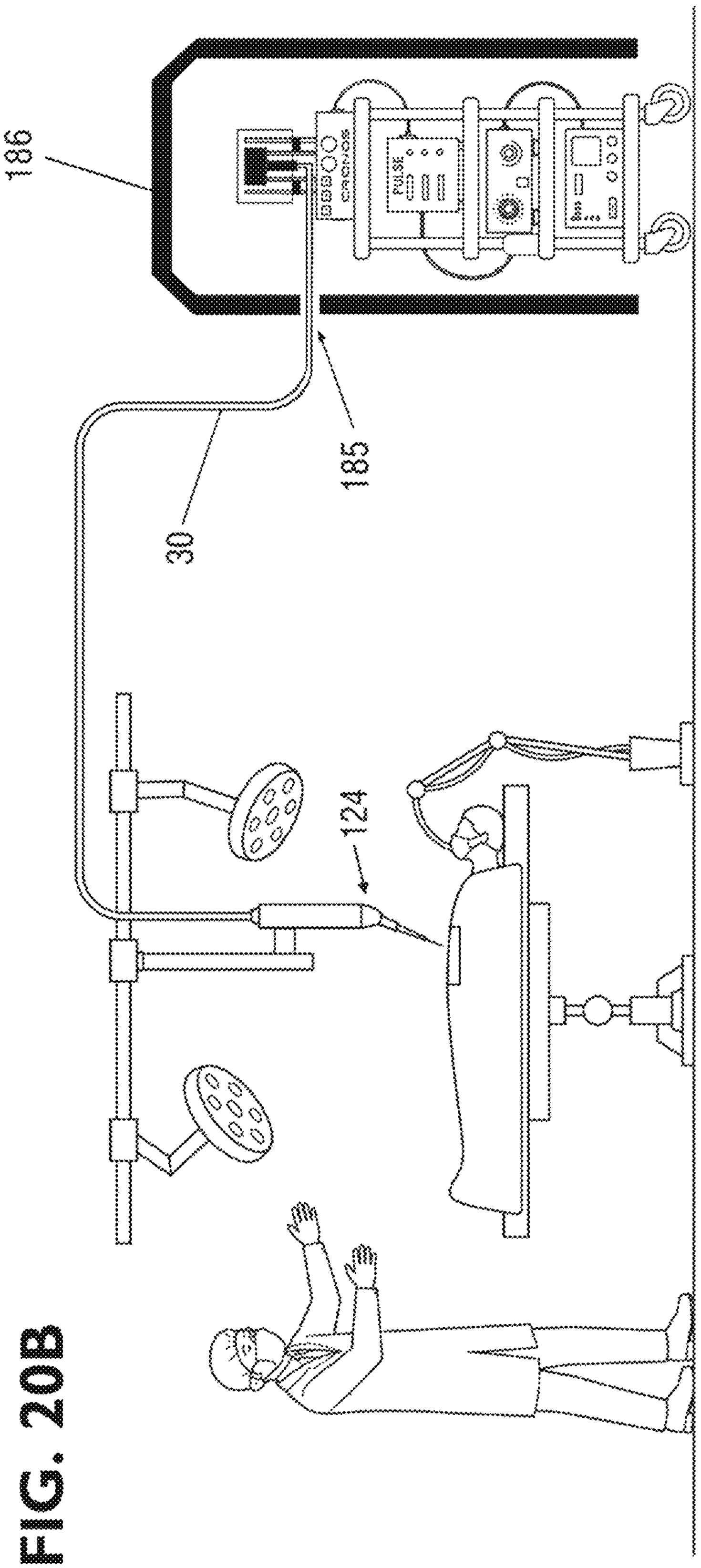

FIGS. 20A and 20B are schematic drawings of robotic systems for treating a patient with UV (e.g., UV-C) light that provide for increase safety.

Figure 21B:
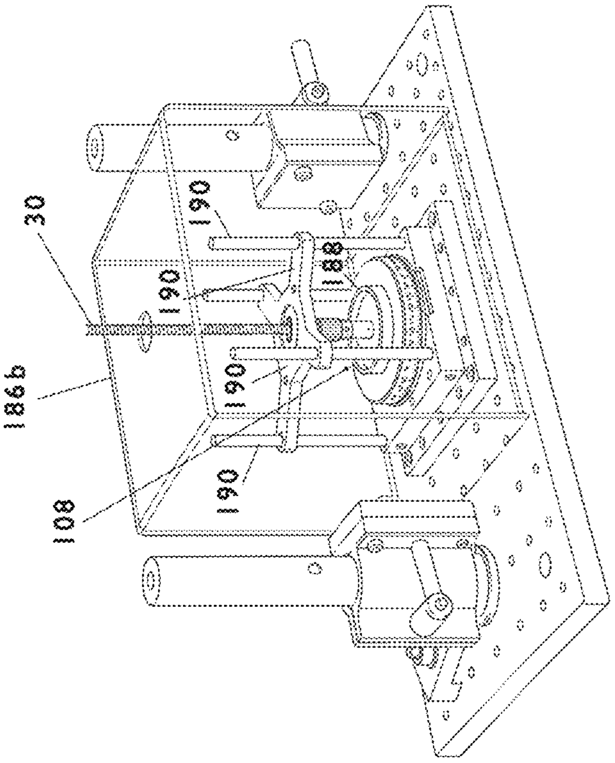
Figure 21A:
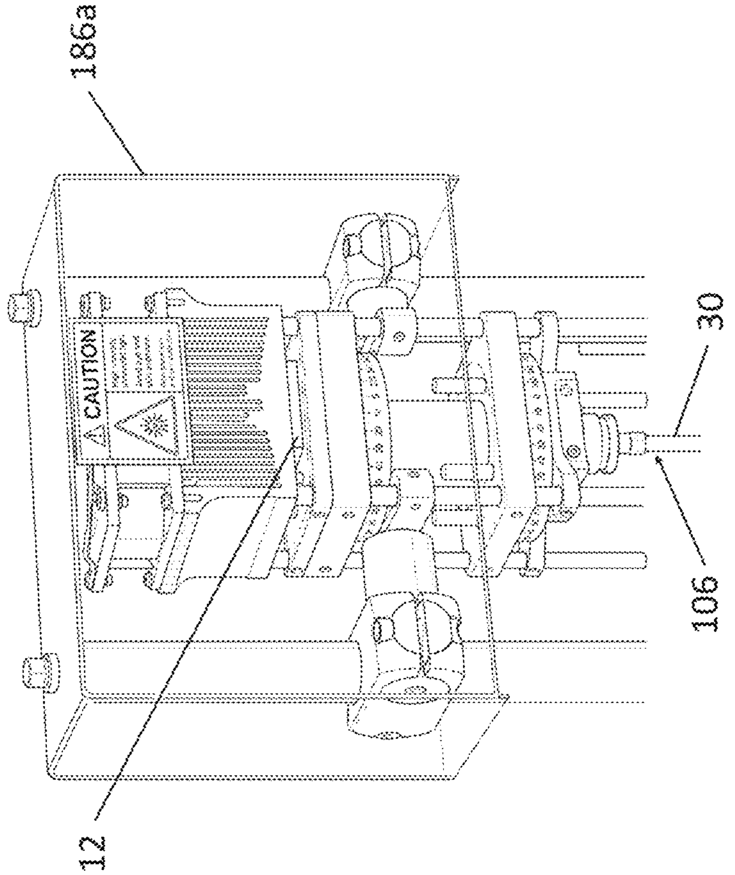

FIGS. 21A and 21B are photographs of the system showing shielding at the light source as well as distal end of the optical fiber/optical fiber line/fiber optic cable.

Figure 22B:
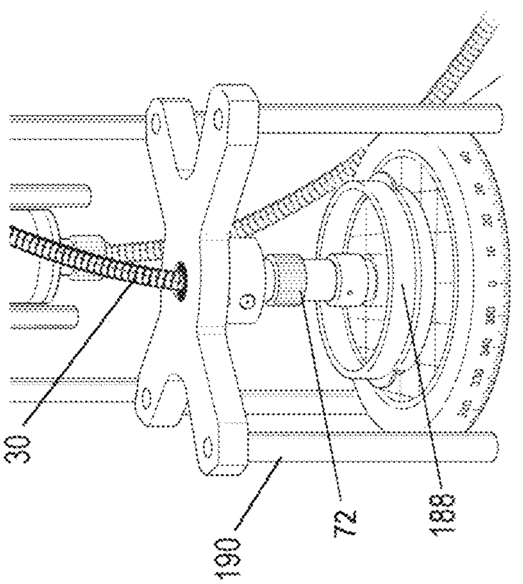
Figure 22A:
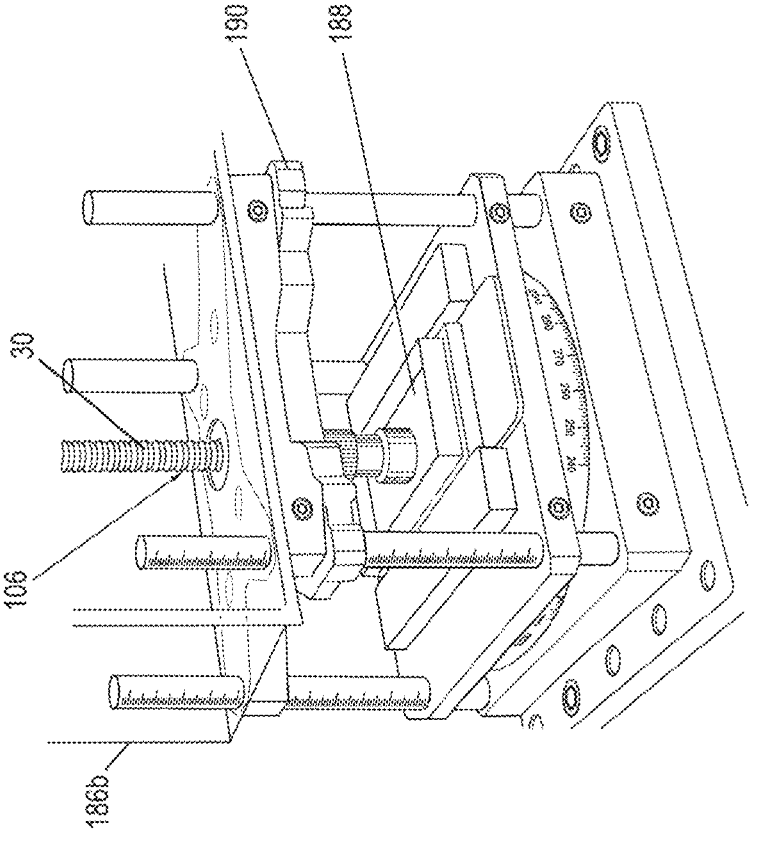

FIGS. 22A and 22B are additional photographs showing a system configured to test samples included on microscope slides, in petri dishes or sample containers using UV light from the distal end of the optical fiber/optical fiber line/fiber optic cable.

Figure 22C:
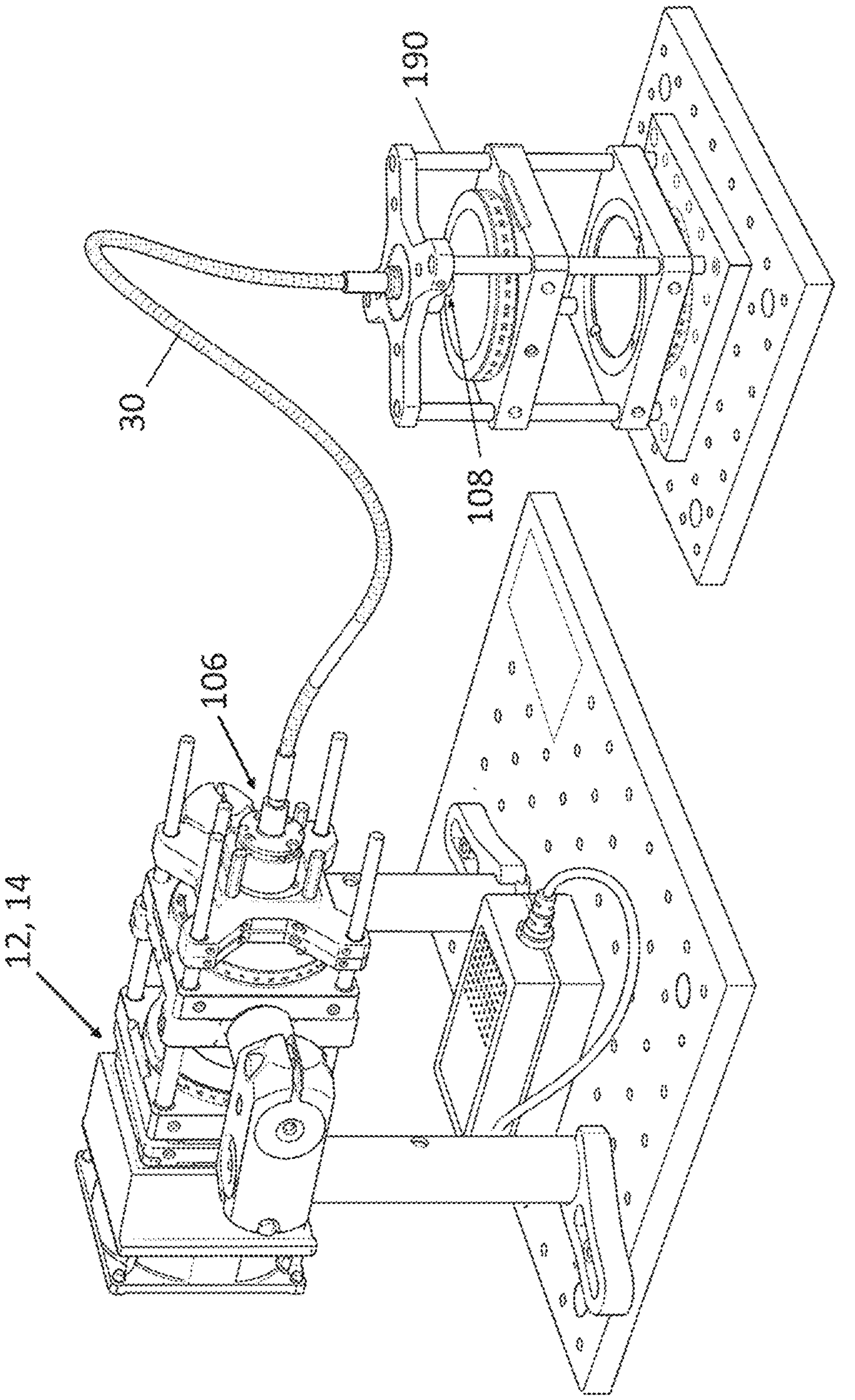
Figure 22D:
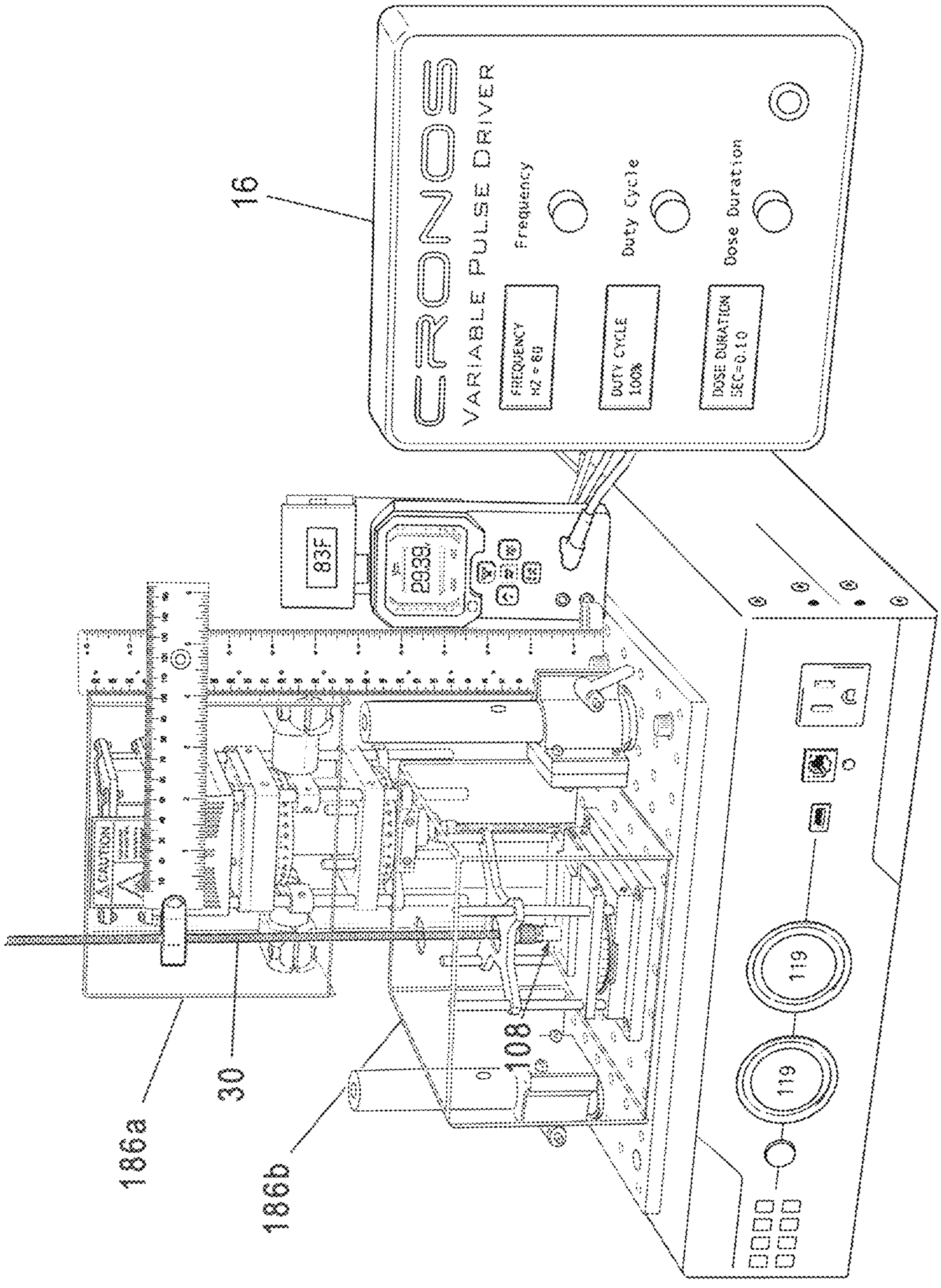

FIGS. 22C and 22D are additional photographs of such a system without the shielding and with the shielding, respectively.

Figure 22E:
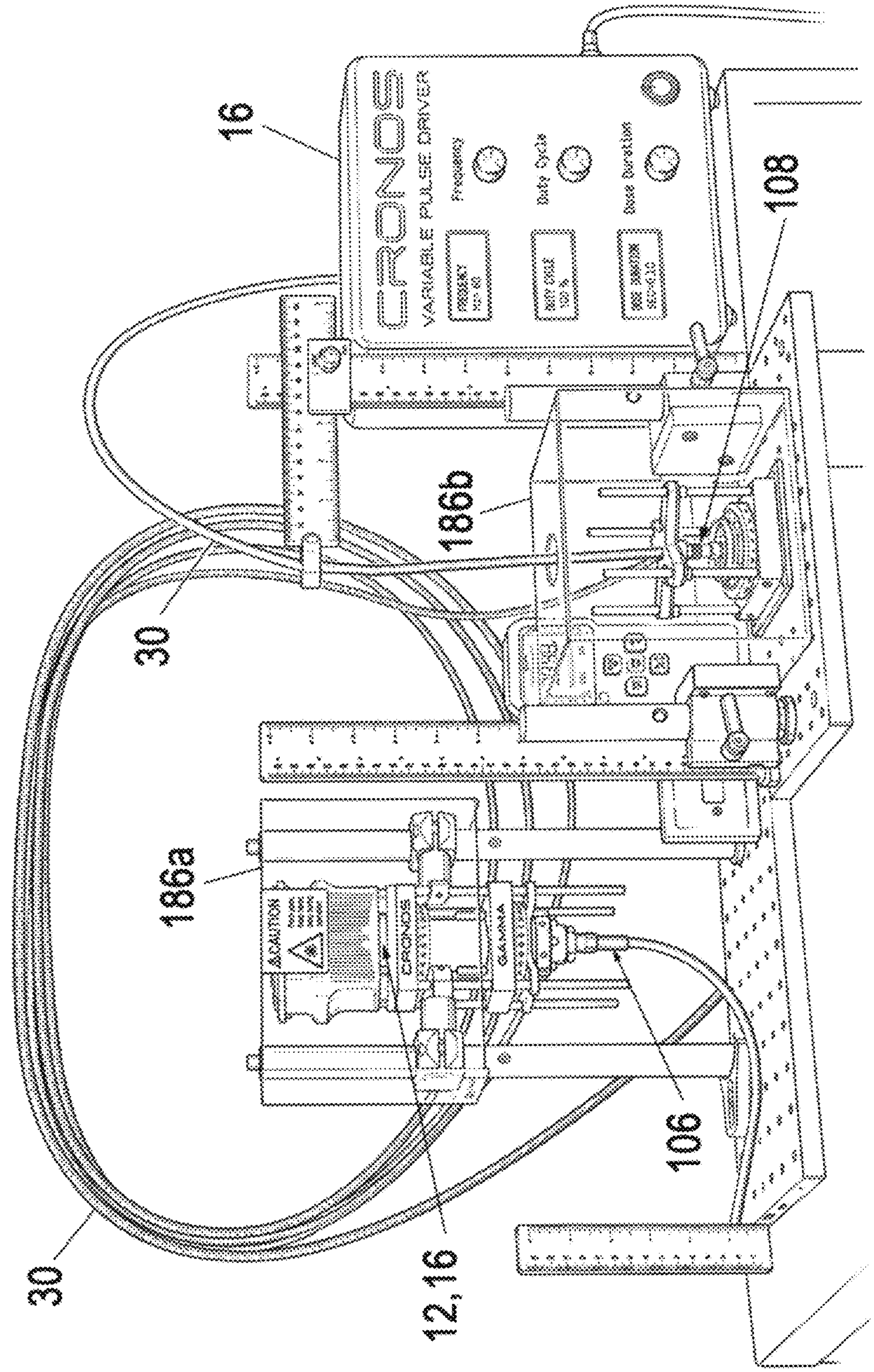

FIG. 22E is a photograph of such a system showing a long length of optical fiber or fiber optic cable or fiber optic line optically coupled to the UV light source. Shielding about the light source (e.g., the one or more light emitters) as well as at the distal end of the optical fiber/fiber optic cable/optical fiber line is readily visible.

Figure 23:
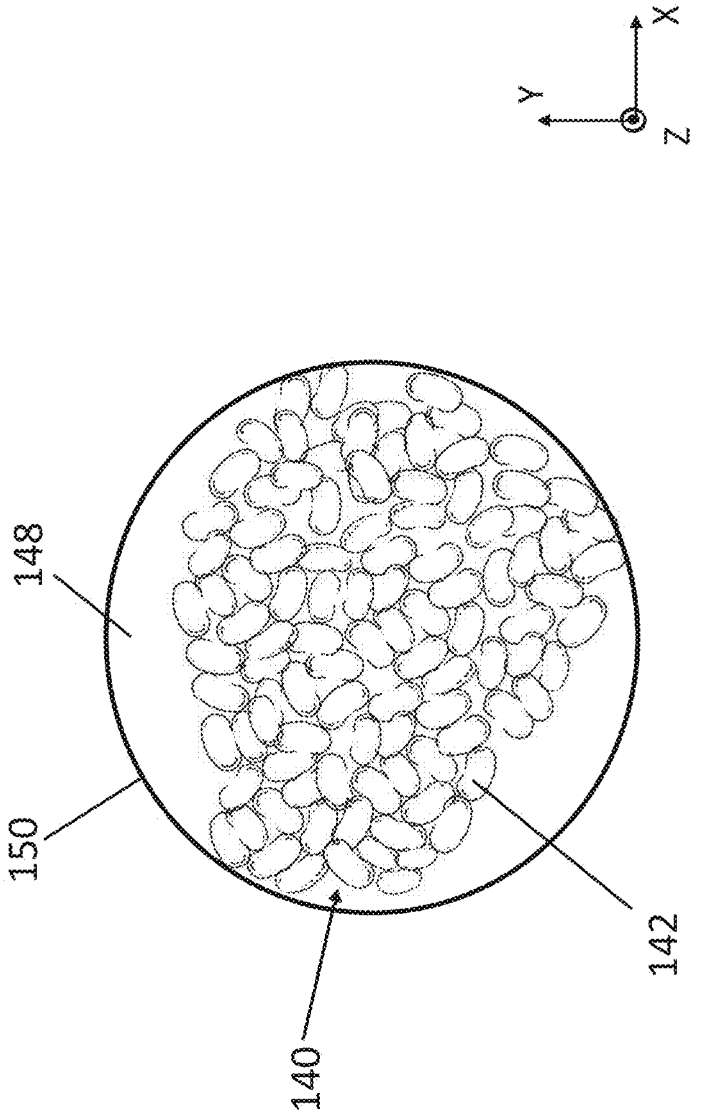

FIG. 23 schematically illustrates a tumor comprising a plurality of cancer cells and a UV-C light beam directed thereon. Systems, methods and devices described herein may be configured to direct light onto the tumor or region of cancerous tissue without excessive exposure of non-cancerous tissue to the UV-C light to reduce damage to such non-cancerous or healthy tissue.

Figure 24:
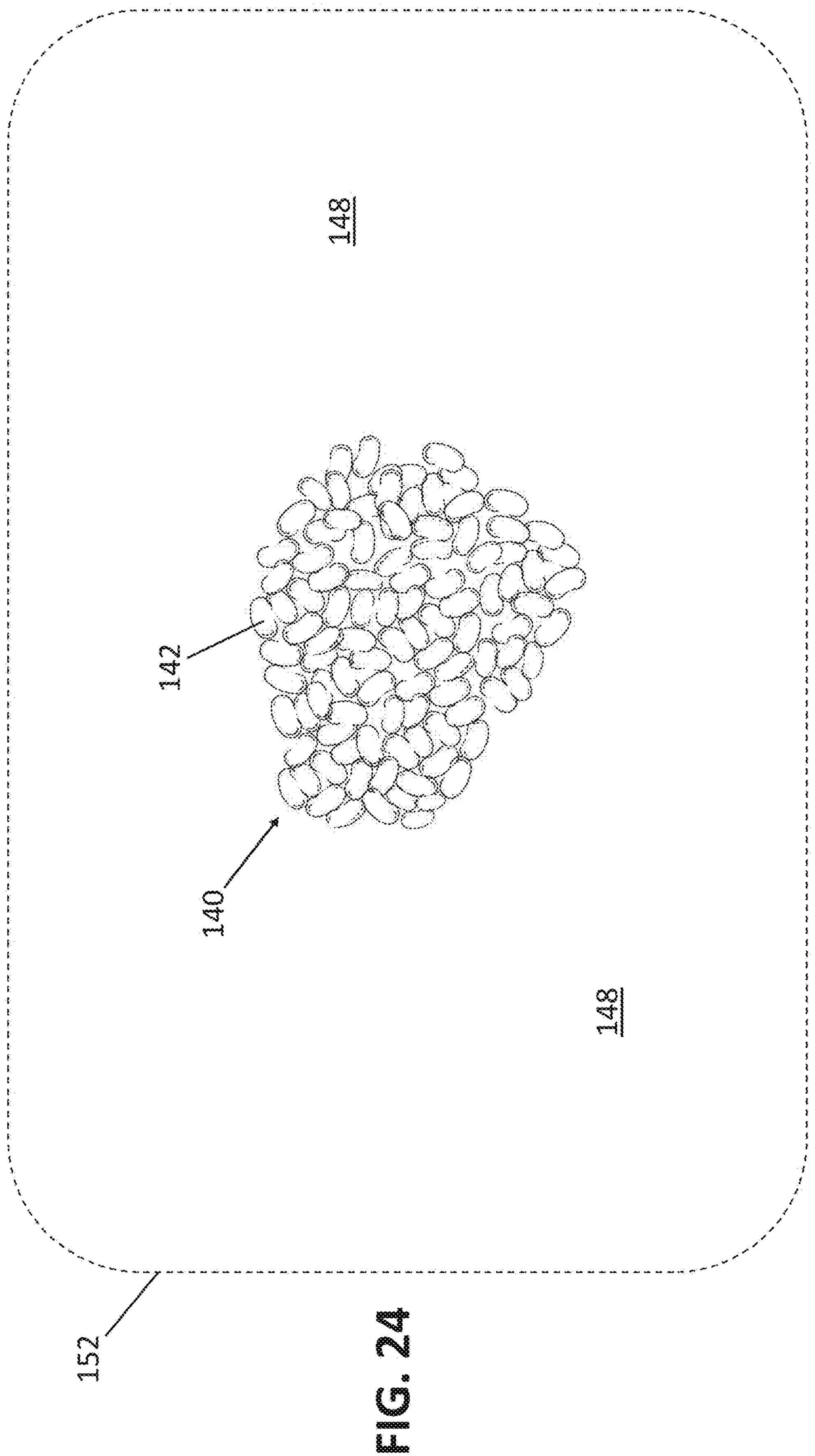

FIG. 24 schematically illustrates a tumor comprising a plurality of cancer cells with "blanket" UV-C illumination directed thereon. In addition to illuminating the tumor or region of cancerous tissue, large portions of non-cancerous tissue are exposed to UV-C light. The UV-C light, for example, covers more non-cancerous tissue than cancerous tissue.

FIG. 25 is a table illustrating how variation in duty cycle of the pulsed UV-C light affects the amount of light directed onto the target.

Figure 26B:
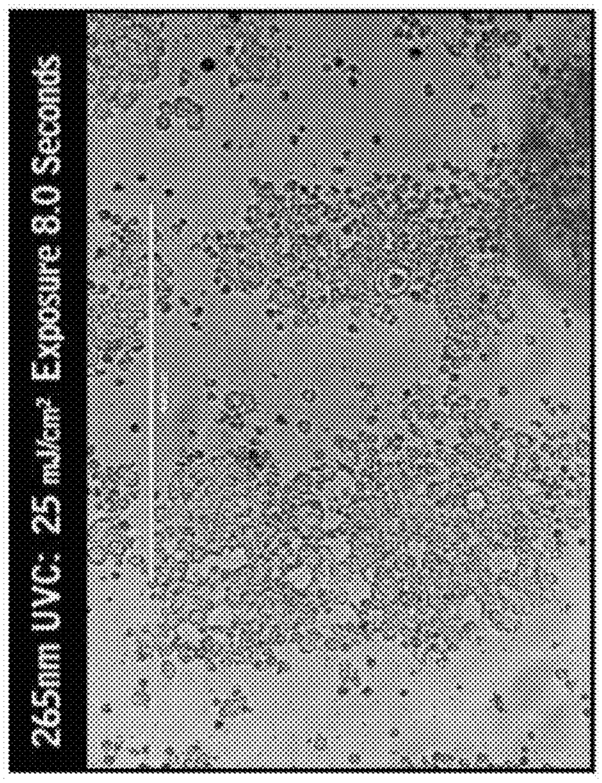
Figure 26A:
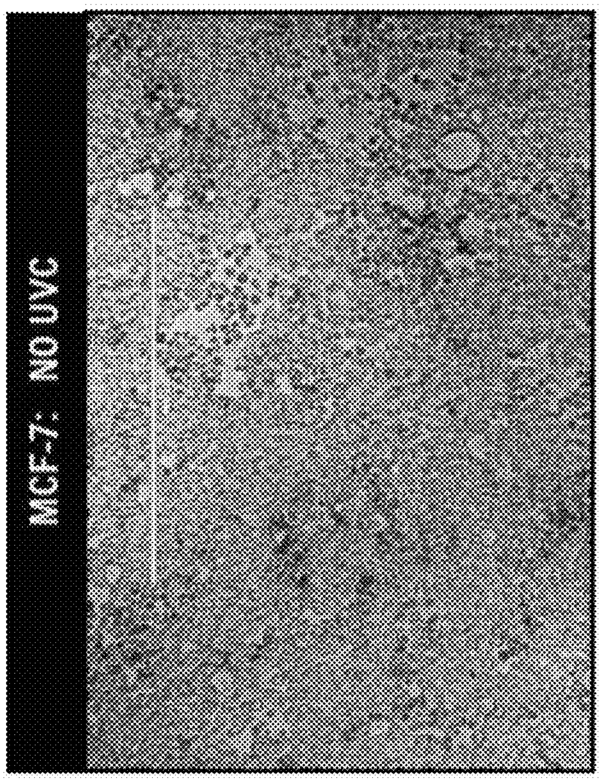

FIG. 26A is a photo of MCF-7 breast cancer cells not exposed to the UV-C light from the UV-C light source.

FIG. 26B is a photo of MCF-7 breast cancer cells after being exposed to 25 $mJ/cm^2$ of UV-C light from the UV-C light source.

Figure 27B:
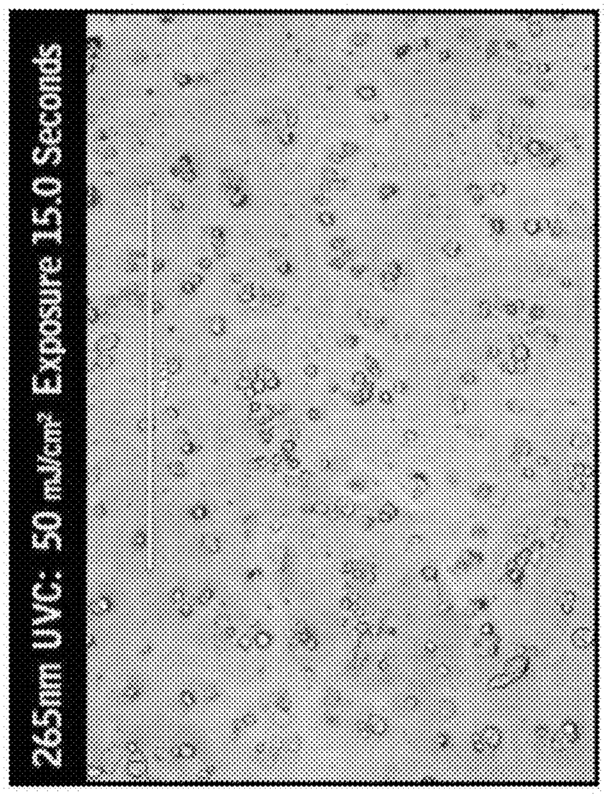
Figure 27A:
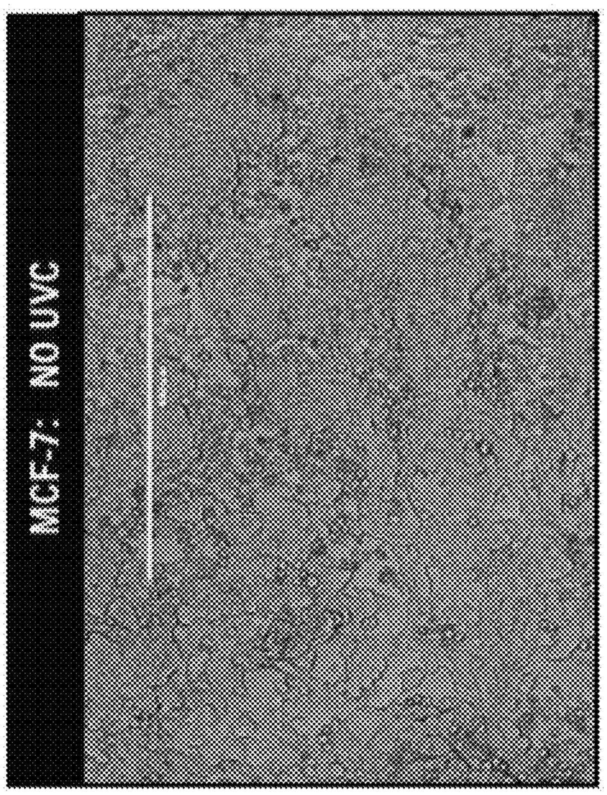

FIG. 27A is a photo of MCF-7 breast cancer cells not exposed to the UV-C light from the UV-C light source.

FIG. 27B is a photo of MCF-7 breast cancer cells after being exposed to 50 $mJ/cm^2$ of UV-C light from the UV-C light source.

Figure 28A:
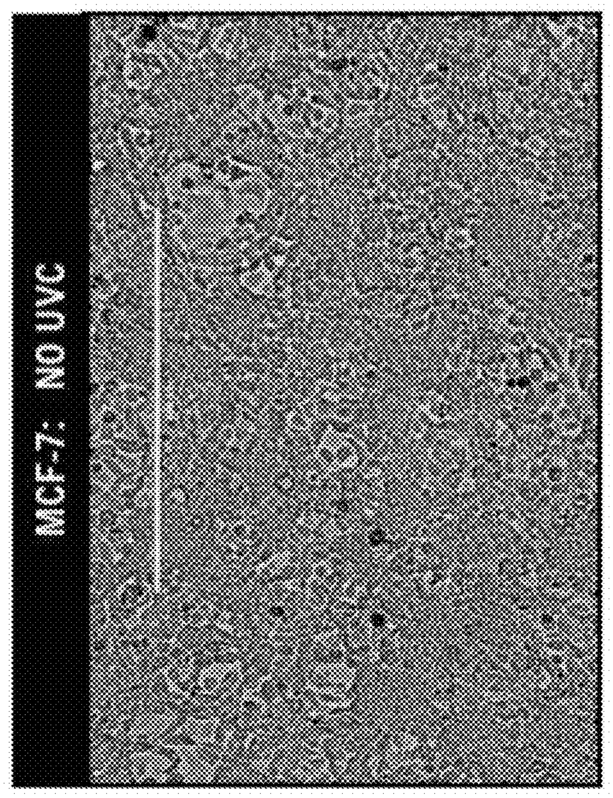

FIG. 28A is a photo of MCF-7 breast cancer cells not exposed to the UV-C light from the UV-C light source.

Figure 28B:
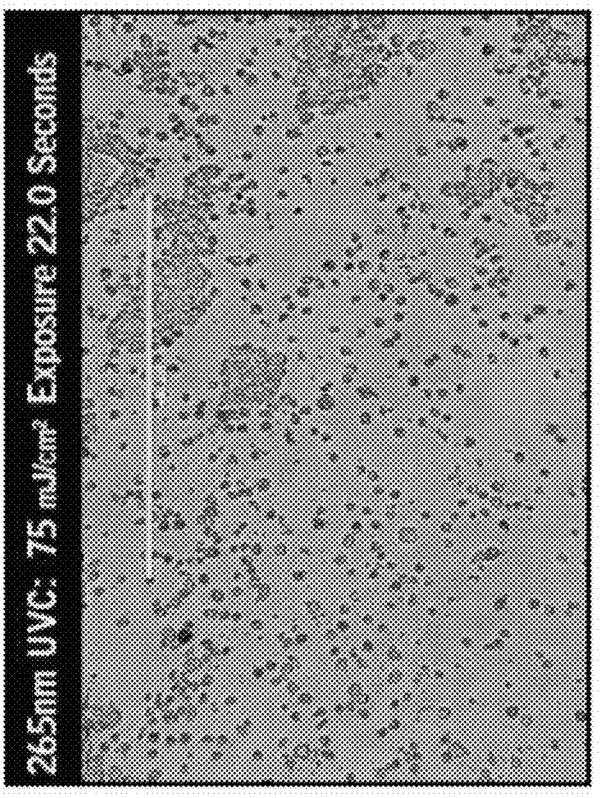

FIG. 28B is a photo of MCF-7 breast cancer cells after being exposed to 75 $mJ/cm^2$ of UV-C light from the UV-C light source.

Figure 29B:
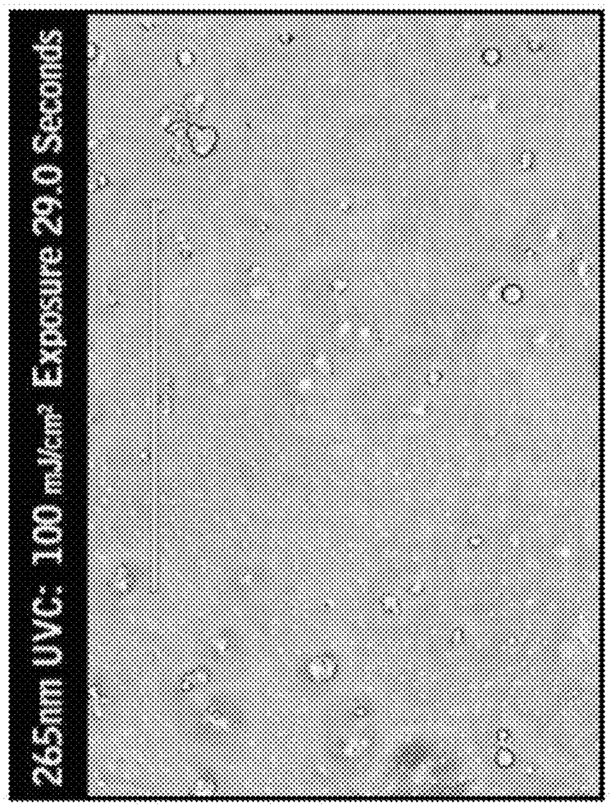
Figure 29A:
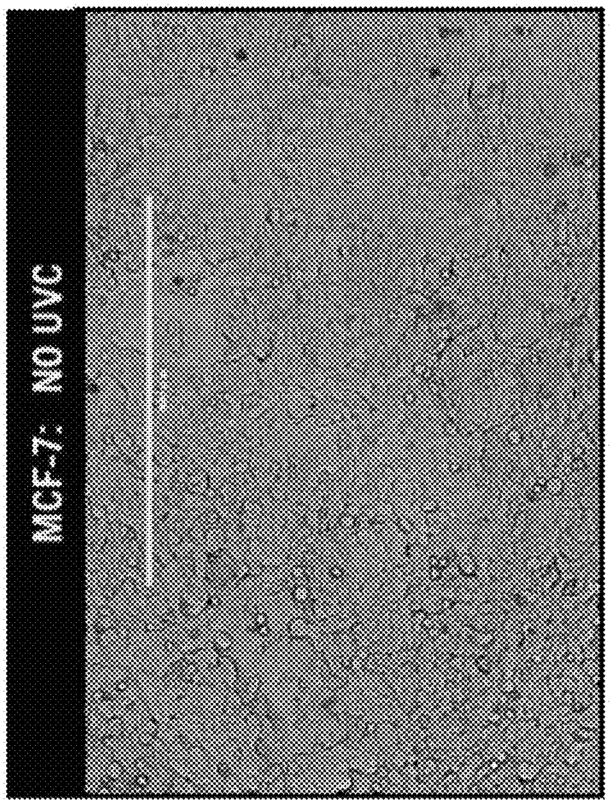
Figure 31A:
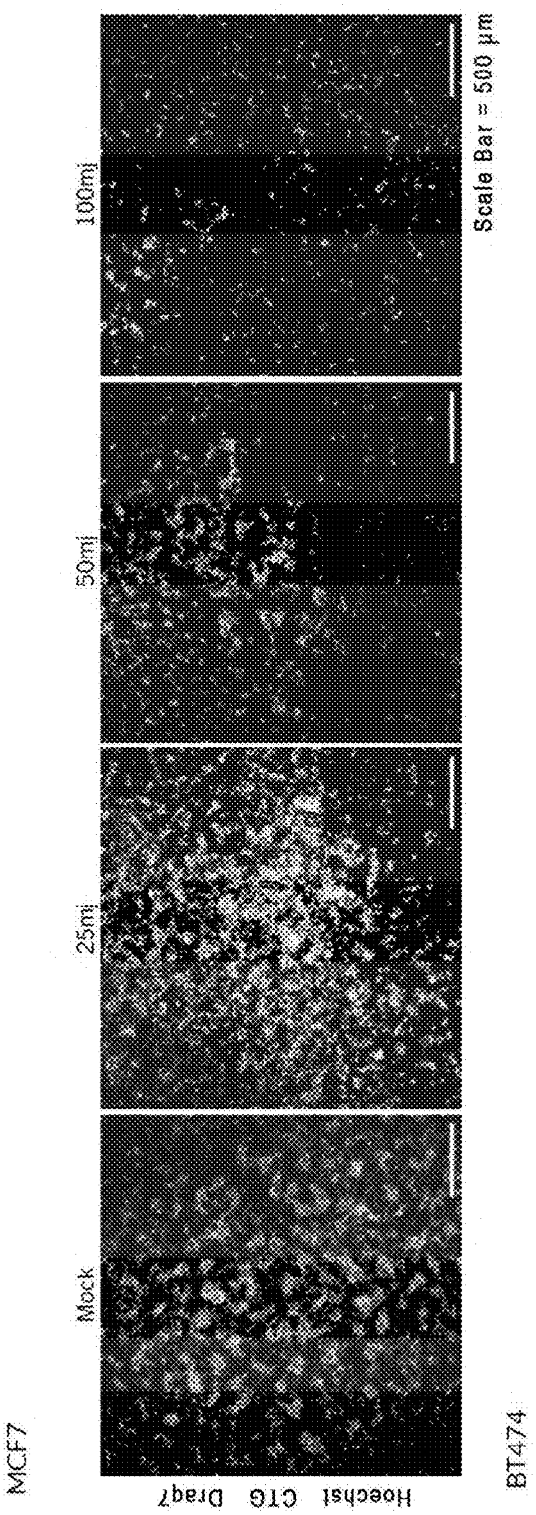
Figure 31B:
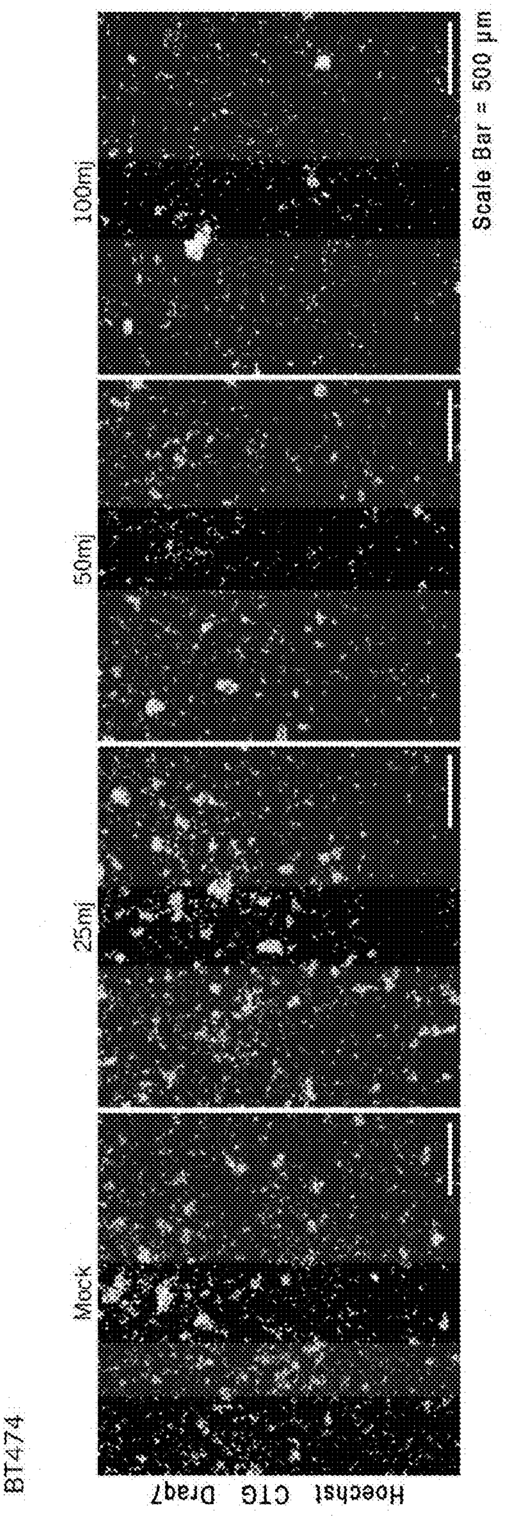
Figure 31C:
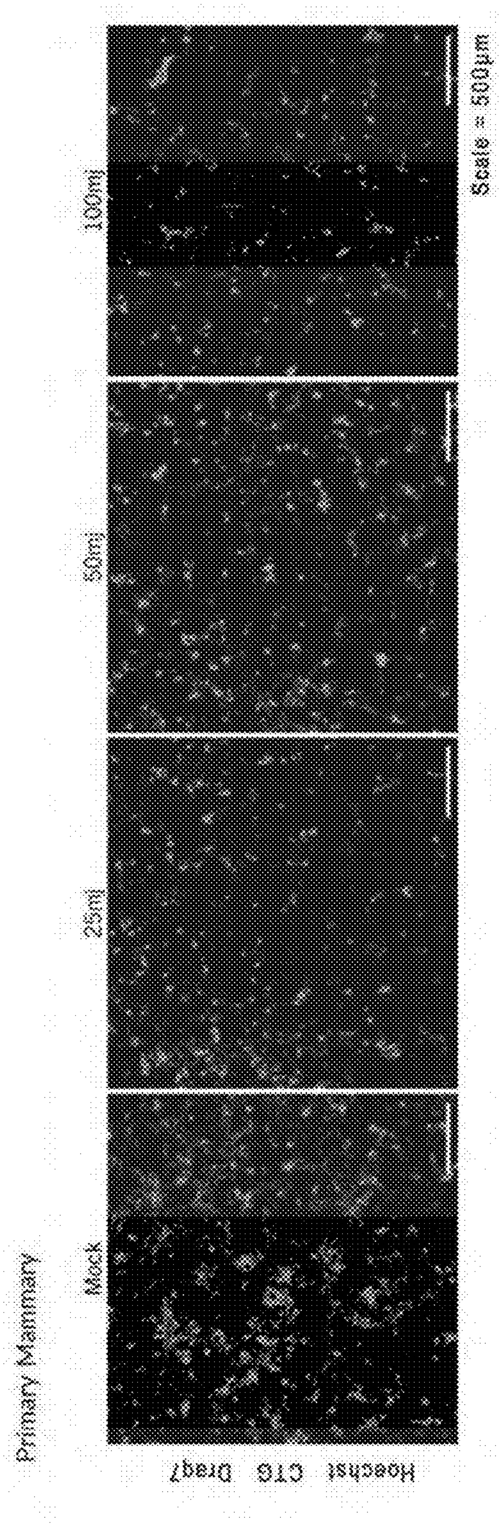
Figure 31D:
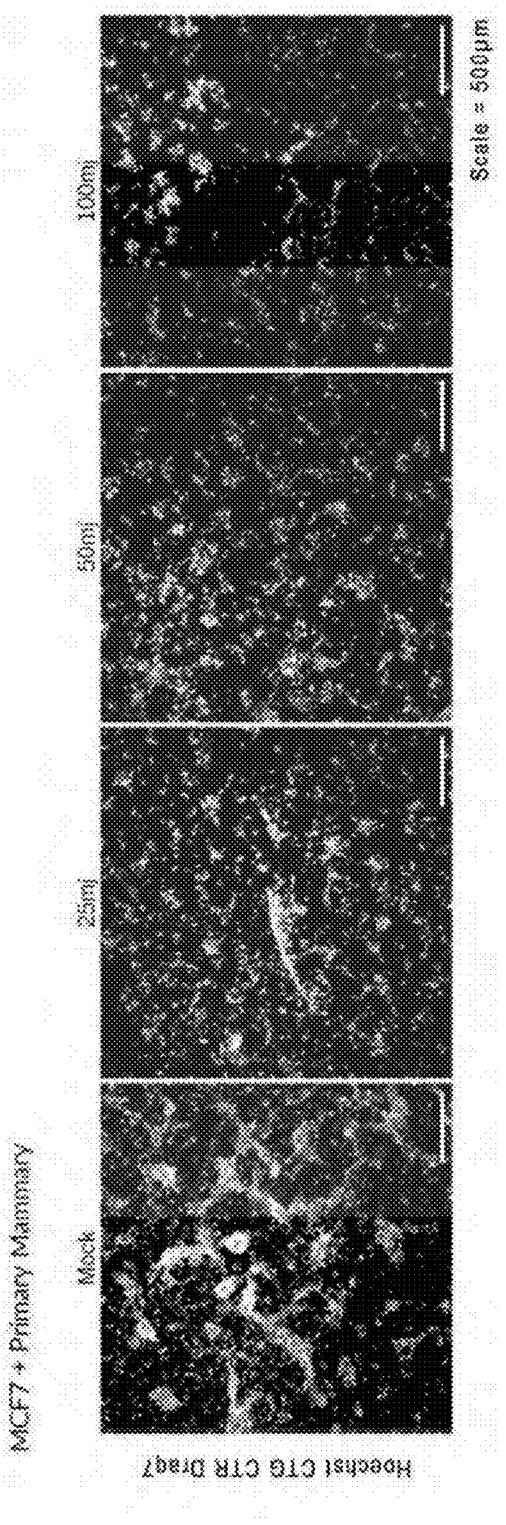
Figure 31E:
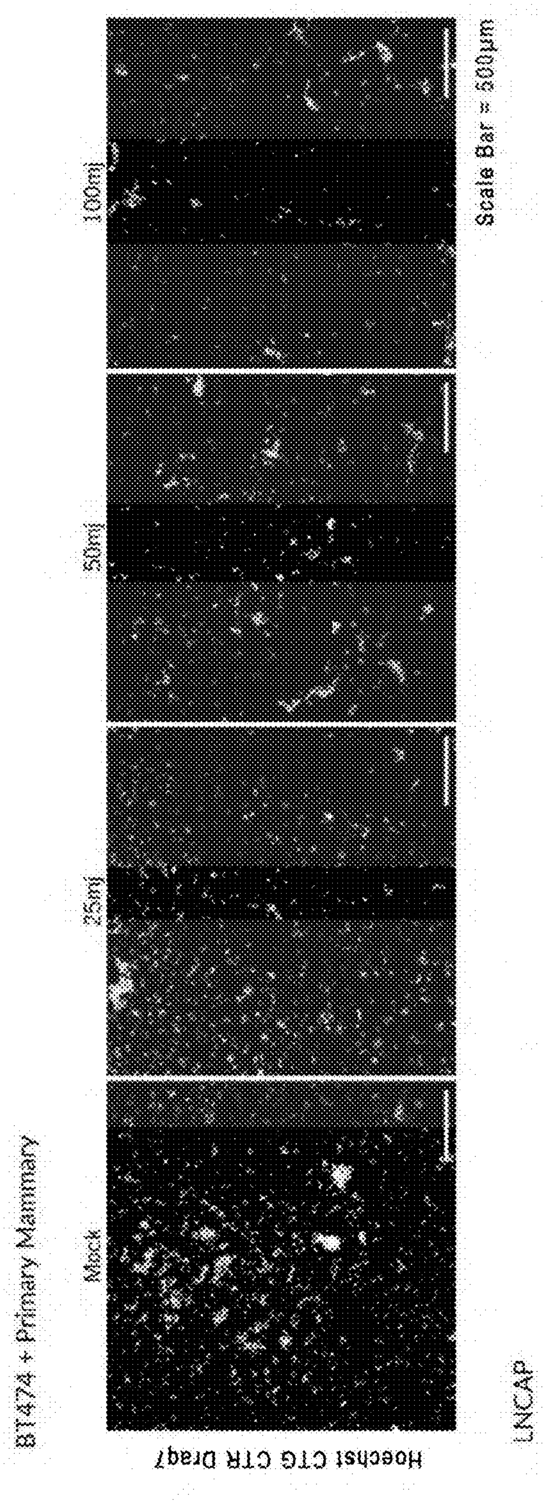
Figure 31F:
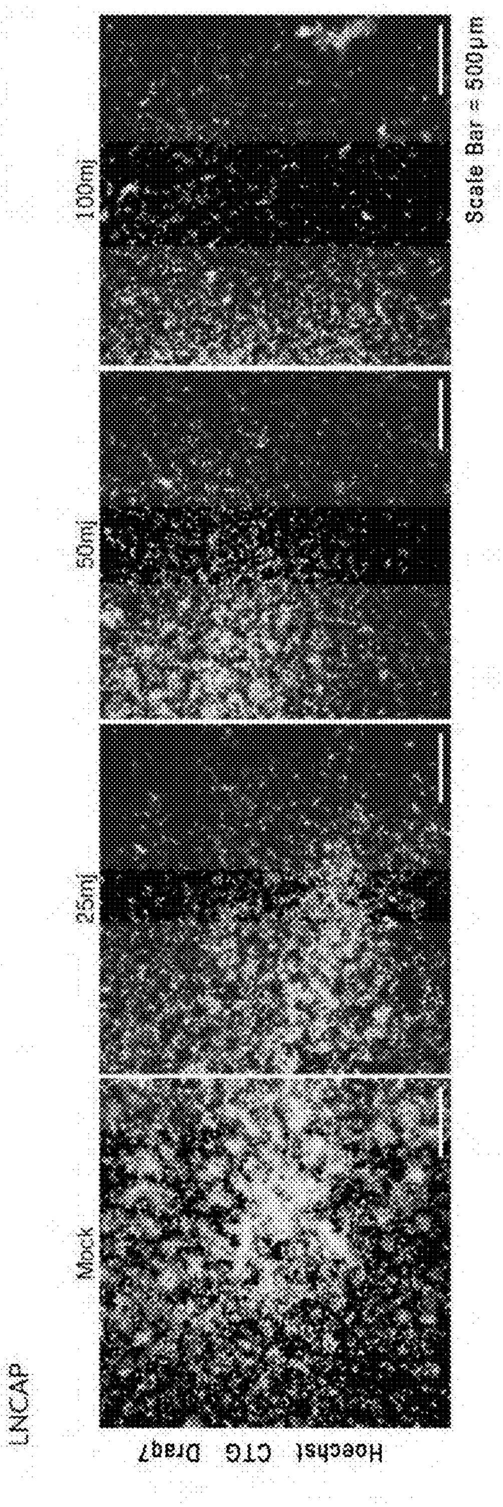
Figure 31G:
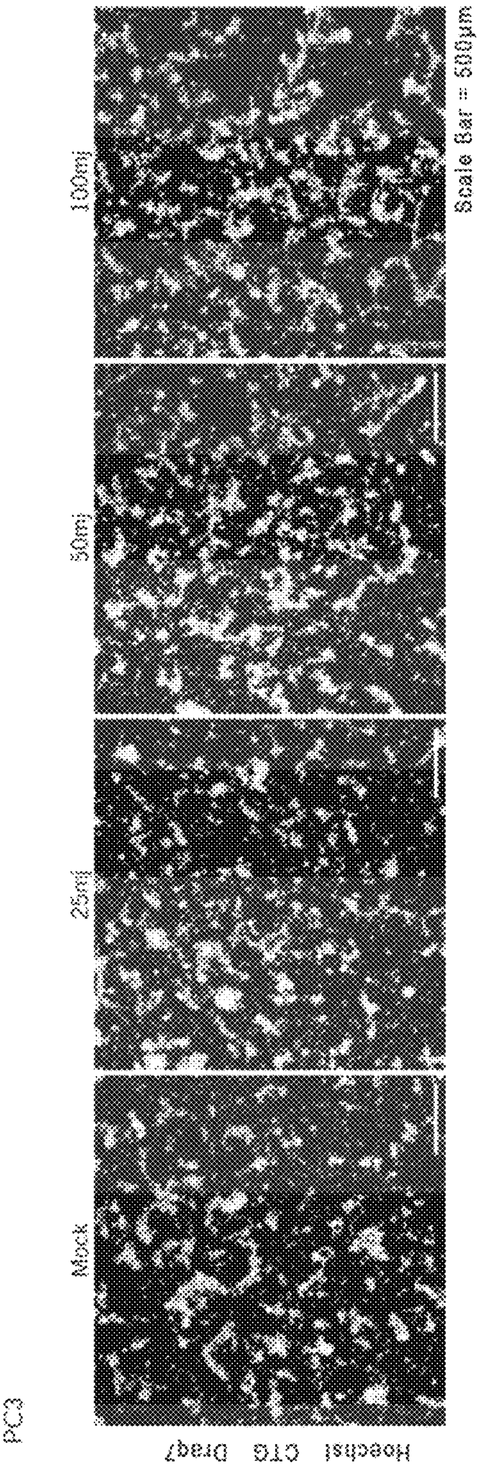
Figure 31H:
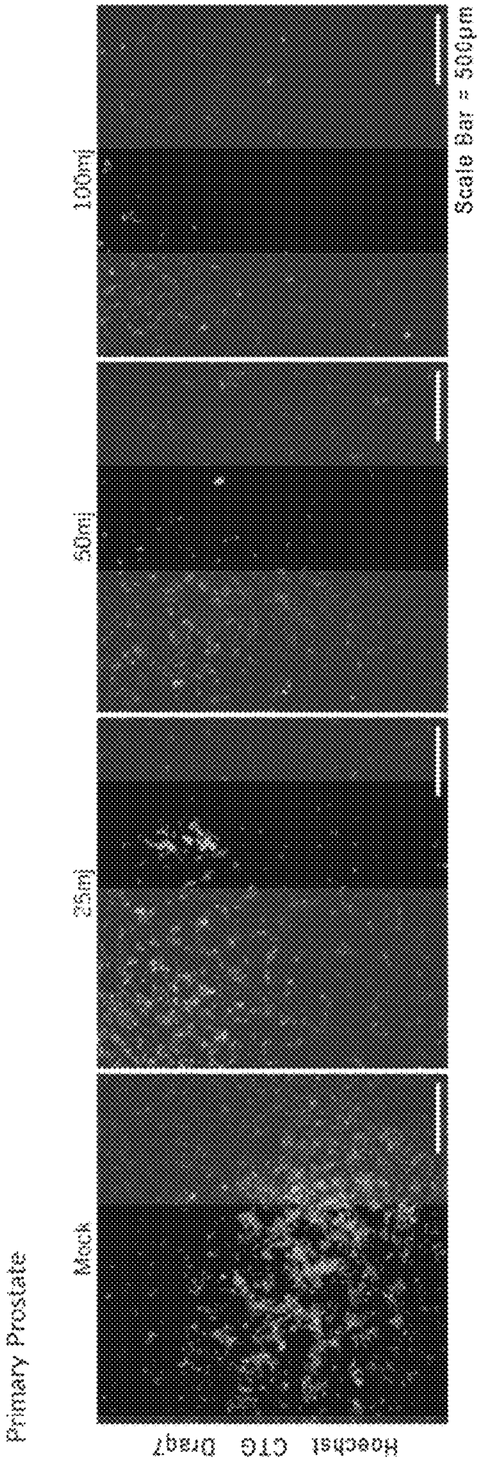
Figure 31I:
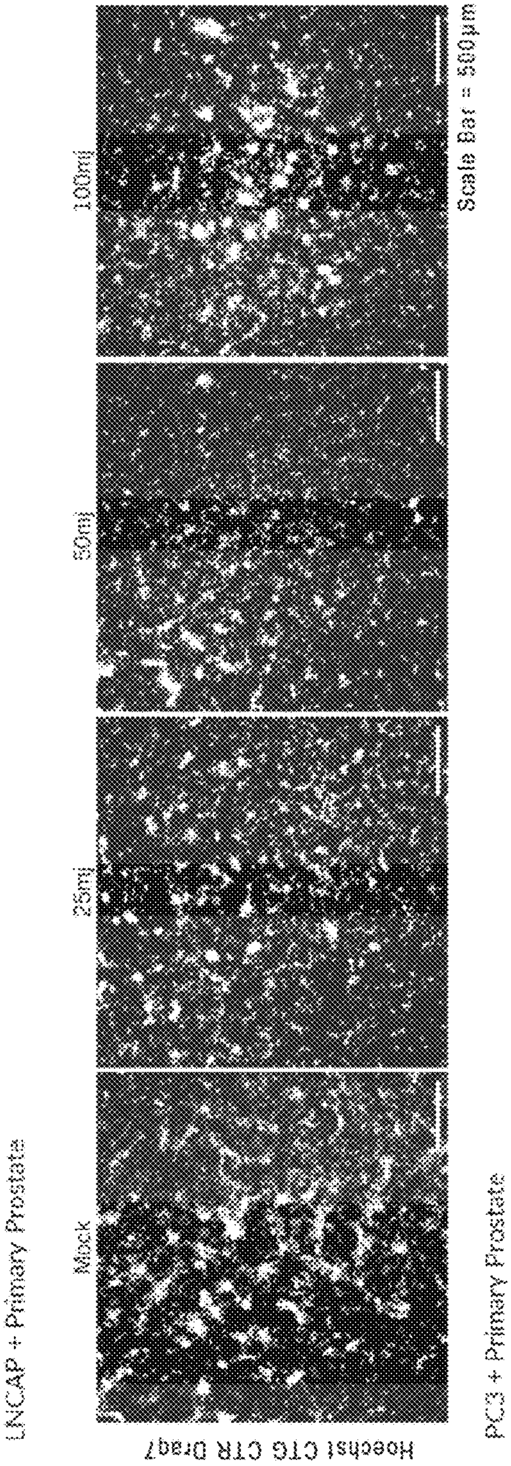
Figure 31J:
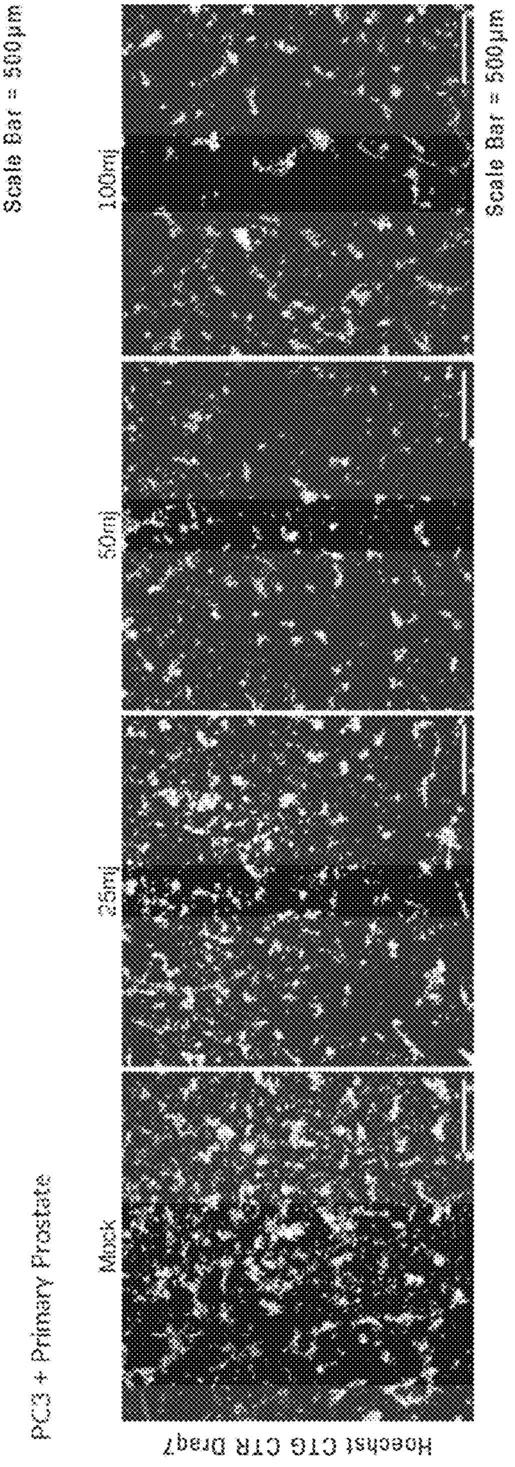
Figure 31K:
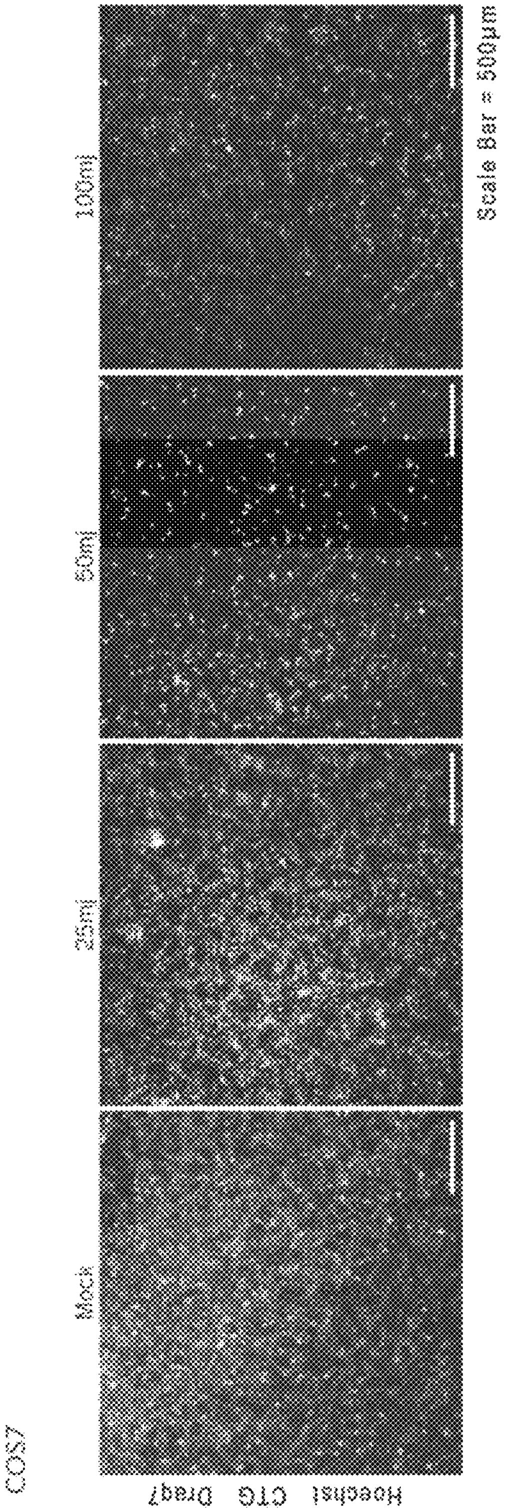

FIG. 29A is a photo of MCF-7 breast cancer cells not exposed to the UV-C light from the UV-C light source.

FIG. 29B is a photo of MCF-7 breast cancer cells after being exposed to 100 $mJ/cm^2$ of UV-C light from the UV-C light source.

FIGS. 30A-30H are plots showing cell count and viability of cells after exposure to UV-C light.

FIGS. 31A-31K are images of showing cells before and after illumination with UV-C light.

DETAILED DESCRIPTION

Various implementations and features of the inventions will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific implementations of the invention. Furthermore, implementations of the invention may comprise several novel features, no single one of which is solely responsible for its desirable attributes or which is essential to practicing the inventions herein described.

Various headings have been included to assist in readability. Such heads are not limiting. The subject matter within the section beneath the heading need not fall within the scope of the and may be different than the heading.

INTRODUCTION

UV-C light is ultraviolet light, for example, having a wavelength range of 100-280 nm. As discussed herein UV-C wavelengths, e.g., in the range of 200 nm to 280 nm, have the potential to inactivate cancer cells. Arguably, total UV fluence received (e.g., radiant energy received by a surface per unit area) may be the main determinant of log reduction, for example, possibly more than pulse frequency, angle, or exposure time. Multiple UVC light emitting diodes (LEDs) can provide high intensity UV-C irradiation in a short time. Accordingly, various systems 10 such as shown, for example, in FIGS. 1, 2, 3A and 3B, are configured to provide UV-C light using an array of UV-C light emitters 12 such as UV-C LEDs.

As described herein, UV-C fluence is a primary consideration when deploying UV-C light sources as medical treatments for destroying, disabling, and/or inactivating harmful cells and/or tissue. Moreover, operational parameters for pulsed UV-C radiance can potentially be selected to achieve the desired high intensity fluence, whilst allowing healthy-cell recovery from the UV-C dose.

Various, although not all, designs described herein are based on UV-C pulsed light e.g., within a range 200 nm-280 nm or 230 nm-280 nm that has been shown to treat cancer cells successfully while allowing non-cancerous cells to survive. In some designs, a more narrow spectrum, for example, centered at 265 nm such as for example 250-280 nm, may be used. DNA, for example, has increased absorption in the range of 260-265 nm as compared to other UV-C wavelengths. In some implementations, different pulsing criteria may be used, differentiating such approaches from continual UV-C blasting.

Without subscribing to any particular scientific theory, pulsing UV-C light can start the production of ROS/OH free radicals (where ROS is Reactive Oxygen Species and OH is diatomic oxygen and hydrogen) that can set in motion a cascade of cellular destruction leading eventually to cell death. In tumor cells such destructive action will continue unabated, however, with less CD95 receptors in non-tumor cells, such non-tumor cells will recover from free radical damage rapidly due to higher levels of endogenous free radical scavengers.

In some implementations, however, the UV-C light is not pulsed and/or configured to be pulse at a frequency higher than 1 Hz or 0.5 Hz or 0.3 Hz or 0.2 Hz or 0.1 Hz, or is not pulsed and/or configured to be pulsed (e.g., 0 Hz). Accordingly, in some implementations, the UV-C light is not pulsed and/or is pulsed and/or configured to be pulsed in a range formed by a pair of these values (e.g., 1 Hz to 0.1 Hz or 0.5 Hz to 0 Hz, etc.). Continual UV-C blasting, at least for a period, may be employed. For example, in some implementations, the UV-C light is switched on and/or configured to be switched on (or to a level of intensity or illuminance above a threshold) for one or more periods of time of at least 0.5 seconds, 0.6 seconds, 0.7 seconds, 0.8 seconds, 0.9 seconds, 1 second, 2 seconds, 3 seconds, 4 seconds, 5 seconds, 6 seconds, 8 second, 9 seconds, 10 seconds, 12 seconds, 15 seconds, 18 seconds, 20 seconds, 25 seconds, 30 seconds, 35 seconds, 40 seconds, 45 seconds, 50 seconds, 1 minute, 2 minutes, 3 minutes, 4 minutes, 5 minutes, 10 minutes, or any range between any of these values or possible longer or shorter (e.g., in a treatment session). In some implementations, the UV-C light is only switched on and/or configured to be switched on (or to a level of intensity or illuminance above a threshold) for periods of time at least 0.5 seconds, 0.6 seconds, 0.7 seconds, 0.8 seconds, 0.9 seconds, 1 second, 2 seconds, 3 seconds, 4 seconds, 5 seconds, 6 seconds, 8 second, 9 seconds, 10 seconds, 12 seconds, 15 seconds, 18 seconds, 20 seconds, 25 seconds, 30 seconds, 35 seconds, 40 seconds, 45 seconds, 50 seconds, 1 minute, 2 minutes, 3 minutes, 4 minutes, 5 minutes, 10 minutes, or any range between any of these values or possible longer or shorter (e.g., in a treatment session).

Various systems, units, devices, components, and methods described herein employ optical fiber to deliver UV light to a patient. As discussed above, the optical fiber may be referred to as an optical fiber line or optical fiber cable (or fiber optic cable). As such, the terms fiber, optical fiber, optical fiber line, optical fiber cable, fiber optic, fiber optic line, fiber optic cable are used interchangeably herein. The optical fiber need not be a single strand of optical fiber and may be comprised of separate parts (e.g., separate strands), for example, stringed, optically connected, optically coupled or concatenated together. The separate portions or strands of optical fiber may be strung together in the longitudinal direction to provide for an elongated waveguide, light pipe, or channel through which light can propagate. The separate or discrete strands of optical fiber may be optically connected or optically coupled together, e.g., via optical connectors and may be butt coupled in some cases. In some designs, optics may be used to connect the strands or discrete portions of optical fiber together. Other ways of stringing, optically coupling or concatenating the separate or discrete portions of optical fiber or strands of optical fiber together are possible. In some implementations, however, the optical fiber comprises a single (e.g., continuous) strand of optical fiber as opposed to discrete or separate parts coupled, e.g., butt coupled together or otherwise optically coupled together.

Light Sources

Figure 1:
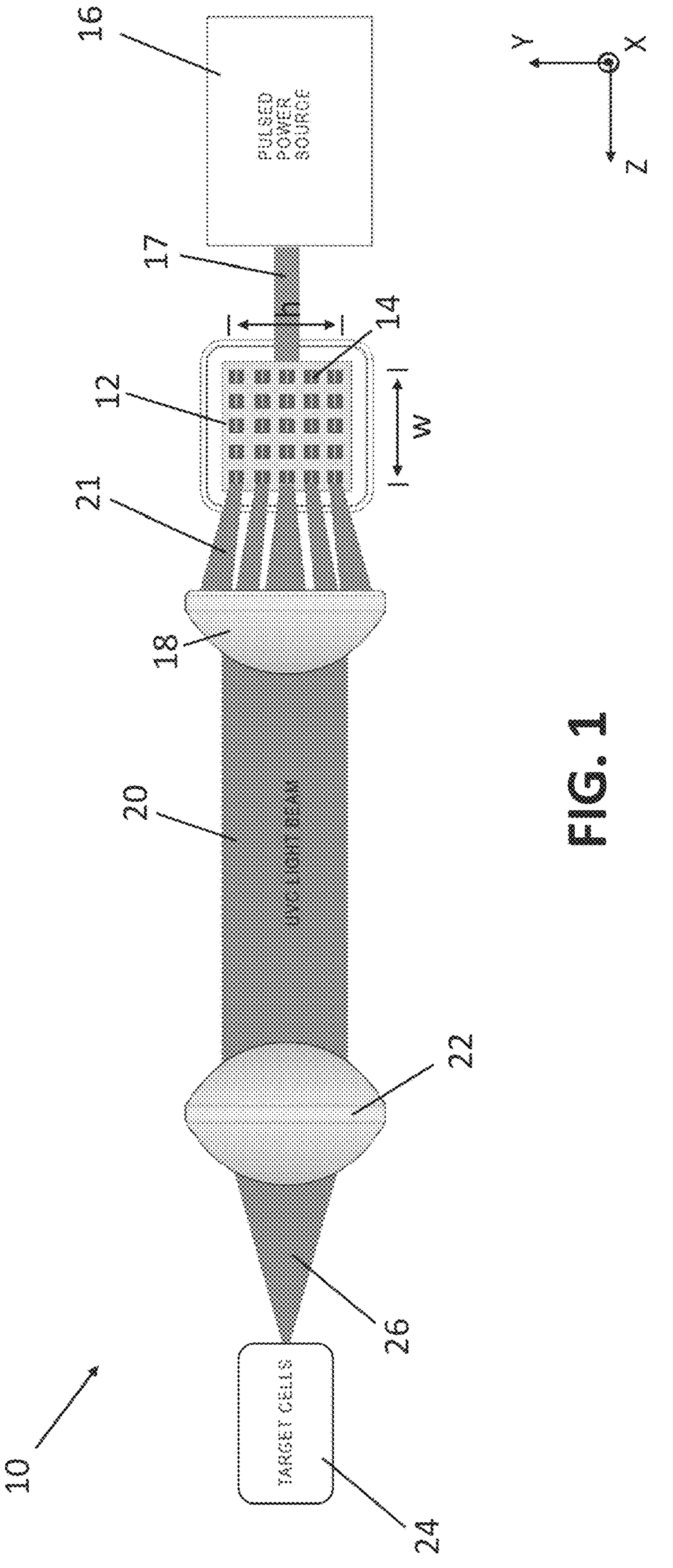
FIG. 1 is a schematic drawing depicting a system configured to output UV-C light. The system includes an array of UV-C light emitters (e.g., UV-C LEDs), collection and focusing optics to collect UV-C light from the plurality of emitters and direct UV-C light onto a target such as cancer cells. The drawing additionally shows driver electronics, e.g., a pulsed power source, to provide electrical power or an electrical signal (e.g., electrical pulses) to the plurality of emitters to cause the emitters to output UV-C light for a desired period of time.
Figure 2:
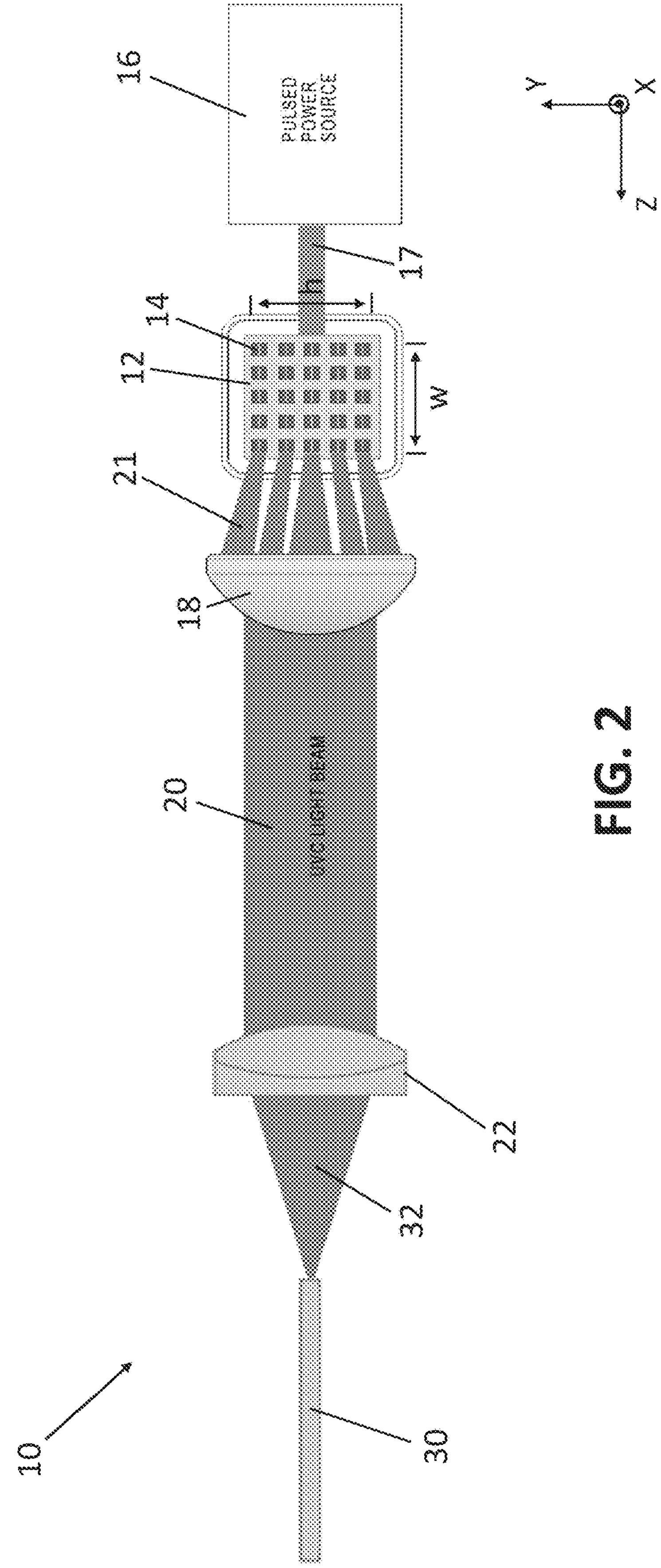
FIG. 2 is a schematic drawing depicting another system configured to output UV-C light. The system includes an array of UV-C light emitters (e.g., UV-C LEDs), collection and coupling optics to collect UV-C light from the plurality of emitters and direct UV-C light into an optical fiber or optical fiber line for delivering the UV-C light to a target such as cancer cells. The drawing additionally shows driver electronics, e.g., a pulsed power source, to provide electrical power or an electrical signal (e.g., electrical pulses) to the plurality of emitters to cause the emitters to output UV-C light for a desired period of time.
Figure 3A:
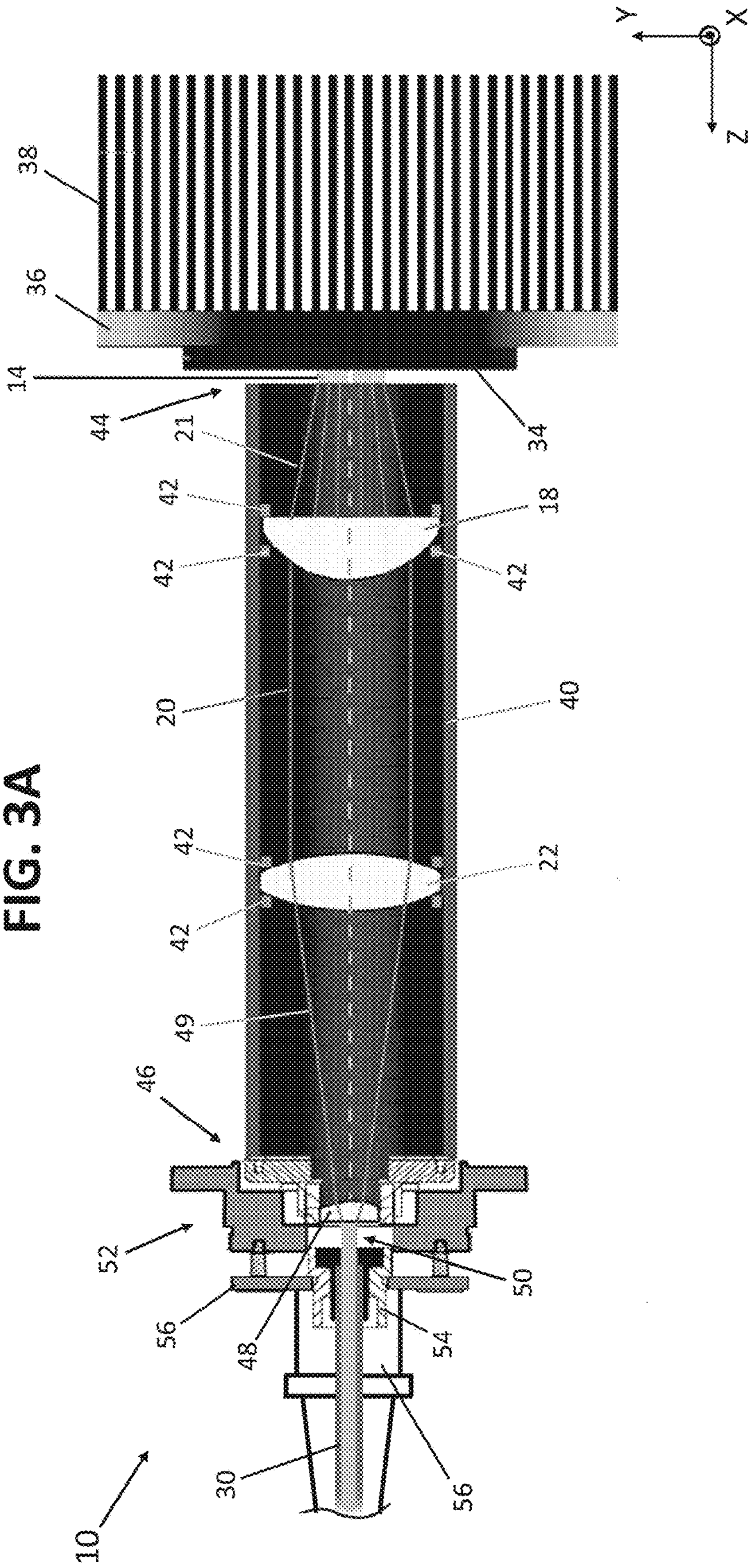
FIG. 3A is a schematic drawing depicting a proximal portion of another system configured to output UV-C light. The system includes an array of UV-C light emitters (e.g., UV-C LEDs), collection and coupling optics to collect UV-C light from the plurality of emitters and direct UV-C light into an optical fiber or optical fiber line. (For illustrative purposes, the optical fiber or fiber optic line is cutoff prior to the end thereof. The distal end of the optical fiber is shown in FIG. 3B.)
Figure 3B:
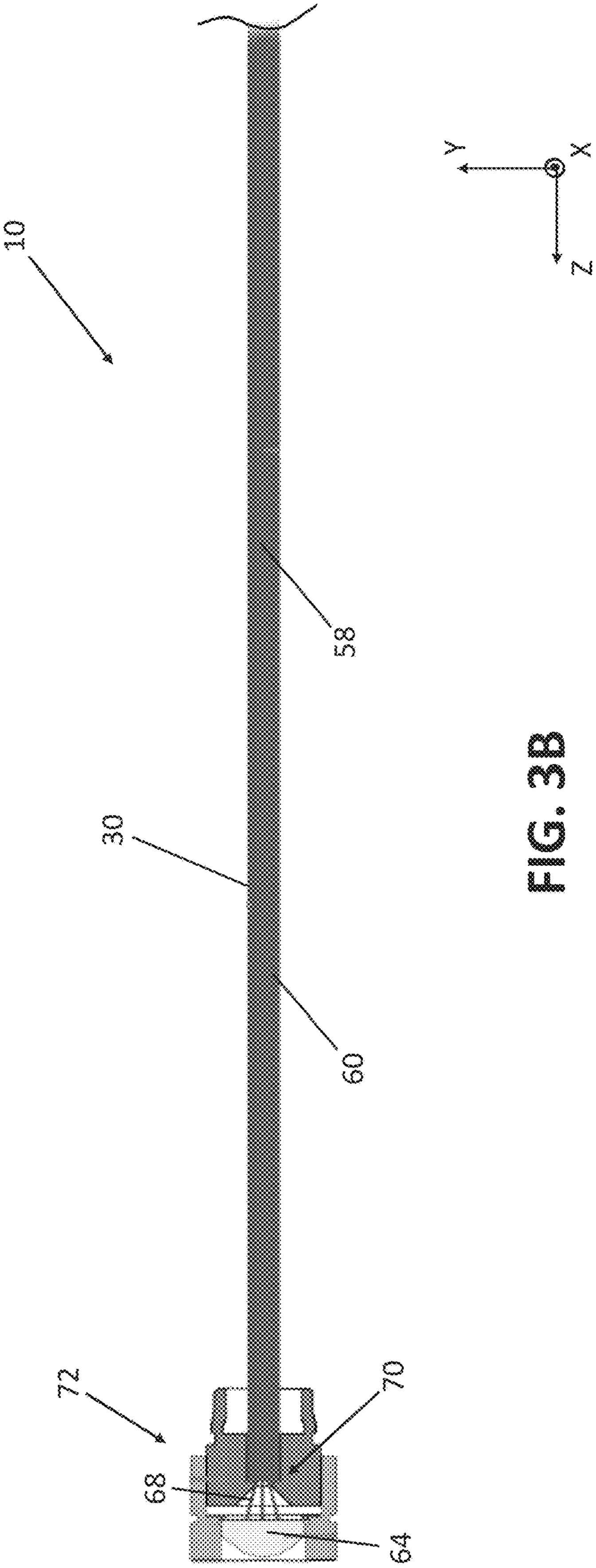
FIG. 3B is a schematic drawing depicting the distal portion of the system configured to output UV-C light that is shown in FIG. 3A.

To provide high levels of UV-C radiation, a UV-C light source 12 comprising a plurality of UV-C light emitters 14, for example, an array of UV-C light emitters, may be employed such as shown in FIGS. 1 and 2 as well as in FIGS. 3A and 3B. The UV-C light emitters 14 may comprise, for example, solid state UV-C emitters such as UV-C light emitting diodes (LEDs). Accordingly, a solid-state array of UV-C LED emitters 12 or UV-C LEDs may be used. The solid-state array 12 may comprise, for example, a semiconductor chip including a plurality of emitters (e.g., LEDs) 14 on a semiconductor substrate. The emitters 14 may be diodes formed by semiconductor junctions. The array of solid-state emitters 12 may have dimensions (e.g., height, h, and width, w, or vice versa) of, 12 millimeters (mm) by 20 millimeters (mm), however, other size arrays are possible. (FIGS. 1 and 2 show the array UV-C light emitters 12 having a width, w, and height, h. For illustrative purposes the array of UV-C light emitters 12 is shown in FIGS. 1 and 2 facing out of the paper and although the array would be facing the collecting lens or collimating lens 18 in various implementations to direct light therein as discussed below.)

The width of the array of UV-C emitters (LEDs) 12 may be measured, for example, from the farthest edges of UV-C emitters or LEDs 14 on opposite sides of the array such as shown, e.g., in FIGS. 1 and 2. Similarly, the height of the array of UV-C emitters (LEDs) 12 may be measured, for example, from the farthest edges of the UV-C emitters or LEDs 14 on opposite top and bottom sides of the array such as shown, e.g., in FIGS. 1 and 2. (The width and height may correspond, for example, to lateral extents of the array of emitters (LEDs) 12 in the X and Y directions, respectively, with thickness of the emitters being in the perpendicular Z direction, light being emitted from the array largely in the Z direction with some divergence in ±X and/or ±Y directions in various implementations.)

The array of UV-C light emitters 12 can have dimensions (e.g., height, h, and width, w, or vice versa), for example, of less than 80 mm×80 mm, 70 mm×70 mm, 60 mm×60 mm, 50 mm×50 mm, 40 mm×40 mm, 30 mm×30 mm, 20 mm×20 mm, 10 mm×10 mm, 5 mm×5 mm, 4 mm×4 mm, 3 mm×3 mm, 2 mm×2 mm, 1 mm×1 mm, 0.5 mm×0.5 mm, 0.4 mm×0.4 mm, 0.3 mm×0.3 mm, 0.2 mm×0.2 mm, 0.1 mm×0.1 mm or any range formed by any of these values or possibly larger or smaller. The array of UV-C emitters or UV-C LEDs 12 in various designs may, for example, be from 70 mm×70 mm to 10 mm×10 mm or from 60 mm×60 mm to 30 mm×30 mm or from 40 mm×40 mm to 20 mm×20 mm or from 10 mm×10 mm to 1 mm×1 mm or from 5 mm×5 mm to 2 mm×2 mm or 5 mm×5 mm to 1 mm×1 mm or 4 mm×4 mm to 0.5 mm×0.5 mm, or 3 mm×3 mm to 0.2 mm×0.2 mm, 2 mm×2 mm to 0.1 mm×0.1 mm. Likewise, the array of UV-C light emitters 12 can have a dimension (e.g., width, w, as opposed to thickness) along a side of 100 mm, 80 mm, 60 mm, 50 mm, 40 mm, 30 mm, 20 mm, 15 mm, 12 mm, 10 mm, 8 mm, 6 mm, 5 mm, 4 mm, 3 mm, 2 mm, 1 mm, 0.5 mm, 0.4 mm, 0.3 mm, 0.2 mm, 0.1 mm or any range formed by any of these values such as from 80 mm to 15 mm or 100 mm to 8 mm, or 60 mm to 10 mm, 10 mm to 1 mm, or 8 mm to 1 mm, or 5 mm to 2 mm, or 5 mm to 1 mm, or 4 mm to 0.5 mm, or 3 mm to 0.2 mm, or 2 mm to 0.1 mm or can be possibly larger or small. The array of UV-C light emitters 12 can have a dimension (e.g., height, h, as opposed to thickness) along another side of 100 mm, 80 mm, 60 mm, 50 mm, 40 mm, 30 mm, 20 mm, 15 mm, 12 mm, 10 mm, 8 mm, 6 mm, 5 mm, 4 mm, 3 mm, 2 mm, 1 mm, 0.5 mm, 0.4 mm, 0.3 mm, 0.2 mm, 0.1 mm or any range formed by any of these values such as from 20 mm to 8 mm or 50 mm to 5 mm or 100 mm to 2 mm, or 10 mm to 1 mm or 8 mm to 1 mm or 5 mm to 1 mm, or 4 mm to 0.5 mm, or 3 mm to 0.2 mm, or 2 mm to 0.1 mm or can be possibly larger or small. However, the array of UV-C light emitters or LEDs 12 need not be square and need not have the same dimension on each side but can be other shapes including, for example, rectangular. The array of UV-C light emitters or LEDs 12 can, for example, have one side with a dimension (e.g., a width, w) from 80 mm to 10 mm or from 60 mm to 15 mm or from 40 mm to 1 mm or from 10 to 2 mm or from 10 mm to 1 mm or 8 mm to 1 mm or from 5 mm to 1 mm, or from 4 mm to 0.5 mm, or 3 mm to 0.2 mm, or 2 mm to 0.1 mm and another side with a dimension (e.g., a height, h) from 80 mm to 4 mm or from 60 mm to 5 mm or from 40 mm to 1 mm or 10 mm to 1 mm or 8 mm to 1 mm or from 5 to 1 mm or from 4 mm to 0.5 mm, or 3 mm to 0.2 mm, or 2 mm to 0.1 mm, however, the two dimensions, e.g., width, w, and height, h, need not be the same, In various implementations, likewise, the area of the array of UV-C light emitters or LEDs 12 (calculate, e.g., by multiplying the length by the width of the array) is less than 2000 $mm^2$, 1500 $mm^2$, 1000 $mm^2$, 800 $mm^2$, 600 $mm^2$, 500 $mm^2$, 400 $mm^2$, 200 $mm^2$, 100 $mm^2$, 50 $mm^2$, 40 $mm^2$, 30 $mm^2$, 25 $mm^2$, 20 $mm^2$, 15 $mm^2$, 12 $mm^2$, 10 $mm^2$, 9 $mm^2$, 8 $mm^2$, 6 $mm^2$, 5 $mm^2$, 4 $mm^2$, 3 $mm^2$, 2 $mm^2$, 1 $mm^2$, 0.5 $mm^2$, 0.1 $mm^2$, 0.05 $mm^2$, 0.01 $mm^2$ or in any range formed by any of these values such as an area from 300 $mm^2$ to 200 $mm^2$ or from 500 $mm^2$ to 100 $mm^2$, or 50 $mm^2$ to 5 $mm^2$, or 40 $mm^2$ to 10 $mm^2$ or 20 $mm^2$ to 10 $mm^2$ or 30 $mm^2$ to 4 $mm^2$, or 25 $mm^2$ to 9 $mm^2$, or from 16 $mm^2$ to 1 $mm^2$, or from 4 $mm^2$ to 0.5 $mm^2$, or from 2 $mm^2$ to 0.1

$mm^2$, or from 1 $mm^2$ to 0.01 $mm^2$ or possibly larger or smaller areas. Any of these arrays of UV-C light emitters 12 can have 2, 3, 4, 5, 6, 7, 8, 9, 10, 11, 12, 13, 14, 15, 16, 18, 20, 22, 24, 26, 28, 30, 32, 34, 36 UV-C light emitters or LEDs 14, or any range formed by any of these numbers (e.g., 2 to 8 UV-C emitters or LEDs, or 4 to 10 UV-C emitters, or 4 to 20 UV-C emitters, etc.) or possible more. The emitters 14 in the array of UV-C emitters 12 may have a spacing (e.g., center to center spacing) of 10 mm, 9 mm, 8 mm, 7 mm, 6 mm, 5 mm, 4 mm, 3 mm, 2 mm, 1 mm, 0.9 mm, 0.8 mm, 0.6 mm, 0.5 mm, 0.4 mm, 0.3 mm, 0.2 mm, 0.1 mm, 0.09 mm, 0.08 mm, 0.06 mm, 0.05 mm, 0.04 mm, 0.03 mm, 0.02 mm, 0.01 mm or any range between any of the values (e.g., from 5 mm to 1 mm or 4 mm to 0.5 mm or from 6 mm to 0.1 mm) or possibly larger or smaller. Although an ordered array of rows and columns is shown in FIGS. 1 and 2, the UV-C emitter array 12 need not be limited to rows and columns such as shown. FIG. 3A, for example, shows an array of UV-C light emitters or a UV-C light emitter array 12 wherein the UV-C emitters (e.g., UV-C LEDs) 14 are not arranged in columns wherein each of the UV-C emitters (UV-C LEDs) is lined up in a column with one or more other UV-C emitters (UV-C LEDs). See, for example, FIG. 5A.

Accordingly, in various implementations, a plurality of light emitters 14 comprises a first group of light emitters such as solid-state UV-C emitters comprising a plurality of UV-C light emitting diodes (LEDs), for example, from 2 to 36 diodes or possibly larger numbers of LEDs. In the example shown in FIGS. 1 and 2, the UV-C emitter array or UV-C LED array 12 comprises 25 emitters or LEDs 14. However, the number of UV-C emitters or LEDs 14 may be less. The UV-C emitter array 12 and/or the plurality of UV-C emitters (or UV-C LEDs) 14 may, for example, comprise 2-10 UV-C emitters or UV-C LEDs or 2-8 UV-C emitters or UV-C LEDs or 2-6 UV-C emitters or UV-C LEDs or 2-4 UV-C emitters or UV-C LEDs or 3-10 UV-C emitters or UV-C LEDs or 3-8 UV-C emitters or UV-C LEDs or 3-6 UV-C emitters or UV-C LEDs or 3-5 UV-C emitters or UV-C LEDs or or 4-10 UV-C emitters or UV-C LEDs or 4-8 UV-C emitters or UV-C LEDs or 4-6 UV-C emitters or UV-C LEDs or 4-5 UV-C emitters or UV-C LEDs or any range formed by any of these ranges or values or may possibly be larger or smaller.

In various implementations, the array of UV-C light emitters 12 outputs radiant flux in the range of from 50 mW to 4000 mW or from 25 mW to 8000 mW. The array may, for example, output radiant flux in the amount of 1 mW, 2 mW, 3 mW, 4 mW, 5 mW, 10 mW, 15 mW, 25 mW, 30 mW, 40 mW, 50 mW, 80 mW, 100 mW, 120 mW, 150 mW, 160 mW, 170 mW, 180 mW, 190 mW, 200 mW, 210 mW, 220 mW, 225 mW, 230 mW, 240 mW, 250 mW, 260 mW, 270 mW, 275 mW, 280 mW, 290 mW, 300 mW, 310 mW, 320 mW, 330 mW, 340 mW, 350 mW, 360 mW, 370 mW, 380 mW, 390 mW, 400 mW, 500 mW, 600 mW, 800 mW, 1000 mW, 1200 mW, 1400 mW, 1500 mW, 1600 mW, 1800 mW, 2000 mW, 2500 mW, 3000 mW, 3500 mW, 4000 mW, 4500 mW, 5000 mW, 5500 mW, 6000 mW, 6500 mW, 7000 mW, 7500 mW, 8000 mW, or any range formed by any of these values (such as for example 100 mW to 1000 mW or 200 mW to 5000 mW, or 400 mW to 4000 mW, 100 mW to 500 mW, 200 mW to 400 mW) or possibly larger or smaller amounts. The output may also be lower. The array may, for example, output radiant flux in the amount of 1 μW, 2 μW, 3 μW, 4 μW, 5 μW, 10 μW, 15 μW, 25 μW, 30 μW, 40 μW, 50 μW, 80 μW, 100 μW, 120 μW, 150 μW, 160 μW, 170 μW, 180 μW, 190 μW, 200 μW, 210 μW, 220 μW, 225 μW, 230 μW, 240 μW, 250 μW, 260 μW, 270 μW, 275 μW, 280 μW, 290 μW, 300 μW, 310 μW, 320 μW, 330 μW, 340 μW, 350 μW, 360 μW, 370 μW, 380 μW, 390 μW, 400 μW, 500 μW, 600 μW, 800 μW, 1000 μW, 1200 μW, 1400 μW, 1500 μW, 1600 μW, 1800 μW, 2000 μW, 2500 μW, 3000 μW, 3500 μW, 4000 μW, 4500 μW, 5000 μW, 5500 μW, 6000 μW, 6500 μW, 7000 μW, 7500 μW, 8000 μW, or any range formed by any of the values set forth herein (such as for example 1 μW to 400 μW or 10 μW to 500 μW, or 20 μW to 1000 μW, 100 μW to 500 μW, 200 μW to 400 μW, 1 μW to 100 mW, or 10 μW to 500 mW) or possibly larger or smaller amounts.

The exposure or dosage can be increased by increasing the duration of time during which the light is applied to the target, e.g., target cells.

In various implementations, the emitter (e.g., LEDs) 14 may be pulsed. Driver electronics (e.g., LED driver electronics) 16 may be electrically coupled to the emitters (e.g., LEDs). In various cases, the driver electronics 16 is configured to output pulses or otherwise can be configured to pulse the emitters/LEDs 14. The driver electronics 16 may comprise, for example, a pulsed power source configured to output pulses. In various designs, the driver electronics, e.g., pulsed power source, 16 is configured to be variable, for example, such that the pulse duration and/or the repetition rate of the optical pulses may be varied and/or selected. For example, the duration of the pulses may be varied and/or the duration between pulses may be varied. Such variation in pulse duration and duration between the pulses may be varied via controls on the pulse power source 16 in some implementations. Similarly, groups of pulses may be applied to the target, the groups of pulses separated from each other by period(s) of time. The number of pulses or the time period(s) during which the group of pulses is applied can be controlled to provide the desired amount of light to the target. Likewise, the time period(s) between the groups of pulses can be controlled. Without subscribing to any scientific theory, the time period(s) between pulses and/or between groups of pulses can enable non-cancerous tissue or cells to have reduced damage, and/or recover from the application of the light pulses, Collecting Optics As illustrated in FIG. 1, collection or collecting optics 18 comprising one or more collection or collecting lenses (e.g. a single lens or a single lens element, a combination of lens elements forming a lens, and/or a lens train, optical train, or optical assembly) may be positioned with respect to the plurality of light emitters 14 to receive light therefrom and project light forward at a reduced divergence angle than emitted from the light emitters 14 and/or plurality of light emitters thereby forming a beam of light in some implementations. The collecting lens 18 may comprise an aspheric lens having one or more aspheric optical surfaces. However, the collecting lens 18 may alternatively or additionally comprise a spherical lens having at least one surface comprising a spherical surface. In various implementations such as shown, a single collection lens 18 collects light from a plurality of UV-C emitters 14 (e.g., from all the UV-C emitters in the array 12) and forms a single beam 20 from this plurality of UV-C emitters (see, e.g., FIG. 1). Likewise, in some designs, a single collection lens 18 has sufficient lateral size (e.g., one or more of width, height, or diameter) to collect the light from the array of UV-C emitters 14 (e.g., light 21 from the separate emitters) and forms a single beam 20 therefrom. The lens 18 may collect light from a plurality of the UV-C emitters (UV-C LEDs) 14, most of the UV-C emitters (UV-C LEDs), or all the UV-C emitters in the UV-C emitter array 12. Similarly, in some designs, a single collecting or collimating lens 18 is paired with the array of UV-C LEDs 14. As illustrated, light 21 from the plurality of UV-C emitters (LEDs) 14, e.g., all the UV-C emitters (LEDs), is collected by the single aperture of the collecting lens 18. In the example shown in FIG. 1, the collection optics or collection lens collects light from 25 separate sources of UV-C rays into a single beam, e.g., collects light from 25 emitters 14 in the emitter array 12 (or 4 emitters in the system 10 shown in FIG. 3A) into a single UV-C light beam. However, as discussed above, in other designs the number of emitters may be larger or smaller. Nevertheless, in various implementations, the collection and/or collimating optics or lens 18 collects light from the UV-C light emitters or UV-C LEDs 14 in the UV-C emitter array 12 into a UV-C beam. Additionally, although a single collecting lens 18 is shown, the collection optics may comprise more than one lens, for example, a plurality of lenses arranged, e.g., longitudinally with respect to each other to form an optical path from the array of UV-C emitters 12 through the lenses, to thereby form a beam of UV-C light.

Accordingly, the collection optics 18 may collect UV-C light 21 from the plurality of UV-C emitters 14 and form a beam 20 from the UV-C light. The collection optics 18 may comprise, for example, collimating optics, for example, one or more collimating lenses configured to collimate light 21 from the plurality of UV-C emitters 14 and form a beam, e.g., a collimated beam 20. In the example shown in FIG. 1, a single collimating lens 18 collects light from the array of UV-C emitters 12 and forms a collimated beam 20 of UV-C light. In various implementations, for example, the collection/collimating optics or collection/collimating lens 18 has positive power and may comprise, e.g., a converging lens with a positive focal length such as a convex lens or a plano convex lens. In some implementations, the collection optics (e.g., collimating lens) 18 may be positioned a focal length away from the array of UV-C light emitters 12 or possibly at a distance from the array of UV-C light emitters that is within 50%, 45%, 40%, 35%, 30%, 25%, 20%, 15%, 10%, 5%, 1%, 0.1%, 0% of the focal length or any range between any of these values or possibly larger or smaller distances away.

In some implementations, the UV-C collecting optics 18 has an aperture or clear aperture (e.g., diameter, width, height, or lateral spatial extent, e.g., in the X and/or Y direction or other direction(s) perpendicular to the Z direction, etc.) of from 4 mm, 5 mm, 6 mm, 7 mm, 8 mm, 9 mm, 10 mm, 12 mm, 14 mm, 15 mm, 16 mm, 17 mm, 18 mm, 19 mm, 20 mm, 21 mm, 22 mm, 24 mm, 25 mm, 26 mm, 27 mm, 28 mm, 29 mm, 30 mm, 32 mm, 34 mm, 36 mm, 38 mm, 40 mm, 50 mm, 60 mm or any range formed by any of these values such as from 16 mm to 36 mm or from 18 mm to 32 mm or possibly larger or smaller. In some implementations, the UV-C collecting optics 18 has a thickness (e.g., in the Z direction) from 0.5 mm, 1 mm, 2 mm, 3 mm, 4 mm, 5 mm, 6 mm, 8 mm, 10 mm, 12, mm, 14 mm, 15 mm, 16 mm, 17 mm, 18 mm, 19 mm, 20 mm, 21 mm, 22 mm, 24 mm, 25 mm, 26 mm, 27 mm, 28 mm, 29 mm, 30 mm, 32 mm, 34 mm, 36 mm, 38 mm, 40 mm, 50 mm, 60 mm or any range formed by any of these values such as from 2 mm to 8 mm, or 6 mm to 15 mm, or from 4 mm to 18 mm or possibly larger or smaller.

Focusing Optics

In various implementations, the UV-C light projection system or unit 10 includes focusing optics 22 comprising, for example, one or more focusing lens (e.g. a single lens or a single lens element, a combination of lens elements forming a lens, and/or a lens train, optical train, or optical assembly) such as shown in FIG. 1. The focusing optics or focusing lens 22 may, for example, have a positive focal length and be positioned to receive light from the collection optics or collection lens 18 so as to focus UV-C light 20 from the collection optics/lens. In various implementations, the focusing optics 22 may focus light from the beam 20 formed by the collection optics or collimating optics 18. In various implementations such as shown, a single focusing lens 22 focuses the single beam 20 from the collecting optics 18 onto the target 24. Likewise, in some designs, a single focusing lens 22 is paired with the collecting optics 18 and the array of UV-C LEDs 12. As illustrated, the light beam, e.g., collimated light beam 20, is received by the single aperture of the focusing lens 22. The focusing lens 22 may comprise an aspheric lens having one or more aspheric optical surface. However, the focusing lens 22 may alternatively or additionally comprise a spherical lens having at least one surface comprising a spherical surface.

Although a single focusing lens 28 is shown, the focusing optics may comprise more than one lens, for example, a plurality of lenses arranged, e.g., longitudinally with respect to each other to form an optical path from the collecting optics 18 through the focusing lenses, to thereby form a focused beam 26 of UV-C light.

This UV-C light 26 may be focused, for example, on the target 24 such as on cancerous tissue and/or target cells like tumor cells. In various implementations, for example, the focusing optics (e.g., focusing lens) 22 comprises a positive lens or converging lens with a positive focal length such as a convex lens (a converging lens) or a bi-convex lens or plano-convex lens. The focusing optics or focusing lens 22 may be positioned a focal length away from the target or possibly at a distance from the target that is within 50%, 45%, 40%, 35%, 30%, 25%, 20%, 15%, 10%, 5%, 1%, 0.1%, 0% of the focal length or any range between any of these values or possibly larger or smaller distances away.

In some implementations, the focusing optics or focusing lens 22 may comprise a lens doublet as shown in FIG. 2. As illustrated, the focusing optics 22 comprises a multiple element lens (e.g., DOUBLET), In the example shown, the focusing optic (e.g., doublet) 22 receives the beam 20 from the collecting optics or collimating optics 18 and reduces the beam to optically couple into a fiber optic 30 and/or other delivery device. The fiber optic 30 may comprise one or a plurality of optical fibers (e.g., an optical fiber bundle). In some implementations, the fiber optic 30 is coupled to or included in an endoscope to facilitate delivery within a body, e.g., a human body.

Example Fiber Systems

FIGS. 3A and 3B show another example system or unit 10 configured to output UV-C light into a fiber optic, e.g., an optical fiber, optical fiber line, fiber optic cable, 30 for delivery, for example, to a target or target tissue or cells 24. The system 10 includes various components as discussed above. Likewise, the discussions above, are applicable to the system 10 shown in FIGS. 3A and 3B unless stated otherwise or shown otherwise in the drawings. The system 10, for example, comprises a UV-C emitter array or UV-C LED array 12 comprising a plurality of UV-C emitters or UV-C LEDs 14. The UV-C emitter array or UV-C LED array 12, however, comprises 4 LEDs. In this example, the UV-C emitter array or UV-C LED array 12, e.g., the four UV-C emitters or UV-C LEDs 14, may emit from 150 mW to 330 mW. In various implementations the UV-C array, e.g., the four UV-C emitters or UV-C LEDs, are configured to output 1 mW, 5 mW, 10 mW, 20 mW, 30 mW, 40 mW, 50 mW, 60 mW, 70 mW, 80 mW, 100 mW, 110 mW, 120 mW, 130 mW, 140 mW, 150 mW, 160 mW, 170 mW, 180 mW, 190 mW, 200 mW, 210 mW, 220 mW, 230 mW, 240 mW, 250 mW, 260 mW, 270 mW, 280 mW, 290 mW, 300 mW, 310 mW, 320 mW, 330 mW, 340 mW, 350 mW, 360 mW, 370 mW, 380 mW, 390 mW, 400 mW, 450 mW, 550 mW, 600 mW, 700 mW, 800 mW, 900 mW, 1000 mW, 1100 mW, 1200 mW, 1500 mW, 2000 mW, 2500 mW or any range formed by any of these values or possibly larger or smaller amounts. In various implementations, for example, the UV-C emitter array or UV-C LED array 12, e.g., the four UV-C emitters or UV-C LEDs 14 are configured from 150 mW and 250 mW, e.g., 200 mW, or from 250 to 330 mW, e.g., 310 mW. However, the output may also be lower. The array may, for example, output radiant flux in the amount of 1 μW, 2 μW, 3 μW, 4 μW, 5 μW, 10 μW, 15 μW, 25 μW, 30 μW, 40 μW, 50 μW, 80 μW, 100 μW, 120 μW, 150 μW, 160 μW, 170 μW, 180 μW, 190 μW, 200 μW, 210 μW, 220 μW, 225 μW, 230 μW, 240 μW, 250 μW, 260 μW, 270 μW, 275 μW, 280 μW, 290 μW, 300 μW, 310 μW, 320 μW, 330 μW, 340 μW, 350 μW, 360 μW, 370 μW, 380 μW, 390 μW, 400 μW, 500 μW, 600 μW, 800 μW, 1000 μW, 1200 μW, 1400 μW, 1500 μW, 1600 μW, 1800 μW, 2000 μW, 2500 μW, 3000 μW, 3500 μW, 4000 μW, 4500 μW, 5000 μW, 5500 μW, 6000 μW, 6500 μW, 7000 μW, 7500 μW, 8000 μW, or any range formed by any of the values set forth herein (such as for example 1 μW to 400 μW or 10 μW to 500 μW, or 20 μW to 1000 μW, 100 μW to 500 μW, 200 μW to 400 μW, 1 μW to 100 mW, or 10 μW to 500 mW) or possibly larger or smaller amounts. The exposure or dosage can be increased by increasing the duration of time during which the light is applied to the target, e.g., target cells, 24.

The UV-C emitters 14 may comprise UV-C light emitting diodes comprising semiconductor formed on a semiconductor substrate. The UV-C emitters 14 and/or substrate may be mounted on and/or in thermal contact with a base 34 such as a metal base (e.g., a base comprising copper or aluminum or combinations thereof or other metals or combinations of metals) or a ceramic base. A heat sink 36 may be in thermal contact with UV-C emitter array 14, e.g., with the base 34 and/or the UV-C emitters 14 and/or semiconductor substrate. The heat sink 36 may comprise, for example, metal and may include one or more, e.g., a plurality of fins 38.

As shown in FIG. 3A, the system or unit 10 includes collection optics (e.g., a collection lens) or collimation optics (e.g., a collimation lens) 18 to collect and reduce the divergence of light 21 from the UV-C emitter array or UV-C LED array 12 and the plurality of UV-C emitters (UV-C LEDs) 14. In the example shown, the collection or collimation optics 18 comprises a positive lens having positive optical power. The collection/collimation lens 18 in this example design comprises a plano-convex lens (with the plano side facing the UV-C emitter array 12 or plurality of UV-C emitters and/or the incoming UV-C light 21) although the lens may be different, e.g., may have the curved surface facing the UV-C emitter array 12 or plurality of UV-C emitters and/or the incoming UV-C light 21 and/or may have a pair of curved surfaces. In this particular example design, the lens 18 has a focal length of 35 mm and a clear aperture or diameter of 25.4 mm, however, the focal length and size may be different. In this example design, the collection or collimating lens 18 is positioned at a distance of 24.5 mm from the UV-C emitter array (e.g., UV-C LED array) 12 and/or the UV-C emitters (e.g. UV-C LEDs) 14 although other distances are possible. Accordingly, the collection or collimating lens 18 may be positioned within a focal length (e.g., effective focal length) to the UV-C emitter array 12 and/or UV-C emitters (UV-C LEDs) 14. Additionally, in other designs, the collection or collimating optics 18 may comprise more than a single lens or lens element such as a plurality of lens elements positioned longitudinally with respect to each other to form a lens, lens train, or lens assembly.

FIG. 3A shows the light from the UV-C emitters (UV-C LEDs) 14 being collimated into a collimated beam 20 by the collection or collimation optics or lens 18. The design shown in FIG. 3A additionally includes focusing optics 22 positioned to receive the light 20 from the collection or collimation optics 18. In this example design, the focusing optics 22 comprises positive optical power configured to cause the beam 20 from the collection or collimation optics 18 to converge. In the example shown, the focusing optics 22 comprises a single lens, a converging lens. In particular, the lens 22 is a bi-convex lens although the lens need not be so limited. In this particular example design, the lens 22 has a focal length of 50 mm and a clear aperture or diameter of 25.4 mm, however, the focal length and size may be different. In this example design, the focusing lens 22 is positioned at a distance of 50 mm from the collection or collimation optics 18 although other distances are possible. For example, in this example, the UV-C light 20 received by the focusing optics 22 is collimated. The distance between the focusing optics or lens 22 could be other distances such as 5 mm, 10 mm, 20 mm or distances different than these can be used and the focusing optics or lens 22 would focus the beam as shown. Still other configurations and/or distances are possible. Additionally, in other designs, focusing optics 22 may comprise more than a single lens or lens element such as a plurality of lens elements positioned longitudinally with respect to each other to form a lens, lens train, or lens assembly.

The system or unit 10 shown in FIG. 3A further comprises one or more housing or tubes 40 in which the collecting or collimation optics or lens 18 and/or the focusing optics or lens 22 are included. The tube(s) 40 may comprise one or more threaded tube(s) with internal and/or external threading for connecting to other tubes and/or components. In the example, the tube 40 has a 1.035 mm diameter and comprises 1.035"-40 thread. Retaining rings 42 may be employed to position the lens 18, 22. In other designs, however, the housing 40 may be different.

The housing, e.g., tube, 40 in this example, has proximal and distal ends 44, 46. The UV-C emitter array (UV-C LED array) 12 and/or plurality of UV-C emitters or UV-C LEDs 14 is at the proximal end 44 of the housing 40. The UV-C light is output from the distal end 46 of the housing.

As illustrated, the optical fiber 30 is at the distal end 46 of the housing or tube 40. The system or unit 10 further comprises coupling optics or a coupling lens 48 positioned to receive UV-C light 49 from the focusing optics 22 to couple or facilitate coupling of the UV-C light into the optical fiber 30. In various implementations, the coupling optics or coupling lens 48 comprises converging optics or a converging lens configured to further focus the UV-C light 49 from the focusing optics 22 onto the proximal end 50 of the optical fiber 30. In some implementations, the coupling optics 48 is configured to increase matching of the light beam 49 with optical fiber 30, for example, with the numerical aperture of the optical fiber and/or may reduce the size of the beam such that the light is coupled into the core of the optical fiber 30. Such coupling optics or coupling lens 48 may be included with a fiber optic input coupling port in some designs. In some designs, the optical fiber 30 is configured to be positioned and/or oriented (translated lateral in x and/or y direction and/or z direction and/or tipped and/or tilted) with respect to the coupling optics 48. In some designs, however, coupling optics, e.g., a coupling lens, 48 in addition to the focusing optics 22 is not employed. Still other configurations are possible.

In this example design, the coupling optics or lens 48 comprises positive optical power configured to cause the beam 20 from the collection or collimation optics 18 to converge. In the example shown, the coupling optics or lens 48 comprises a single lens, a converging lens. In particular, the lens 48 is a plano-convex lens (with the curved side facing the focusing optics 22 and/or the incoming UV-C light 49) although the lens need not be so limited. In this particular example design, the coupling lens 48 is smaller than the focusing lens 22 and/or the collection or collimating lens 18. For example, the coupling lens 48 has a focal length of 10 mm and a clear aperture or diameter of 6 mm, however, the focal length and size may be different. The coupling optics may be achromatic in some implementations. The coupling lens 48 may additionally or alternatively comprise an aspheric lens having one or more aspheric optical surfaces. However, the coupling lens 48 may additionally or alternatively comprise a spherical lens having at least one surface comprising a spherical surface. In this example design, the coupling lens 48 is positioned at a distance of 38 mm from the focusing optics 22 although other distances are possible. Additionally, in other designs, coupling optics 48 may comprise more than a single lens or lens element.

The system or unit 10 further comprises a fiber optic coupling port 52 at the distal end 46 of the housing or tube 40. The fiber optic input coupling port 52 is configured to receive the optical fiber 30, e.g., the proximal end 50 of the fiber optic. The fiber optic input coupling port 52 may include a receptacle or elongate (possibly threaded) connector 54 for receiving an optical fiber 30, such as an optical fiber connector, e.g., a FC/PC or SMA connector, 56, which may be configured to receive an optical fiber patch cable or other optical fiber. In some designs, the receptacle 54 includes a threaded elongate connector or nipple but other designs are possible. In this example design, the coupling optics or coupling lens 48 is in the fiber optic input coupling port 52. In the example shown, the receptacle 54 is included in an adjustable tip/tilt plate that can be adjusted for example to alter the tip and tilt as well as potentially the longitudinal distance of the proximal end 50 of the optical fiber 30 to the coupling lens 48. Other designs, however, may be different. For example, the housing 40 and/or fiber optic coupling port 52 may be different. Similarly, the fiber connector 56 may be different.

As discussed above, the optical fiber need not be a single strand of optical fiber and may be comprised of separate parts (e.g., separate strands), for example, stringed, optically connected, optically coupled or concatenated together. The separate portions or strands of optical fiber may be strung together in the longitudinal direction to provide for an elongated waveguide, light pipe, or channel through which light can propagate. The separate or discrete strands of optical fiber may be optically connected or optically coupled together, e.g., via optical connectors and may be butt coupled in some cases. Optics may be used to connect the strands or discrete portions of optical fiber together. Other ways of stringing, optically coupling or concatenating the separate or discrete portions of optical fiber or strands of optical fiber together are possible. In some implementations, however, the optical fiber comprises a single continuous strand of optical fiber as opposed to discrete or separate parts coupled, e.g., butt coupled together or otherwise optically coupled together.

Also, as discussed above, the optical fiber may be referred to as an optical fiber line or optical fiber cable (or fiber optic cable). The terms fiber, optical fiber, optical fiber line, optical fiber cable, fiber optic, fiber optic line, fiber optic cable, etc. are used interchangeably herein.

Example Optical Fibers

Figure 4:
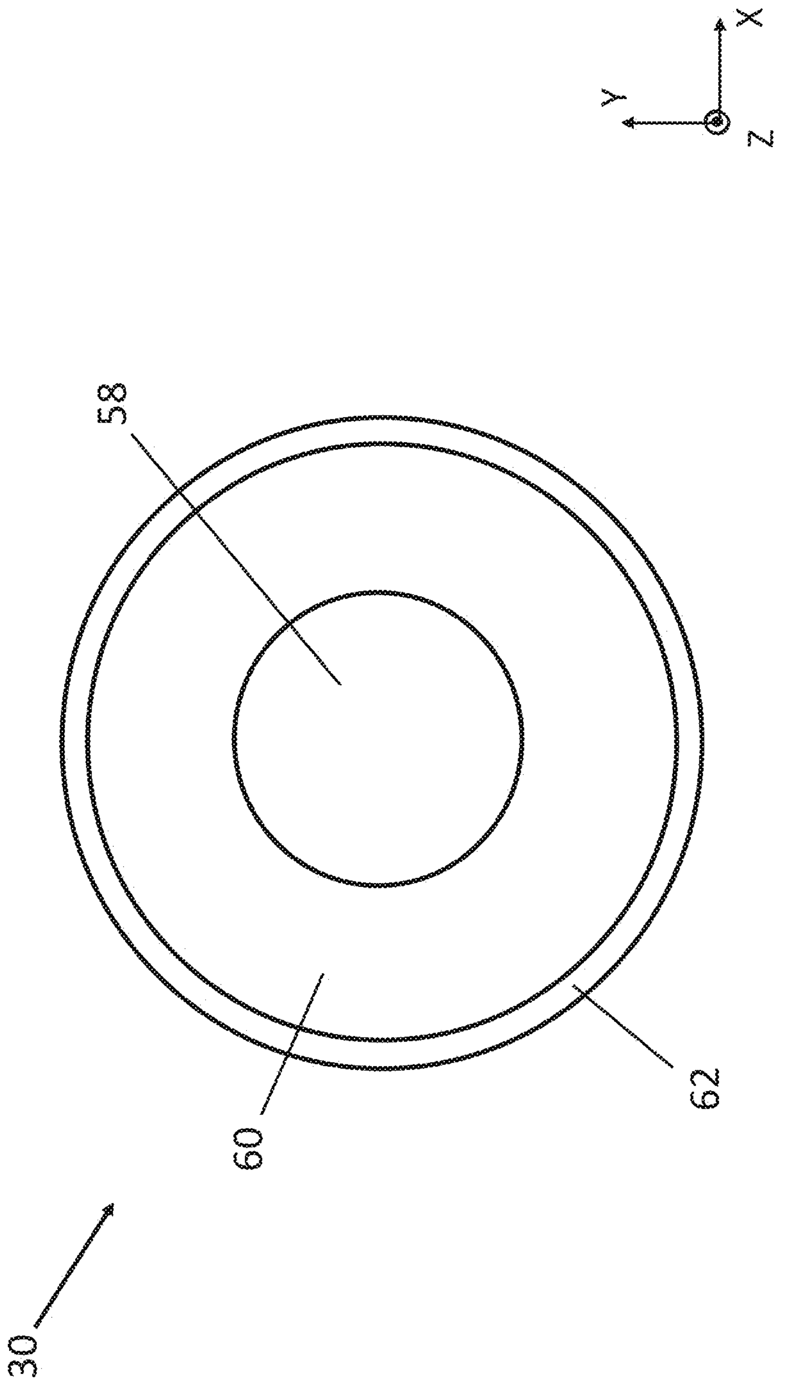
FIG. 4 is a schematic cross-sectional view of an optical fiber or optical fiber line such as shown in FIGS. 3A and 3B for conveying UV-C light to the target, such as target tissue and/or target cells.

FIG. 3B shows a more distal portion of the optical fiber 30. This optical fiber 30 may comprise, for example, a multimode optical fiber. The system or unit 10, mainly the optical fiber 30, is split between FIGS. 3A and 3B for illustrative purposes (e.g., to be able to include more detail). FIG. 4 also shows a cross-section of the optical fiber 30. The optical fiber 30 comprises a core 58 and a cladding 60. In addition, the optical fiber 30 may have a coating 62 such as a polymer coating on the cladding. In one example, the length of the optical fiber 30 is 70 mm. However, the length of the optical fiber 30 may be different. For example, the optical fiber 30 may be 4 inches, 5 inches, 6 inches, 7 inches, 8 inches, 9 inches, 10 inches, 11 inches, 1 foot, 13 inches, 14 inches, 15 inches, 16 inches, 17 inches, 18 inches, 20 inches, 21 inches, 22 inches 2 feet, 2.5 feet, 3 feet, 3.5 feet, 4 feet, 4.5 feet, 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, 60 feet, 70 feet, 75 feet, 80 feet, 90 feet, 100 feet, 110 feet, 120 feet, or any range formed by any of these values or possibly larger or smaller. Longer optical fiber may enable the light emitters 14 be to a distance from the patient and user (e.g., physician, surgeon, technician) and others (e.g., nurses, technicians, etc.) thereby potentially reducing exposure to stray UV-C light from the light emitters. In various implementations, for example, the UV-C light emitters 14 may be in a separate room than the patient and/or user thereby reducing exposure to stray UV-C light. In some implementations, shielding may be employed to block stray UV-C light from the UV-C light emitters 14. Such shielding may be opaque and/or have reduced transmission for UV-C light. Such shielding may comprise metal or plastic such as, for example, Plexiglass or polymethyl methacrylate (PMMA). The shielding may, for example, comprise material that is ⅛ in thick, ¼ inch thick or ⅜ inch thick or ½ inch thick. The thickness may for example be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 20 mm, 22 mm, 25 mm, 30 mm, or any range formed by any of these values such as from 2 mm to 16 mm or from 4 mm to 14 mm or possibly larger or smaller. The UV-C light source (e.g., the UV-C light emitters 14) may therefore comprise or be encased in a housing comprising material that reduces transmission of stray UV-C light. In some designs, the UV-C light emitters 14 and/or power supply 16 are in a housing on wheels that can be moved easily to different locations. The optical fiber 30 can extend therefrom and can extend to a location where the patient will be treated. Accordingly, in some cases, the distal end of the optical fiber 30, e.g., the head of the endoscope and/or the handheld output tool, delivery device or handpiece, is in an operating room or treatment room while the UV-C light emitters 14 are in an adjacent room or closet. In some implementations, a ring or tubular shield may be provided between the one or more light emitter 14 and the optics, e.g., collecting lens 18, possibly between the baseplate 34/heatsink 36 and the tube 40, to block stray light. This ring may, for example, comprise an elastic material such as rubber or neoprene or may comprise plastic or metal or other materials that provide reduced transmission of UV-C light. Other configurations or arrangements are possible.

Although not shown in FIG. 3B, the optical fiber 30 may include a protective sheath that is around the optical fiber. In some implementations, this optical fiber 30 may be included in an endoscope and/or be part of an endoscope. Likewise, in some implementations, this optical fiber 30 may be included in an endoscope sheath.

The optical fiber 30 is configured to transmit UV-C light. Accordingly, the optical fiber 30, and in particular, the core 58 of the optical fiber may, for example, be optically transmissive to light having a wavelength or wavelengths in the range of 200-280 nm such as 250-280 nm such as for example 265 nm. In certain implementations, the optical fiber 30 and/or the core 58 is optically transmissive to UV-C wavelengths in a range from 250 to 280 nm, such as 250 nm, 255 nm, 260 nm, 261 nm, 262 nm, 263 nm, 264 nm, 265 nm, 266 nm, 267 nm, 268 nm, 269 nm, 270 nm, 275 nm, 280 nm or any range formed by any of these values such as 255 to 275 nm or 260 to 270 nm. In some implementations, for any one of these wavelengths or any range of wavelengths formed by any of these wavelength values, the material comprising the core 58, e.g., silica, has an optical transmission per 700 mm or 1000 mm length of fiber 30 of at least 1%, 2%, 3%, 4%, 5%, 6%, 8%, 10%, 12%, 15%, 18%, 20%, 25%, 30%, 35%, 40%, 45%, 50%, 55%, 60%, 65%, 70%, 75%, 80%, 85%, 90%, 95%, 97%, 98%, 99%, 99.9%, 99.99%, 99.999%, 99.9999%, 99.99999% of any range formed by any of these percentages. In certain implementations, the optical fiber 30 and/or the core 58 is optically transmissive to UV-C wavelengths in a range from 200 to 280 nm, such as 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm or any range formed by any of these values such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or possible higher or lower wavelengths. In some implementations, for any one of these wavelengths or any range of wavelengths formed by any of these wavelength values, the material comprising the core 56, e.g., silica, has an optical transmission per 700 mm or 1000 mm length of fiber of at least 1%, 2%, 3%, 4%, 5%, 6%, 8%, 10%, 12%, 15%, 18%, 20%, 25%, 30%, 35%, 40%, 45%, 50%, 55%, 60%, 65%, 70%, 75%, 80%, 85%, 90%, 95%, 97%, 98%, 99%, 99.9%, 99.99%, 99.999%, 99.9999%, 99.99999% of any range formed by any of these percentages.

In some implementations, high OH optical fiber, optical fiber having hydroxyl (OH) content in the core material that is at least 100 ppm, 200 ppm, 300 ppm, 400 ppm, 500 ppm, 600 ppm, 700 ppm, 800 ppm, 900 ppm, 1000 ppm, 2000 ppm, 3000 ppm, 4000 ppm, 5000 ppm, 6000 ppm, 8000 ppm, 9000 ppm, 10,000 ppm, or any range formed by any of these values, such as 600-800 ppm OH, may be employed, although other values and ranges larger or smaller are possible. In some implementations, low OH optical fiber, optical fiber having hydroxyl (OH) content in the core material that is no more than 20 ppm, 10 ppm, 5 ppm, 2 ppm, 1.5 ppm, 1.2 ppm, 1 ppm, 0.9 ppm, 0.8 ppm, 0.7 ppm, 0.6 ppm, 0.5 ppm, 0.4 ppm, 0.3 ppm, 0.2 ppm, 0.1 ppm, 0.09 ppm, 0.08 ppm, 0.07 ppm, 0.06 ppm, 0.05 ppm, 0.04 ppm, 0.03 ppm, 0.02 ppm, 0.01 ppm, 0.005 ppm, 0.002 ppm, 0.001 ppm, or any range formed by any of these values, such as 0.8 to 0.08 ppm OH or 0.5 to 0.05 ppm, may be employed, although other values and ranges larger or smaller are possible.

In various implementations, the cladding 60 comprises glass such as doped glass. Such doping may control the index of refraction of the cladding 60. In some designs, the cladding 60 is doped with fluorine and comprises fluorine doped glass. In some designs, the numerical aperture (NA) of the optical fiber 30 is 0.22. However, the NA may be different.

In various designs, the optical fiber 30 is multimode fiber. Moreover, in various designs, the core 58 has a width or lateral spatial extent (e.g., in X and/or Y directions) such as a diameter that is sufficiently large to convey sufficient UV-C light to the target and/or target tissue. The size (e.g., width, diameter, lateral spatial extent) of the core 58 may, for example, be larger than 500 micrometers (μm) or larger. The core 58 may, for example, be 50 μm, 75 μm, 100 μm, 125 μm, 150 μm, 200 μm, 250 μm, 260 μm, 275 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1050 μm, 1100 μm, 1150 μm, 1200 μm, 1250 μm, 1300 μm, 1350 μm, 1400 μm, 1450 μm, 1500 μm, 1550 μm, 1600 μm, 1650 μm, 1800 μm, 1850 μm, 1900 μm, 1950 μm, 2000 μm, 3000 μm, 4000 μm, 5000 μm, 6000 μm, 7000 μm, 8000 μm, 9000 μm, 10,000 μm, 12,000 μm, 15,000 μm, or any range formed by any of these values (e.g., from 650 μm to 1500 μm or 700 μm to 1300 μm, 800 to 1200 μm, 900 μm to 1100 μm) or possible larger or smaller. In one example, the core 58 is 1000 μm. In various implementations, the fiber core 58 comprises fused silica.

The optical fiber 30 may have a variety of different lengths. The optical fiber may, for example, be 4 inches, 5 inches, 6 inches, 7 inches, 8 inches, 9 inches, 10 inches, 11 inches, 1 foot, 13 inches, 14 inches, 15 inches, 16 inches, 17 inches, 18 inches, 20 inches, 21 inches, 22 inches 2 feet, 2.5 feet, 3 feet, 3.5 feet, 4 feet, 4.5 feet, 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, or any range formed by any of these values (such as from 6 inches to 3 feet or from 1 foot to 6 feet or from 4 feet to 8 feet or from 3.5 feet to 6.5 feet or from 5 feet to 15 feet or from 15 feet to 20 feet, or from 20 feet to 30 feet or from 10 feet to 30 feet) or possibly larger or smaller. In some implementations, for example, the light source may be in a different room than the patient and/or user (e.g., physician, surgeon, technician). Accordingly, in some implementations, the distal end of the optical fiber may be in a different room than the proximal end of the optical fiber and/or the plurality of emitters (e.g. LED).

As discussed above, in some implementations, a coating 62 surrounds the cladding 60. Such a coating 62 may comprise, for example, polymer in some designs. The coating 62 may, for example, comprise acrylate. Such a coating 62 is sterilizable by Ethylene Oxide (ETO) and potentially other methods suitable for medical applications such as medical treatments (e.g., cancer treatments).

As discussed above, the optical fiber need not be a single strand of optical fiber and may be comprised of separate parts (e.g., separate strands), for example, stringed, optically connected, optically coupled or concatenated together. The separate strands of optical fiber may be optically connected or optically coupled together, e.g., via optical connectors, and may be butt coupled in some cases. In some implementations, optics may be used to connect the strands or portions of optical fiber together.

Thus, in some implementations, the optical fiber comprises separate portions that are coupled together, e.g., via one or more optical connectors, and the separate or discrete portions of optical fiber may be butt coupled. Likewise, the portions of the optical fiber may be separate and/or separable. In some implementations, however, the optical fiber comprises a single continuous strand of optical fiber as opposed to discrete or separate parts coupled, e.g., butt coupled together or otherwise optically coupled together.

Also, as discussed above, the optical fiber may be referred to as an optical fiber line or optical fiber cable (or fiber optic cable). The terms fiber, optical fiber, optical fiber line, optical fiber cable, fiber optic, fiber optic line, fiber optic cable, etc. are used interchangeably herein.

The system or unit 10 further comprises output optics or an output lens 64 positioned to receive UV-C light 68 output from the distal end 70 of the optical fiber 30. In this example design, the output optics or lens 64 comprises positive optical power configured to cause the UV-C light 68 from the distal end 70 of the optical fiber 30 to reduce its divergence, possibly collimating or focusing the light. In the example shown, the output optics or lens 64 comprises a single lens, a converging lens. In particular, the lens 64 is a plano-convex lens (with the plano side facing the distal end 70 of the optical fiber 30 and/or the incoming UV-C light 68) although the lens need not be so limited. In this particular example design, the output lens 64 is smaller than the focusing lens 22 and/or the collection or collimating lens 18. For example, the output lens 64 has a focal length of 10 mm and a clear aperture or diameter of 6 mm, however, the focal length and/or size may be different. The output optics 64 may be achromatic in some implementations. The output lens 64 may additionally or alternatively comprise an aspheric lens having one or more aspheric optical surface. However, the output lens 64 may additionally or alternatively comprise a spherical lens having at least one surface comprising a spherical surface. In this example design, the output lens 64 is positioned at a distance of 0.5 to 5 mm from the distal end 70 of the optical fiber 30 although other distances are possible. Additionally, in other designs, output optics 64 may comprise more than a single lens or lens element.

In the example system or unit 10 shown in FIG. 3B, the output lens 64 is included in a fiber optic output assembly (or lens holder) 72 which, in some implementations, comprises a handheld output tool or portion thereof. In various designs, a user such as a physician or surgeon may manipulate this handheld output tool to deliver the UV-C light to the target, e.g., to the cancerous tissue or cells. In some implementations, this handheld output tool, delivery device or handpiece may have a body which may be contoured to, e.g., ergonomically, fit the user's hand. The handheld output tool, delivery device or handpiece may comprise, for example, a wand, head, or probe, in some cases. As discussed above, in some implementations the output lens 64 may be configured to collimate the UV-C light 68 from the distal end 70 of the optical fiber 30. Accordingly, this fiber optic output assembly or probe 72 may be referred to as a collimator assembly or probe. In some implementations, the output lens 64 is configured to focus the light, for example, onto the target (e.g., target tissue such as cancerous tissue or cells). Accordingly, in various implementations, the output lens 64 is configured to reduce the divergence of UV-C light output from the distal end 70 of the optical fiber 30.

In certain implementations, the system or unit 10 may be configured to adjust the output beam size. For example, the handheld output tool, delivery device or handpiece 114 and/or the endoscope 102 may be configured to adjust the output beam size directed onto the target. In some cases, for example, the output lens 64 may be interchangeable to adjust the beam size. The handheld output tool, delivery device or handpiece 114 and/or the endoscope 102 may, for example, be configured to receive different lenses to adjust the beam size. Accordingly, one or more additional lenses may be included, for example, in a kit together with the handheld output tool, delivery device or handpiece 114 and/or the endoscope 102. The kit may include different lenses, e.g., output lenses 64, having different parameters, e.g., focal lengths and/or aperture sizes such as diameters. Different ones of the lenses may be used in different situations to provide different size beams. For example, if the tumor is larger or smaller, an output lens 64 that produces a larger or smaller beam size or width at the target may be employed. Accordingly, the user (e.g., physician, nurse, technician, etc.) may reconfigure the system 10 by switching lenses 64 to vary the beam size of light exiting the system and/or directed onto the target. Other configurations are possible to provide variable beam size output from the system 10.

The output assembly 72 is configured to receive the distal end 70 of the optical fiber 30, which may comprise a patch cable having a fiber connector at the distal end thereof. The fiber optic output assembly 72 may thus include an adaptor, such as an FC/PC or SMA adapter, to receive the distal end of the optical fiber 30. Other configurations, however, are possible. The optical fiber 30 need not comprise a patch cable, nevertheless a lens holder 72 may be configured to receive the optical fiber 30 and position the lens 64 at the distal end of the fiber. Thus, the output assembly 72 may comprise a lens holder. In various designs, therefore, the fiber optic output assembly or lens holder 72 houses and positions the output lens 64 to receive UV-C light 68 output by the distal end 70 of the optical fiber 30. In some cases, the fiber optic output assembly 72 can be manipulated to direct the UV-C light output by the output lens 64 to the target, e.g., the target tissue and/or target cells 24. In some such implementations, the fiber optical output assembly 72 may be integrated with a handheld UV-C light delivery device or tool or handpiece for such purpose. A medical practicianer such as physician (e.g., a surgeon) may hold the handheld output tool, delivery device, or handpiece and move the tool or handpiece to expose the target tissue and/or different portions of the target tissue 24 to UV-C light. The optical fiber 30 may move with movement of the tool or handpiece. Although the UV-C light may in some instances be applied to an external feature of the body, such as the skin, in other cases such as open surgery, a surgical incision is made and the UV-C light is applied to tissue within the body accessed through the surgical site. UV-C light may also be applied to tissue via minimally invasive surgery. The optical fiber 30 may be inserted through a small incision of the body to provide UV-C to disease tissue (e.g., cancerous tissue). The optical fiber 30 may be included as part of an endoscope or laparoscope, etc. Likewise, the optical fiber 30 and the fiber optical output assembly 72 may be part of an endoscope, for example, the head or distal end thereof, to provide endoscopic delivery of the UV-C light to the target 24. In some implementations, an optical fiber 30 transmissive to UV-C light, such as a fused silica optical fiber, having a sufficiently large core 58 as described herein to transmit sufficient UV-C light therethrough may accompany an optical fiber bundle or lens train that provides an imaging path for the endoscope or laparoscope. As described above, the distal end of the optical fiber 30 may be part of a tool such as a handheld tool or handpiece that is inserted into the body, for example, by the physician (e.g., surgeon). Imaging optics at the distal end of the endoscope may collect light to image the target 24 or other parts of the inside of the body. This light collected by the imaging lens may be relayed to the proximal end of the endoscope by one or more relay lens or optical fiber bundle to a camera on the proximal end of the endoscope or to an ocular for direct viewing the images of the target or other part of the body. In some designs, however, the camera may be at the distal end of the endoscope or handheld tool or handpiece to obtain images of the body. One or more electrical wires, lines or cables may be used to convey one or more signals containing image data obtained by the camera.

The optical fiber 30 may, however, be included with other delivery devices. For example, at least the output of the optical fiber 30, e.g., the distal end of the optical fiber output could be mounted on one or more translation stages (e.g., X-Y translation stages) or scanners to translate the position of the output of the optical fiber and thus the UV-C light output therefrom. Alternatively, one or more translation stages or scanners may be employed to translate and/or scan the UV-C light beam even if an optical fiber 30 is not employed. A system such as shown in FIG. 1 may, for example, be mounted on a translation stage or a scanner and may be employed to deflect a beam output from a system such as shown in FIG. 1. In some implementations, the optical fiber 30 is included on an articulated arm or robotic arm. Likewise, the optical fiber 30 may be included in a robotic system such as a robotic assisted surgery system where the surgeon manipulates one or more robotic arms or robotic surgery systems that are more autonomous at least in part. Still other variations are possible.

Example Light Emitter Arrays

Figure 5A:
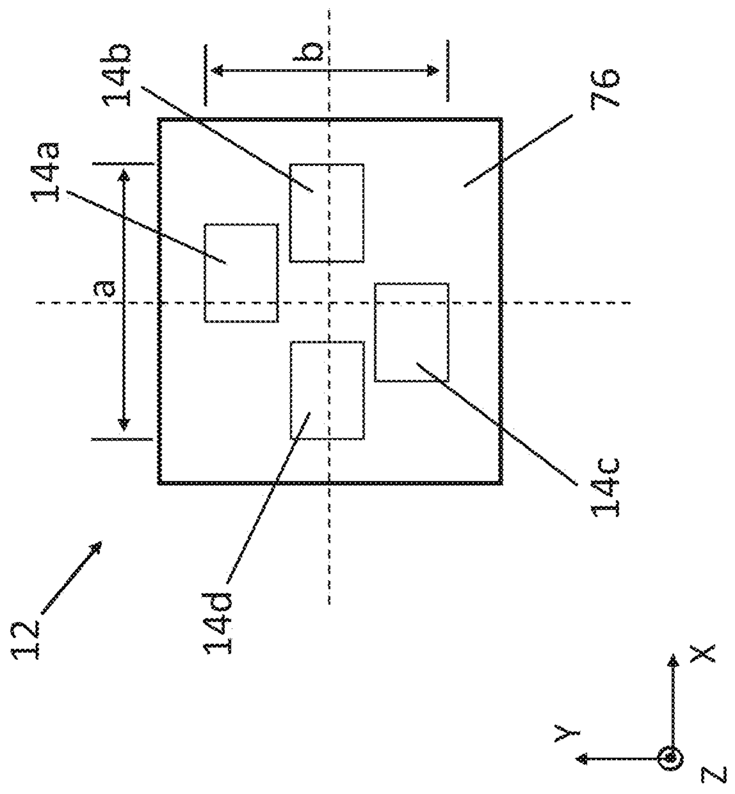
FIG. 5A is a schematic front view of the plurality of light emitters (e.g., UV-C LEDs) in a UV-C emitter array.

A schematic front view of an example UV-C emitter array 12 comprising a plurality of UV-C emitters 14 is depicted in FIG. 5A. In particular, an example UV-C LED array 12 comprising four UV-C LEDs 14*a*, 14*b*, 14*c*, 14*d* is shown. The LEDs 14 comprise semiconductor material on a substrate 76 such as a semiconductor substrate. In one example, the LED 14 comprises III-V semiconductor material such as AlGaN/AlN structures. Other materials may be used. In the example shown, the four diodes are in a space or area having a dimension of 2.7 mm×2.4 mm (a×b). The diodes themselves are 1 mm×0.8 mm. Although an ordered array of rows and columns is shown in FIGS. 1 and 2, as illustrated by FIG. 5A, the UV-C emitter array 12 need not be limited to rows and column such as shown in FIGS. 1 and 2. FIG. 5A, for example, shows UV-C emitters (e.g., UV-C LEDs) 14 in the array of UV-C light emitters or a UV-C light emitter array 12 that are not arranged in columns. Each of the UV-C emitters (UV-C LEDs) 14 in the UV-C emitter array or UV-C LED array 12 are not lined up in a column with one or more other UV-C emitters (UV-C LEDs). Instead, the first (top) row has a single LED 14*a*, the second (middle) row has the two LEDs 14*b*, 14*d*, and the third (bottom) row has a single LED 14*c*. The single LED 14*a* in the first (top) row is offset from both the two LEDs 14*b*, 14*d* in the second (middle) row (e.g., the centers of the LEDs are offset with respect to each other). The single LED 14*a* in the first (top) row is also offset from the single LED 14*c* in the third (bottom) row (e.g., the centers of the LEDs are offset with respect to each other). Additionally, the single LED 14*c* in the third (bottom) row is offset from both the two LEDs 14*b*, 14*d* in the second (middle) row (e.g., the centers of the LEDs are offset with respect to each other).

Figure 5B:
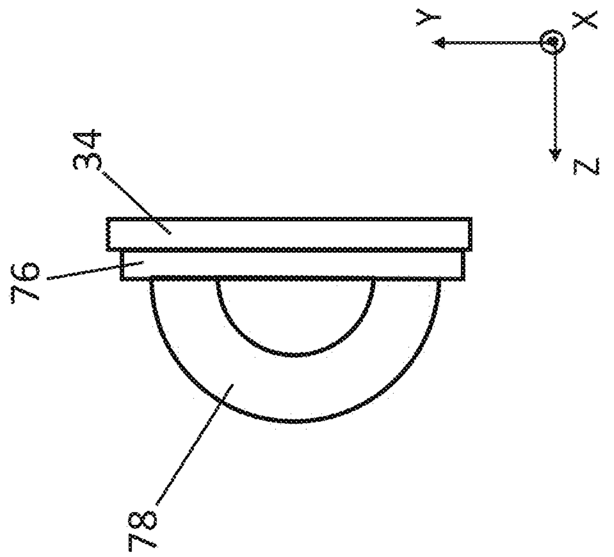
FIG. 5B is a schematic cross-sectional view of the UV-C emitter array such as shown in FIG. 5B additionally showing a glass window or dome over the UV-C emitters.

FIG. 5B shows a cross-section of a UV-C emitter array or UV-C LED array 12 such as shown in FIG. 5A. The semiconductor substrate 76 on which the LEDs 14*a*-14*d* are fabricated is shown together with the base 34, which may comprise metal or ceramic. A heat sink 36 (possibly with fins 38) such as shown in FIG. 3A may be thermally coupled with the base 34 to extract heat therefrom. A window or dome 78 that is optically transparent to UV-C light is shown in the schematic cross-section depicted in FIG. 5B. This window or dome 78 may comprise, for example, fused silica. This window or dome 78 may provide for a seal such as a hermitic seal.

Wavelength Spectrums

Figure 5C:
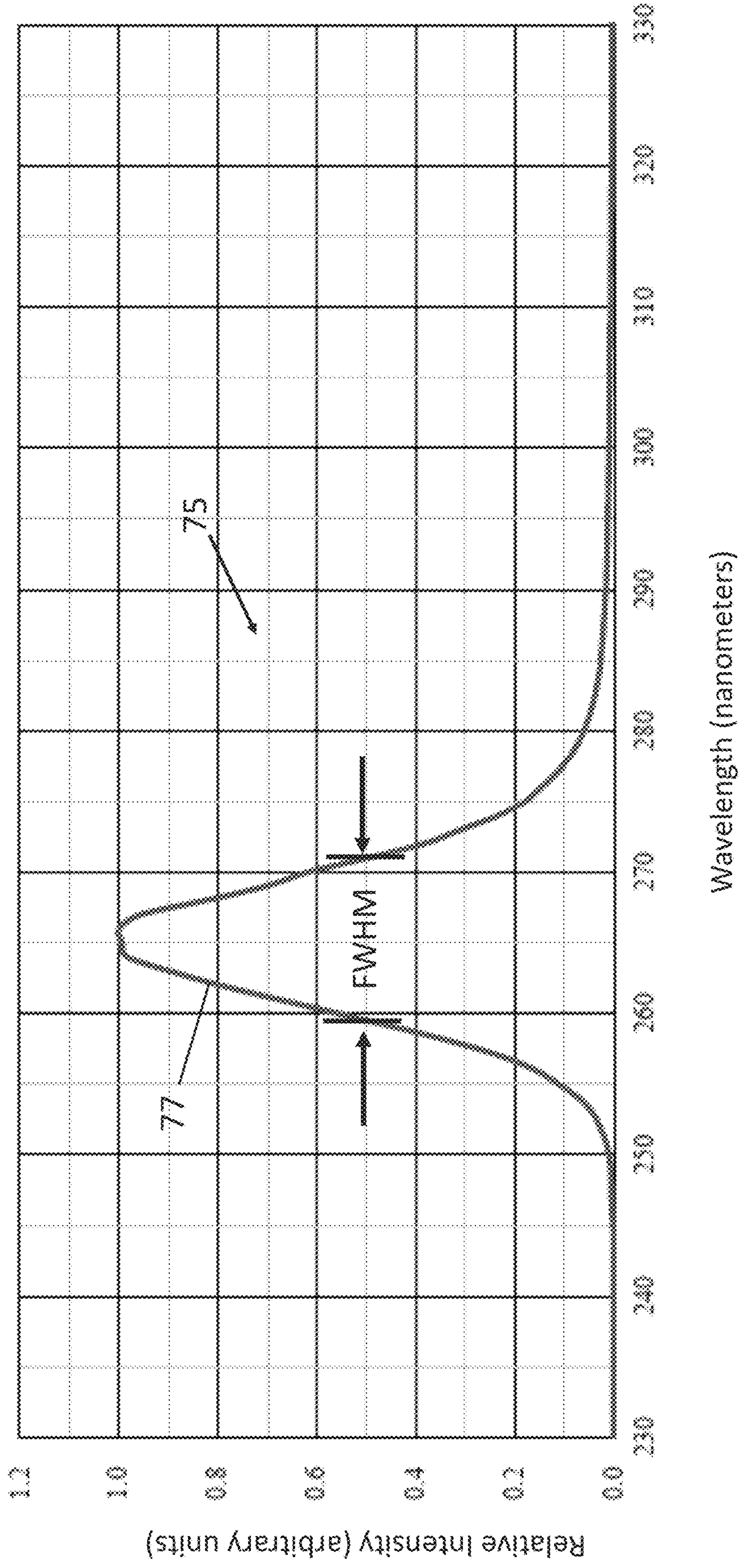
FIG. 5C is plot on axes of relative intensity (arbitrary units) versus wavelength (nanometers) showing an example wavelength distribution of light output by a UV-C LED.

FIG. 5C depicts an emission spectrum 75 for a UV-C emitter 14 such as a UV-C LED or a plurality (e.g., an array 12) of such UV-C emitters (e.g., UV-C LEDs). The emission spectrum 75 has a peak 77 in the UV-C spectrum. In this example, the UV-C peak 77 is centered about 265 nm and has a spectral bandwidth (FWHM) of 11.5 or 12 nm. The emission below 250 nm and above 310 nm is negligible. In fact, the transmission above 290 nm appears less than 2.5% or 3%. Accordingly, these UV-C emitters emit mostly in the UV-C as compared to other UV wavelengths as well as compared to visible wavelengths.

Accordingly, in various implementations, the one or more UV-C emitters emit more than 40% or 50% (e.g., of the peak intensity, which is normalized to be unity) at 260 nm and/or 270 nm. The one or more UV-C emitters emit more than 90% or 95% or 97% or 98% or 99% (of the peak intensity) or in any range formed by any of these values at 265 nm. The one or more UV-C emitters emit more than 70% or 75% or 80% (of the peak intensity) or in any range formed by any of these values at 262 nm. However, the one or more UV-C emitters may emit less than 90% or 85% or 80% (of the peak intensity) or in any range formed by any of these values at 262 nm.

Additionally, the one or more UV-C emitters emit less than 25% or 20% (of the peak intensity) or in any range formed by any of these values at 255 nm and/or 275 nm. The one or more UV-C emitters may emit less than 10% (of the peak intensity) at 250 nm and 280 nm. Similarly, the one or more UV-C emitters emit less than 5% or 4% or 3% or 2% or 1% (of the peak intensity) or in any range formed by any of these values at 245 nm, 240 nm, 235 nm, 230 nm or in any range formed by any of these values. Additionally, the one or more UV-C emitters emit less than 5% or 4% or 3% or 2.5% or 2% (of the peak intensity) or in any range formed by any of these values at 285 nm or 290 nm, 235 nm, 230 nm or in any range formed by any of these values. Furthermore, the one or more UV-C emitters emit less than 2% or 1% (of the peak intensity) at 295 nm or 300 nm, 305 nm, 310 nm, 320 nm, 330 nm or in any range formed by any of these values. Any one or more of these spectral limitations are applicable to the one or more UV-C emitters.

Moreover, in various implementations, one or more UV-C emitters (e.g., one or more UV-C LEDs), the UV-C emitter array (e.g., UV-C LED array) 12 and/or the plurality of UV-C emitters (e.g. UV-C LEDs) 14 emit UV-light having a wavelength within a wavelength range of 250 and 280 nm. In certain implementations, the one or more UV-C emitters (e.g., one or more UV-C LEDs) 14, the UV-C emitter array 12 and/or UV-C emitters 14 emit UV light having a spectrum or peak in the UV-C centered at about 265 nm. In certain implementations, the one or more UV-C emitters (e.g., one or more UV-C LEDs), the UV-C emitter array 12 and/or UV-C emitters 14 emit UV-C light having a spectral peak or spectrum having a spectral width as measured at full width half maximum (FWHM) that is about, at least or at most 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, or in a range between any of these values or possibly larger or smaller. In some implementations, the one or more UV-C emitters (e.g., one or more UV-C LEDs), the UV-C emitter array 12 and/or UV-C emitters 14 emit UV-C light having a spectrum or spectral peak having a spectral width as measured at full width half maximum (FWHM) that is about, at least, or at most 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, or in a range between any of these values or possibly larger or smaller.

In some implementations, the UV or UV-C peak or spectrum is centered at a UV-C wavelength other than 265 nm, but possibly within the range of from 250 nm to 280 nm. The peak may be centered, for example, at 250 nm, 250.5 nm, 251 nm, 251.5 nm, 252 nm, 252.5 nm, 253 nm, 253.5 nm, 254 nm, 254.5 nm, 255 nm, 255.5 nm, 256 nm, 256.5 nm, 257 nm, 257.5 nm, 258 nm, 258.5 nm, 259 nm, 259.5 nm, 260 nm, 260.5 nm, 261 nm, 261.5 nm, 262 nm, 262.5 nm, 263 nm, 263.5 nm, 264 nm, 264.5 nm, 265 nm, 265.5 nm, 266 nm, 266.5 nm, 267 nm, 267.5 nm, 268 nm, 268.5 nm, 269 nm, 269.5 nm, 270 nm, 270.5 nm, 271 nm, 271.5 nm, 272 nm, 272.5 nm, 273 nm, 273.5 nm, 274 nm, 274.5 nm, 275 nm, 276.5 nm, 276 nm, 276.5 nm, 277 nm, 277.5 nm, 278 nm, 278.5 nm, 279 nm, 279.5 nm, 280 nm or in any range formed by any of these values or possibly larger or smaller. Similarly, much or most of the light (e.g., energy, power, radiant flux) output by the one or more UV-C emitters (e.g., one or more UV-C LEDs), the array and/or the UV-C light emitters (e.g., UV-C LEDs) and/or output by the optical fiber and/or system and/or directed onto the target area (e.g., target tissue and/or cancerous tissue) 24 such as 40% or more, 45% or more, 50% or more, 55% or more, 60% or more, 65% or more, 70% or more, 75% or more, 80% or more, 85% or more, 90% or more, 95% or more, 98% or more, 99% or more, 100%, or any range formed by any of these values (e.g., 40%-95% or 50% to 98% or 60% to 99% or 70% to 100% or 75% to 100%), may be in any range formed by any of 250 nm, 250.5 nm, 251 nm, 251.5 nm, 252 nm, 252.5 nm, 253 nm, 253.5 nm, 254 nm, 254.5 nm, 255 nm, 255.5 nm, 256 nm, 256.5 nm, 257 nm, 257.5 nm, 258 nm, 258.5 nm, 259 nm, 259.5 nm, 260 nm, 260.5 nm, 261 nm, 261.5 nm, 262 nm, 262.5 nm, 263 nm, 263.5 nm, 264 nm, 264.5 nm, 265 nm, 265.5 nm, 266 nm, 266.5 nm, 267 nm, 267.5 nm, 268 nm, 268.5 nm, 269 nm, 269.5 nm, 270 nm, 270.5 nm, 271 nm, 271.5 nm, 272 nm, 272.5 nm, 273 nm, 273.5 nm, 274 nm, 274.5 nm, 275 nm, 275.5 nm, 276 nm, 276.5 nm, 277 nm, 277.5 nm, 278 nm, 278.5 nm, 279 nm, 279.5 nm, 280 nm (e.g., from 250 nm to 280 nm or 255 nm to 275 nm, or 260 to 270 nm, or 258 nm to 272 nm) or possibly larger or smaller or higher or lower wavelengths. In some implementations, visible light may additionally be included, for example, as a guide for the practicianer (e.g., the physician, surgeon etc.) as UV-C light is invisible to the eye.

Accordingly, in some cases, much or most of the UV light and/or UV-C light (e.g., energy, power, radiant flux) output by the one or more UV-C emitters (e.g., one or more UV-C LEDs), the array and/or the UV-C light emitters (e.g., UV-C LEDs) and/or output by the optical fiber and/or directed onto the target area (e.g., target tissue and/or cancerous tissue) 24 such as 40% or more, 50% or more, 60% or more, 70% or more, 80% or more, 90% or more, 95% or more, 98% or more, 99% or more, 100%, or any range formed by any of these values (e.g., 40%-95% or 50% to 98% or 60% to 99% or 70% to 100%), may be in any range formed by any of 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm (e.g., from 250 nm to 280 nm or 255 nm to 275 nm, or 260 to 270 nm, or 258 nm to 272 nm) or possibly larger or smaller. In some implementations, however, visible light may additionally be included, for example, as a guide for the user (e.g., the physician, surgeon etc.) as UV-C light is invisible to the eye. Nevertheless, in various implementations, most of the UV light may comprise UVC light. And most of the UVC light may be in the range between 250 nm and 280 nm for certain designs.

Other designs, however, are possible. In some designs, for example, one or more UV-C emitters (e.g., one or more UV-C LEDs), the UV-C emitter array (e.g., UV-C LED array) 12 and/or the plurality of UV-C emitters (e.g. UV-C LEDs) 14 emit UV-light having a wavelength within a wavelength range of 200 and 250 nm. In certain implementations, the one or more UV-C emitters (e.g., one or more UV-C LEDs), the UV-C emitter array 12 and/or UV-C emitters 14 emit UV light having a spectrum or peak in the UV-C centered at about 207 nm or 222 nm. In certain implementations, the one or more UV-C emitters (e.g., one or more UV-C LEDs), the UV-C emitter array 12 and/or UV-C emitters 14 emit UV-C light having a spectral peak or spectrum having a spectral width as measured at full width half maximum (FWHM) that is about 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm or in a range between any of these values or possibly larger or smaller. In some implementations, the one or more UV-C emitters (e.g., one or more UV-C LEDs), the UV-C emitter array 12 and/or UV-C emitters 14 emit UV-C light having a spectrum or spectral peak having a spectral width as measured at full width half maximum (FWHM) that is about 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 100 nm, 110 nm, 120 nm, 130 nm, 140 nm, 150 nm, 175 nm, 200 nm, or in a range between any of these values (e.g., from 5 to 20 nm or 10 to 30 nm, or 10 to 50 nm or from 10 to 80 nm or from 10 to 100 nm or from 10 to 120 nm) or possibly larger or smaller.

In some implementations, the UV or UV-C peak or spectrum is centered at a UV-C wavelength other than 207 nm or 222 nm, but possibly within the range of from 200 nm to 250 nm. The peak may be centered, for example, at 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm or any range formed by any of these values such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or possible higher or lower wavelengths. Similarly, much or most of the light (e.g., energy, power, radiant flux) output by the one or more UV-C emitters (e.g., one or more UV-C LEDs), the array and/or the UV-C light emitters (e.g., UV-C LEDs) and/or output by the optical fiber and/or system and/or directed onto the target area (e.g., target tissue and/or cancerous tissue) such as 40% or more, 45% or more, 50% or more, 55% or more, 60% or more, 65% or more, 70% or more, 75% or more, 80% or more, 85% or more, 90% or more, 95% or more, 98% or more, 99% or more, 100%, or any range formed by any of these values (e.g., 40%-95% or 50% to 98% or 60% to 99% or 70% to 100% or 75% to 100%), may be in any range formed by any of 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or possible higher or lower wavelengths. In some implementations, visible light may additionally be included, for example, as a guide for the practicianer (e.g., the physician, surgeon etc.) as UV-C light is invisible to the eye.

Accordingly, in some cases, much or most of the UV light and/or UV-C light (e.g., energy, power, radiant flux) output by the one or more UV-C emitters (e.g., one or more UV-C LEDs), the array and/or the UV-C light emitters (e.g., UV-C LEDs) and/or output by the optical fiber and/or directed onto the target area (e.g., target tissue and/or cancerous tissue) such as 40% or more, 50% or more, 60% or more, 70% or more, 80% or more, 90% or more, 95% or more, 98% or more, 99% or more, 100%, or any range formed by any of these values (e.g., 40%-95% or 50% to 98% or 60% to 99% or 70% to 100%), may be in any range formed by any of 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or possible higher or lower wavelength. In some implementations, however, visible light may additionally be included, for example, as a guide for the user (e.g., the physician, surgeon etc.) as UV-C light is invisible to the eye. Nevertheless, in various implementations, most of the UV light may comprise UVC light (e.g., in the range from 200 to 280 nm). And most of the UVC light (and/or UV light) may be in the range between 200 to 250 nm or 200 to 230 nm or 200 to 235 nm for certain designs although as described above some or most of the UVC light (or UV light or light) may be in the range of from 250 to 280 nm. In some implementations, the one or more UV-C emitters (e.g., UV-C LEDs), the UV-C emitter array (UV-C LED array), and/or the plurality of UV-C emitters (UV-C LEDs) may emit UV-C light in any combination of these ranges e.g., 200 to 250 nm and 250 to 280 nm or 200 to 230 nm and 250 to 280 nm or 200 to 235 nm and 250 to 280 nm. In various implementations, the one or more UV-C emitters (e.g., one or more UV-C LEDs), the UV-C emitter array 12 and/or UV-C emitters 14 emit UV-C light having a spectrum or spectral peak having a spectral width as measured at full width half maximum (FWHM) that is at least (or at most) 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 100 nm, 110 nm, 120 nm, 130 nm, 140 nm, 150 nm, 175 nm, 200 nm, or in a range between any of these values (e.g., from 5 to 20 nm or 10 to 30 nm, or 10 to 50 nm or from 10 to 80 nm or from 10 to 100 nm) or possibly larger or smaller.

Guiding Using Visible Light

As referred to above, visible light may be useful to guide the physician in knowing where UV-C light is being directed. In some implementations, the perimeter of the visible light beam at the target location matches the perimeter of the UV-C light to within 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1% of the size of the beam UV-C beam or any ranges formed by any of these values or possible larger or smaller. Accordingly, the one or more UV-C emitters (e.g., UV-C LEDs) may emit visible light in some designs. The one or more UV-C emitter may, for example, emit blue or violet in addition to UV-C light.

Figure 5D:
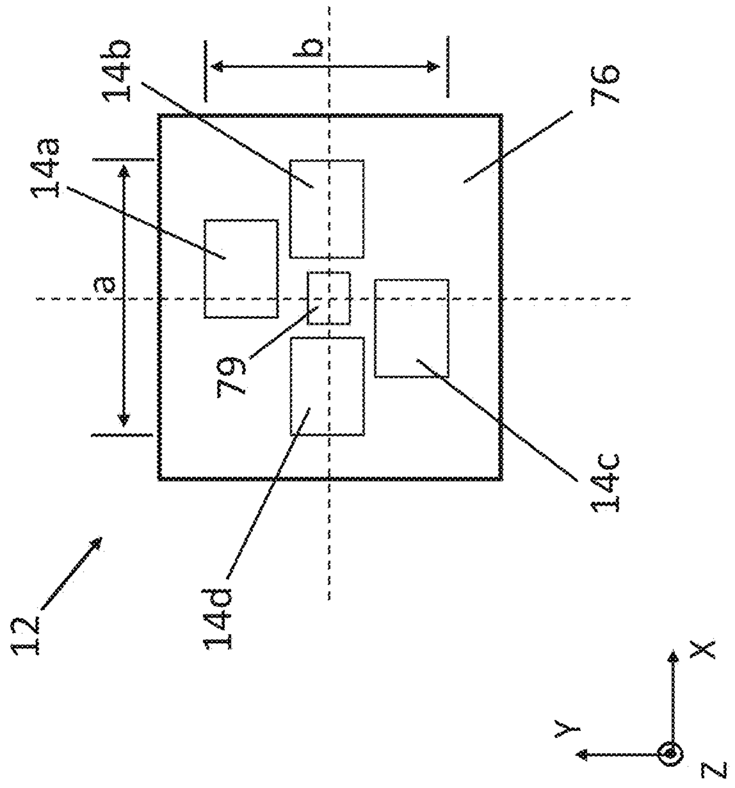
FIG. 5D is a schematic front view of the plurality of light emitters (e.g., UV-C LEDs) in a UV-C emitter array further comprising a visible light emitter (e.g., a visible LED, such as a red LED, green LED, blue LED or violet LED).

However, in other implementations, such as shown in FIG. 5D, at least one separate visible light emitter (e.g. visible light LED) 79 may be included with the UV-C emitters (UV-C LEDs). As discussed above, the UV-C emitters (UV-C LEDs) may emit at most negligible amounts of visible light. The at least one visible light emitter 79 may be configured to output a visible light beam coincident with and having the same size (e.g., to within 15%, 12%, 10%, 9%, 8%, 7%, 6%, 5%, 4%, 3%, 2%, 1%, 0.5%, 0.1%) at the target 24 as the UV-C light beam so that the physician or medical profession can know where the invisible UV-C light is incident on the patient. In some implementations, the beam size of the at least one visible light emitter 79 may be adjustable independent of the beam size of the UV-C emitters 14, for example, to match the beam sizes of the visible and UV-C light beams at the target. In some implementations, the beam size of both the visible light emitter 79 and the UV-C emitters 14 are adjustable, for example, by adjusting optics receiving light from the UV-C emitters and/or the visible light emitters 79. As discussed above, in some implementations, the perimeter of the visible light beam at the target location matches the perimeter of the UV-C light to within 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1% of the size of the beam UV-C beam or any ranges formed by any of these values or possible larger or smaller. Other configurations are possible.

Driver Electronics

As discussed above, the UV-C emitter array (e.g., UV-C LED array) 12 is driven by driver electronics 16, which may comprise a pulsed power source that provides electrical pulses to the UV-C emitters or LEDs 14 such that the UV-C emitters output pulses of UV-C light. The electronics, for example, the pulse power source, 16 may provide the ability to alter the duration or period of time, $T_{on}$, during which the UV-C light and/or optical pulses are applied and/or the duration or period of time $T_{off}$ between when the UV-C light and/or optical pulses are applied. The driver electronics may in some implementations comprise an AC power source. Alternatively, the driver electronics may comprise a non-pulsed power source, e.g. a constant power source or DC power source. Such a non-pulsed or constant or DC power supply may apply DC or constant electrical power to the UV-C emitters (e.g., UV-C LEDs). This DC or constant power provided by the driver electronics 16 to the UV-C emitters may be turned on or be above a threshold amount for continuous periods of time, for example, of 1 second, 2 seconds, 3 seconds, 4 seconds, 5 seconds, 6 seconds, 8 seconds, 9 seconds, 10 seconds, 12 seconds, 15 seconds, 20 seconds, 25 seconds, 30 seconds, 40 seconds, 50 seconds, 60 seconds, 120 seconds or for a time in any range between any of these values or possible longer or shorter although the DC or constant power may be turned off or reduced below the threshold amount at the end of such period of time. Constant or continuous amounts of UV-C light may thus be applied to the target for such amounts of time. The DC power or constant power and correspondingly, the UV-C light may subsequently be turned on again or increased above the threshold amount with the UV-C light being directed to the same or different target (e.g., target cells) or portions thereof. This process may be repeated multiple times in one treatment session or in different respective treatment sessions. For example, the power provided by the driver electronics 16 to the UV-C emitters may be turned on or be above a threshold amount for continuous periods of time, for example, of 1 second, 2 seconds, 3 seconds, 4 seconds, 5 seconds, 6 seconds, 8 seconds, 9 seconds, 10 seconds, 12 seconds, 15 seconds, 20 seconds, 25 seconds, 30 seconds, 40 seconds, 50 seconds, 60 seconds, 120 seconds or for periods of time in any range between any of these values or possible longer or shorter and the power may be turned off or reduced below the threshold amount at the end of such period in a first treatment session (or at a first target location). The power provided by the driver electronics 16 to the UV-C emitters may be turned on or be above a threshold amount for continuous periods of time, for example, of 1 second, 2 seconds, 3 seconds, 4 seconds, 5 seconds, 6 seconds, 8 seconds, 9 seconds, 10 seconds, 12 seconds, 15 seconds, 20 seconds, 25 seconds, 30 seconds, 40 seconds, 50 seconds, 60 seconds, 120 seconds or for time periods in any range between any of these values or possible longer or shorter and the power may be turned off or reduced below the threshold amount at the end of such period in a second treatment session (or at a second target location, e.g., in a given treatment session). Constant or continuous amounts UV-C light may thus be applied to the target(s), for example, for these amounts of time.

Figure 6A:
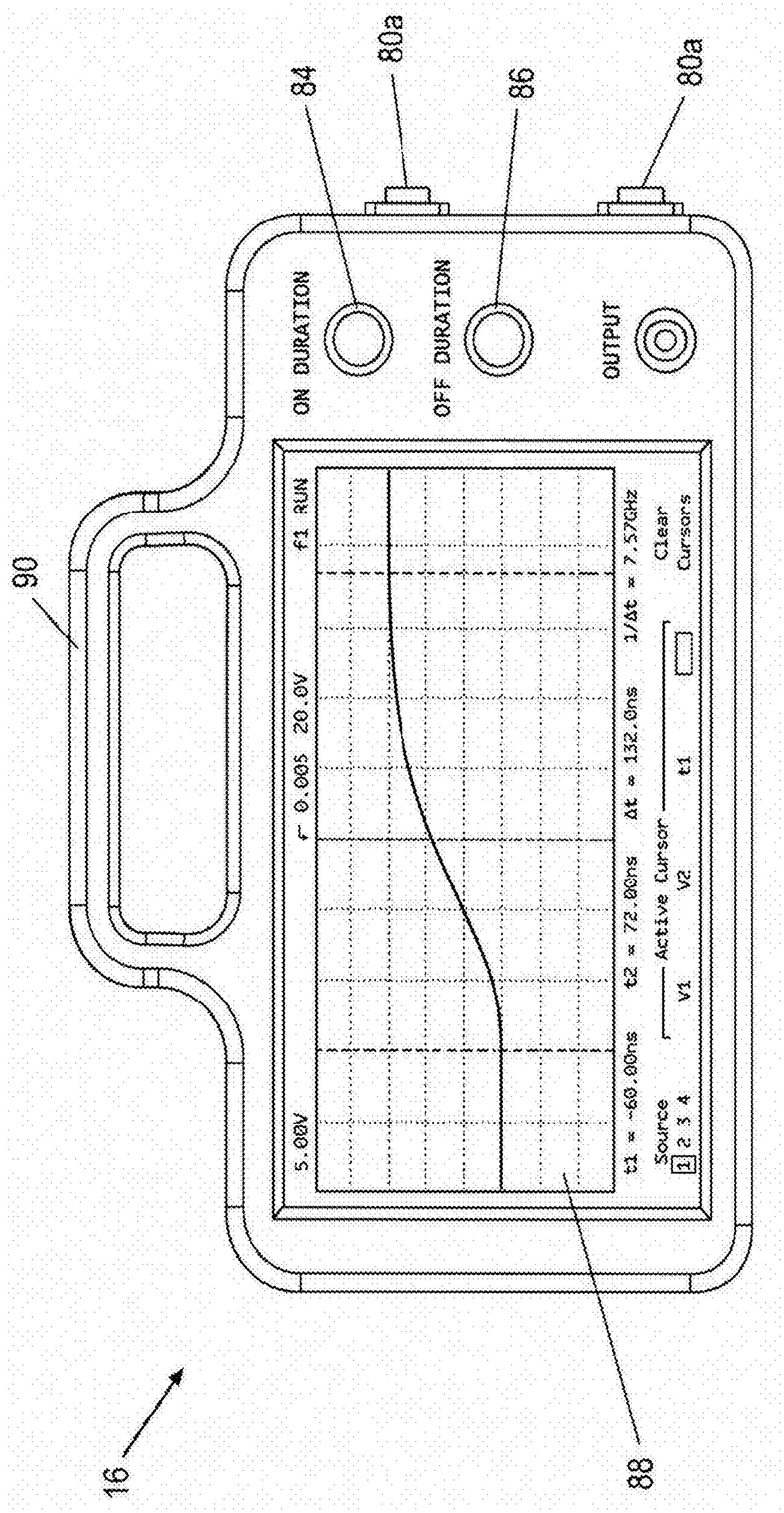
FIGS. 6A-6C are front, side, and back views, respectively, of an electrical power supply, e.g., pulsed power source or pulse generator, configured to provide electrical power (e.g., electrical pulses) to the UV-C emitters such that the UV-C emitters output UV-C light (e.g., UV-C light pulses). The example pulsed power source shown includes controls for varying the duration of the pulses or groups of pulses as well as the duration between pulses or groups of pulses. In various implementations, the frequency of the pulses may also be varied.
Figure 6B:
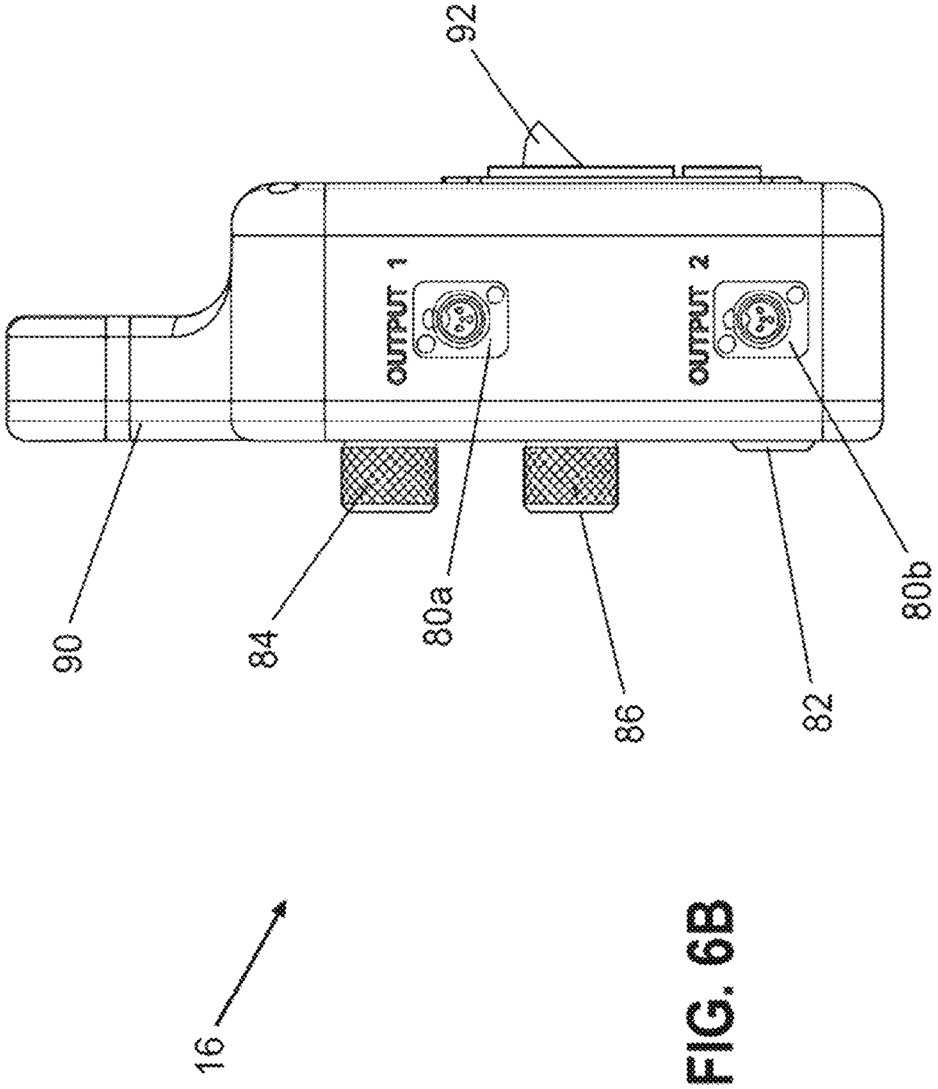
Figure 6C:
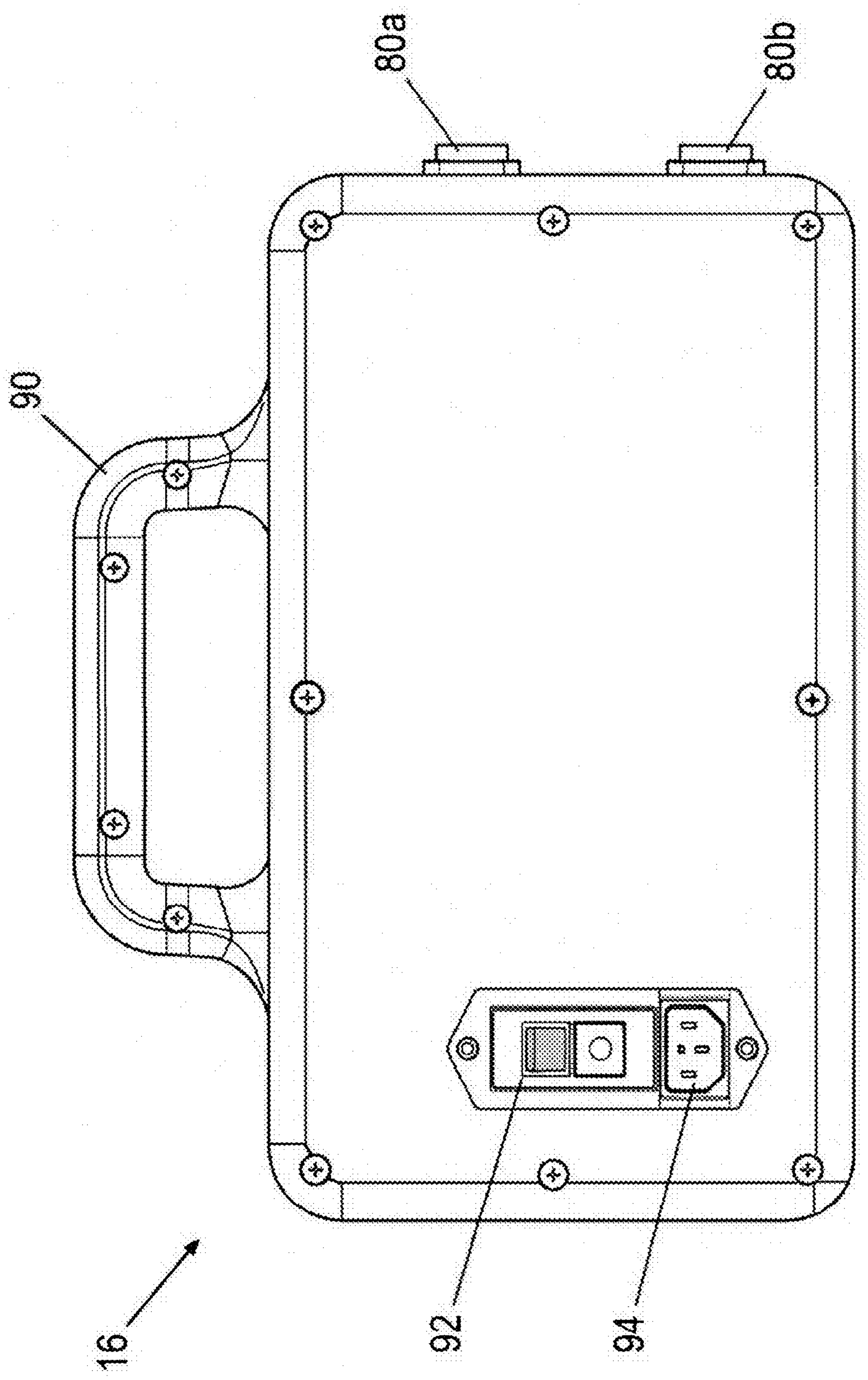

FIGS. 6A-6C show an example pulsed power source 16 that may be used to drive a plurality of UV-C emitters (LEDs) 14. FIG. 6A is a front view, FIG. 6B is a side view, and FIG. 6C is a back view. The pulsed power source 16 includes two electrical outputs 80*a*, 80*b*, which can be coupled to respective electrical cables to provide electrical signals to UV-C emitters (e.g., UV-C LEDs). The two electrical outputs 80*a*, 80*b* provide the ability to drive two emitter arrays (e.g., UV-C LED arrays) 12.

The pulsed power source 16 further includes controls 84 and 86, respectively, to control duration or period of time, $T_{on}$, during which the UV-C light, for example, optical pulses, are applied as well as the duration or period of time or delay, $T_{off}$, between when the optical pulses are applied. See FIG. 6A. In some implementations, the UV-C light or pulses are on for a period of time, $T_{on}$, during which the UV-C light or optical pulses are output by the UV-C emitter array 12 and off for a period of time, $T_{off}$. In some such designs, no UV-C light may be emitted from the UV-C emitter array/UV-C LED array between pulses and/or groups of pulses. The controls 84, 86 can control the duration or length of these two time periods, $T_{on}$ and $T_{off}$. (In some other designs, the UV-C light and/or pulses are not be turned on and off but instead during one period, $T_{high}$, the UV-C light and/or pulses exceed a non-zero threshold amount. Between such periods of higher light output, the UV-C emitter array 12 or UV-C emitters 14 output UV-C light below the threshold amount or below another lower threshold amount. This later period may be referred to as $T_{low}$.)

Other variations are possible. The pulsed power source 16 may for example have controls for control of one or more of frequency such as pulse frequency or repetition rate (rep rate) (e.g., 60 Hz, etc.), duty cycle (e.g., 50%) and/or dose duration (e.g., 40 seconds). The pulse power source 16 may have knobs, dials, switches, etc., to control one or more of these parameters or other parameters (e.g., brightness, etc.) or may be configured to control one or more of these parameters or other parameters with a keypad, touch screen, or may be responsive to voice commands via, e.g., voice recognition.

Figure 6D:
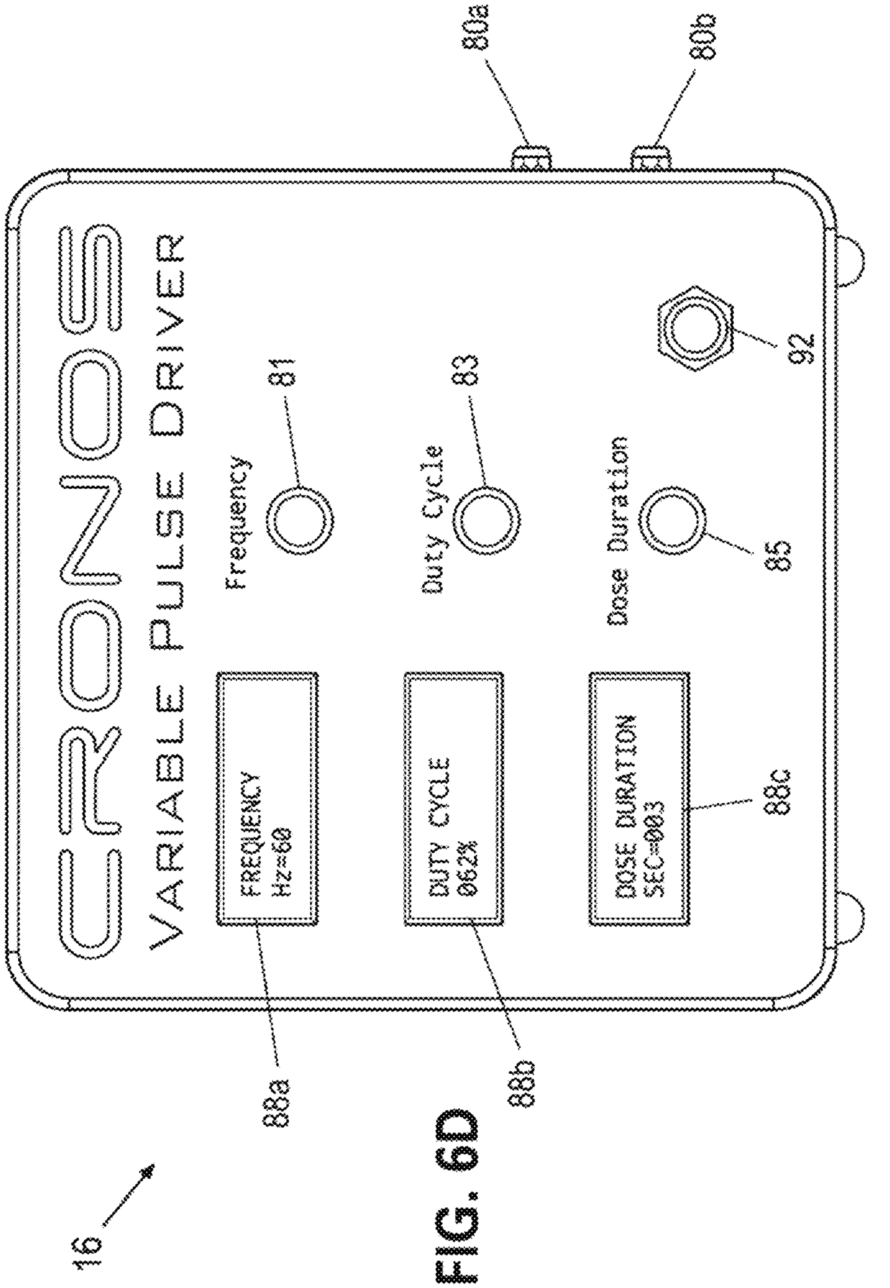
FIGS. 6D-6F are front, side, and perspective views, respectively, of another electrical power supply, e.g., pulsed power source or pulse generator, configured to provide electrical power (e.g., electrical pulses) to the UV-C emitters such that the UV-C emitters output UV-C light (e.g., UV-C light pulses). The example pulsed power source shown also includes controls for varying the frequency or repetition rate, the duty cycle, and the duration of the pulses or groups of pulses.
Figure 6E:
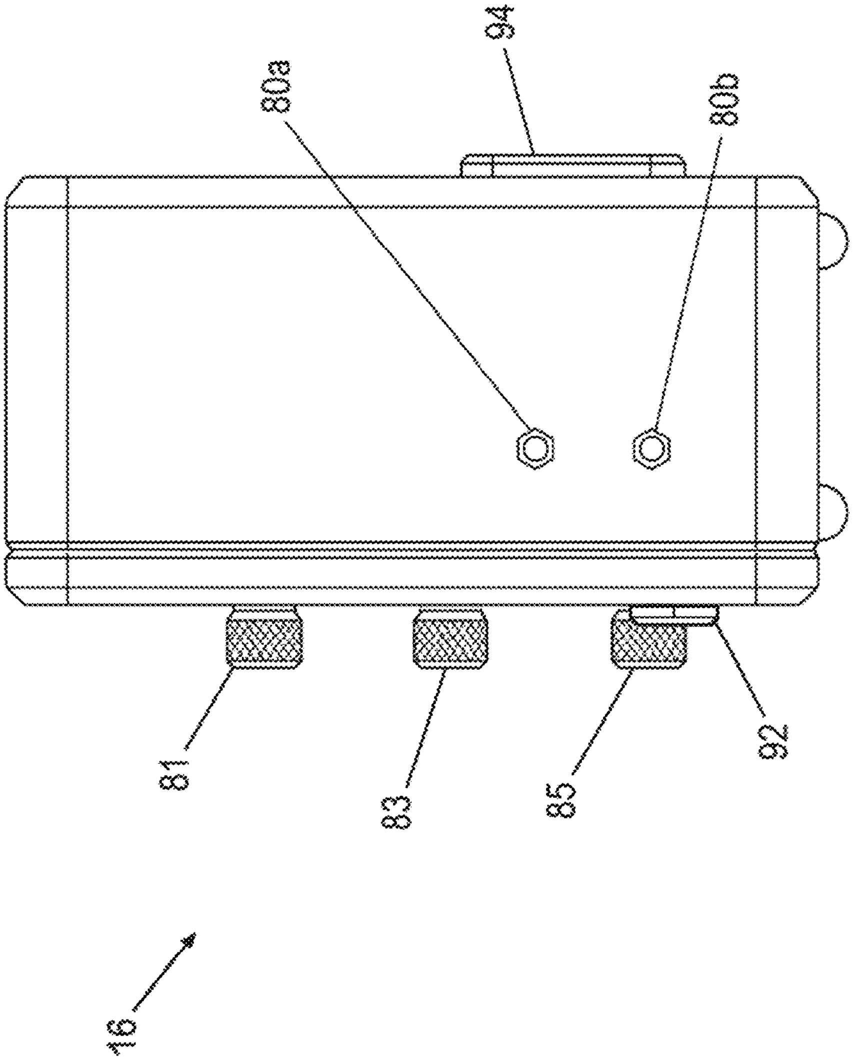
Figure 6F:
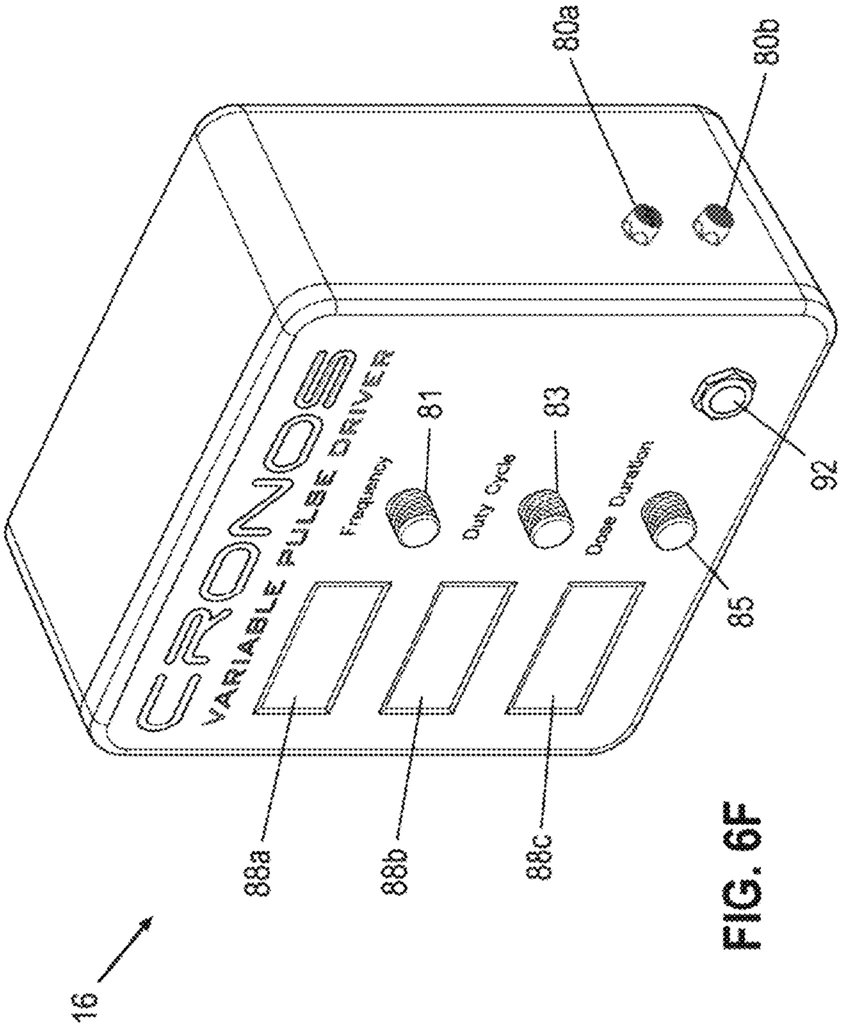

Another example of a pulsed power source 16 that may be used to drive a plurality of UV emitters (e.g., LEDs) 14 is shown in FIGS. 6D-6F. FIG. 6D is a front view, FIG. 6E is a side view, and FIG. 6F is a perspective view. This pulsed power source 16 includes two electrical outputs 80*a*, 80*b*, which can be coupled to respective electrical cables to provide electrical signals to UV emitters (e.g., UV-C LEDs). In one example, the electrical outputs 80*a*, 80*b* are coaxial connectors (e.g., four pin coaxial connectors). In some designs, the two outputs 80*a*, 80*b* may output the same electrical signal to drive two emitter arrays (e.g., UV LED arrays) 12 with the same signal. In other implementations, the two electrical outputs 80*a*, 80*b* provide the ability to drive two emitter arrays (e.g., UV LED arrays) 12 such as, for example, included in two separate devices like an endoscope and a laparoscope with two independent signals, for example, having different parameters such as different, first and second pulse frequencies, different, first and second duty cycles, different, first and second pulse durations, or any combination thereof. Other parameters may be different in the two signals. Additionally, although two electrical outputs 80*a*, 80*b* are shown, the variable pulsed power supply may include more or less electrical outputs.

The pulsed power source 16 in the example shown in FIGS. 6D-6F further includes controls 81, 83, 85, respectively, to control or set the frequency or repetition rate (rep rate) of the pulses or groups of pulses, the duty cycle of the pulses or groups of pulses, and the dose duration or the cumulative time during which the UV-C light, for example, optical pulses, are applied or are above a threshold amount. In this example, the pulse power source 16 also includes a plurality of displays. For example, in FIGS. 6D and 6F, three displays 88*a*, 88*b*, 88*c*, such as LED or LCD displays, which may show the values of the different parameters selected, are shown. The displays 88*a*, 88*b*, 88*c* in this example show the frequency or repetition rate (rep rate) of the pulses or groups of pulses, the duty cycle of the pulses or groups of pulses, and the dose duration or the cumulative time during which the UV-C light, for example, optical pulses, are applied or are above a threshold amount. However, other parameters may be shown. In addition, although three displays are shown, more or less displays may be included in the pulsed power source 16. Other variations are possible.

The pulsed power driver 16 shown in FIGS. 6D-6F includes an on-off switch 92 on the front and a receptacle 94 for receiving AC electrical power on the back. Other configurations, however, are possible.

The pulsed power source 16 shown in FIGS. 6A-6C also include a display 88. This pulsed power source 16 is compact and may include a handle 90 for carrying although different implementation need not include a handle. On the back of the example pulsed power supply 16 in FIGS. 6A-6C is a power switch 92 and an AC electrical power input for receiving electrical power to power the pulse power source. In certain implementations, the pulsing frequency or repetition rate (rep rate) may be 47-63 Hz (e.g., 60 Hz), however, other pulse frequencies and frequency ranges are possible.

UV Transmissive Optics

In various designs, the transmissive optics (e.g., lenses) such as the collecting optics or collecting lens or lenses (e.g., collimating optics or collimating lens or lenses) 18 and/or the focusing optics or focusing lens or lenses 22 and/or the coupling optics or coupling lens or lenses 48 and/or the output optics or output lens or lenses 64 or any one or more of these or combination of these lenses or lens elements may comprise material transmissive to UV-C light such as the wavelengths recited herein. Such UV-C transmissive materials that may be employed for these lenses or optics are discussed below.

As discussed above, the one or more UVC LEDs 14 may emit light having a wavelength in the UVC wavelength range and in certain implementations herein emit light in the range of from 250 nm to 280 nm, 250 nm to 275 nm, 260 nm to 270 nm, for example, possibly having a peak wavelength in one or more of these range, e.g., possibly at 265 nm. Likewise, the lens(es) (e.g., collecting lens(es), collimating lens(es) 18, focusing lens(es) 22, coupling lens(es) 48, output lens(es) 64, or any combination of these, etc.) may comprise material optically transmissive to UVC light such as light in the wavelength range of UVC light emitted by the UVC emitters or LEDs. In some implementations, for example, the lens(es) comprise a fused silica lens or lenses comprising fused silica, which is transmissive to UVC light. In some implementations, for example, the lens(es) are optically transmissive (for example, at least 50%, 55%, 60%, 65%, 70%, 75%, 80%, 85%, 90%, 95%, 98%, 99%, 100%, transmissive or any range formed by any of these percentages) to light in the wavelength range of from 220 nm to 290 nm, 220 nm to 280 nm, 250 nm to 280 nm (e.g., 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, etc. or any range formed by any of these values), 250 nm to 275 nm, 260 nm to 275 nm, 260 nm to 270 nm, e.g., 265 nm, or any range formed by any of these values.

In certain implementations, the lens(es) (e.g., collecting lens(es), collimating lens(es) 18, focusing lens(es) 22, coupling lens(es) 48, output lens(es) 64, or any combination of these, etc.) are optically transmissive (for example, at least 50%, 55%, 60%, 65%, 70%, 75%, 80%, 85%, 90%, 95%, 98%, 99%, 100%, transmissive or any range formed by any of these percentages) to light in the wavelength range of from 200 nm to 290 nm, 200 nm to 280 nm, 200 nm to 250 nm (e.g., 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, etc.) or any range formed by any of these values such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or possible higher or lower wavelengths.

As discussed above, in some implementations, the lens (es) (e.g., collecting lens(es) 18, collimating lens(es), focusing lens(es) 22, coupling lens(es) 48, output lens(es) 64, or any combination of these, etc.) comprises fused silica. In various implementations, the lens(es) may comprise fused silica glass having a transmittance (e.g., internal transmittance or transmittance corrected to reduce or possibly eliminate the effects of scattering and of reflection from surfaces) of UVC light with 245-280 nm wavelength (e.g., 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm or any range formed by any of these values), of least 95% for a 10 mm thickness of the fused silica glass although in other implementations this transmittance is at least 50%, 55%, 60%, 65%, 70%, 75%, 80%, 85%, 90%, 94%, 96%, 98%, 99%, 99.9%, or 100% or any range formed by any of these values or possibly more or less. In various implementations, the OH (e.g., Hydroxyl) content is not larger than 5 ppm although in other implementations the OH content is not larger than 0 ppm, 0.01 ppm, 0.05 ppm, 0.5 ppm, 0.1 ppm, 1 ppm, 2 ppm, 3 ppm, 4 ppm, 6 ppm, 8 ppm, 10 ppm, 20 ppm, 30 ppm, 40 ppm, 50 ppm, 60 ppm, 70 ppm, 80 ppm, 90 ppm, 100 ppm, 125 ppm, 150 ppm, 200 ppm, 300 ppm, 400 ppm, or 500 ppm or any range formed by any of these values or possibly more or less. Additionally, in various implementations, a content of Li, Na, K, Mg, Ca and Cu each are smaller than 0.1 ppm although in some implementations the content of any one or more, possibly each, of Li, Na, K, Mg, Ca and Cu are not larger than or smaller than 0 ppm, 0.001 ppm, 0.005 ppm, 0.01 ppm, 0.05 ppm, 0.1 ppm, 0.2 ppm, 0.3 ppm, 0.4 ppm, 0.5 ppm, 0.6 ppm, 0.7 ppm, 0.8 ppm, 0.9 ppm, 1 ppm, 1.25 ppm, 1.50 ppm, 2.00 ppm, 3.00 ppm, 4.00 ppm, or 5.00 ppm or any range formed by any of these values or possibly more or less.

In some implementations, the glass has a viscosity coefficient at 1215° C. of at least $10^{11.5}$ Pas; and a Cu ion diffusion coefficient of not larger than $1\times10^{-10}$ $cm^2$/sec in a depth range of greater than 20 μm up to 100 μm, from the surface, when left to stand at 1050° C. in air for 24 hours. However, the glass need not be so limited as other implementations are possible.

In some case, the glass may be fabricated by crystobalitizing powdery silica raw material and then, fusing the crystobalitized silica material in a non-reducing atmosphere. However, the method of manufacture should not be so limited.

In some implementations, the fused silica glass may exhibit a high transmittance of ultraviolet, visible and infrared rays, may have high purity and heat resistance, and may exhibit a reduced diffusion rate of metal impurities or any combination of these traits.

Thermal dynamics (e.g., heating or thermal loads) of the UV-C projection unit or light source can be controlled (e.g., reduced) by passive and/or active heat dissipation. Examples of passive heat dissipation include heat sinks such as metal heat sinks and/or thermally conductive fins such as metal fins. For example, metal heat sinks having metal fins may be employed. Active heat dissipation may include, for example, fans or other configurations that provide air cooling.

Drive Signals and Outputs

Advantageously, this UV-C emitter array 12 augmented by optics to collect, collimate, and/or focus UV-C light emitted by the emitter array with or without the use of an optical fiber 30 to convey UV-C light can achieve the high fluence rate useful for fast cellular deactivation. Radiant exposure or radiant fluence of, for example, 100 mJ/$cm^2$ can be output at the distal end of the optical fiber and through the output lens and directed onto the target area. Such radiant exposure or radiant fluence should be sufficient to destroy cancer cells in 10-20 seconds, 20-30 seconds or 25-30 seconds (e.g. 29 seconds) or 30-40 seconds or 30-35 seconds (e.g., 32.5 seconds) or any range formed by any of these values or possibly more or less time. Radiant exposures or radiant fluences of 1 mJ/$cm^2$, 2 mJ/$cm^2$, 3 mJ/$cm^2$, 4 mJ/$cm^2$, 5 mJ/$cm^2$, 6 mJ/$cm^2$, 8 mJ/$cm^2$, 9 mJ/$cm^2$, 10 mJ/$cm^2$, 12 mJ/$cm^2$, 15 mJ/$cm^2$, 18 mJ/$cm^2$, 20 mJ/$cm^2$, 25 mJ/$cm^2$, 30 mJ/$cm^2$, 40 mJ/$cm^2$, 50 mJ/$cm^2$, 60 mJ/$cm^2$, 60 mJ/$cm^2$, 70 mJ/$cm^2$, 80 mJ/$cm^2$, 90 mJ/$cm^2$, 100 mJ/$cm^2$, 110 mJ/$cm^2$, 120 mJ/$cm^2$, 130 mJ/$cm^2$, 140 mJ/$cm^2$, 150 mJ/$cm^2$, 160 mJ/$cm^2$, 170 mJ/$cm^2$, 180 mJ/$cm^2$, 190 mJ/$cm^2$, 200 mJ/$cm^2$, 210 mJ/$cm^2$, 220 mJ/$cm^2$, 230 mJ/$cm^2$, 240 mJ/$cm^2$, 250 mJ/$cm^2$, or radiant exposures or radiant fluences in any range for by any of these values or possible larger or smaller may be output from the system 10, for example, through the output optics or lens 64 at the distal end of the optical fiber 30 and/or directed onto the target tissue 24.

Figure 7A:
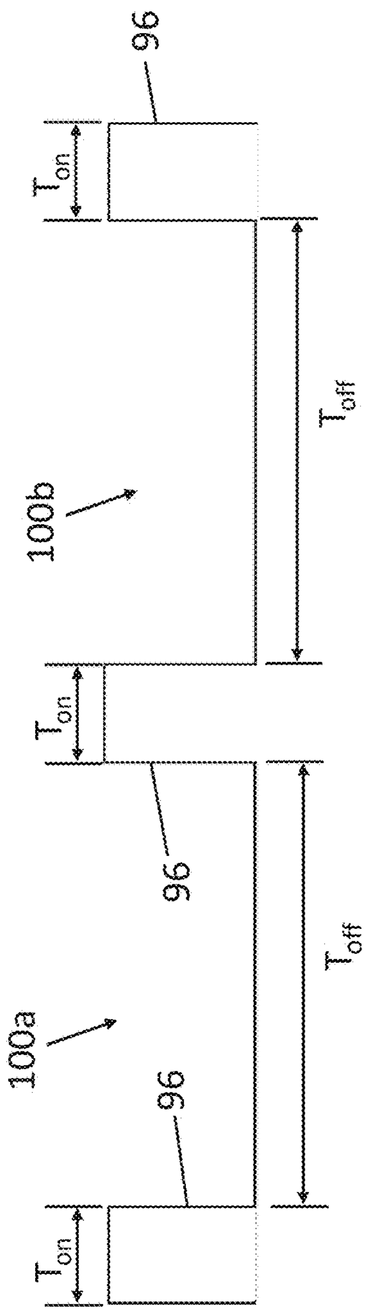
FIGS. 7A and 7B are plots of electrical signal versus time illustrating the electrical signal provided by the power supply (e.g., pulsed power source) to drive the UV-C light emitters (e.g., UV-C LEDs). The power supply can turn on and off the UV-C light applied for periods of time, $T_{on}$ and $T_{off}$, respectively. The duration, $T_{on}$ or $T_{high}$, over which the light is applied (or is above a threshold level) is twice as large in the example driving signal shown in FIG. 7B as the example driving signal shown in FIG. 7A. However, the duration over which the light is not applied (or is below a threshold level), as in $T_{off}$, is the same in both FIG. 7A and FIG. 7A. Thus, the exposure and total fluence is twice as much in the example shown in FIG. 7B as in 7A. These plots in FIGS. 7A and 7B also correspond to the intensity, radiant exposure, radiant fluence, and/or luminance of light output by the array of light emitters and/or that are directed at the target (e.g., cancer cells).
Figure 7B:
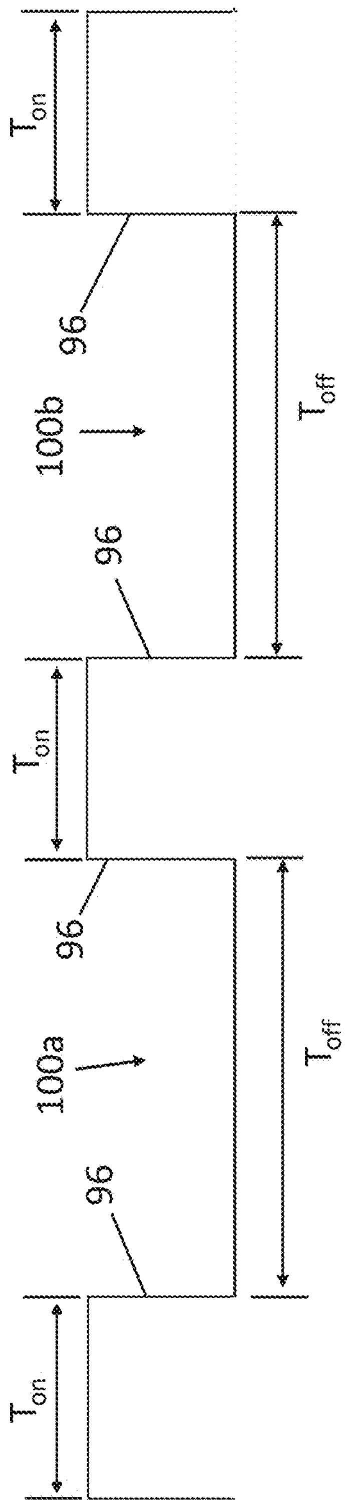

As discussed above, the period during which the UV-C light and/or UV-C pulses are produced by the UV-C emitter array (e.g. UV-C LED array) 12 and/or are coupled into the optical fiber 30 to exit at the distal end 70 thereof and/or directed onto the target area (e.g., cancerous tissue and/or cells) 24 may be controlled by the signal and/or power applied by the electronics 16 driving the UV-C emitter array and the plurality of UV-C emitters 14. FIGS. 7A and 7B illustrate two example electrical signals provided by the driver electronics (e.g., pulsed power source) 16 and applied to the UV-C emitters (e.g., UV-C LEDs) 14. As shown, during a period, $T_{on}$ (or $T_{high}$), a sufficiently high current and/or voltage is applied to the UV-C emitters 14 to cause the output of UV-C light to be above a threshold amount. The result is that during this period, $T_{on}$ (or $T_{high}$), UV-C light or UV-C light pulses 96 are output by the UV-C emitters 14, possibly coupled into the optical fiber 30, and delivered to the target 24, The radiant exposure or radiant fluence of this UV-C light may be sufficiently high to damage and/or destroy tissue or cells. These cells may be cancer cells. Non-cancerous cells may also be affected by exposure to this UV-C light. Accordingly, without subscribing to any particular scientific theory, the UV-C light or UV-C light pulses 96 may be shut off for a period of time, $T_{off}$ (or $T_{low}$), to allow the non-cancerous cells to recover. As discussed above, the driver electronics (e.g., the pulsed power source) 16 may be configured to control the duration, $T_{on}$ (or $T_{high}$), over which the UV-C light or UV-C pulses 96 are applied to the diseased tissue as well as the time period, $T_{off}$ (or $T_{low}$), during which the UV-C light or UV-C pulses are not applied to the target area, possibly to allow healthy cells to recover from the high intensity expose to the UV-C light. FIGS. 7A and 7B illustrate, for example, how the period of time, $T_{on}$ (or $T_{high}$), over which the UV-C pulses 96 are applied to the diseased tissue can be increased. The exposure of the diseased tissue to the UV-C light can thus be increased. In this particular example, the time period, $T_{off}$ (or $T_{low}$), during which the UV-C light or UV-C pulses 96 are not applied to the target area 24, does not change. However, in certain implementations, the driver electronics, e.g., the pulsed power source, 16 may be adjusted to alternatively or additionally change the time period, $T_{off}$ (or $T_{low}$), during which the UV-C light or UV-C pulses 96 are not applied to the target area 24. Thus, either or both $T_{on}$ (or $T_{high}$) and/or $T_{off}$ (or $T_{low}$) may be modified or adjusted. Likewise, either or both $T_{on}$ (or $T_{high}$) and/or $T_{off}$ (or $T_{low}$) need not be constant but may be varied, for example, during a single treatment session and/or from one treatment session to another.

(As discussed above, in some implementations, the pulses 96 need not be turned on or off but rather the brightness of the UV-C light pulses can be alternately increased above a non-zero threshold level to be therapeutically effective and reduced below the non-zero threshold amount. Thus, the periods, $T_{on}$ and $T_{off}$ may instead be replaced with the periods $T_{high}$ and $T_{low}$ where light pulses 96 of a high intensity are alternated with light pulses of a low lower intensity. Other possible programs are possible.)

As discussed above in connection with FIGS. 7A and 7B, the period during which the UV-C light is produced by the UV-C emitter array (e.g. UV-C LED array) 12 and/or are coupled into the optical fiber 30 to exit at the distal end 70 thereof and/or directed onto target area (e.g., cancerous tissue and/or cell) 24 may be controlled by the signal and/or power applied by the electronics 16 driving the UV-C emitter array and the plurality of UV-C emitters 14. In some implementations, a plurality of pulses 96 is output in a group 98. Groups 98*a*, 98*b*, 98*c* of such pulses 96 are shown in FIGS. 8A and 8B.

In particular, FIGS. 8A and 8B illustrate two example electrical signals provided by the driver electronics (e.g., pulsed power source) 16 and applied to the UV-C emitters (e.g., UV-C LEDs) 14. As shown, during a period, $T_{on}$ (or $T_{high}$), pulses of sufficiently high current and/or voltage are applied to the UV-C emitters 14 to output UV-C light, e.g., UV-C light pulses, above a threshold amount. The result is that during this period, $T_{on}$ (or $T_{high}$), groups 98*a*, 98*b*, 98*c* of UV-C light pulses 96 are output by the UV-C emitters 14, possibly coupled into the optical fiber 30, and delivered to the target 24. The radiant exposure or radiant fluence of this UV-C light may be sufficiently high to damage and/or destroy tissue or cells. These cells may be cancer cells. Non-cancerous cells may also be affected by exposure to this UV-C light. Accordingly, without subscribing to any particular scientific theory, the UV-C light pulses 96 may be shut off for a period of time, $T_{off}$ (or $T_{low}$), to allow the non-cancerous cells to recover. As discussed above, the electronics (e.g., the pulsed power source) 16 may be configured to control the duration, $T_{on}$ (or $T_{high}$), over which the UV-C pulses 96 are applied to the diseased tissue as well as the time period, $T_{off}$ (or $T_{low}$), during which the UV-C pulses are not applied to the target area, possibly to allow healthy cells to recover from the high intensity exposure to the UV-C light. FIGS. 8A and 8B illustrate, for example, how the period of time, $T_{on}$ (or $T_{high}$), over which the UV-C pulses 96 are applied to the diseased tissue can be increased. The exposure of the diseased tissue to the UV-C light can thus be increased. In this particular example, the time period, $T_{off}$ (or $T_{low}$), during which the UV-C pulses 96 are not applied to the target area 24, does not change. However, in some implementations, the electronics, e.g., the pulsed power source, 16 may be adjusted to alternatively or additionally change the time period, $T_{off}$ (or $T_{low}$), during which the UV-C pulses 96 are not applied to the target area 24. Thus, either or both $T_{on}$ (or $T_{high}$) and/or $T_{off}$ (or $T_{low}$) may be adjusted modified or adjusted. Likewise, either or both $T_{on}$ (or $T_{high}$) and/or $T_{off}$ (or $T_{low}$) need not be constant but may be varied, for example, during a single treatment session and/or from one treatment session to another.

(As discussed above, in some implementations, the pulses 96 need not be turned on or off but rather the brightness of the UV-C light pulses can be alternately increased above a non-zero threshold level to be therapeutically effective and reduced below the non-zero threshold amount or below another non-zero threshold amount. Thus, the periods, $T_{on}$ and $T_{off}$ may instead be replaced with periods $T_{high}$ and $T_{low}$ where groups of light pulses 96 of a high intensity are alternated with low intensity light such as groups of light pulses of a low lower intensity or constant low intensity light, etc. Other possible programs are possible.)

Different cell types may be tested with various wavelengths of UV-C and/or different pulsing periods (e.g., exposure times, repetition rates, etc.) to determine useful dosage responses. As referenced above, various designs of the UV-C light emission unit may comprise a power source such as the pulsed power source 16 that can regulate the desired application of pulses 96 of UV-C radiation at rates or periods (e.g. $T_{on}$ or $T_{high}$) or exposure times, for example, from 100 microseconds (10") up to 10 seconds (see, e.g., FIG. 4) or any range therebetween (e.g., any range formed by any of the values in the chart such as from 200 microseconds to 900 millisecond or from 200 milliseconds to 8 seconds). Other exposure times, periods or rates, larger or smaller, are also possible. Although Chart 1 in FIG. 9 references 265 nm, the wavelength is not so limited and the values in the chart may be applicable for other wavelengths of UV-C light.

In various designs that output light in a manner shown in FIG. 7A, 7B, 8A or 8B, the user or practitioner, e.g., a physician, surgeon, medical professional, etc., may control the duration during which the pulses or group of pulses are applied, for example, by pressing a button or using a switch, a pedal, or touchscreen, etc. Other types of controls may be used to control the duration during which the pulses or group of pulses are applied, including but not limited to keypads, voice recognition, etc.

For various implementations, the durations for applying UV-C light or pulses for treatment of tumor cells may be determined by the power output at the target 24 of the system 10 comprising the UVC light source 12. For breast cancer cells, for example, a total cumulative UVC energy per unit area of 100 mJ/cm$^2$ may cause cell death. If the energy output is 5 milliJoule (mJ) per cm$^2$ per 100 milliseconds (ms) time period (e.g., $T_{on}$ or $T_{high}$) then 20 applications (e.g., $T_{on}$ or $T_{high}$) may be used. This energy may possibly be pulsed with 100 ms pulses (e.g., with multiple periods, $T_{on}$ or $T_{high}$) with 900 ms gaps periods, or delays, $T_{off}$ or $T_{low}$ between the periods, $T_{on}$ or $T_{high}$, during which the UV-C light and/or pulses 96 are applied. For example, in FIGS. 7A, $T_{on}$ or $T_{high}$ may be equal to 100 ms while $T_{off}$ or $T_{low}$ is equal to 900 ms. These values are simply examples and the periods, $T_{on}$ or $T_{high}$ and/or $T_{off}$ or $T_{low}$, may vary. The period of time during which UV-C light is applied or applied above a threshold amount $T_{on}$ or $T_{high}$, may be different; the amplitude of the pulse may also be different. Similarly, the period of time during which UV-C light is not applied or is below a threshold amount, $T_{off}$ or $T_{low}$, may be different. Also, while FIGS. 7A-7B show electrical signals that may be output by the driver electronics (e.g., pulsed power source) 16 and/or delivered to the UV-C array (e.g., UV-C LED array) 12 and/or plurality of UVC emitters (e.g., UV-C LEDs) 14, these figures and plots also correspond to the UV-C light output of the system such as output from the optical fiber and, for example, the amount of light, e.g., radiant exposure, radiant fluence, luminance, etc., directed onto the target area 24, the waveforms of which are similar in shape. Such optical output may, for example, comprise a plurality of UV-C light pulses 96 having periods $T_{on}$ or $T_{high}$ and/or separations therebetween, $T_{off}$ or $T_{low}$. Such number of pulses provides for the exposure time during which the tissue is exposed to the UV-C light. This exposure time may, for example, range from at least 0.1 μs, 0.2 μs, 0.3 μs, 0.4 μs, 0.5 μs, 0.6 μs, 0.7 μs, 0.8 μs, 0.9 μs, 1 μs, 2 μs, 3 μs, 4 μs, 5 μs, 6 μs, 7 μs, 8 μs, 9 μs, 10 μs, 20 μs, 30 μs, 40 μs, 50 μs, 60 μs, 70 μs, 80 μs, 90 μs, 100 μs or 0.1 ms, 0.2 ms, 0.3 ms, 0.4 ms, 0.5 ms, 0.6 ms, 0.7 ms, 0.8 ms, 0.9 ms, 1 ms, 2 ms, 3 ms, 4 ms, 5 ms, 6 ms, 7 ms, 8 ms, 9 ms, 10 ms, 20 ms, 30 ms, 40 ms, 50 ms, 60 ms, 70 ms, 80 ms, 90 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s, 200 s, 300 s, 400 s, 500 s or times in any range between any of these values, such as from 0.2 ms to 900 ms or from 200 ms to a 1 s or from 1 s to 40 s or other times, larger or smaller.

Similarly, a total cumulative UVC energy per unit area of 100 mJ/cm$^2$ that may cause cell death may be achieved by groups 98 of pulses 96 such as shown in FIG. 8A, for example, if the energy per unit area output is 5 milliJoule (mJ) per cm$^2$ per 200 milliseconds (ms) time period (e.g., $T_{on}$ or $T_{high}$) for the group 98 of pulses 96 then 20 groups of pulses (e.g., $T_{on}$ or $T_{high}$) may be applied for example if the duty cycle is 50%. The time period for the group 98 of pulses 96 may be larger than for pulses such as shown in FIG. 7A to accommodate for the duty cycle of the pulses in the group of pulses such as shown in FIG. 8A. These values are simply examples and the periods, $T_{on}$ or $T_{high}$ and/or $T_{off}$ or $T_{low}$, may vary. The period of time during which UV-C light is applied or applied above a threshold amount $T_{on}$ or $T_{high}$, may be different; the amplitude of the pulse may also be different. Similarly, the period of time during which UV-C light is not applied or is below a threshold amount, $T_{off}$ or $T_{low}$, may be different. Also, while FIGS. 8A-8B show electrical signals that may be output by the driver electronics (e.g., pulse power source) 16 and/or delivered to the UV-C array (e.g., UV-C LED array) 12 and/or plurality of UVC emitters (e.g., UV-C LEDs) 14, these figures and plots also correspond to the UV-C light output of the system such as output from the optical fiber and, for example, the amount of light, e.g., radiant exposure, radiant fluence, luminance, etc., directed onto the target area 24, the waveforms of which are similar in shape. Such optical output may, for example, comprise a plurality of groups 98 of UV-C light pulses 96 having periods $T_{on}$ or $T_{high}$ and/or separations therebetween, $T_{off}$ or $T_{low}$. Such number of groups as well as the size or duration of the group of pulses together with the duty cycle provides for the exposure time during which the tissue is exposed to the UV-C light. This exposure time may, for example, range from at least μs 0.1 ms, 0.2 ms, 0.3 ms, 0.4 ms, 0.5 ms, 0.6 ms, 0.7 ms, 0.8 ms, 0.9 ms, 1 ms, 2 ms, 3 ms, 4 ms, 5 ms, 6 ms, 7 ms, 8 ms, 9 ms, 10 ms, 20 ms, 30 ms, 40 ms, 50 ms, 60 ms, 70 ms, 80 ms, 90 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s, 200 s, 300 s, 400 s, 500 s or times in any range between any of these values, such as from 0.2 ms to 900 ms or from 200 ms to a 1 s or from 1 s to 40 s or other times, larger or smaller.

The frequency and/or possibly the duty cycle of the pulses or groups of pulses may be varied. Example frequencies or repetition rates (rep rates) may include 5 Hz, 10 Hz, 20 Hz, 30 Hz, 40 Hz, 50 Hz, 60 Hz, 70 Hz, 80 Hz, 90 Hz, 100 Hz, 110 Hz, 120 Hz or frequencies/rep rates in any range formed by any of these values or possible larger and/or smaller. Similarly, the duty cycle may include 10%, 20%, 30%, 40%, 50%, 60%, 70%, 80%, 90% or duty cycles in any range formed by any of these values or possible larger and/or smaller.

In some implementations, the UV-C light may be applied for a duration of time ($T_{on}$ or $T_{high}$), for example, the emitters (e.g., LEDs) 14 may be turned on for a duration of time such as shown in FIG. 10. This duration may for example, be for example, 1 s, 2 s, 3 s, 4 s, 5 s, 6 s, 7 s, 8 s, 9 s, 10 s, 20 s, 30 s, 40 s, 50 s, 60 s, 70 s, 80 s, 90 s, 100 s, 200 s, 300 s, 400 s, 500 s or any range between any of these values or possibly for larger or smaller times. The light emitted during this period may be referred to as a pulse. Likewise, the current applied to the UV-C emitters (e.g., LEDs) 14 may be referred to as a pulse. This current and resultant UV-C light may also be referred to as DC because of the longer time span. The practitioner, e.g., a physician, surgeon, medical professional, etc., may apply the UV-C Slight by, for example, pressing a button or using a switch, a pedal, or touchscreen, etc., to control the duration. In the example shown in FIG. 10, the UV-C light is turned on for a period of time $T_{on}$ and then turned off as indicated by the references to $T_{off}$ surrounding the instance of $T_{on}$. As discussed above, in other cases, the UV-C light may be above a threshold when the button switch, pedal, or touchscreen etc. is activated and below the threshold or another threshold when the button, switch, a pedal, or touchscreen, etc. is set to another state (e.g., not pressed, pressed again). Other configurations are possible.

In various implementations described herein, the current applied to the UV-C emitters (e.g., LEDs) 14 may, for example, be 100 mA, 150 mA, 200 mA, 250 mA 300 mA, 350 mA, 400 mA, 450 mA, 500 mA, 550 mA, 600 mA, 650 mA, 700 mA, 750 mA, 800 mA or in any range formed by any of these values or possibly larger or smaller. Such currents may be output by the driver electronics (e.g., the pulsed power source) 16.

Empirical determination of the energetic light application time, $T_{on}$ and $T_{high}$, and the non-energetic gap time, e.g., $T_{off}$ and $T_{low}$, may be used to fine-tune the useful or optimal dose response curve where an increased or maximum yield of destroyed, disabled, dead, or non-viable tumor cells is achieved along with potentially a reduced or minimum number of non-tumor cell deaths or damage. The duration of these periods, $T_{on}$ or $T_{high}$ and/or $T_{off}$ or $T_{low}$, likely vary from cell type to cell type and also potentially depending on whether the cells are cancerous or non-cancerous.

In one example method for performing such measurements, a timer can measure the period (e.g., $T_{on}$ or $T_{high}$) during which the UV-C pulses 96 are applied. For example, a duration (e.g., $T_{on}$ or $T_{high}$) during which energetic pulses 96 are applied to injure, destroy, or disable cells or render cells non-viable may be 100 ms and a gap (e.g., $T_{off}$ or $T_{low}$) between consecutive applications of such energetic pulses may 900 ms. Other durations (e.g., $T_{on}$ or $T_{high}$) such as 200 ms and 500 ms blasts also with 900 ms gaps (e.g., $T_{off}$ or $T_{low}$) may be tested. The gap times may be beneficial for the survivability of the non-cancerous cells. Accordingly, the gap times (e.g., $T_{off}$ or $T_{low}$) may also be varied and tested to accommodate (e.g., increase) survivability of the non-cancerous cells possibly up to, for example, 2 seconds. Experimentation may allow useful, effective, beneficial and/or possibly optimal blasting, dosing, or application time (e.g., $T_{on}$ or $T_{high}$) and gaps times (e.g., $T_{off}$ or $T_{low}$), for example, with an objective of determining that the instrument 10 is capable of delivering a series of pulses or groups of pulses resulting in tumor cell death or non-viability and non-tumor cell viability. The above times, however, are examples, and should not be construed as limiting.

Accordingly, experimentation may be useful to determine an appropriate range of timings for different types of cells. Likewise, the duration (e.g., $T_{on}$ or $T_{high}$) during which energetic pulses 96 are applied to injure, destroy, or disable cells or render cells non-viable may include any of or any range formed by any of the values disclosed herein including those in the chart shown in FIG. 9 although the duration may possibly be larger or smaller. Similarly, the gap in time (e.g., $T_{off}$ or $T_{low}$) between consecutive applications of such energetic pulses or groups of pulses for injuring, destroying or disabling cells or rendering cells non-viable may include any of those disclosed herein including those in the chart shown in FIG. 9 or any range formed by any of those values although the duration may possibly be larger or smaller. Although the chart refers to 265 nm LED pulse rates, the chart is not limited to 265 nm and may apply to other UV-C wavelengths or wavelength ranges such as those set forth herein.

Cancer Treatments/Therapys

Methods for treating cancer by applying UV-C radiation are described herein. Such methods may be employed to potentially treat a wide variety of cancers including but not limited to brain tumors and brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, leukemia, liver cancer, liver metastases, lymphoma, melanoma, male breast cancer, oral cancer, ovarian cancer, pancreatic cancer, pancreatic cysts, pituitary gland tumors and adenomas, rectal cancer, salivary gland cancer, skin cancer, skull base tumors, soft tissue sarcoma, fibrosarcoma, choriocarcinoma, spine tumors and spinal cancer, squamous cell carcinoma, stomach (gastric) cancer, throat cancer, thryroid cancer, glioma, uterine cancer and uterine sarcoma. The systems, methods and devices described herein may be employed to potentially treat such cancers. Accordingly, the discussions above with regard to the various parameters, such as for example, wavelength (nm), exposure or dose or dosage (mJ/cm$^2$), exposure time(s), duration of pulses or groups of pulses and/or duration between pulses or groups of pulses, etc. apply to the methods of treatment such as the method of treatment of cancer such as described above as well as other cancers.

Various treatments such as for tumors or other cancerous tissues are in vivo. However, the systems, devices and methods described herein are not so limited. In some implementations, for example, the UV-C treatment is ex vivo or where a medium is removed from the patient's body and illuminated with UV-C light to destroy or disable cancer cells or render cancer cells non-viable. The medium can then be returned to the body of the patient. For example, to treat leukemia, blood or bone marrow may be removed from the body of the subject, patient, person or animal and exposed to UV-C light such from solid state UV-C emitters 14 (e.g., LEDs) as described herein. The blood or marrow may then be returned to the body. Other methods are possible. Accordingly, the discussions herein with regard to the various parameters, such as for example, wavelength (nm), exposure or dose or dosage (mJ/cm$^2$), exposure time(s), duration of pulses or groups of pulses and/or duration between pulses or groups of pulses, etc. apply to the ex vivo methods of treatment or methods where a medium is removed from the body and exposed to UV-C light such as the methods of treatment of cancer like leukemia as described herein.

More on Wavelengths

Accordingly, various implementations described herein comprise a UV-C projection unit comprising one or a plurality of pulsed light emitters such as light emitting diodes (LEDs), such as variable LEDs, emitting 265 nm wavelength light collimated into a single beam by UV-C LED projection optics. However, other variations are possible. The wavelength output by the UV-C projection unit or system, for example, may vary. 265 nm need not be the dominant nor central wavelength and in some cases might not be included. Other UV-C wavelengths are possible and may include wavelengths in the range of 250 nm to 280 nm or possibly 200 nm to 280 nm. Accordingly, the central wavelength of the UV-C light or of the UV light or of the light output by the system 10 or the optical fiber 30 or directed onto the target (e.g., cancerous tissue or cells) may be (or be at least or at most) 250 nm, 250.5 nm, 251 nm, 251.5 nm, 252 nm, 252.5 nm, 253 nm, 253.5 nm, 254 nm, 254.5 nm, 255 nm, 255.5 nm, 256 nm, 256.5 nm, 257 nm, 257.5 nm, 258 nm, 258.5 nm, 259 nm, 259.5 nm, 260 nm, 260.5 nm, 261 nm, 261.5 nm, 262 nm, 262.5 nm, 263 nm, 263.5 nm, 264 nm, 264.5 nm, 265 nm, 265.5 nm, 266 nm, 266.5 nm, 267 nm, 268.5 nm, 268 nm, 268.5 nm, 269 nm, 269.5 nm, 270 nm, 270.5 nm, 271 nm, 271.5 nm, 272 nm, 272.5 nm, 273 nm, 273.5 nm, 274 nm, 274.5 nm, 275 nm, 275.5 nm, 276 nm, 276.5 nm, 277 nm, 277.5 nm, 278 nm, 278.5 nm, 279 nm, 279.5 nm, 280 nm, or be in any range (e.g., from 260 nm to 270 nm or 255 nm to 275 nm) formed by any of these values. The bandwidth of the spectrum or central peak, for example, at Full Width Half Peak (FWHP) may be 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 110 nm, 120 nm, or any range formed by any of these values or possible larger or smaller.

In some designs, the central wavelength of the UV-C light or of the UV light or of the light output by the system 10 or the optical fiber 30 or directed onto the target 24 (e.g., cancerous tissue or cells) may be (or be at least or at most) 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, etc.) or any range formed by any of these values such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm or 200 nm to 280 nm, 200 nm to 290 nm or possible higher or lower wavelengths. The bandwidth of the spectrum or central peak, for example, at Full Width Half Peak (FWHP) may be 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 110 nm, 120 nm, 130 nm, 140 nm, 150 nm, 175 nm, 200 nm, or any range formed by any of these values or possible larger or smaller.

Endoscopes

As discussed above, in various implementations, the UV-C light may be provided to the cancerous tissue and/or cells using an endoscope. An example system 10 that includes an endoscope 102 is shown in FIG. 11. The endoscope 102 includes an optical fiber 30 such as described herein, e.g., comprising a fused silica core 58, to convey UV-C light from a UV-C light source 12 comprising, for example, one or a plurality of UV-C emitters 14 (e.g., UV-C array). As shown, the UV-C light source 12 may be located at the proximal end 106, 50 of the endoscope 102 and optical fiber 30. In this example, the UV-C light source 12 is shown housed together with drive electronics 16 for providing electrical power (e.g., current) to the UV-C emitters 14.

As discussed above, UV-C light from the UV-C light source 12 is output at the distal end 70 of the optical fiber 30 and the distal end 108 of the endoscope 102. In the example shown, the endoscope 102 includes an endoscope head or endpiece 110 at the distal end 108 of the endoscope. This endoscope head or endpiece 110 may include, for example, optics such as an output lens 64 for reducing the divergence of (e.g., collimating, focusing, etc.) UV-C light 68 emitted from the distal end of the optical fiber 30. The endoscope 102 may also include optics for imaging, for example, the inside of the body and thus may have one or more imaging lenses at the distal end 108 thereof. Similarly, the endoscope 102 may include one or more relay lenses or an optical fiber bundle to convey an image from the distal end 108 toward the proximal end 106 of the endoscope where a sensor array or optical detector array such as a CCD array or CMOS sensor array may be located to capture images of the inside of the body or an ocular permitting the user to view the image. In alternative designs, the camera may be at the distal end 108 of the endoscope 102. The camera, for example, may be on the head or tip or endpiece 110 of the endoscope 102. The camera may include, for example, an optical detector array or sensor array such as a CCD array or CMOS sensor array and imaging optics (e.g. one or more imaging lens) to form images of the body thereon. In some implementations, the endoscope 102 may be configured to provide illumination (e.g., visible light illumination such as white light illumination) to illuminate the tissue on the inside of the body and facilitate image formation thereof. The illumination may be provided by one or more light sources on the distal end 108 (e.g., endpiece 110) of the endoscope 102. The light, such as visible light, may be provided by, for example, one or more LEDs at the distal end 108 (e.g., endpiece 110) of the endoscope 102. The endoscope 102 may therefore include one or more electrical connections throughout the length of the endoscope 102, for example to send electrical power to the one or more light sources at the distal end 108 of the endoscope and/or to receive signals from a camera on the distal end of the endoscope. The endoscope 102 may further include an outer protective sheath that contains, for example, at least the optical fiber 30 therein and/or possibly other components such as one or more relay lenses or optical fiber bundles for conveying an image from the distal end 108 to the proximal end 106 of the endoscope and/or one or more electrically conducting lines, wires, cables, etc. A wide range of designs, design features and other variations are possible.

Advantageously, an endoscope 102 may have small profile so as to permit entry into orifices of the body as well as through small incisions or openings. Accordingly, an endoscope 102 may provide for minimally invasive procedures which may cause less damage to the body and likewise heal sooner. In various implementations, the endoscope 102 has (e.g., at the distal end 108 thereof) a cross-sectional width or diameter, for example, measured along the maximum lateral extent of the endoscope in the transverse direction orthogonal to the length (or longitudinal direction, e.g., z direction in FIG. 11) at the distal end of the endoscope of no more than 50 mm, 45 mm, 40 mm, 35 mm, 30 mm, 28 mm, 25 mm, 24 mm, 22 mm, 21 mm, 20 mm, 18 mm, 16 mm, 15 mm, 14 mm, 12 mm, 10 mm, 9 mm, 8 mm, 7 mm, 6 mm, 5 mm, 4.5 mm, 4 mm, 3.5 mm, 3 mm, 2.5 mm, 2 mm, 1.5 mm, 1 mm, 0.9 mm, 0.8 mm, 0.6 mm, 0.5 mm, 0.4 mm, 0.3 mm, 0.2 mm or in any range formed by any of these values such as from 1 to 10 mm, or 2 mm to 15 mm or 4 mm to 20 mm, or 5 mm to 30 mm, or possibly larger or smaller. Similarly, the head 110 of the endoscope 102 or the endpiece may, in various implementations, have (e.g., at the distal end 108 thereof) a cross-sectional width or diameter, for example, measured along the maximum lateral extent of the endpiece in the transverse direction orthogonal to the length (or longitudinal direction, e.g., z direction in FIG. 11) of the endpiece and/or the endoscope at that location of no more than 50 mm, 45 mm, 40 mm, 35 mm, 30 mm, 28 mm, 25 mm, 24 mm, 22 mm, 21 mm, 20 mm, 18 mm, 16 mm, 15 mm, 14 mm, 12 mm, 10 mm, 9 mm, 8 mm, 7 mm, 6 mm, 5 mm, 4.5 mm, 4 mm, 3.5 mm, 3 mm, 2.5 mm, 2 mm, 1.5 mm, 1 mm, 0.9 mm, 0.8 mm, 0.6 mm, 0.5 mm, 0.4 mm, 0.3 mm, 0.2 mm or in any range formed by any of these values such as from 1 to 10 mm, or from 2 mm to 15 mm or 4 mm to 20 mm, or 5 mm to 30 mm, or possibly larger or smaller.

Handheld Delivery Devices

Also, as described above, the system 10 such as shown in FIGS. 12A and 12B may be configured for the user (e.g., physician, surgeon, technician, etc.) to manually apply a beam of UV-C light 112 to the target tissue 24, which may, for example, be on the skin or may be exposed during open surgery or otherwise, for example, wherein tissue is readily accessible such as in the mouth, ear, nose or through one or more incision. The system 10 includes an optical fiber 30 such as described herein, e.g., comprising a fused silica core 58, to convey UV-C light from a UV-C light source 12 comprising, for example, one or a plurality of UV-C emitters 14 (e.g., UV-C array). As shown, the UV-C light source 12 may be located at the proximal end 106 of the optical fiber 30. In this example, the UV-C light source 12 is shown housed together with drive electronics 16 for providing electrical power (e.g., current) to the UV-C emitters 14.

As discussed above, UV-C light 112 from the UV-C light source 12 is output at the distal end 108 of the optical fiber 30. In the example shown, the system 10 includes a handheld output tool, delivery device, or handpiece 114 at the distal end 108 of the optical fiber 30. In various designs, a user such as a physician or surgeon may manipulate this handheld output tool, delivery device or handpiece to direct UV-C light 112 to the target, e.g., to the cancerous tissue or cells 24. In some implementations, this handheld output tool or handpiece 114 may have a body or portion thereof 116 that may be configured, for example, contoured to, e.g., ergonomically, to fit the user's hand and/or provide a grip for enhanced manual control. The handheld output tool, delivery device, or handpiece 114 may comprise, for example, a wand, head, or probe, in some cases.

Advantageously, in some implementations, the handheld output tool, delivery device, or handpiece 114 may have small profile. In various implementations, the handheld output tool, delivery device, or handpiece 114 may have a cross-sectional width or diameter, for example, measured along the maximum lateral extent of the handpiece in the transverse direction orthogonal to the length (or longitudinal direction, e.g., z direction in FIGS. 12A and 12B) of the handpiece and/or the endoscope at that location of no more than 150 mm, 120 mm, 110 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 24 mm, 22 mm, 21 mm, 20 mm, 18 mm, 16 mm, 15 mm, 14 mm, 12 mm, 10 mm, 9 mm, 8 mm, 7 mm, 6 mm, or in any range formed by any of these values such as from 10 mm to 30 mm or 15 mm to 40 mm, or 20 mm to 60 mm, or 20 mm to 80 mm, or possibly larger or smaller.

As discussed above, in some implementations, one or more output lenses 64 may be configured to reduce divergence of UV-C light 112 from the distal end 106, 70 of the optical fiber 30. Such output lens(es) 64 may be included in the handheld output tool, delivery device, or handpiece 114. In some implementations, the output lens(es) 64 is configured to focus or collimate or otherwise reduce the divergence of the light 112 and/or size of the beam directed, for example, onto the target (e.g., target tissue such as cancerous tissue or cells) 24.

In some implementations, the handheld output tool, delivery device, or handpiece 114 may include a button or switch 118 to activate the application of UV-C light 112. Activating the switch or switch 118, for example, may provide light to be output from the handheld output tool, delivery device, or handpiece 114. As discussed above, in some designs, the system 10 includes a pedal that is configured to be depressed to control illumination. In some implementations, when the button, switch 118 or pedal is depressed or switch is placed in one state, UV-C light 112 is output or pulses of UV-C light are output from the handheld output tool, delivery device, or handpiece 114. In some implementations, when the button, switch 118 or pedal is no longer depressed or pressed again or the switch is in another state, UV-C light 112 or pulses of UV-C light are no longer output from the handheld output tool, delivery device, or handpiece 114. In other designs, the button or switch or pedal may cause illumination to be provided for a set amount of time or set number of pulses. This amount of time or number of pulses may be varied with other controls such as a touchscreen, keypad, or other knobs, buttons, or switches or possibly via voice recognition (e.g., voice activated).

This button or switch 118 may, for example, be configured to be turned on using the thumb on the hand of the user that is holding the handheld output tool, delivery device, or handpiece 114. In some implementations, the handheld output tool, delivery device, or handpiece 114 is configured to provide an ergonomical fit for the thumb and/or other portions of the hand to the handpiece, for example, for the thumb to depress or switch (e.g., activate) the button or switch.

As described above, although the UV-C light may in some instances be applied to an external feature of the body, such as the skin. In other cases, such as open surgery, one or more surgical incisions are formed and the UV-C light 112 is applied to tissue within the body accessed through the surgical site formed by the one or more incisions. UV-C light 112 may also be applied to tissue via minimally invasive surgery. As such, a tube 120 such as a canula or catheter, which may be rigid or flexible, such as for a laparoscope may be included at the distal end of the handheld output tool, delivery device, or handpiece 114 such as shown in FIGS. 13A and 13B. Such a tube 120 may, for example, fit into a small incision formed in a patient, for example, in minimally invasive surgery. Such a tube 120 may be useful for entering an orifice of the body, e.g., mouth, nose, ears, etc.

Advantageously, the tube 120 may have a small profile so as to permit entry into orifices of the body as well as through small incisions or openings. Accordingly, a tube 120 may provide for minimally invasive procedures which may cause less damage to the body and likewise heal sooner. In various implementations, the tube 120 has (e.g., at the distal end thereof) a cross-sectional width or diameter, for example, measured along the maximum lateral extent of the tube in the transverse direction orthogonal to the length (or longitudinal direction, e.g., z direction in FIGS. 13A and 13B) of the tube of no more than 50 mm, 45 mm, 40 mm, 35 mm, 30 mm, 28 mm, 25 mm, 24 mm, 22 mm, 21 mm, 20 mm, 18 mm, 16 mm, 15 mm, 14 mm, 12 mm, 10 mm, 9 mm, 8 mm, 7 mm, 6 mm, 5 mm, 4.5 mm, 4 mm, 3.5 mm, 3 mm, 2.5 mm, 2 mm, 1.5 mm, 1 mm, 0.9 mm, 0.8 mm, 0.6 mm, 0.5 mm, 0.4 mm, 0.3 mm, 0.2 mm, 0.1 mm, 0.05 mm, 0.01 mm or in any range formed by any of these values such as from 1 to 10 mm, or 2 mm to 12 mm, or 3 mm to 15 mm, or 6 mm to 20 mm, or 10 to 30 mm, or possibly larger or smaller.

In various implementations although not all, the optical fiber 30 may extend through a portion or most of the length or the entire length of the tube 120 to bring UV-C light to the distal end of the tube. In various cases, however, output optics such as one or more output lenses 64 may be included, for example, at the distal end of the tube 120 to reduce divergence of (e.g., to collimate or focus) the UV-C light exiting the optical fiber 30. In some designs, the fiber may not extend within the tube but may nevertheless direct UV (e.g., UV-C) light therein. Optics, such as an one or more output lenses 64 may be included in the tube, canula, or catheter 120. In various implementations, this tube, canula, or catheter, 120 having a smaller lateral spatial extent (e.g., width, diameter, etc.) than other portions of the handheld output tool, delivery device, or handpiece 114 such as the grip 116, may at least provide a low profile extension that may offer increased visibility and maneuverability such that the UV-C light 112 may directed to the target 24 with increased ease and/or precision.

The handheld output tool, delivery device, or handpiece 114 may in some implementations such as shown in FIGS. 14A and 14B include a pistol grip 122. Such a pistol grip 122 may, for example, provide enhanced control in some cases. In such designs where the handheld output tool, delivery device, or handpiece 114 is provided with a pistol grip 122, the button or switch 118 may be a trigger type switch 123 that can be readily pulled by the index finger of the user's hand holding the pistol grip. A handheld output tool, delivery device or handpiece 114, with and without a rigid or flexible tube 120 (e.g., canular, catheter, etc.) at the distal end thereof, is shown in FIGS. 14B and 14A, respectively. Other designs, however, are possible.

Robotics

Systems 10 described herein may be implemented on robotic arms and/or in robotics such as robotic surgery systems. FIG. 15A, for example, illustrates an articulated arm or robotic arm 124 supporting an optical fiber 30 connected to one or more UV-C light emitters 14 such as a UV-C emitter array 12. In the example design shown, the articulated arm 124 comprises a plurality of segments 126 coupled together by pivoting joints 128 such that one segment can rotate with respect to another segment, thereby proving for movement of the position and/or orientation of an output head or endpiece 130 of the system 10. UV-C light 112 from the distal end 70 of the optical fiber 30 exits at the output head or endpiece 130 and can be directed to the subject (e.g., the patient) 132. The optical fiber 30 extends from the UV-C light emitters 14, e.g., the UV-C light LED array 12, across the plurality of segments 126, which support the optical fiber 30, to the head 130 of the articulated arm. In this example, the UV-C light 112 is shown directed to the head of the subject or patient 132, however, other portions of the body may be exposed to, e.g., treated by, the UV-C light. Additionally, while the patient 132 is shown supine on an operating table 134 in this example, the patient may be seated or otherwise situated or oriented.

The articulated arm 124 is shown supported on a column 136 with base 138, however, other configurations, including, for example, ceiling mounted may be employed. The articulated arm 124 may include motors or actuators to cause the arm to move such that the distal end thereof and, in particular, the head or endpiece 130 may be positioned and/or oriented to provide UV-C light 112 to the target, e.g., cancerous tissue or cells 24. The articulated arm 124 may in some designs be controlled by a physician (e.g., surgeon) or other medical profession, for example, using a joystick, mouse, one or more pedals or other input and/or may be pre-programmed such as in robotic assisted surgery or be automatic or autonomous or partially automatic or partially autonomous, FIG. 15B shows a similar design as that depicted in FIG. 15A, implemented on a robotic arm 124 and/or in robotics such as robotic surgery systems. The articulated arm or robotic arm 124 supports an optical fiber 30 connected to one or more UV-C light emitters 14 such as a UV-C emitter array 12. The system 10 shown in FIG. 15B further comprises a tube 120, such as a canula or catheter, at the distal end of the output head or endpiece 130. Such a tube 120 may, for example, fit into a small incision formed in a patient, for example, in minimally invasive surgery, such as laparoscopy. UV-C light 112 may thereby be applied to tissue via minimally invasive surgery. Such a tube 120 may also be useful for entering an orifice of the body, e.g., mouth, nose, ears, etc. In various implementations, the tube 120 has (e.g., at the distal end thereof) a cross-sectional width or diameter, for example, measured along the maximum lateral extent of the tube in the transverse direction orthogonal to the length (or longitudinal direction) of the tube of no more than 50 mm, 45 mm, 40 mm, 35 mm, 30 mm, 28 mm, 25 mm, 24 mm, 22 mm, 21 mm, 20 mm, 18 mm, 16 mm, 15 mm, 14 mm, 12 mm, 10 mm, 9 mm, 8 mm, 7 mm, 6 mm, 5 mm, 4.5 mm, 4 mm, 3.5 mm, 3 mm, 2.5 mm, 2 mm, 1.5 mm, 1 mm, 0.9 mm, 0.8 mm, 0.6 mm, 0.5 mm, 0.4 mm, 0.3 mm, 0.2 mm, 0.1 mm, 0.05 mm, 0.01 mm or in any range formed by any of these values such as from 1 to 8 mm, or 2 mm to 10 mm, or 5 mm to 20 mm, or 8 mm to 30 mm, or possibly larger or smaller. In various implementations, the optical fiber 30 may extend through the tube 120 to bring UV-C light to the distal end of the tube or at least partially through the tube. Output optics such as one or more output lenses 64 may be included, for example, in the tube 120, e.g., at the distal end of the tube 120, to reduce divergence of (e.g., to collimate or focus) the UV-C light exiting the optical fiber 30. In some implementations, the optical fiber 30 does not extend into the tube 120. The tube 120, however, may include output optics such as one or more output lenses 64 to reduce divergence of (e.g., to collimate or focus) the UV-C light exiting the optical fiber 30.

As discussed above, a longer optical fiber 30 may enable the UV-C light emitters 14 to be a distance from the patient and user or operator (e.g., physician, surgeon, technician) and others (e.g., nurses, technicians, etc.) thereby potentially reducing exposure to stray UV-C light from the light emitters. In various implementations, for example, the UV-C light emitters 14 may be in a separate room than the patient and/or user thereby reducing exposure to stray UV-C light. In some implementations, shielding may be employed to block stray UV-C light from the light emitters 14. Such shielding may be opaque and/or have reduced transmission for UV-C light. Such shielding may comprise metal or plastic such as for example Plexiglass or polymethyl methacrylate (PMMA) or acrylic. The shielding may, for example, comprise material that is ¼ inch thick or ⅜ inch thick or ½ inch thick. The thickness may for example be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 20 mm, 22 mm, 25 mm, 30 mm, or any range formed by any of these values such as from 2 mm to 16 mm or from 4 mm to 14 mm or possibly larger or smaller. The shielding may, for example, be located on two, three, four, five, or six or more sides of the UV light source 12 and/or UV light emitters 14. The shielding may, for example, be included on the front and sides of the UV light source 12 and/or UV light emitters 14 and/or on the front, sides, and top of the UV light source 12 and/or UV light emitters 14 in various designs. In some implementations the UV-C light source 12 may be encased in a housing comprising material that reduces transmission of stray UV-C light. In some designs, the UV-C light emitters 14 and/or power supply 16 are in a housing on wheels that can be moved to different locations. The optical fiber 30 can extend therefrom and can extend to a location where the patient will be treated. Accordingly, in some cases, the distal end of the optical fiber 30, e.g., the head or endpiece 110 of the endoscope 102 (see, e.g., FIG. 11) and/or the handheld output tool, delivery device or handpiece 114 (see, e.g., FIGS. 12A-14B) and/or the end 130 of the articulated or robotic arm 124 (see, e.g., FIGS. 15A-15B), is located in an operating room or treatment room while the UV-C light emitters 14 are in an another (e.g., adjacent) room or closet. In some implementations a ring or tubular shield may be provided between the one or more UV-C light emitter 14 and the optics, e.g., collecting lens 18, possibly between the baseplate 34/heatsink 38 and the tube 40, to block stray light. This ring may, for example, comprise an elastic material such as rubber or neoprene or may comprise plastic or metal or other materials that have reduced transmission of UV-C light. Other configurations or arrangements are possible.

Endoscope Designs

As discussed above, in various implementations UV-C light from the UV-C light source 12 is output at the distal end 70 of the optical fiber 30 and the distal end 108 of the endoscope 102. FIG. 16A depicts an example distal end 108 of an endoscope 102 including the endoscope head or endpiece 110. FIG. 16A also shows part of a flexible insertion tube 160 of the endoscope 102, which houses the optical fiber 30 configured to transmit UV, e.g., UV-C, light to the distal end 108 of the endoscope 102. This endoscope head or endpiece 110 includes an output for UV (UV-C) light to be directed to target tissue such as a cancerous tissue or one or more tumors 24. This endoscope head or endpiece 110 may include, for example, optics such as an output lens 64 for reducing the divergence of (e.g., collimating, focusing, etc.) UV-C light 68 emitted from the distal end 108 of the optical fiber 30 that is to be directed onto the target 24.

The endoscope 102 may also include optics for imaging, for example, the inside of the body and thus may have one or more imaging lenses 162 at the distal end 108 of the endoscope. Similarly, the endoscope 102 may include one or more relay lenses or an optical fiber bundle to convey an image from the distal end 108 toward the proximal end 106 of the endoscope where a sensor array or 2D optical detector array such as a CCD array or CMOS sensor array may be located to capture images of the inside of the body or an ocular is located permitting the user to view the image. In alternative designs, the camera may be at the distal end 108 of the endoscope 102. The camera, for example, may be on the head or tip or endpiece 110 of the endoscope 102. The camera may include, for example, a 2D optical detector array or sensor array such as a CCD array or CMOS sensor array and imaging optics (e.g. one or more imaging lens) 162 to form images of the body on the 2D optical sensor array.

In some implementations, the endoscope 102 may be configured to provide illumination (e.g., visible light illumination such as white light illumination) to illuminate the tissue on the inside of the body and facilitate image formation thereof. The illumination may be provided by one or more light sources 164 at the distal end 108 (e.g., on the endpiece 110) of the endoscope 102. The light, such as visible light, may be provided by, for example, one or more LEDs at the distal end 108 (e.g., on the endpiece 110) of the endoscope 102. Although one light source 164 at one location at the distal end 108 of the endoscope 102 (e.g., on the endpiece 110) is shown, in other designs, more than one light source at more than one location may be included on the endpiece.

To provide electrical connection to the light source 164 and/or camera at the distal end 108 of the endoscope 102 (e.g., in the endpiece 110), the endoscope 102 may include one or more electrical or conductive pathways (e.g., electrical or conductive lines, wires, cable, etc.) along the length of the endoscope 102 (e.g., within the flexible insertion tube 160). Such electrical or conductive pathways, e.g., electrical or conductive lines, wires, cable, etc., may, for example, send electrical power to the one or more light sources 164 at the distal end 108 of the endoscope 102 and/or receive signals from a camera located in the endpiece 110 at the distal end of the endoscope. The endoscope 102 may further include an outer protective sheath, which may form at least part of the flexible insertion tube 160 that contains, for example, at least the UV transmissive optical fiber 30 therein and/or possibly other components such as one or more relay lenses or optical fiber bundles for conveying an image from the distal end 108 to the proximal end 106 of the endoscope 102 and/or one or more electrically conducting lines, wires, cables, etc., to transport power to and/or signals from the camera at the distal end 108 of the endoscope and/or power to one or more light sources (e.g., LED) 164 at the distal end.

In various designs, the endoscope 102 may provide one or more irrigation channels 166 having an output at the distal end 108 of the endoscope, for example, in the endpiece or endoscope head 110 as shown in FIG. 16A. The irrigation channel 166 may convey fluid such as water (e.g., saline water) to the area where UV light is to be provided (e.g., the tumor or cancerous tissue and/or surrounding area). This fluid (e.g., liquid) output from the irrigation channel 166 may be used to wash away blood or other fluids or matter and/or clean debris from the target tissue and potentially surrounding area. In various designs, at least part of the irrigation channel 166 may therefore be within and extend along the flexible insertion tube 160 to provide fluid from the proximal end 106 to the distal end 108 of the endoscope 102. Part of the irrigation channel 166 may, for example, comprise an irrigation line within the flexible insertion tube 160. The irrigation channel 166 may be in fluid connection with a supply of fluid and may be a supply of fluid at a pressure such that fluid ejected from the output of the channel within the endpiece 110 of the endoscope 102 is of sufficiently high pressure to clear or remove fluid, particles, debris, etc., from the target tissue and potentially surrounding area. The endoscope 102 may thus have a connector at the proximal end 106 thereof configured to connect with a source of fluid such as a source of high pressure fluid such as a hospital fluid line (e.g., a pipe, tube or conduit in the operating or treatment room via a suitable connector). The endoscope 102 may include other features such as a suction line to remove fluid and/or matter from the body at the location of the target tissue 24 and/or area nearby. A wide range of designs, design features and other variations are possible.

Output Protectors/Covers

In some implementations, for example, a cover 168 may be included in front of the UV output. For example, a cover 168 may be included in front of the UV transmissive fiber and/or in front of output optics (e.g., output lens 64). Such a cover 168 may provide protection and/or reduce obstructions from being deposited or formed on or adhered to the output optics 64 or UV transmissive fiber 30 or window in front thereof (see, e.g., FIG. 16B). This cover 168 may be movable or switchable such that in a first state the cover is configured to provide protection for the optics (e.g., output lens 64) and/or UV (e.g., UV-C) transmissive optical fiber 30 and/or window and in a second state the cover is at least partially if not mostly or completely removed from protecting the output optics and/or optical fiber or window. As such obstructions that would otherwise block the UV light output, for example, the optics 64 and/or fiber 30 and/or UV transmissive window, may be removed to allow the UV light to pass through the optical output of the endpiece 110 of the endoscope 102. The cover 168 may be configured to be moved between these first and second states without removing the cover (or, e.g., the endoscope 102 or distal end thereof) from the body of the patient. A control (electrical, mechanical, hydraulic, etc.) that is located outside the body may be used to move the cover 168 when the distal end 108 of the UV-C light projection unit 10 is in the body.

In some implementations, the cover 168 comprises one or more, for example, 2, 3, 4, etc., segments, sections or portions that in a first state can be moved into place in front of the optics (e.g., output lens 64) and/or fiber 30 and/or UV transmissive window and can be moved, in a second state, to another position where the segment(s) or section(s) or portion(s) provide less coverage in front of the optics and/or fiber and/or window. In some implementations, the cover 168 may comprise, for example, an iris. Motors or other actuators, such a hydraulically driven actuators, may be employed to move the cover 168 or segments/sections/portions thereof into place in front of the optics (e.g., output lens 64) and/or fiber 30 and/or window and to another position that provides less coverage in front of the optics and/or fiber and/or UV transmissive window. Such motors or actuators may, for example, be electrical, mechanical or hydraulic. In some implementations, the cover 168 or portion or portions thereof (e.g., a segment of the cover) may be biased in one position or another, for example, using a spring or other flexible but resilient material. Also, although the cover 168 has been described as providing protection to the optics (e.g., output lens 64) and/or fiber 30, as discussed above, a UV (e.g., UV-C) transmissive window may also be included in front of such optics and/or UV transmissive fiber and the cover may provide protection for said window.

Extensions

In the example design shown in FIG. 16A, the endpiece 110 includes a portion 170 (which may be referred to herein as an extension) that extends more distal that includes the UV (e.g., UV-C) output. This UV or UV-C output may include, for example, the output lens 64 and/or distal end 108 of the UV transmissive optical fiber 30 and/or a window such as a UV (e.g., UV-C) transmissive window. This extension 170 brings the output of the UV light closer to the target area 24 than, for example, the location of the camera or imaging optics 162, which may have a different working distance than the output optics 64. Similarly, this extension 170 may allow the output of UV (e.g., UV-C) light to be closer to the target 24 while the irrigation channel 166 and/or illumination source 164 can be more distant from the target tissue so as to provide irrigation and/or illumination to a wider area than the target and/or the beam of UV light. In other designs, however, this extension may be longer or shorter or may not be included. Accordingly, in some designs, the output of the UV light (e.g., output lens 64) is at the same longitudinal distance from the target tissue as the camera or imaging optics 162, the illumination source 164, or the irrigation channel 166 or any combination thereof.

While such features as those shown in FIGS. 16A and 16B may be described in connection with the endoscope 102 and the distal end 108 thereof, such features are applicable to designs that include a tube 120, for example, on a handheld output tool, delivery device or handpiece 114 such as shown in FIGS. 13A and 13B, 14A and 14B as well as 15B, which may comprise, for example, a canula or catheter, which may be rigid or flexible. Accordingly, such tubes 120 and/or the end thereof may include visualization systems (e.g., cameras and/or imaging optics 162), illumination (LEDs) sources 164, irrigation channels 166, a UV (e.g., UV-C) output such as output optics 64, a UV transmissive fiber 30, and/or window, or any combination thereof. Similarly, the UV (e.g., UV-C) transmissive optical fiber 30, electrically conductive lines for signal and/or power, irrigation lines or channels 166, relay lenses and/or optical fiber bundles, or any combination thereof may be included in the tube 120.

Medical Procedures

FIGS. 17A-17F schematically illustrate examples of the endoscope 102 being inserted into the human body in different scenarios to treat different ailments such as different forms of cancer. FIG. 17A, for example, schematically illustrates an endoscope 102 within the stomach 172 to treat cancerous tissue 175 (e.g., one or more tumors) therein. As shown, the endoscope 102 can access the stomach 172 through the esophagus. An enlarged view 174 of the UV (UV-C) light directed onto the cancer 175 is also shown. FIG. 17B is another schematic illustration of the use of an endoscope 102 configured to deliver UV (e.g., UV-C) light to cancerous tissue 175 within the stomach 172 (which is enlarged in this illustration for purposes of clarity and ease of viewing). FIG. 17B shows the endoscope 102, which includes the UV transmissive optical fiber 30, having a sufficiently long length optically connected to the UV light emitters 12. The pulse driver, e.g., variable pulse driver 16 is also shown together with other electronics 177. The other electronics 177 may include, for example, power supplies, camera electronics for receiving image data from the endoscope camera and for driving a display 176 (also shown) or other electronics.

FIG. 17C shows the endoscope 102, which includes the UV (e.g., UV-C) transmissive optical fiber 30, inside a colon 178 to, for example, direct UV (e.g., UV-C) light onto cancerous tissue 175 such as one or more cancer tumors. FIG. 17D shows the endoscope 102 treating breast cancer. In this example, the endoscope 102 with the UV (e.g., UV-C) transmissive optical fiber 30 is inserted through an incision proximal to or in the breast tissue 180 to provide access of the distal end 108 of the endoscope 102 to the tumor(s) 175. In this procedure, UV, e.g., UV-C, light is output from the distal end 108 of the endoscope 102 and directed onto the tumor(s) 175. FIG. 17E illustrates an endoscope 102 treating prostrate cancer. FIG. 17E shows the distal end 108 of the endoscope 102 proximal one or more tumor 175 in the prostrate 182. UV, e.g., UV-C light, is output by the distal end 108 of the endoscope 102 and directed onto the cancerous tissue 175.

As discussed above, in various circumstances, UV or UV-C light is delivered to the cancerous tissue 175 using a handheld output tool, delivery device or handpiece 114. FIG. 17F, for example, illustrates a handheld output tool, delivery device or handpiece 114 inserted through an incision to administer UV or UV-C light within the body, e.g., to cancer on a breast.

Safety

The system 10 has very high intensity UV-C light output and a very high intensity LED light source 12. Consequently, operators and bystanders without Personal Protective Equipment (PPE) may have symptoms of UV (e.g., UV-C) exposure in only a few minutes. With full UV resistant PPE, symptoms including tingling on the skin (erythema), and irritation to the eyes (photophobia and photokeratitis) may occur in 10 minutes. Longer exposure may result in nausea, occurring to some operators and bystanders within 20 minutes of system operation. Threshold limit values for UV radiation were also measured and in some cases overexposure to UV-C radiation may be possible if not properly address.

Long Fibers

As discussed above, to address such concerns, an optical fiber 30 transmissive to UV (e.g., UV-C) light having increased length may be employed such that the patient, operator, surgeon(s), other physician(s), nurse(s), technician (s), other medical practitioner(s) or any combination thereof are a distance from the UV (e.g., UV-C) light source 12. This optical fiber 30 may for example, be at least 2 feet, 2.5 feet, 3 feet, 3.5 feet, 4 feet, 4.5 feet, 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, 60 feet, 70 feet, 75 feet, 80 feet, 90 feet, 100 feet, 110 feet, 120 feet, or any range formed by any of these values or possibly larger or smaller. Longer optical fiber may enable the light emitters 14 be to a distance from the patient and user (e.g., physician, surgeon, technician, etc.,) and others (e.g., nurses, technicians, etc.) thereby potentially reducing exposure to stray UV-C light from the UV light emitters 14. Thus, in various implementations, the optical fiber 30 is at least 3 feet, 3.5 feet, 4 feet, 4.5 feet or at least 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, 60 feet, 70 feet, 75 feet, 80 feet, 90 feet, 100 feet, 110 feet, 120 feet, or any range formed by any of these values or possibly larger or smaller.

FIG. 18, for example, schematically illustrates a system 10 that includes an optical fiber 30 having an increased length such as a length of 25 feet. The light source 12 can thus be positioned a distance from the patient, surgeon(s), physician(s), nurse(s), technician(s) or any one or more of these such that exposure to UV (e.g., UV-C) radiation is reduced and safe. Although, in this and other examples, the UV (e.g., UV-C) transmissive optical fiber is 25 feet, the optical fiber may have other lengths such as, for example, at least 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, 60 feet, 70 feet, 75 feet, 80 feet, 90 feet, 100 feet, 110 feet, 120 feet, or any range formed by any of these values or possibly larger or smaller. Having an optical fiber 30 with a long length permits the location of the light source 12 to be remote from the delivery of the UV light to the patient. Accordingly, the UV (e.g., UV-C) light source 12 may be remote from the operating table, surgical and/or exam lights, display 176 such as camera display (e.g., display configured to display images obtained by endoscope camera or camera on handheld output tool, delivery device or handpiece 114), anesthesia machine, EKG and/or ECG machines, and/or other surgical equipment or other equipment for use in connection with the treatment. The system 10 may thus, in some implementations, include one or more remote controls 181 to allow the system and/or components thereof, e.g., the variable pulse source, emitters, etc., to be controlled remotely, a distance from the remote control and thus the operator (e.g., surgeon, physician, nurse, technician, medical professional, etc.). Such a remote control may, for example, permit adjustment of one or more parameters of the UV light delivered such as the frequency or repetition rate of the pulses or groups of pulses, duration of the pulses or groups of pulses, duty cycle of the pulses or groups of pulses, separation between pulses or groups of pulses, output level (e.g., power, strength, intensity level, radiance, radiant flux, fluence, exitance, luminance) or any one or more of these.

Having a long optical fiber 30 may also facilitate the placement of the light source 12 in a separate room 183 such as schematically illustrated in FIG. 19A. The light source 12 can thus be positioned in different room 183 than (and thus a distance from) the distal end 108 of the optical fiber 30, the patient, physician(s), nurse(s), technician(s) or any one or more of these such that exposure of persons to UV (e.g., UV-C) radiation is reduced and the procedure in likewise more safe. Accordingly, the UV (e.g., UV-C) light source 12 may be remote from the operating table, surgical and/or exam lights, display 176 such as camera display (e.g., display configured to display images obtained by endoscope camera or camera on handheld output tool, delivery device or handpiece 114), anesthesia machine, EKG and/or ECG machines, and/or other surgical equipment. In some implementations, the room where the UV light is delivered to the patient and the room 183 where the light source 12 are located are separated by a wall 184 that provides shielding. In some cases, this wall 184 may be reinforced with shielding material. Locating the light source 12 and possible the proximal end 106 of the optical fiber 30 in a separate, possibly enclosed, room 183 can dramatically reduce the risk of operator exposure to harmful UV radiation. Exposure of the patient and/or bystanders in the operating or treatment room such as nurses, technicians, and other medical professionals, to stray UV light may also be reduced. In some implementations, the room 183 may be smaller than the operating, treatment room, or room where the procedure takes place and may for example be a closet or the size of a closet. As shown in FIG. 19A, in various implementations an opening or hole 185 in the wall 184 permits passage of the optical fiber 30.

Although, in this and other examples, the UV (e.g., UV-C) transmissive optical fiber 30 is 25 feet, the optical fiber may have other lengths such as, for example, at least 5 feet, 5.5 feet, 6 feet, 6.5 feet, 7 feet, 7.5 feet, 8 feet, 8.5 feet, 9 feet, 9.5 feet, 10 feet, 10.5 feet, 11 feet, 12 feet, 14 feet, 15 feet, 16 feet, 18 feet, 20 feet, 21 feet, 22 feet, 24 feet, 25 feet, 26 feet, 27 feet, 28 feet, 30 feet, 35 feet, 40 feet, 50 feet, 60 feet, 70 feet, 75 feet, 80 feet, 90 feet, 100 feet, 110 feet, 120 feet, or any range formed by any of these values or possibly larger or smaller. Having an optical fiber 30 with a long length permits the location of the light source 12 to be remote from the delivery of the UV light to the patient, for example, in another room than the operating room or room where the treatment or procedure takes place. Accordingly, the UV (e.g., UV-C) light source 12 may be remote from the distal end 108 of the optical fiber 30, operating table, surgical and/or exam lights, display 176 such as camera display (e.g., display configured to display images obtained by endoscope camera or camera on handheld output tool, delivery device or handpiece 114), anesthesia machine, EKG and/or ECG machines, and/or other surgical equipment. As discussed above, the system 10 may thus include one or more remote controls 181 to allow the system 10 and/or components thereof, e.g., the variable pulse source, emitters, etc., to be controlled remotely, a distance from the remote control and thus the operator (e.g., physician, nurse, technician, medical professional, etc.). Such a remote control 181 may, for example, permit adjustment of one or more parameters of the UV light delivered such as the frequency or rate of the pulses or groups of pulses, duration of the pulses or groups of pulses, duty cycle of the pulses or groups of pulses, separation between the pulses or groups of pulses, output level (e.g., power, radiant flux, strength, intensity level, radiance, fluence, exitance, luminance) or any one or more of these.

The optical fiber may form part of the endoscope. A portion of the optical fiber may form part of the endoscope while a portion of the optical fiber may be outside the endoscope and/or connected thereto. In some cases, most of the optical fiber is not within the endoscope but extends from the light source to the endoscope.

In some implementations, a portion of the optical fiber is coupled to the endoscope via an optical connector and may be butt coupled. Thus, the portions of the optical fiber may be separate and/or separable. As discussed above, the optical fiber need not be a single strand of optical fiber and may be comprised of separate parts (e.g., separate strands), for example, strung, optically coupled, optically connected or concatenated together. The separate strands of optical fiber may be optically coupled or optically connected together, e.g., via optical connectors and may be butt coupled in some cases. In some implementations, optics may be used to optically couple the strands or portions of optical fiber together. In some implementations, however, the optical fiber comprises a single fiber strand as opposed to discrete or separate parts coupled, e.g., butt coupled together or otherwise optically coupled together. As discussed above, the optical fiber may be referred to as an optical fiber line or optical fiber cable (or fiber optic cable). The terms fiber, optical fiber, optical fiber line, optical fiber cable, fiber optic, fiber optic line, fiber optic cable, etc. are used interchangeably herein.

Shielding

As discussed above, in some implementations, the system 10 may include shielding to reduce the amount of stray UV (e.g., UV-C) light emitted from the light source 12 into ambient. FIG. 19B, for example, schematically illustrates shielding 186 disposed about the light source 12 comprising the UV emitter(s) 14 as well as the proximal end 106 of the optical fiber 30. In this specific example, the shielding 186 also covers other components such as the variable pulse source 16 and other electronics 177. In this example, components including the light source 12 comprising one or more UV (e.g., UV-C) emitters 14 as well as the pulse power source 16 and electronics 177 are on a mobile assembly with wheels or casters such that the equipment may be readily moved, for example, from one room to another or to different locations within a room. The shielding 186, however, blocks stray light emitted by the light source 12 and/or from the coupling between the one or more UV light emitter(s) 14 and the proximal end 106 of the optical fiber 30, and/or other potential sources of leakage of UV light. Assembling the components, for example, light source 12, optical fiber 30, optics such as lenses and mounts for supporting and/or aligning such optical components and/or including such components in a housing may not sufficiently limit stray UV light and consequent exposure of individuals near to the light source 12 and/or proximal end 105 of the optical fiber 30. The shielding 186, to be effective at reducing leakage may, for example, be sealed in a manner to limit the number and/or size of openings through which UV light leaks or passes. In some cases, for example, the opening 185 in the shielding 186 through which the optical fiber 30 passes is sealed in a manner to block stray UV light from the light source 12 and the coupling of the light source to the proximal end 106 of the optical fiber.

In various implementations, the shielding 186 is suitably located, comprises suitable material, is sufficiently thick and/or is sufficiently complete (e.g., with reduced number or without sources of leakages such as openings) to reduce UV emissions from the system (other than the light emitted through the core at the distal 108 of the optical fiber 30) to less than less than 200 mW/cm$^2$, less than 100 mW/cm$^2$, less than 50 mW/cm$^2$, less than 20 mW/cm$^2$, less than 10 mW/cm$^2$, less than 5 mW/cm$^2$, less than 2 mW/cm$^2$, 1 mW/cm$^2$ or less, less than 1 mW/cm$^2$, less than 0.5 mW/cm$^2$, less than 0.1 mW/cm$^2$, less than 0.05 mW/cm$^2$, less than 0.01 mW/cm$^2$, less than 0.005 mW/cm$^2$, less than 0.004 mW/cm$^2$, less than 0.003 mW/cm$^2$, less than 0.002 mW/cm$^2$, less than 0.001 mW/cm$^2$, less than 0.0005 mW/cm$^2$, less than 0.0004 mW/cm$^2$, less than 0.0003 mW/cm$^2$, less than 0.0002 mW/cm$^2$, less than 0.0001 mW/cm$^2$, less than 0.00005 mW/cm$^2$, less than 0.00001 mW/cm$^2$, 0.000005 mW/cm$^2$, 0.000001 mW/cm$^2$, or 0 J/m$^2$ or any range between or formed by any of these values (e.g., from 0.5 mW/cm$^2$ to 0 mW/cm$^2$, 0.0001 mW/cm$^2$ to 0 mW/cm$^2$,) although possible larger or smaller when the light source 12 and one or more light emitters 14 are producing sufficient light such that 0.01 mW/cm$^2$, 0.02 mW/cm$^2$, 0.03 mW/cm$^2$, 0.04 mW/cm$^2$, 0.05 mW/cm$^2$, 0.06 mW/cm$^2$, 0.08 mW/cm$^2$, 0.1 mW/cm$^2$, 0.2 mW/cm$^2$, 0.3 mW/cm$^2$, 0.4 mW/cm$^2$, 0.5 mW/cm$^2$, 0.6 mW/cm$^2$, 0.8 mW/cm$^2$, 1 mW/cm$^2$, 2 mW/cm$^2$, 3 mW/cm$^2$, 4 mW/cm$^2$, 5 mW/cm$^2$, 6 mW/cm$^2$, 8 mW/cm$^2$, 10 mW/cm$^2$, 12 mW/cm$^2$, 15 mW/cm$^2$, 20 mW/cm$^2$, 25 mW/cm$^2$, 30 mW/cm$^2$, 40 mW/cm$^2$, 50 mW/cm$^2$, 60 mW/cm$^2$, 70 mW/cm$^2$, 75 mW/cm$^2$, 80 mW/cm$^2$, 90 mW/cm$^2$, 100 mW/cm$^2$, 120 mW/cm$^2$, 125 mW/cm$^2$, 130 mW/cm$^2$, 140 mW/cm$^2$, 150 mW/cm$^2$, 160 mW/cm$^2$, 180 mW/cm$^2$, 200 mW/cm$^2$, 225 mW/cm$^2$, 250 mW/cm$^2$, 275 mW/cm$^2$, 300 mW/cm$^2$, 350 mW/cm$^2$, 400 mW/cm$^2$, 450 mW/cm$^2$, 500 mW/cm$^2$, 600 mW/cm$^2$, 800 mW/cm$^2$, 1000 mW/cm$^2$, 1200 mW/cm$^2$, 1500 mW/cm$^2$, 2000 mW/cm$^2$, 3000 mW/cm$^2$, 4000 mW/cm$^2$, 5000 mW/cm$^2$, or any range formed by any of these values, is output from the distal end of the optical fiber. These values and ranges (e.g., of leakage or system emissions excluding light output the distal end of the optical fiber 30, such as stray emission,) may pertain to or be for measurements performed a distance from the shielding 186, or from the emitters, and/or from the proximal end 106 or the distal end 108 of the UV transmissive optical fiber 30 of 50 centimeters (cm), 200 cm, 180 cm, 150 cm, 120 cm, 110 cm, 100 cm, 90 cm, 80 cm, 70 cm, 60 cm, 50 cm, 40 cm, 30 cm, 25 cm, 20 cm, 18 cm, 16 cm, 15 cm, 14 cm, 12 cm, 10 cm, 9 cm, 8 cm, 6 cm, 5 cm, 4 cm, 3 cm, 2 cm, 1 cm, 0.5 cm, 0.1 cm, 0 cm, or 96 inches, 84 inches, 78 inches, 72 inches, 66 inches, 60 inches, 54 inches, 48 inches, 42 inches, 36 inches, 30 inches, 24 inches, 18 inches, 12 inches, 6 inches, 2 inches, 1 inch, 0.5 inch, or in any range formed between any of these values or possible farther or closer (e.g., where an operator, patient, or bystander such as physician, nurse, technician, or other health care provider may be situated). The measurement wavelength may be in the UV, e.g., UV-C range, such as at any of the wavelengths recited herein including, for example, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm or any range formed by any of these values or possible larger or smaller wavelengths. The shielding 186 may be configured to limit exposure to a person (e.g., operator, patient, physician, nurse, technician, medical professional, within a distance of 10 feet, 9 feet, 8 feet, 6 feet, 5 feet, 4 feet, 3 feet, 2 feet, 1 foot, 0.5 feet, 0.1 foot, of the UV-C light emitters or of the proximal end 106 or distal end 108 of the optical fiber/optical fiber line/fiber optic cable 30 or any range formed by any of these values, to 60 J/m$^2$ (6 mJ/cm$^2$) or less, 50 J/m$^2$ (5 mJ/cm$^2$) or less or 40 J/m$^2$ (4 mJ/cm$^2$) or less or 35 J/m$^2$ (3.5 mJ/cm$^2$) or 30 J/m$^2$ (3.0 mJ/cm$^2$) or less, or 25 J/m$^2$ (2.5 mJ/cm$^2$) or less or 20 J/m$^2$ (2.0 mJ/cm$^2$) or 15 J/m$^2$ (1.5 mJ/cm$^2$) or less or 10 J/m$^2$ (0.10 mJ/cm$^2$) or less, or 5 J/m$^2$ (0.5 mJ/cm$^2$) or less, or 1 J/m$^2$ (0.1 mJ/cm$^2$) or 0.5 J/m$^2$ (0.05 mJ/cm$^2$) or less, or 0.1 J/m$^2$ (0.01 mJ/cm$^2$) or less, or 0.05 J/m$^2$ (0.005 mJ/cm$^2$) or less, or 0.01 J/m$^2$ (0.001 mJ/cm$^2$) or less, or 0.005 J/m$^2$ (0.0005 mJ/cm$^2$) or less, or 0.001 J/m$^2$ (0.0001 mJ/cm$^2$) or less, or 0.0005 J/m$^2$ (0.00005 mJ/cm$^2$) or less, or 0.0001 J/m$^2$ (0.00001 mJ/cm$^2$) or less, or 0 J/m$^2$ or any range formed by any of these values or possibly more or less, for example, when said light emission in said UV wavelength range from the (e.g., distal end of) the optical fiber is 1 mJ/cm$^2$, 2 mJ/cm$^2$, 3 mJ/cm$^2$, 4 mJ/cm$^2$, 5 mJ/cm$^2$, 6 mJ/cm$^2$, 8 mJ/cm$^2$, 9 mJ/cm$^2$, 10 mJ/cm$^2$, 12 mJ/cm$^2$, 15 mJ/cm$^2$, 16 mJ/cm$^2$, 20 mJ/cm$^2$, 25 mJ/cm$^2$, 30 mJ/cm$^2$, 40 mJ/cm$^2$, 50 mJ/cm$^2$, 60 mJ/cm$^2$, 70 mJ/cm$^2$, 80 mJ/cm$^2$, 90 mJ/cm$^2$, 100 mJ/cm$^2$, 120 mJ/cm$^2$, 150 mJ/cm$^2$, 180 mJ/cm$^2$, 200 mJ/cm$^2$, 300 mJ/cm$^2$, 400 mJ/cm$^2$, 500 mJ/cm$^2$, 800 mJ/cm$^2$, 1000 mJ/cm$^2$ or any range formed by any of these values or possibly larger or smaller. The period of such emissions may be over a period of 12 hours, 10 hours, 8 hours, 6 hours, 4 hours, or 2 hours, 1 hour, 0.5 hour, 20 minutes, 15 minutes, 10 minutes, 5 minutes, 3 minutes, 2 minutes, 1 minute, 50 seconds, 40 seconds, 30 seconds, 20 seconds, 10 second, 5 seconds, 4 seconds, 3 seconds, 2 second, 1 seconds, 0.5 seconds, 0.1 seconds, or any range formed by any of these values or possible larger or smaller. The wavelength may be in the UV, e.g., UV-C range, such as at any of the wavelengths recited herein including, for example, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm or any range formed by any of these values or possible larger or smaller wavelengths. Accordingly, such emissions may be a wavelength range formed by any of the wavelengths above or wavelengths or wavelength ranges listed or included elsewhere herein such as at 262 nm, 265 nm, or 270 nm or in a range from 260 nm to 270 nm, or 260 to 280 nm, or 250 to 280 nm, or 250 to 290 nm, or 250 to 300 nm, or 255 to 315 nm, 280 to 290 nm, or 290 nm to 300 nm, or 250 to 300 nm, or 207 to 315 nm or 280 to 320 or 200 to 320 nm or any range formed by any of these values. These emissions may be for an region or area of 0.1 $ft^2$, 0.5 $ft^2$, 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, 12 $ft^2$, 16 $ft^2$, 20 $ft^2$, 25 $ft^2$, 28 $ft^2$, 36 $ft^2$, 40 $ft^2$, 49 $ft^2$, 55 $ft^2$, 64 $ft^2$, 81 $ft^2$, 100 $ft^2$, 121 $ft^2$, 144 $ft^2$, 200 $ft^2$, 400 $ft^2$, 500 $ft^2$, 800 $ft^2$, 900 $ft^2$, 1000 $ft^2$, or any range formed by any of these values or possibly larger or smaller. The emissions may be for a solid angle of 0.1 steradian, 0.2 steradian, 0.3 steradian, 0.4 steradian, 0.5 steradian, 0.6 steradian, 0.7 steradian, 0.8 steradian, 0.9 steradian, 1 steradian, 0.1π steradian, 0.2π steradian, 0.3π steradian, 0.4π steradian, 0.5π steradian, 0.6π steradian, 0.7π steradian, 0.8π steradian, 0.9π steradian, 1π steradian, 1.1π steradian, 1.2π steradian, 1.3π steradian, 1.4π steradian, 1.5π steradian, 1.6π steradian, 1.7π steradian, 1.8π steradian, 1.9π steradian, 2π steradian, 2.1π steradian, 2.2π steradian, 2.3π steradian, 2.4 steradian, 2.5π steradian, 2.6π steradian, 2.7π steradian, 2.8π steradian, 2.9π steradian, 3π steradian, 3.1π steradian, 3.2π steradian, 3.3π steradian, 3.4π steradian, 3.5π steradian, 3.6π steradian, 3.7π steradian, 3.8π steradian, 3.9π steradian, 4π steradian, or any range formed by any of these values or possibly larger or smaller. These emissions may be for an angular extent in one direction of 25°, 35°, 45°, 60°, 75°, 90°, 120°, 150°, 180°, 210°, 240°, 270, 300°, 330°, 360°, or any range formed by any of these values or possibly larger or smaller and/or for an angular extent in another (e.g., orthogonal) direction of 25°, 35°, 45°, 60°, 75°, 90°, 120°, 150°, 180°. For example, these emissions may be measured over an area, solid angle or angular range or ranges, between the UV light source 12 (e.g., UV emitters 14) and the patient and/or operator (and/or other bystanders such as doctors, nurse, technicians, medical professionals or healthcare provider). UV light emission from the UV light source 12, e.g., the UV light emitters 14, may be blocked, attenuated, absorbed, reflected, or any combination thereof by the shielding such that UV emission or light in the wavelength region output by the UV light source (e.g., UV emitters) excluding light emitted from the distal end of the optical fiber, for example, UV light leakage from the system, is reduced and may be negligible to reduce health risks to the patient and/or operator (and/or bystanders). Accordingly, the light levels may be measured and cited herein at a particular distance from, e.g., the light emitters 14, the distal end 70, 106 of the optical fiber 30, the proximal end 50, 108 of the optical fiber 30 and/or over an angular region or angular extent in one and/or two directions, over a solid angle or over an area or any combination thereof in various cases.

Thus, excluding output from a distal end 70, 108 of said optical fiber 30, light emission from the system 10 with the shielding 186 in place in said UV wavelength ranges discussed above and elsewhere herein may be 60 $J/m^2$ (6 $mJ/cm^2$) or less, 50 $J/m^2$ (5 $mJ/cm^2$) or less or 40 $J/m^2$ (4 $mJ/cm^2$) or less or 35 $J/m^2$ (3.5 $mJ/cm^2$) or 30 $J/m^2$ (3.0 $mJ/cm^2$) or less, or 25 $J/m^2$ (2.5 $mJ/cm^2$) or less or 20 $J/m^2$ (2.0 $mJ/cm^2$) or 15 $J/m^2$ (1.5 $mJ/cm^2$) or less or 10 $J/m^2$ (0.10 $mJ/cm^2$) or less, or 5 $J/m^2$ (0.5 $mJ/cm^2$) or less, or 1 $J/m^2$ (0.1 $mJ/cm^2$) or 0.5 $J/m^2$ (0.05 $mJ/cm^2$) or less, or 0.1 $J/m^2$ (0.01 $mJ/cm^2$) or less, or 0.05 $J/m^2$ (0.005 $mJ/cm^2$) or less, or 0.01 $J/m^2$ (0.001 $mJ/cm^2$) or less, or 0.005 $J/m^2$ (0.0005 $mJ/cm^2$) or less, or 0.001 $J/m^2$ (0.0001 $mJ/cm^2$) or less, or 0.0005 $J/m^2$ (0.00005 $mJ/cm^2$) or less, or 0.0001 $J/m^2$ (0.00001 $mJ/cm^2$) or less, or 0 $J/m^2$ or any range formed by any of these values or possibly more or less over a solid angle, for example, of 0.1 steradian, 0.2 steradian, 0.3 steradian, 0.4 steradian, 0.5 steradian, 0.6 steradian, 0.7 steradian, 0.8 steradian, 0.9 steradian, 1 steradian, 0.1π steradian, 0.2π steradian, 0.3π steradian, 0.4π steradian, 0.5π steradian, 0.6π steradian, 0.7π steradian, 0.8π steradian, 0.9π steradian, 1π steradian, 1.1π steradian, 1.2π steradian, 1.3π steradian, 1.4π steradian, 1.5π steradian, 1.6 steradian, 1.7π steradian, 1.8π steradian, 1.9π steradian, 2π steradian, 2.1π steradian, 2.2π steradian, 2.3π steradian, 2.4π steradian, 2.5π steradian, 2.6π steradian, 2.7π steradian, 2.8π steradian, 2.9π steradian, 3π steradian, 3.1π steradian, 3.2π steradian, 3.3π steradian, 3.4π steradian, 3.5π steradian, 3.6π steradian, 3.7π steradian, 3.8π steradian, 3.9 steradian, 4π steradian, or any range formed by any of these values or possibly larger or smaller at a distance from the shielding 186, or from the emitters 14, and/or from the proximal end 106 or the distal end 108 of the UV transmissive optical fiber 30 of, for example, 250 centimeters (cm), of 200 cm, 180 cm, 150 cm, 120 cm, 110 cm, 100 cm, 90 cm, 80 cm, 70 cm, 60 cm, 50 cm, 40 cm, 30 cm, 25 cm, 20 cm, 18 cm, 16 cm, 15 cm, 14 cm, 12 cm, 10 cm, 9 cm, 8 cm, 6 cm, 5 cm, 4 cm, 3 cm, 2 cm, 1 cm, 0.5 cm, 0.1 cm, 0 cm, or 96 inches, 84 inches, 78 inches, 72 inches, 66 inches, 60 inches, 54 inches, 48 inches, 42 inches, 36 inches, 30 inches, 24 inches, 18 inches, 12 inches, 6 inches, 2 inches, 1 inch, 0.5 inch, or in any range formed between any of these values or possible farther or closer when said light emission in said UV wavelength range from the optical fiber (e.g., the distal end of the optical fiber/optical fiber line/fiber optic cable) is, for example, 1 $mJ/cm^2$, 2 $mJ/cm^2$, 3 $mJ/cm^2$, 4 $mJ/cm^2$, 5 $mJ/cm^2$, 6 $mJ/cm^2$, 8 $mJ/cm^2$, 9 $mJ/cm^2$, 10 $mJ/cm^2$, 12 $mJ/cm^2$, 15 $mJ/cm^2$, 16 $mJ/cm^2$, 20 $mJ/cm^2$, 25 $mJ/cm^2$, 30 $mJ/cm^2$, 40 $mJ/cm^2$, 50 $mJ/cm^2$, 60 $mJ/cm^2$, 70 $mJ/cm^2$, 80 $mJ/cm^2$, 90 $mJ/cm^2$, 100 $mJ/cm^2$, 120 $mJ/cm^2$, 150 $mJ/cm^2$, 180 $mJ/cm^2$, 200 $mJ/cm^2$, 300 $mJ/cm^2$, 400 $mJ/cm^2$, 500 $mJ/cm^2$, 800 $mJ/cm^2$, 1000 $mJ/cm^2$ or any range formed by any of these values or possible larger or smaller.

The shielding 186 may reduce the UV light at any of the wavelengths or wavelength ranges described above by at least 75% 80%, 90%, 92%, 94%, 95%, 96%, 97%, 98%, 99%, 99.5%, 99.6%, 99.7%, 99.8%, 99.9%, 99.95%, 99.99%, 99.992%, 99.995%, 99.999%, 99.9995%, 99.9997%, 99.9998%, 99.9999%, 99.99999%, 100% or any range formed by any of these values. The shielding 186 may reduce UV light at any of the wavelengths or wavelength ranges described above to less than 25%, 20%, 15%, 10%, 5%, 4%, 3%, 2%, 1%, 0.5%, 0.1%, 0.05%, 0.01%, 0.005%, 0.001%, 0.0005%, 0.0001%, 0, of the amount output by the any one or more of the light source 12, the light emitters 14, the distal end of the optical fiber 30, etc., or any range formed by any of these values.

Accordingly, in some implementations, shielding 186 may be employed to block stray UV-C light from the UV-C light emitters 14. Such shielding 186 may be opaque and/or have reduced transmission for UV-C light. Such shielding 186 may comprise metal or plastic such as, for example, acrylic, plexiglass or polymethyl methacrylate (PMMA). The shielding may, for example, comprise material that is at least ⅛ in thick, ¼ inch thick or ⅜ inch thick or ½ inch thick. The thickness may for example be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 20 mm, 22 mm, 25 mm, 30 mm, or any range formed by any of these values such as from 2 mm to 16 mm or from 4 mm to 14 mm or possibly larger or smaller. For example, the shielding 186 may have a minimum thickness 5 mm in some implementations or designs.

The UV-C light source 12 (e.g., the UV-C light emitters 14) may therefore comprise or be encased in a housing comprising material that reduces transmission of stray UV-C light. In some designs, the UV-C light emitters 14 and/or power supply are in a housing on wheels that can be moved easily to different locations. The shielding 186 may surround the UV-C light source 12, e.g., the UV-C light emitters 14. The shielding 186 may, for example, be in front, behind, above, on opposite lateral sides of the UV-C light source 12, e.g., the UV-C light emitters 14, or any combinations of these such the in front of, behind, above, and on opposite lateral sides of the UV-C light source 12, e.g., the UV-C light emitters 14. In some designs, the shielding 186 may be below the behind, above, on opposite lateral sides of the UV-C light source 12, e.g., the UV-C light emitters 14. Similarly, the shielding 186 may, for example, be in front, behind, above, on opposite lateral sides of the interface between the UV-C light source 12, e.g., the UV-C light emitters 14, and the proximal end 106 of the UV transmissive optical fiber 30 or any combinations of these such the in front of, behind, above, and on opposite lateral sides of the interface between the UV-C light source 12, e.g., the UV-C light emitters 14 and the proximal end of the optical fiber. In some designs, the shielding 186 may be below the UV-C light source 12, e.g., the UV-C light emitters 14 and/or the interface between the UV-C light source 12, e.g., the UV-C light emitters 14 and the proximal end of the UV (e.g., UV-C) transmissive optical fiber 30. In some implementations, a wall 184 separating the room where the light source 12 is located and where the patient is to be treated (e.g., operating or procedure room) is reinforced or includes such shielding as described above. Accordingly, the shielding may be on 1 side, 2 sides, 3 sides, 4 sides, 5 sides, 6 sides, of the light source 12, the one or more emitters 14, the proximal end 50, 106 of the optical fiber 30, the distal end 70, 108 of the optical fiber 30, the coupling between the light source and/or emitters and the proximal end of the optical fiber or any combination of these. Separate shielding such as first and second shielding, such as a shielding for the UV light source 12, UV emitters 14 and/or proximal end 50, 106 of the optical fiber 30 and additional shielding for the distal end 70, 108 of the optical fiber may be included in the system. Alternatively, the same shielding may be used for both UV light source 12/UV emitters 14, the proximal end 50, 106 of the optical fiber 30 as well as the distal end 70, 108 of the optical fiber.

In some implementation, the shielding 186 comprises polycarbonate, which may comprise a polyester in which dihydric (or polyhydric) phenols are joined through carbonate linkages. Ultraviolet light may be strongly absorbed by this specific UV resistant polycarbonate. Testing has resulted in UV-C shielding reducing up to 99.995% of the 265 nm radiance. A 3 second exposure of UV-C leakage that measured 79.55 mJ/cm$^2$ at array 12 of UVC emitters 14 was reduced to 0.0041 mJ/cm$^2$ at a distance of 10 mm from a 3.2 mm transparent shield. In another case, 0.0 mJ/cm$^2$ was measured over a period of 3 seconds 10 mm from the shield as compared to 8.13 mJ/cm$^2$ for a 3 second exposure at the coupling between the UV light source 12 and the proximal end 50 of the optical fiber 30 (e.g., at the fiber optic collimating port). In another case, 0.0 mJ/cm$^2$ was measured over a period of 30 seconds 2 inches (e.g., 50 mm) from the shield as compared to 171.5569 mJ/cm$^2$ for a 30 second exposure at the coupling between the UV light source 12 and the proximal end 50 of the optical fiber 30 (e.g., at the fiber optic collimating port).

By contrast, without subscribing to any scientific theory, according to literature, the standard for occupational exposure to ultraviolet radiation is based on the Threshold Limit Values (TLV) published by the American Conference of Governmental Industrial Hygienists. Such TLV are relative to a monochromatic source of radiation at 270 nm. Th exposure at this wavelength in 8 hours is 30 J/m$^2$ (3 mJ/cm$^2$) and the effective irradiance which will produce this exposure in 1 milliwatt/m$^2$. At a wavelength of 260 nm, the TLV may be 46 J/m$^2$ (4.6 mJ/cm$^2$).

To make plastic or polymer shielding material (e.g., polycarbonate) UV stable, UV stabilizers and/or light absorbers may be incorporated therein that protect the material from degradation caused by ultraviolet (UV) radiation. Some commonly used chemicals include UV absorbers (UVA), and Hindered Amine Light Stabilizers (HALS). The UV Absorbers (UVA) may absorb UV radiation and dissipate the UV radiation as heat, reducing the occurrence of and/or preventing the UV radiation from breaking down the polymer structure. Examples UV Absorbers (UVA) include Benzotriazoles (e.g., Tinuvin 329, Tinuvin 234), Benzophenones (e.g., BP-12, BP-6), and Triazines (e.g., Cyasorb UV-1164, Tinuvin 1577). Without subscribing to any particular scientific theory, hindered amine light stabilizers (HALS) may work by scavenging free radicals generated by UV exposure, thus reducing the incidence of and/or preventing degradation. Some HALS for polycarbonate include, Tinuvin 622, Chimassorb 944, Hostavin N30. By combining UV absorbers with HALS, the lifespan of shielding 186 such as plastic or polymer shielding (e.g., polycarbonate shielding) can be extended.

Coatings and surface treatments may also be provided. For additional protection, for example, UV-resistant coatings (e.g., acrylic or silicone hard coats with UV blockers) and/or co-extruded layers of UV-stabilized polymer or plastic such as polycarbonate (PC) may be used (e.g., used as shielding 186 and/or applied to the shielding).

Accordingly, various design described provide the system 10 with shielding 186, which may mitigate long-term UV exposure risks, including DNA damage, skin cancer risks, and ocular harm. OSHA, FDA, and medical safety regulations impose stringent requirements on UV-based medical devices to provide for operator and patient safety. The system's built-in shielding 186 can assist in compliance with such regulations and enhance exposure safety and risk mitigation.

Remote Operation

As discussed above, the optical fiber 30 can extend from the UV light source 12 and can extend to a location where the patient will be treated a safe distance away from the light source 12 and the coupling between the light source and the proximal end 106 of the optical fiber. This distance may be, for example, at least 2 or 3 feet, possible 4 or 5 feet or more, such as 8 or 10 or 15 or 20 or 25 or more feet from the light source 12 and/or the coupling between the light source and the proximal end of the optical fiber 30. This distance in combination with the shielding 186, such as shown in FIG. 19B, may provide increase protection. FIG. 19B, for example, shows a medical practitioner such as the operator a distance from the light source 12 to reduce exposure to stray UV light from the light source and the coupling between the light source and the proximal end 106 of the optical fiber 30 or other components in the system. Also, as discussed above, the system 10 shown in FIG. 19B includes shielding 186 to reduce escape of stray light from the system 10 and harmful exposure of the operator or user such as a medical practitioner (e.g., physician) or other medical professionals (other doctors, nurses, technicians, etc.) and/or the patient and/or bystanders.

As discussed above and shown in FIG. 19A, in various implementations, the UV-C light emitters 14 and/or proximal end of the optical fiber 30 and/or the coupling therebetween may be in a separate room 183 than the patient/or user and/or others thereby reducing exposure to stray UV-C light. In some cases, for example, the distal end 108 of the optical fiber 30, e.g., the head 110 of the endoscope 102 and/or the handheld output tool, delivery device or handpiece 114, is in an operating room or treatment room while the UV-C light emitters 14 are in an adjacent room or closet. Nevertheless, shielding 186 may be included and may surround the light source 12 and/or the coupling between the light emitters 14 and the proximal end **10*t*6 of the optical fiber 30**.

Various designs herein thus prioritize operator safety by allowing treatment procedures to occur remotely, mitigating long-term UV exposure risks, including DNA damage, skin cancer risks, and/or ocular harm. In some configurations, the system separate-room operation feature allows the system 10 to satisfy the highest safety standards for occupational UV exposure, a potentially and important factor in regulatory approvals and/or commercial adoption.

Integrating a long, e.g., at least 5, 10, 15, 20, or 25 foot fiber optic cable can facilitate remote operation (see, e.g., FIG. 18) possibly from a mobile shielded assembly (see, e.g., FIG. 19B). In one configuration, including the light source 12 in a separate, enclosed room can dramatically reduce the risk of operator exposure to harmful UV radiation. In some implementations, the wall 184 separating the rooms may include shielding 186 (e.g., plastic shielding). The operator and patient can thus be placed in a fully shielded environment.

As discussed above, the optical fiber may form part of the endoscope. A portion of the optical fiber may form part of the endoscope while a portion of the optical fiber may be outside the endoscope and/or connected thereto. In some cases, most of the optical fiber is not within the endoscope but extends from the light source to the endoscope.

In some implementations, a portion of the optical fiber is coupled to the endoscope via an optical connector and may be butt coupled. As discussed above, the portions of the optical fiber may be separate and/or separable. The optical fiber need not be a single strand of optical fiber and may be comprised of separate parts (e.g., separate strands), for example, strung, optically coupled, optically connected or concatenated together. The separate or discrete strands of optical fiber may be optically coupled or connected together, e.g., via optical connectors and may be butt coupled in some cases. For some designs, optics may be used to connect the strands or portions of optical fiber together. In some implementations, however, the optical fiber comprises a single (e.g., continuous) strand of optical fiber as opposed to discrete or separate parts coupled, e.g., butt coupled together or otherwise optically coupled together. As discussed above, the optical fiber may be referred to as an optical fiber line or optical fiber cable (or fiber optic cable). The terms fiber, optical fiber, optical fiber line, optical fiber cable, fiber optic, fiber optic line, fiber optic cable, etc. are used interchangeably herein.

Example Robotic Systems

Using robotic systems 10 may also enhance safety by reducing exposure of the physician and/or other medical professionals (e.g., nurses, technicians, other doctors) to stray UV light. FIGS. 20A and 20B, for example, schematically illustrate robotic systems for treating a patient with UV (e.g., UV-C) light. In both FIGS. 20A and 20B, the robotic system includes a UV (e.g., UV-C) transmissive optical fiber 30 configured to deliver UV light to the patient, for example, to one or more tumors or cancerous tissue. In various implementations, the operator (e.g., physician, surgeon, etc.) may control the movement of the robotic system, for example, in a robotic assisted system. Alternatively, the robotic system may be autonomous or fully robotic. Accordingly, the various systems, devices and methods describe herein may be employed for robotic assisted surgery and/or used or integrated in robotic assisted surgery systems. The operator, e.g., the physician or surgeon, can thus be remote from the distal end 108 of the optical fiber 30 where the UV (e.g., UV-C) light exits the optical fiber and is directed onto the patient. The robotic system 10 can likewise reduce the exposure of the operator to the UV light as the operator (e.g., physician) does not need to be next to the patient to deliver the UV light. Additionally, in some cases, the light source 12 and/or optical coupling between the light source and the optical fiber 30 can be included in another room 183 (see, e.g., FIG. 20A). A wall 184, possibly with UV shielding 186, may separate the two rooms.

Furthermore, in some implementations, the system 10 may include shielding 186 even if the light source 12 is in the same room as the patient. The light source 12 and/or coupling between the light emitter(s) 14 and the proximal end 106 of the optical fiber 30 may, for example, be encased in or have shielding 186 on a number (e.g., 1, 2, 3, 4, 5, 6, etc.) of sides (e.g., top, front, back, left and right lateral sides, bottom or any combination of these) such as shown in FIG. 20B. In some cases, the source 12 and/or coupling between the light emitter(s) 14 and the proximal end 106 of the optical fiber 30 may be encased in or have shielding 186 on a number (e.g., 1, 2, 3, 4, 5, 6, etc.) of sides (e.g., top, front, back, left and right lateral sides, bottom or any combination of these) and also be included in a separate room 183 and/or be separated by a wall 184. In various instances, the optical fiber 30 may be of sufficient length, and may be, for example, at least 3 feet, 4 feet, 5 feet, 6 feet, 8 feet, 9 feet, 10 feet, 12 feet, 14 feet, 15 feet, 16 feet, 18 feet, 20 feet, 21 feet, 22 feet, 24 feet, 25 feet, 30 feet, 40 feet, 50 feet, or any range formed by any of these values or possibly longer or shorter.

Examples of Shielding

FIGS. 21A and 21B illustrate some examples of such UV light shielding 186. FIG. 21A, for example, shows UV light shielding 186 disposed about the light source 12, the one or more UV emitters 14 as well as other components such as the heat sink, fan, and at least part of the housing or tube(s) in which the collecting optics or collecting lens 18 is included. In this example, this shielding 186 comprises plastic or polymer material, e.g., polycarbonate. This polycarbonate may be a polyester in which dihydric (or polyhydric) phenols are joined through carbonate linkages. Ultraviolet light is strongly absorbed by this specific UV resistant polycarbonate. As discussed above, the shielding material, for example, the plastic or polymer shielding material (e.g., polycarbonate), may include UV stabilizers and/or light absorbers that protect the material from degradation caused by ultraviolet (UV) radiation and/or enhance UV light absorption.

In this example, the UV light shielding 186 is substantially optically transmissive or transparent to visible light (although it need not be). The UV light shielding 186 comprises a plurality of sides, e.g., plates in this example, that are sealed, e.g., fused or bonded, together. The UV light shielding 186 in FIG. 21A is shown in front of, to the rear of, on the left and right lateral sides of, as well as on top of the UV light source 12, e.g., the UV light emitters 14. In this example, stray UV emission in excess of 70 mJ/cm$^2$ was measurable without the shielding 186, however, less than 0.01 mJ/cm$^2$ (e.g., 0.004 mJ/cm$^2$ was measured when the shielding was in place). This measurement of stray UV emission may be performed, for example, at 10 mm from the LED and at 10 mm from the shielding surface. However, the measurement may be conducted at other distances from the light emitters 14, the proximal end 50, 106 of the fiber 30, or the distal end 70, 108 of the optical fiber, such as 2 cm, 5 cm, 10 cm, 20 cm, 30 cm, 40 cm, 50 cm, 60 cm, 70 cm 80 cm, 90 cm, 100 cm, 125 cm, 150 cm, 175 cm, 200 cm, 250 cm, 300 cm, or 1 foot, 2 feet, 3 feet, 4 feet, 5 feet, 6 feet, 7 feet, 8 feet, 9 feet, 10 feet, or any range formed by any of these value or possibly larger or smaller distances.

The shielding 186 may be larger or smaller. For example, the shielding 186 may also cover at least a portion of the proximal end 106 of the UV transmissive optical fiber 30. For example, the shielding 186 may cover at least 0.5 cm, 1 cm, 2 cm, 3 cm, 4 cm, 5 cm, 8 cm, 10 cm, 12 cm, 15 cm, 20 cm, 30 cm, 40 cm, 50 cm, 60 cm, 70 cm, 80 cm, 100 cm of the proximal end of the UV transmissive optical fiber 30 or any range formed by any of these values or possibly larger or smaller. The shielding 186 may shield more or less components in the system such as the light source 12, the light emitters 14, the collecting lens 18, the focus lens 22, the coupling lens 48, the coupling between the proximal end 106 of the fiber 30 and the UV light source 12, the UV light emitters 14, the proximal end of the fiber or any combination thereof.

FIG. 21B shows UV light shielding 186 disposed about the distal end 108 of the optical fiber 30 including possibly output optics 64. In this example, this shielding 186 also comprises plastic or polymer material, e.g., polycarbonate. This polycarbonate may be a polyester in which dihydric (or polyhydric) phenols are joined through carbonate linkages. Ultraviolet light is strongly absorbed by this specific UV resistant polycarbonate. The plastic or polymer shielding material may (e.g., polycarbonate) may include UV stabilizers and/or light absorbers that protect the material from degradation caused by ultraviolet (UV) radiation and/or enhance UV light absorption.

The UV light shielding 186 shown in FIG. 21B is substantially optically transmissive or transparent to visible light (although it need not be). The UV light shielding 186 comprises a plurality of sides, e.g., plates in this example, that are sealed, e.g., fused or bonded, together. The UV light shielding 186 in FIG. 21B is shown in front of, to the rear of, on the left and right lateral sides of, as well as on top of the distal end 108 of the fiber and possibly of the output lens 64.

The shielding 186 may be larger or smaller. For example, the shielding 186 may cover at least 0.5 cm, 1 cm, 2 cm, 3 cm, 4 cm, 5 cm, 8 cm, 10 cm, 12 cm, 15 cm, 20 cm, 30 cm, 40 cm, 50 cm, 60 cm, 70 cm, 80 cm, 100 cm of the distal end 108 of the UV transmissive optical fiber 30 or any range formed by any of these values or possibly larger or smaller. The shielding 186 may be closer to or farther from the proximal end 108 of the optical fiber 30 and/or the output optics 64 or any combination thereof.

In the example shown in FIG. 21B, the distal end 108 of the optical fiber 30 is configured to be positioned with respect to samples 188 such as included on a microscope slide, in a petri dish or sample (e.g., biopsy) container. Such samples 188 included on a microscope side, in a petri dish or sample container may be supported on a support, platform or sample holder. The support, platform or sample holder could be translated and/or rotated in various implementations. The distal end of the optical fiber may be mounted on a mount. This mount may be movable. For example, this mount may be translated in the lateral (x and/or y) directions and/or in the longitudinal (z) direction.

Systems and Configurations for Testing Samples and/or Setting Parameters

The system 10 such as shown in FIG. 21B as well as FIGS. 22A and 22B is configured to direct UV (e.g., UV-C) light onto a sample or specimen 188 such as a biopsy or sample similar to the cancerous tissue of the patent. See also FIGS. 22C and 22D, which are additional photographs of such a system 10 without the shielding and with the shielding 186*a*, 186*b*. FIG. 22E is another photograph of such a system showing a long length of optical fiber or fiber optic cable 30 optically coupled to the UV light source 12. Shielding 186*a*, 186*b* about the light source (e.g., the one or more light emitters) 14 as well as at the distal end 70 of the optical fiber/optical fiber cable 70 is readily visible. This configuration may be particularly useful for determining one or more parameters of the system 10, such as of the light source 12 (e.g., radian flux, power, intensity, brightness) and variable pulsed source 16 (e.g., frequency/rep rate, duration, duty cycle, separation, of the pulses or groups of pulses, etc.) that are effective in treating (e.g., destroying or deactivating) cancerous tissues and/or tumors and/or preserving the health of non-cancerous tissue.

For example, conducting an in vitro biopsy study to test UV (e.g., UV-C) light at specific radiances, frequencies, and/or pulse durations, etc. for increased cell death, e.g., increased or optimal apoptosis, would be highly beneficial for refining the system's effectiveness. Different types of cancer cells may respond uniquely to UV-C light potentially based on, for example, their cell cycle, DNA repair mechanisms, sensitivity to radiation-induced damage or any combination thereof. Controlled in vitro testing can help establish a useful or effective, possibly optimal, dose, frequency/rep rate of pulses or groups of pulses, exposure time or any combination thereof for safe and effective treatment. Precise targeting of the specific type of cancer cells may thus be enabled. In some cases, for example, a dose-response relationship can be studied and a dose that provides increased or optimized effectiveness can be determined. The effectiveness and potentially safe of other parameters can also be studied for the particular cancer type.

Advantageously, a biopsy of the patient, e.g., of the patient's cancerous tissue, can also allow testing UV-C light directly on live cancerous cells (e.g., breast, prostate) to determine which radiance frequency and pulse settings induce increase or maximum cell death such as apoptosis while reducing or minimizing collateral damage to surrounding healthy cells. Biopsied tumor cells from different patients can be tested, leading to specific UV-C therapy protocols based on individual tumor characteristics. Thus, such a system 10 and/or configuration of the system can provide the potential for personalized cancer treatment.

Such a system 10 or system configuration can potentially have other uses and provide other advantages such as, for example, validation for clinical and/or FDA approval as well as enhancing precision for robotic integration. Generating repeatable, lab-controlled cell death (e.g., apoptosis) data may be useful for regulatory approval. The results can also support preclinical trials, facilitating the transition into in vivo animal models and eventually human trials. As discussed above, the system 10 can be included in and/or integrated with a surgical robotic systems such as a robotic assisted surgery system (e.g., like the Da Vinci). Knowing the exact UV-C radiance and duration needed for cell death or apoptosis can help develop precise software controls for robotic systems and applications.

In various implementations, a system 10, possibly a different or separate system from the one that is used to direct UV (UV-C) light onto the patient or possibly the same system, can be utilized to study the effect of the UV light on one or more samples. The system 10 can similarly employ a light source 12 comprising one or more UV (e.g., UV-C) light emitters 14. The system 10 can have any one or more or any combination of the features described herein. The system 10 can, for example, include an optical fiber 30 that is 25 feet long, optically coupled or connected to the UV or UV-C light source 12. Having such a system that includes features the same as the system to be used on the patient, can be helpful in increasing applicability of test results. Accordingly, the system 10 may include many or most of the features the same as the system to be used on the patient. Likewise, using the same system for both testing one or more samples and applying the UV light to the patient can be beneficial.

In some cases, one or more samples are tested on the same or different system as is to be used to treat the patient (e.g., applying the UV light to the tumor(s) or cancerous tissue in or on the patient's body.) In some cases, values for parameters use to control the system 10 such as the light source 12, e.g., one or more UV light emitters 14 possibly via the driver electronics 16 may be determined based on information obtained by testing samples 188 with the system. For example, different values of parameters can be tested to determine the effectiveness of a treatment using those or similar parameter values. As discussed above, examples of such parameters may include optical power, radiant flux, intensity, amount of light, output by the light source 12 or distal end 70, 108 of the optical fiber 30. Pulse parameters such as frequency or repetition rate of pulses or groups of pulses, duration of pulses or groups of pulses, separation between pulses or groups of pulses, duty cycle, or other parameters or factors or any combination of these may be tested. Values used when illuminating a sample can be assessed for their effectiveness in damaging, destroying, disabling, deactivating or suppressing tumors, or cancer cells. Similarly, assessments can be made with regard to reducing the damage to healthy tissue. Information can be obtained from such tests on samples 188 performed by exposing samples such as cancer cell samples and/or healthy tissue to UV light output from the distal end 70, 108 of the optical fiber 30. Such information can be used to determine settings for the system 10 and/or treatment, for example, for the UV light source 12 (e.g., one or more UV emitters), the driver electronics or pulsed power source 16, and/or procedure or protocol. In addition to possibly setting parameters of the system 10 such as output power of or amount of UV light output by the light source 12/light emitters 14 and/or pulse parameters, etc., other features of the treatment can be determined such as the beam size, the scan format or method, the dosage, the duration of exposure, the treatment regimen or any combination of these.

In various cases cancer cell samples of the same type of cancer as the patient's cancerous tissue may tested. Such cell samples may be of the same cancer line as well. Such cell samples may be obtained from a lab or vendor or may be biopsies obtained from the patient (e.g., from the patient's cancerous tissue or cells and/or healthy tissue or cells for example nearby).

In some cases, the treatment of the patient, e.g., one or more sessions of exposing the patient (e.g., tumors, cancerous tissue, or cancerous cells of the patient) may be performed shortly after testing samples 188. Likewise, in some cases, one or more parameters of the system 10 (e.g., optical power, amount of light, pulse duration, rep rate, etc.) used for treatment or other treatment parameters of the treatment (e.g., beam size, duration, how many sessions, length of sessions, dosage etc.) may be selected and applied to the treatment shortly after samples are tested. The value(s), thus, may be used in directing light in the UV wavelength range that is output from the optical fiber 30 on the body of the patient within 30 days, 20 days, 14 days, 12 days, 10 days, 8 days, 7 days, 6 days, 5 days, 4 days, 2 days 1 day, 18 hours, 12 hours, 10 hours, 8 hours, 6 hours, 4 hours, 3 hours, 2 hours, 1 hour, 30 minutes, 10 minutes, 5 minutes of the testing of the sample(s), (e.g., of directing the UV or UV-C light that was output from the optical fiber onto the sample) or any range formed by any of these values (e.g., within 1 to 7 days, within 1-2 days, within 24 hours to 30 minutes, within 12 hours to 10 minutes, etc.) or possible longer or short time periods. That is, in some cases, the treatment may be performed shortly after, for example, within 30 days, 20 days, 14 days, 12 days, 10 days, 8 days, 7 days, 6 days, 5 days, 4 days, 2 days 1 day, 18 hours, 12 hours, 10 hours, 8 hours, 6 hours, 4 hours, 3 hours, 2 hours, 1 hour, 30 minutes, 10 minutes, or 5 minutes of when the sample(s) are tested on the system 10 or another similar system, or any range formed by any of these values (e.g., within 1 to 7 days, within 1-2 days, within 24 hours to 30 minutes, within 12 hours to 10 minutes, etc.). The values used for the treatment may be selected based on values of different parameters tested on the samples. One or more of the same values may be used for the treatment as was tested. Or different values may be determined based on the values tested, for example, using extrapolation or interpolation or other techniques.

As discussed herein, these tests can be performed by exposing the sample 188 to UV light from the distal end 70, 108 of the optical fiber 30. In some cases, the optical fiber 30 (e.g., distal end 70, 108 thereof) can be mounted on a mount 190 disposed with respect to the sample 188 to direct light from the distal end of the optical fiber onto the sample. The sample 188 may be on a sample support, possible a sample stage. Either or both the mount 190 and/or support (e.g., sample) can be moved laterally or longitudinally with respect to each to the provide UV light from the distal end 70, 108 of the optical fiber 30 to perform the tests. In some cases, the endoscope 102, 110 and/or handheld delivery device 114 (e.g., distal end thereof) can be secured to the mount 190 to direct light out of the endoscope or handheld delivery device onto the sample to simulate more accurately the actual conditions of the treatment. Other variations, however, are possible.

Likewise, in various implementations, this device 10 can deliver UC (e.g., UV-C) light through direct exposure and fiber optic application to simulate surgical precision. The system 10 can be employed to concentrate UV-C light directly on live cancerous cells (e.g., breast, prostate) in sample container (e.g., biopsy container, petri dishes, etc.) to determine which parameter such as radiance frequency and pulse settings induce increase possibly maximum cancer cell death or inactivation (e.g., increased or maximum apoptosis)

while potentially reducing or minimizing collateral damage to surrounding healthy cells. This system 10 can be used to determine the appropriate (e.g., effective, safe and/or optimal) UV-C radiance frequency, intensity, pulse duration or any combination therefor for inducing death or deactivation (e.g., apoptosis) in specific tumor cells, while reducing or minimizing damage to healthy cells.

Such a system 10 can enable in vitro studies to be performed that could facilitate a comparison of UV or UV-C efficacy to traditional chemo or radiation therapy to demonstrate advantages in targeted treatment, reduced side effects, and enhanced cancer kill (e.g., apoptosis) rates.

Some tumors cell types are available for selections and testing. Examples of biopsy samples from specific cancer types include breast cancer cells (e.g., MCF-7, MDA-MB-231) and prostate cancer cells (e.g., LNCaP, PC-3). Other target tumor types may be possible based on clinical relevance. Tumor cells can be cultured in a controlled in vitro environment. Healthy cell controls from the same tissue type can be included. These tumor cells and healthy cells can be exposed to UV (e.g., UV-C) light to test the efficacy and/or safety of the UV light treatment. The parameters of the UV light (e.g., wavelength, intensity, pulse parameters) can be varied and tested. The UV-C exposure setup may be similar to that used to treat the patient. The system 10 may, for example, comprise a light source 12 comprising one or more UV (e.g., UV-C) emitter 14. A variable pulse supply 16 may be used to generate pulses of UV (e.g., UV-C) light. The system 10, for example, the variable pulse controller 16 and/or other electronics can be configured to vary frequency/rep rate, power or intensity, and durations and/or separations between pulses or groups of pulses. Pulse durations may range, for example, from 1 ms to 10 seconds (with varied intervals). The energy doses may vary in the range between 0.1 mJ/cm$^2$ to 100 mJ/cm$^2$ or more. To determine the effect of the UV light on the cancer or tumor cell samples, microscopic & molecular analysis may be performed. With live-cell imaging, real-time morphological changes can be observed. Tests such as Western blot/qPCR can be used to Check expression of apoptosis-related genes (BAX, BCL-2, Caspase-3, P53).

Expected outcomes of these tests may be the identification of the most effective UV-C parameters, such as pulse parameters, e.g., frequency/rep rate, power, intensity, and duration and/or separation of pulses or groups of pulses, for cell death, destruction, and/or inactivation (e.g., apoptosis). Additionally, an understanding of the impact of UV light (e.g., UV-C light) on cancerous vs. healthy cells may be developed.

The ability of UV (e.g., UV-C) light expose to induced death, destruction, deactivation, and/or apoptosis in biopsied tumor cells may be studied. Apoptosis & cell viability assessment may be provided by a number of methods. MTT assay and/or Alamar Blue assay, for example, may be employed to measure cell viability post-treatment. Annexin V/PI staining may be used to identify early and late apoptosis. TUNEL assay may detect DNA fragmentation in apoptotic cells. Flow cytometry analysis may be used to quantify cell cycle arrest and apoptosis rates. ROS detection assay may assess oxidative stress induced by UV-C light.

After in vitro success, some additional possible next steps may include in vivo testing to evaluate UV (e.g., UV-C) light application in animal tumor models. The system 10 may be further refined, for example, to improve and/or optimize UV-C delivery parameters for robotic and/or fiber optic applications. The tests described above, can potentially assist in clinical trial planning. In vitro and in vivo data can be used, for example, to prepare for regulatory approval (e.g., FDA pre-submission).

As discussed above, the variable pulse power source 16 may provide the ability to vary pulse parameters such as, for example, frequency/rep rate, duration, separation, duty cycle of pulse or groups of pulses or any combination of these. The system 10 may also be configured to alter the power, intensity, radiant flux or signal strength of the UV (e.g., UV-C) light delivered to the patient. Accordingly, such samples positioned at the distal end of the UV (e.g., UV-C) transmissive optical fiber 30 to receive light therefrom can be tested to determine the effect of different parameter settings on the death, destruction, or inactivation of the cancer cells or tumor cells as well as potentially the effect on non-cancerous or healthy tissue or cells. The system 10 can thus be configured to receive such samples and position the distal end 108 of the optical fiber 30 to direct UV (e.g., UV-C) light on said samples. FIGS. 21A, 22A, and 22B show the distal end 108 of the optical fiber 30 in systems 10 configured to direct light on samples 188 in sample containers such as petri dishes or biopsy containers for testing purposes. As shown, the systems 10 include a mount 190 for positioning the distal end 108 of the UV transmissive optical fiber 30 with respect to the sample 188, e.g., above the sample, to direct UV light from the UV light source 12 on the sample. In some cases, the mount 190 is adjustable to adjust the distance in the longitudinal direction (z-direction) from the distal end 108 of the optical fiber 30 to the sample 188. In some designs, the sample 188 is on a stage that can be translated laterally (e.g., in the x or y directions) and/or on a rotation state configured to rotate in the azimuthal direction about the longitudinal axis. In some implementations, the support or platform on which the sample is placed can be translated, for example, laterally (e.g., in x and/or y directions) and/or rotated.

Additionally, as discussed above UV (e.g., UV-C) light leakage, secondary UV reflections and scattered radiation can pose unintended risks to medical personnel and even adjacent patients. This system 10, nevertheless, may advantageously reduce and/or minimize these risks by confining UV exposure to a controlled and isolated environment.

The proximal and distal shielding 186*a*, 186*b* shown in FIGS. 21A and 21B as well as 22A and 22B is designed to offer sufficient shielding during short duration of UV exposure whilst testing the effect of UV (e.g., UV-C light) on samples 188 and/or using different dosage, rates of pulses or groups of pulses, durations of pulses or groups of pulses, duty cycles of pulses or groups of pulses, etc. The pulse durations may, in some cases, be up to 30 seconds possibly limited to a few times per day to tune the device for increased or maximum UV induced cancer cell death rate. During these tests, operators can utilize PPE including full UV resistant polycarbonate faceplate, clothing and gloves. PPE may also be worn and/or recommended to be worn by operators and/or bystanders (e.g., surgeons, physicians, nurses, technicians, and others) present when UV (e.g., UV-C) light is output from the UV light source 12 (e.g., UV emitter). The systems 10 described herein can provide that ambient UV does not escape into unintended areas or at least sufficiently curtail the incidence of such stray light reaching physicians, nurses, technicians or other medical professionals including the operator of the system 10 during testing of biopsies or other samples 188. As shown in FIGS. 21B, 22A, and 22B, shielding 186*b* may be provided at the distal end 108 of the optical fiber 30. The shielding 186*b* may comprises plastic or polymer such as polycarbonate or acrylic with a thickness of 5 mm or more and may be transparent to visible light or may comprise a metal housing/encapsulation. In the example shown in FIGS. 21B and 22A-22B, the shielding 186*b* may comprise a plurality plastic plates sealed together (e.g., bonded or fused). In the example shown, the plates are on one or more (e.g., 1, 2, 3, 4, 5, 6, etc.) sides such as in front of and to the rear of distal end 108 of the optical fiber 30 as well on left and right sides of the distal end of the optical fiber as well as above the distal end of the optical fiber. Other configurations are possible, for example, the shielding 186*b* may have a tubular shape that is a right circular cylinder. Still other shapes and configurations are possible.

In the example shown, the shielding 186*a*, 186*b* is substantially optically transmissive or is transparent to visible light. Having the shielding 186*b* at the distal end 70, 108 of the optical fiber 30 may be useful in enabling the operator or user to position the sample with respect to the distal end of the fiber and to monitor the illumination.

Optics Materials

As discussed above, the optics, for example, lenses, may comprise material that is optically transmissive to UV light such as UV-C light or other wavelengths recited herein and have reduced loss (e.g., absorption, scattering, or combinations thereof) at such wavelengths. Glass, acrylic, polycarbonate, for example, absorb UV light including UV-C light such that attenuation limits the ability to destroy cancer cells after transmission through optics and/or optical fiber comprising such materials. Additionally, some materials such as PMMA may degrade under prolonged exposure to UV, e.g., UV-C, light.

Sapphire, quartz, fused silica, or special UV-grade fluoropolymers are among the limited materials capable of transmitting UV-C effectively. UV-C light (e.g., 200-280 nm) is strongly absorbed by many common optical materials. As discussed above, optical materials such as, for example, glass, acrylic, polycarbonate, and PMMA absorb UV-C or degrade under exposure. For UV-C transmission, fused silica, synthetic quartz, or UV-transparent polymers may be employed.

Fused silica, quartz, sapphire, and specific fluoropolymers (like Teflon AF) are among the materials that effectively transmit UV-C light. The terms "fused silica" and "fused quartz" refer to two different types of silica glass. For example, fused quartz (Type I/II) may be made by melting natural or purified crystalline silica, while fused silica (Type III/IV) may be a synthetic material made from a chemical precursor. For optical applications, the key difference between fused quartz and fused silica is their levels of impurities that contribute to absorption, with fused quartz having more impurities such as Al, alkalis, and transition metals. UV-C transparent optics can, for example, be made from synthetic fused silica or sapphire. Fused silica can be made by a variety of methods, including but not limited to flame hydrolysis. Impurities, in the form of metallic ions or hydroxyl groups (OH) can cause greater absorption and influence the viscosity of the glass. Greater absorption leads to loss of transmission.

As discussed above, increased hydroxyl (OH—) content in fused silica lenses can reduce UV transmission. Likewise, low Hydroxyl rates or amounts provide for higher UV-C transmissive lenses and optics. The hydroxyl (OH—) content in fused silica lenses has a significant impact on UV transmission, particularly in the deep UV (DUV) and vacuum UV (VUV) ranges (wavelengths below 250 nm). The presence of hydroxyl groups affects absorption, transmission efficiency, and overall optical performance. Accordingly, in various implementations described herein, the OH content in the fused silica comprising the optics such as one or more lenses (e.g., collecting lens 18, focusing lens 22, coupling lens 48 output lens 64, or any combination thereof) is OH<10 ppm. Such low OH content provides high UV transmission, particularly in the 200-250 nm wavelength range. The reduced UV absorption makes lenses and optics comprising such low OH fused silica useful for UV-C (e.g., 265 nm). Lower-OH content, such as ≤1 ppm, may further reduce absorption and scattering losses.

The hydroxyl (OH—) groups in fused silica introduce absorption peaks in the UV spectrum, particularly, at 140 nm-185 nm (strong absorption in VUV) and 210 nm-250 nm (moderate absorption affecting deep UV transmission). Without subscribing to any particular scientific theory, OH-content may affect phonon interactions, potentially leading to increased Rayleigh scattering and reduced optical clarity in the UV range. Regardless of the absorption mechanism, high-OH fused silica can have UV absorption losses.

The hydroxyl (OH—) content in fused silica lenses thus affects UV transmission performance of the system 10, particularly for deep UV and UV-C applications. While high-OH fused silica significantly reduces transmission and increases absorption losses, low-OH fused silica can increase UV-C efficiency.

Accordingly, in various designs, the transmissive optics (e.g., lenses) such as the collecting optics or collecting lens or lenses (e.g., collimating optics or collimating lens or lenses) 18 and/or the focusing optics or focusing lens or lenses 22 and/or the coupling optics or coupling lens or lenses 48 and/or the output optics or output lens or lenses 64 or any one or more of these or combination of these lenses or lens elements may comprise material transmissive to UV-C light such as at the wavelengths recited herein. Such UV-C transmissive materials that may be employed for these lenses or optics are discussed below.

As discussed above, the one or more UVC LEDs 14 may emit light having a wavelength in the UVC wavelength range and in certain implementations discussed herein emit light in the range of from 250 nm to 280 nm, 250 nm to 275 nm, 260 nm to 270 nm, for example, possibly having a peak wavelength in one or more of these range, e.g., possibly at 265 nm. Likewise, the lens(es) (e.g., collecting lens(es), collimating lens(es) 18, focusing lens(es) 22, coupling lens (es) 48, output lens(es) 64, or any combination of these, etc.) may comprise material optically transmissive to UVC light such as light in the wavelength range of UVC light emitted by the UVC emitters or LEDs. In some implementations, for example, the lens(es) comprise a fused silica lens or lenses comprising fused silica, which is transmissive to UVC light. In some implementations, for example, the lens(es) are optically transmissive (for example, at least 50%, 55%, 60%, 65%, 70%, 75%, 80%, 85%, 90%, 95%, 98%, 99%, 100%, transmissive or any range formed by any of these percentages) to light in the wavelength range of from 220 nm to 290 nm, 220 nm to 280 nm, 250 nm to 280 nm (e.g., 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, etc.), 250 nm to 275 nm, 260 nm to 275 nm, 260 nm to 270 nm, e.g., 265 nm, or any range formed by any of these values.

In certain implementations, the lens(es) (e.g., collecting lens(es), collimating lens(es) 18, focusing lens(es) 22, coupling lens(es) 48, output lens(es) 64, or any combination of these, etc.) are optically transmissive (for example, at least 50%, 55%, 60%, 65%, 70%, 75%, 80%, 85%, 90%, 95%, 98%, 99%, 100%, transmissive or in any range formed by any of these percentages) to light in the wavelength range of from 200 nm to 290 nm, 200 nm to 280 nm, 200 nm to 250 nm (e.g., 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 240 nm, 241 nm, 242 nm, 243 nm, 244 nm, 245 nm, 246 nm, 247 nm, 248 nm, 249 nm, 240 nm, 241 nm, 242 nm, 243 nm, 244 nm, 245 nm, 246 nm, 247 nm, 248 nm, 249 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, etc.) or any range formed by any of these values such as from 200 nm to 210 nm or from 200 to 220 nm or from 200 to 230 nm or from 210 to 230 nm or 220 to 230 nm, or 220 to 250 nm or 210 to 250 nm or 200 to 250 nm or 200 to 270 nm, 200 to 300 nm, 260 to 315 nm, or possible higher or lower wavelengths.

As discussed above, in some implementations, the lens (es) (e.g., collecting lens(es) 18, collimating lens(es), focusing lens(es) 22, coupling lens(es) 48, output lens(es) 64, or any combination of these, etc.) comprises fused silica. In various implementations, the lens(es) may comprise fused silica glass having a transmittance (e.g., internal transmittance or transmittance corrected to reduce or possibly eliminate the effects of scattering and of reflection from surfaces) of UVC light in the range of 245 to 280 nm or 260 nm to 270 nm or 290 nm to 315 nm or 300 nm to 330 nm (e.g., 245 nm, 246 nm, 247 nm, 248 nm, 248 nm, 250 nm, 251 nm, 252 nm, 253 nm, 254 nm, 255 nm, 256 nm, 257 nm, 258 nm, 259 nm, 260 nm, 261 nm, 262 nm, 263 nm, 264 nm, 265 nm, 266 nm, 267 nm, 268 nm, 269 nm, 270 nm, 271 nm, 272 nm, 273 nm, 274 nm, 275 nm, 276 nm, 277 nm, 278 nm, 279 nm, 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, or any range formed by any of these values), of least 95% for a 10 mm thickness of the fused silica glass although in other implementations this transmittance is at least 50%, 55%, 60%, 65%, 70%, 75%, 80%, 85%, 90%, 94%, 96%, 98%, 99%, 99.9%, or 100% or any range formed by any of these values or possibly more or less. In various implementations, the OH (e.g., Hydroxyl) content is not larger than 5 ppm although in other implementations the OH content is not larger than 0.05 ppm, 0.01 ppm, 0.5 ppm, 1 ppm, 2 ppm, 3 ppm, 4 ppm, 5 ppm, 6 ppm, 8 ppm, 10 ppm, 20 ppm, 30 ppm, 40 ppm, 50 ppm, 60 ppm, 70 ppm, 80 ppm, 90 ppm, 100 ppm, 125 ppm, 150 ppm, 200 ppm, 300 ppm, 400 ppm, or 500 ppm or any range formed by any of these values or possibly more or less. Additionally, in various implementations, a content of Li, Na, K, Mg, Ca and Cu each are smaller than 0.1 ppm although in some implementations the content of any one or more, possibly each, of Li, Na, K, Mg, Ca and Cu are smaller than 0.001 ppm, 0.005 ppm, 0.01 ppm, 0.05 ppm, 0.1 ppm, 0.2 ppm, 0.3 ppm, 0.4 ppm, 0.5 ppm, 0.6 ppm, 0.7 ppm, 0.8 ppm, 0.9 ppm, 1 ppm, 1.25 ppm, 1.50 ppm, 2.00 ppm, 3.00 ppm, 4.00 ppm, or 5.00 ppm, or 6.00 ppm, or 7.00 ppm, or 8.00 ppm, or 9.00 ppm, or 10 ppm, or 12 ppm, or 15 ppm or any range formed by any of these values or possibly more or less.

In some implementations, the glass has a viscosity coefficient at 1215° C. of at least $10^{11.5}$ Pa·s; and a Cu ion diffusion coefficient of not larger than $1\times10^{-10}$ $cm^2$/sec in a depth range of greater than 20 μm up to 100 μm, from the surface, when left to stand at 1050° C. in air for 24 hours. However, the glass need not be so limited as other implementations are possible.

In some cases, the glass may be fabricated by crystobalitizing powdery silica raw material and then, fusing the crystobalitized silica material in a non-reducing atmosphere. However, the method of manufacture should not be so limited.

In some implementations, the fused silica glass may exhibit a high transmittance of ultraviolet, visible and infrared rays, may have high purity and heat resistance, and may exhibit a reduced diffusion rate of metal impurities or any combination of these traits.

Variable Beam Size

As discussed above, the size of the UV light beam delivered to the target area, for example, the cancerous tissue, one or more tumors, and possibly some adjacent or surrounding tissue can be adjusted. The size of the UV beam may be altered, for example, by changing the optical power and/or focal length of the output optics 64. The optical power and/or focal length may be changed by substituting out one output lens 64 for another. A first output lens 64 may, for example, have a first optical power and/or focal length that provides a first beam size (e.g., width, diameter, etc.) and a second output lens may have a second optical power and/or focal length that provides a second beam size (e.g., width, diameter, etc.) different than the first beam size. The first or second output lens 64 may be employed to obtain the first or second beam sizes. Additional output lenses 64 can be used in the alternative to obtain additional different beam sizes. A kit of output lenses 64 may include 2, 3, 4, 5, 6, 7, 8, 9, 10, 12, 15, 18, 20 or more lenses, or any range formed by any of these values or possibly a larger or smaller number of lenses. Different lenses from the kit may be used at different times to provide different beam sizes (e.g., widths, diameters, etc.), some larger, some smaller.

In some designs, the lenses may be included in an attachment such as a cap that fits on, over, and/or in front of, the distal end 30 of the optical fiber to position the lens in place at the distal end of the optical fiber. Different attachments (e.g., caps) with different lenses may be attached to provide different beam width. For example, a first attachment with the first lens may be removed from the distal end 108 of the optical fiber 30 and replaced with a second attachment with the second lens to change the optical power and/or focal length from the first optical power and/or focal length to the second optical power and/or focal length. The operator and/or other medical professional such as nurse, technician, etc. may switch out the attachments (e.g., caps) to provide different optical powers and/or focal lengths. The operator and/or other medical professional may for example select from 2, 3, 4, 5, 6, 7, 8, 9, 10, 12, 15, 18, 20 or more lenses and/or attachments (e.g., end caps), or any range formed by any of these values. The operator and/or medical professional may, for example, select the lens 64 and/or attachment based on the size of the target area, e.g., the size of the tumor or tumors, the size of the area of cancerous tissue, or a slightly larger to account for margins or regions of non-cancerous tissue adjacent and/or surrounding the cancerous tissue. The lens and/or attachment may be selected, for example, to provide a beam at the target that has a lateral size that is about the lateral size of the cancerous tissue (e.g., tumor or tumors) and/or the cancerous tissue (e.g., tumor or tumors) plus a margin thereabout or regions of non-cancerous tissue adjacent and/or surrounding the cancerous tissue. Alternatively or additionally, a lens 64 may be used that provides a beam smaller than the region of cancerous tissue (e.g., tumor or tumors), or smaller than the regions of cancerous tissue plus a margin, the region of cancerous tissue plus adjacent and/or surrounding non-cancerous tissue. For example, a lens may be used that will provide a concentrated beam the size of a portion of the cancerous tissue area and different portions of the cancerous tissue may be exposed to UV light at different times by moving the beam to those locations.

Other approaches to altering the beam size are possible. For example, a second output lens 64 may be added to a first output lens at the distal end 108 of the optical fiber 30. For example, a first output lens 64 may be located at the distal end 108 of the optical fiber 30 that provides a first beam size (e.g., width, diameter, etc.). To obtain a second beam size (e.g., width, diameter, etc.), a second output lens 64 may be added to the first output lens. The combination of the first and second output lenses 64 may have an aggregate or effective optical power and/or focal length that is different than the focal length and/or optical power of the first lens without the second output lens added thereto. In some implementations, for example, the second lens may be included in an attachment that can be attached to the distal end 108 of the optical fiber 30 to add the second output lens to the first output lens. A first beam size provided by the first output lens 64 alone may be different than a second beam size provided by the second output lens in addition to the first output lens. The second beam size may be larger or smaller than the first beam size. Likewise, the first and/or second output lenses may be positive or negative in power and/or focal length and may have different optical power and/or focal lengths and/or optical power and/or focal lengths of different signs (e.g., positive and negative optical power and/or focal lengths). A kit of output lenses 64 to be attached to a first output lens may include 2, 3, 4, 5, 6, 7, 8, 9, 10, 12, 15, 18, 20 or more lenses, or any range formed by any of these values. Different lenses from the kit may be added to the first output lens at different times to provide different beam sizes (e.g., widths, diameters, etc.), some larger, some smaller. The different lenses may have different optical powers and/or focal lengths and/or optical powers and/or focal lengths of different signs. As discussed above, the different additional lenses may be included in different attachments that can be selected and attached to the distal end 108 of the optical fiber 30 with the first output lens at the end of the optical fiber.

Other techniques for changing the optical power and/or focal length of the output optics 64 at the distal end 108 of the optical fiber 30 may be employed. An adjustable lens assembly may be included at the distal end of the optical fiber. For example, a plurality of output lenses 64 may be included at the distal 108 end of the optical fiber 30 and a longitudinal distance between at least two lenses may be changed to alter the aggregate optical power or effective focal length and the beam size (e.g., beam width, diameter, etc.) at the target tissue. The change in longitudinal distance and/or the change in the beam size may be caused by manually altering the longitudinal distance between lenses. In other designs, the longitudinal distance and/or the change in the beam size may be controlled remotely with remote control (e.g., electrically, hydraulically, mechanically, etc.,). Other configurations, however, are possible.

An adjustable lens assembly at the distal end of the optical fiber may comprises a lens or plurality of lenses that are moved together, for example, with respect to the optical fiber to alter the beam size. The longitudinal distance between the lens or plurality of lenses and the end of the optical fiber may be changed to alter the beam size. The change in longitudinal distance and/or the change in the beam size may be caused by manually altering the longitudinal distance between the lens(es) and the optical fiber. In other designs, the longitudinal distance and/or the change in the beam size may be controlled remotely with remote control (e.g., electrically, hydraulically, mechanically, etc.,). Other configurations, however, are possible.

Directing Beam Onto Target

Advantageously, the systems 10 described herein can produce a beam of UV-C light having a beam size that is reduced so as to reduce exposure of healthy tissue to UV-C light. FIG. 23 shows, for example, a tumor 140 comprising a plurality of cancer cells 142 being illuminated by a beam 148 of UV-C light having a diameter, width, or lateral extent that is similar to the size of the tumor. The UV-C light beam 148 depicted in FIG. 23, for example, has a perimeter 152 and the diameter, width, or lateral extent that is within 35%, 30%, 25%, 20%, 15%, 10%, 5%, 4%, 3% 2%, 1% of the maximum lateral extent of the tumor. In this example, the UV-C light beam 148 is larger than the tumor. However, in various implementations, the area of the tumor is greater than 40%, 50%, 60%, 70%, 80%, 90%, 95%, 98%, 99%, 100% of the area of the beam at the target, or any range formed by any of these values or possibly larger or smaller. The diameter, width, or lateral extent (e.g., in the x and/or y directions) of the UV-C light beam 148 at the target, for example, measured FWHM, may be less than 60 mm, 50 mm, 40 mm, 30 mm, 20 mm, 25 mm, 20 mm, 15 mm, 10 mm, 9 mm, 8 mm, 6 mm, 5 mm, 4 mm, 3 mm, 2 mm, 1 mm, 0.5 mm, 0.25 mm, 0.1 mm or any range formed by any of these values, for example, from 3 mm to 0.5 mm or from 1 mm to 6 mm or from 2 mm to 10 mm or possible larger or smaller, for example, such that the excess amounts of healthy tissue is not exposed to the UV-C light from the UV-C emitters 14.

In contrast, FIG. 24 shows blanket UV-C illumination provided, for example, by a Xenon tube. The size of the UV-C beam 148 is large compared to the tumor 140. As a result, portions of healthy tissue larger than the size of the tumor 140 itself are exposed to UV-C light. FIG. 23 shows, for example, the tumor 140 comprising a plurality of cancer cells 142 being illuminated by a beam 148 of UV-C light having a width, diameter, or lateral extent that is multiple times larger than the size of the tumor. This drawing, however, is schematic, and the perimeter 152 of the beam 148 may be substantially larger than shown.

Compact Designs

In addition, to potentially providing a smaller beam size, solid state UV-C light emitters 14 (with or without the use of an optical fiber) may also provide a low profile for the system 10. In some implementations, for example, the system 10 can fit within a suitcase or be of similar size. In various implementations, for example, the system 10 (with or without the optical fiber) may be less than 80 cm, 70 cm, 60 cm, 50 cm, 40 cm, 30 cm, 20 cm, 10 cm, in one dimension (e.g., length) or any range formed by any of these values such as from 20 to 60 cm or 30 to 50 cm, or possibly larger or smaller. In various implementations, for example, the system 10 (with or without the optical fiber) may be less than 80 cm, 70 cm, 60 cm, 50 cm, 40 cm, 30 cm, 20 cm, 10 cm, 5 cm, in another dimension (e.g., height) or any range formed by any of these values such as from 10 to 50 cm or 20 to 40 cm, or possibly larger or smaller. In various implementations, for example, the system 10 (with or without the optical fiber) may be less than 80 cm, 70 cm, 60 cm, 50 cm, 40 cm, 30 cm, 20 cm, 10 cm, 5 cm, 4 cm, 3 cm, 2 cm, 1 cm, in another dimension (e.g., width) or any range formed by any of these values such as from 5 to 40 cm or 10 to 30 cm, or possibly larger or smaller. Accordingly, the system 10 (with or without the optical fiber) may have a volume 5,000,000 $cm^3$, 4,000,000 $cm^3$, 3,000,000 $cm^3$, 2,000,000 $cm^3$, 1,900,000 $cm^3$, 1,800,000 $cm^3$, 1,700,000 $cm^3$, 1,600,000 $cm^3$, 1,500,000 $cm^3$, 1,400,000 $cm^3$, 1,300,000 $cm^3$, 1,200,000 $cm^3$, 1,100,000 $cm^3$, 1,000,000 $cm^3$, 900,000 $cm^3$, 800,000 $cm^3$, 700,000 $cm^3$, 600,000 $cm^3$, 500,000 $cm^3$, 450,000 $cm^3$, 400,000 $cm^3$, 350,000 $cm^3$, 300,000 $cm^3$, 250,000 $cm^3$, 200,000 $cm^3$, 190,000 $cm^3$, 180,000 $cm^3$, 170,000 $cm^3$, 160,000 $cm^3$, 150,000 $cm^3$, 140,000 $cm^3$, 130,000 $cm^3$, 120,000 $cm^3$, 100,000 $cm^3$, 110,000 $cm^3$, 90,000 $cm^3$, 80,000 $cm^3$, 75,000 $cm^3$, 70,000 $cm^3$, 64,000 $cm^3$, 60,000 $cm^3$, 55,000 $cm^3$, 50,000 $cm^3$, 45,000 $cm^3$, 40,000 $cm^3$, 35,000 $cm^3$, 30,000 $cm^3$, 24,000 $cm^3$, 20,000 $cm^3$, 18,000 $cm^3$, 16,000 $cm^3$, 15,000 $cm^3$, 14000 $cm^3$, 12000 $cm^3$, 10000 $cm^3$, 8000 $cm^3$, of or any range formed by any of these values such as from 800,000 $cm^3$ to 100,000 $cm^3$ or 200,000 $cm^3$ to 20,000 $cm^3$, 30,000 $cm^3$ to 10,000 $cm^3$, or possibly larger or smaller. Other shapes and sizes are possible.

In some implementations, the weight of the system may be no more than 200 pounds (lbs.), 175 lbs., 150 lbs., 140 lbs., 130 lbs., 120 lbs., 110 lbs., 100 lbs., 90 lbs., 80 lbs., 70 lbs., 60 lbs., 50 lbs., 45 lbs., 40 lbs., 35 lbs., 30 lbs., 25 lbs., 15 lbs., 10 lb., or any range formed by any of these values such as from 80 lbs. to 20 lbs., or from 50 lbs. to 10 lbs. or from 40 lbs. to 15 lbs. or possibly more or less. Other systems 10, for example, may potentially weigh more or less.

Additionally, various designs described herein, for example, the endoscope 102 and/or the handheld output tool, delivery device or handpiece 114, with or without the tube 120, have a sufficiently small size to be able to be used in minimally invasive procedures. The output head or endpiece 110 of the endoscope 102 and/or the tube 120 on the handheld output tool, delivery device or handpiece 114 may be 30 mm, 25 mm, 20 mm, 18 mm, 15 mm, 12 mm, 10 mm, 9 mm, 8 mm, 6 mm, 5 mm, 4 mm, 3 mm, 2 mm, 1 mm, 0.9 mm, 0.5 mm, 0.2 mm or in any range formed by any of these values such as from 10 mm to 0.5 mm, or from 4 mm to 1 mm, or possibly larger or smaller. Such small size can enable the physician or user to easily manipulate the output end of the system 10, for example, to navigate around surgical or medical components and/or anatomical features or access or reach the target tissue.

Test Results

FIG. 25 shows how variation in duty cycle affects the output of the system 10 and the exposure time for providing a specific dosage (100 $mJ/cm^2$) of UV-C light with that duty cycle. To obtain the results shown in the table in FIG. 18, a UV-C LED array 12 was optically coupled into a four meter long optical fiber having a fused silica core 58 with a 1000 micron core diameter. The LED array 12 was driven with 500 mA of current at 60 Hz. The amount of light was measured at the output at the distal end of the optical fiber 30, for example, where the target cancer cells would be located. This amount of light for the different duty cycles tested is listed in the third column from the left labeled $mW/cm^2$. The voltages measured for the LEDs changed with the change in duty cycle, decreasing with duty cycle. (The voltmeter measuring this voltage may show a lower output voltage when the duty cycle is less than 100%, because the voltmeter may be unable to react quickly enough to capture the peak voltage of the pulse. Rather, the voltmeter may be obtaining an average voltage, which includes both the on time and the off time of the pulses resulting in a lower voltage.)

As discussed above, the chart shows how the output in $mW/cm^2$ (third column from right) varies with duty cycle (second column from left). Understandably, the amount of light reduces with reduction in duty cycle. The chart also shows the calculations for the total time of exposure (second column from right) for obtaining 100 $mJ/cm^2$ to kill cancer cells based on the amount of light produced for a given duty cycle. The chart demonstrates that the total time of exposure (second column from right) for obtaining 100 $mJ/cm^2$ increases as the duty cycle is reduced. For example, when the duty cycle is 10%, 317 seconds of exposure provide 100 $mJ/cm^2$ whereas when the duty cycle is 90%, 31.5 seconds provides 100 $mJ/cm^2$, and when the duty cycle is 100%, 28.1 seconds provides 100 $mJ/cm^2$. Results may vary. The chart also lists a benchmark exposure amount of 29.0 seconds (fourth column from the right), which is a calculated duration of exposure for obtaining 100 $mJ/cm^2$ at 100% duty cycle.

The temperature was also measured. Temperature measurements were obtained close to the junction of the LED substrate and heatsink 36. The tests indicate that lower output coincides with lower temperatures e.g. 73° F. When increased output was produced, the temperature was measured to be 80-85° F.

FIGS. 26-29 demonstrate the effects of exposing breast cancer cells to UV-C light from a system such as disclosed herein. In particular, breast cancer cells from the MCF-7 cell line were exposed to UVC-light coupled into an optical fiber 30. The UV-C light was produced by a UV-C LED array 12 and was optically coupled into a 12 foot long optical fiber 30 having a fused silica core 58 with a 1000 micron core diameter. The output of the optical fiber 30 was directed onto the MCF-7 breast cancer cells, which were in 35 mm Petrie dishes. The output lens 64 at the distal end of the optical fiber 30 provided a 2-3 mm diameter beam of UV-C light on the breast cancer cells. The optical fiber 30 was positioned such that the output lens 64 was a distance of 2 mm from the cells and the beam of light was incident on the center of the Petrie dish. The UV-C light had a spectral output as shown in FIG. 5C with a central wavelength of 265 nm.

FIGS. 26A and 26B show a comparison of the density of MCF-7 breast cancer cells prior to exposure to the UV-C light with the density of MCF-7 breast cancer cells after exposure to the UV-C light for 8 seconds. The radiant exposure of the breast cancer cells to the UV-C light is estimated to be 25 $mJ/cm^2$ in FIG. 26B.

FIGS. 27A and 27B show a comparison of the density of MCF-7 breast cancer cells prior to exposure to the UV-C light with the density of MCF-7 breast cancer cells after exposure to the UV-C light for 15 seconds. The radiant exposure of the breast cancer cells to the UV-C light is estimated to be 50 mJ/cm$^2$ in FIG. 27B.

FIGS. 28A and 28B show a comparison of the density of MCF-7 breast cancer cells prior to exposure to the UV-C light with the density of MCF-7 breast cancer cells after exposure to the UV-C light for 22 seconds. The radiant exposure of the breast cancer cells to the UV-C light is estimated to be 75 mJ/cm$^2$ in FIG. 28B.

FIGS. 29A and 29B, show a comparison of the density of MCF-7 breast cancer cells prior to exposure to the UV-C light with the density of MCF-7 breast cancer cells after exposure to the UV-C light for 29 seconds. The radiant exposure of the breast cancer cells to the UV-C light is estimated to be 100 mJ/cm$^2$ in FIG. 29B.

The density of MCF-7 breast cancer cells appears to be reduced with exposure to the UV-C light.

Additional Test Results

Additional testing was performed to observe the impact of UV exposure on cell viability in cancerous and healthy cells. UV-C light on breast cancer and prostrate cancer lines were tested using a system such as shown in FIGS. 21A-21B.

The conclusions of this additional study are that the effects of UV irradiation on cell viability were different for different cell lines tested. Some cell lines showed a high degree of cell death in response to UV irradiation, while others were relatively more resistant. UV irradiation caused significant cell death in both primary human mammary and primary human prostate epithelial cells in monoculture. In cocultures with cancer cell lines, primary cell death was still present but was less pronounced.

The two different prostate cancer cell lines exhibited markedly different levels of cell death, as did to the two different breast cancer cell lines tested. This implies that a cell line's unique genetic background may be as significant in determining susceptibility to UV irradiation as any other variable.

Morphology of cells was notably different in monocultures vs. cocultures, as was the tendency of dead cells to remain present in the samples.

Most cell lines did not show a clear UV dose-dependent cell death response, suggesting that under these experimental conditions 25 mj was a “threshold” dose.

The response of the cell lines were as follows.

Primary human mammary epithelial cells: In monoculture, widespread cell death occurred in response to all doses of UV radiation. In cocultures with MCF7 or BT474 cell lines, cell death still occurred but was less pronounced than in monoculture.

Primary human prostate epithelial cells: In monoculture, widespread cell death occurred in response to all doses of UV radiation. In cocultures with LNCAP or PC3 cell lines, cell death still occurred but was less pronounced than in monoculture.

MCF7 cells: In monoculture, widespread cell death occurred in response to all doses of UV radiation. In coculture with primary human mammary epithelium, widespread cell death occurred in response to all doses of UV radiation.

BT474 cells: In monoculture, cell viability was minimally affected in response to all doses of UV radiation. In coculture with primary human mammary epithelium, cell viability was minimally affected in response to all doses of UV radiation.

LNCAP cells: In monoculture, cell viability was minimally affected in response to all doses of UV radiation. In coculture with primary human mammary epithelium, cell viability was minimally affected in response to all doses of UV radiation.

PC3 cells: In monoculture, widespread cell death occurred in response to all doses of UV radiation. In coculture with primary human mammary epithelium, cell death was surprisingly not significant.

The experimental design was as follows.

MCF7, COS7, LNCAP, PC3 and BT474 cells were loaded with 10 μM CellTracker Green dye while primary human mammary epithelial cells and primary human prostate epithelial cells were loaded with 10 μM CellTracker Red dye for 30 minutes at 37 degrees.

CellTracker dyes were removed and the cells washed 2× with PBS to remove all excess dye. Cells were split using TrypLE Express and counted.

For monocultures, 125,000 cells per well were seeded into poly-1-lysine coated Ibidi 3-well chamber slides. For co-cultures, 62,500 cells of each line were seeded per well. Cells were incubated overnight in a 37 degree cell culture incubator.

16 hours after cell seeding, cells were treated with UV radiation. On a one-by-one basis, cell culture media was removed from each slide and slides were placed in the device chamber at a predetermined X/Y/Z position with the target area centered over each well. After each slide was treated, cell culture media was replenished and the slides were incubated overnight in a 37 degree cell culture incubator. Three energy levels were tested: 100 millijoules (29 seconds), 50 millijoules (15 seconds) and 25 millijoules (8 seconds) per well. Control cells were treated identically except the UV device was not turned on; instead, the slides were placed in the device chamber for either 29/15/8 seconds per well as measured by a timer.

24 hours after irradiation, slides were treated with 3 μM DRAQ7 dye (to label dead cells) for 10 minutes at room temperature before being fixed for 30 minutes at room temperature using 4% PFA containing 1/1000 Hoechst nuclear dye. Fixative was removed, slides were washed 3×/well with PBS and silicone chamber gaskets were removed. 1 drop of ProLong Diamond Antifade mounting media was placed on each cell-containing region and a 24×60 mm glass coverslip overlaid. Slides were cured overnight protected from light before being imaged.

Image analysis was as follows.

The entire well of each chamber was scanned using a Yokogawa CQ1 spinning disc confocal microscope fitted with a 4× objective. Images were gathered using 1×1 binning for maximum resolution and stitched into single images in the Yokogawa CellPathfinder software suite. Analysis was restricted to a 2.5 mm×2.5 mm region of interest (ROI) that corresponds to the irradiated zone of the chamber. Each stitched image ROI was subjected to the following algorithmic analysis.

Analysis Overview:

Images were stitched into a single, full-chamber image.

The analysis region was restricted to a 2.5 mm×2.5 mm ROI corresponding to the irradiated region of the well.

The 4-channel data within the ROI is focused on for the following steps:

An erosion/dilation background subtraction is conducted using the Hoechst channel prior to identification of all Nuclei within the ROI using an adaptive thresholding paradigm.

Using the Nuclei as primary object ‘seeds’ the CellTracker channels are used to delineate Cell Bodies for each cell.

A machine-learning based algorithm then assigned each cell to one of four classes:

CellTracker Green only (Viable cell)

CellTracker Green+Draq7 (Dead cell)

CellTracker Red only (Viable cell)

CellTracker Red+Draq7 (Dead cell)

By isolating the Draq7 channel, the fidelity of the live/dead assignment can be confirmed.

Analysis Masks for only the Draq7 positive cells can be viewed to further confirm the gating paradigm.

FIG. 30A-30B plots of cell counts in effort to characterize viability.

FIGS. 31A-31K are representative images after different exposure level or doses of the different cell lines. Below is a summary of the results.

The effects of UV irradiation on cell viability were different for each cell line tested. Some cell lines showed a high degree of cell death in response to UV irradiation, while others were relatively more resistant.

UV irradiation caused significant cell death in both primary human mammary and primary human prostate epithelial cells in monoculture. In cocultures with cancer cell lines, primary cell death was still present but was less pronounced.

The two different prostate cancer cell lines exhibited markedly different levels of cell death, as did to the different breast cancer cell lines tested. This implies that a cell line's unique genetic background may be as significant in determining susceptibility to UV irradiation as any other variable.

Morphology of cells was notably different in monocultures vs. cocultures, as was the tendency of dead cells to remain present in the samples.

Most cell lines did not show a clear UV dose-dependent cell death response, suggesting that under these experimental conditions 25 mj was a "threshold" dose.

Many Variations

A wide variety of variations of the designs, configurations and implementations of the systems, devices and methods described herein are possible. For example, although multiple lenses are shown, for example, collector lens 18 collecting UV-C light from the UV-C emitters 14/emitter array 12, focusing lens 22 focusing UV-C light, and/or coupling lens 48 coupling UV-C light into the optical fiber 30, for example, in FIGS. 1, 2, and 3A, more or less lenses or lens elements may be used. For example, a lens may collect UV-C light from one or more UV-C light emitters 14 and focus the UV-C light down. Likewise, the collecting optics or collecting lens 18 collimate and/or focus the UV-C light down for directing onto the target 24 and/or the optical fiber 30. Other variations are possible.

As discussed above, the pulsed power source 16 may, for example, have controls and one or more of the frequency/rep rate such as pulse frequency, (e.g., 60 Hz, etc.), duty cycle (e.g., 50%) and/or dose duration (e.g., 40 seconds) may be varied with such controls. However, the pulse power source 16 may have knobs, dials, switches, etc., to control other parameters (e.g., brightness, etc.) in addition and/or in alternative. Additionally, the pulse power source 16 may, for example, have controls such as a keypad, touch screen, or the pulse power source 16 may be responsive to voice commands via, e.g., voice recognition. Other types of controls may be employed. Additionally, the control of such parameters is not limited to the pulse power source 16. Other electronics may provide such control.

Additionally, although a plurality of UV-C emitters 14 such as in an array of UV-C emitters 12 are described herein, in some implementations, the system, devices and/or methods described herein may employ a single UV-C emitter 14 such as a single solid state UV-C emitter like a single UV-C LED, for example, if the UV-C emitter is sufficiently powerful and/or is capable of emitting sufficient light. Accordingly, any of the designs, methods, or implementations described herein with respect to a plurality of UV-C emitters may apply to one or more UV-C emitters. Likewise, the systems, devices, units, methods, etc., and any characteristics, components, and/or features thereof described herein may apply to systems, devices, units, methods, etc. with at least one UV-C light emitter (e.g., at least one UV-C LED) or one or more UV-C light emitter (e.g., one or more UV-C LED) or one UV-C light emitter (e.g., one UV-C LED) and/or the characteristics, components, and/or features thereof.

Additionally, while various systems, devices, components, and methods have been discussed herein in connection with UV-C light, other types of UV light such as UV-B light may used. Accordingly, any of the systems, devices, methods, components, features discussed herein with regard to UV-C light, may apply more broadly to UV light and specifically apply to UV-B light (e.g., any one or more wavelength in the range of from 280-320 nm). Accordingly, some, much, most or all of the light (e.g., energy, power, radiant flux) output by the one or more light emitters, such as one or more UV light emitters (e.g., one or more UV LEDs), array of UV light emitters and/or the one or more UV light emitters (e.g., one or more UV LEDs) and/or transmitted through and/or output by the optical fiber and/or system and/or directed onto the target area (e.g., target tissue and/or cancerous tissue) such as 1% or more, 5% or more, 10% or more, 20% or more, 30% or more, 40% or more, 45% or more, 50% or more, 55% or more, 60% or more, 65% or more, 70% or more, 75% or more, 80% or more, 85% or more, 90% or more, 95% or more, 98% or more, 99% or more, 100%, or any range formed by any of these values (e.g., 5-10%, 10-20%, 20-30%, 40%-95% or 50% to 98% or 60% to 99% or 70% to 100% or 75% to 100%), may be in any range formed by any of 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 311 nm, 312 nm, 313 nm, 314 nm, 315 nm, 316 nm, 317 nm, 318 nm, 319 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, such as from 280 nm to 290 nm or from 290 to 300 nm or from 300 to 310 nm or from 310 to 320 nm or 310 to 325 nm, or 280 to 320 nm or 260 to 310 nm or 260 to 320 nm or 281 to 290 nm or 281 to 300 nm or possible higher or lower wavelengths. Likewise, in various implementations the one or more lenses (collecting optics or lens(es), focusing optics or lens(es), coupling optics or lens(es), output optics or lens(es) etc.) and/or the optical fiber are optically transmissive any such wavelengths (e.g., UV-B wavelengths). Accordingly, the system may emit UV light other than UV-C light such as UV-B light. The light source 12 and/or emitters 14 may emit UV light other than UV-C light such as UV-B light. The optical fiber 30 and/or the optics such as lenses may be optically transmissive to UV light other than UV-C light such at UV-B light. Such UV-B light may, for example, supplement the UV-C light. In some implementations, however, UV-B light instead of UV-C light is used. Other wavelengths, UV and/or non-UV wavelengths may also be included, for example, output the light source 12, transmitted by the optical fiber 30 and/or lens(es), output by the optical fiber and/or system 10, directed onto the target tissue (e.g., tumor(s) or cancerous tissue) 24 or any combination of these.

As discussed above, various systems, designs and methods described herein may potentially be employed to treat cancer. Accordingly, in various implementations, the systems, devices, units (e.g., UV-C light projection unit) described herein are configured for medical use. For example, the system, device or unit may include an outer surface on at least a portion thereof that is sterile. This portion may be at the distal end of the system, device, or unit. This portion may be configured to contact the patient and may, for example, be the outer surface of the endoscope (e.g., the outer surface of the sheath of the endoscope) or the outer surface of the tube of a laparoscope or the end of a handheld output tool, delivery device or handpiece. Similarly, at least a portion of the system, device or unit may be sterilizable. For example, the system, device, or unit may include an outer surface on at least a portion thereof that is sterilizable. This portion may be at the distal end of the system, device or unit. This portion may be configured to contact the patient and may, for example, be the outer surface of the endoscope (e.g., the outer surface of the sheath of the endoscope) or the outer surface of the tube of a laparoscope or the end of a handheld output tool, delivery device or handpiece. Likewise, the unit or device may be included in sterile packaging.

Additionally, although the UV-C light projection unit may be employed to treat cancer, the UV-C light projection unit need not be limited to such a particular application. The UV-C light projection unit may be employed in other applications, for example, that involve high UV-C fluences as well. Advantageously, the UV-C light projection unit may also be compact.

EXAMPLES

The following is a numbered list of example implementation that are within the scope of this disclosure. The examples that are listed should in no way be interpreted as limiting the scope of the potential implementations. Various features of the examples that are listed can be removed, added, or combined to form additional implementations, which are part of this disclosure.

Part I

1. A UV-C light projection unit comprising:
   an array of UV-C light emitters, said UV-C light emitters comprising UV-C light emitting diodes (LEDs) configured to emit light having a wavelength in the range of 250 to 280 nm that diverges; and
   UV-C collecting optics disposed to receive light emitted by said array of UV-C light emitters and to transmit said light and reduce said divergence.
2. The UV-C light projection unit of Example 1, wherein said array of UV-C light emitters has dimensions from 5 mm×10 mm to 50 mm×60 mm.
3. The UV-C light projection unit of Examples 1 or 2, wherein said UV-C light emitters of said array of UV-C light emitters extend across an area of 64 $mm^2$ to 2000 $mm^2$.
4. The UV-C light projection unit of Example 1, wherein said UV-C light emitters of said array of UV-C light emitters extend across an area of 0.01 $mm^2$ to 125 $mm^2$.
5. The UV-C light projection unit of Example 1, wherein said UV-C light emitters of said array of UV-C light emitters extend across an area of 0.1 $mm^2$ to 64 $mm^2$.
6. The UV-C light projection unit of Example 1, wherein said UV-C light emitters of said array of UV-C light emitters extend across an area of 0.25 $mm^2$ to 36 $mm^2$.
7. The UV-C light projection unit of any of the examples above, wherein said UV-C light emitters of said array have a center-to-center spacing of from 0.1 mm to 8 mm.
8. The UV-C light projection unit of any of the examples above, wherein said UV-C light emitters of said array have a center-to-center spacing of from 0.5 mm to 8 mm.
9. The UV-C light projection unit of any of the examples above, wherein said UV-C light emitters of said array of UV-C light emitters are formed on a single semiconductor substrate.
10. The UV-C light projection unit of any of the examples above, wherein said unit can fit in a suitcase.
11. The UV-C light projection unit of any of the examples above, wherein said UV-C collecting optics comprises one or more UV-C lenses.
12. The UV-C light projection unit of any of the examples above, wherein said UV-C collecting optics has positive optical power.
13. The UV-C light projection unit of any of the examples above, wherein said UV-C collecting optics comprises an aspheric lens comprising at least one aspheric surface configured to refract UV-C light.
14. The UV-C light projection unit of any of the examples above, wherein said UV-C collecting optics comprises a UV-C collimating optics configured to form a collimated beam from light from said array of UV-C light emitters.
15. The UV-C light projection unit of Example 14, wherein said UV-C collimating optics has a focal length and is positioned a focal length away from said array of UV-C light emitters such that said UVC collimating lens forms a collimated beam from light from said array of UV-C light emitters.
16. The UV-C light projection unit of Example 14, wherein said UV-C collimating optics has a focal length and is positioned less than a focal length away from said array of UV-C light emitters.
17. The UV-C light projection unit of Example 14, wherein said UV-C collimating optics has a focal length and is positioned a distance from 0.2 to 0.4 of the focal length away from said array of UV-C light emitters.
18. The UV-C light projection unit of any of the examples above, wherein said UV-C collecting optics comprises a single lens.
19. The UV-C light projection unit of any of the examples above, further comprising electronics configured to pulse said array of UV-C light emitters such that said array of UV-C light emitters emits pulses of UV-C light.
20. The UV-C light projection unit of any of Examples 1-18, further comprising electronics configured to cause said array of UV-C light emitters to output a pulse of UV-C light having a duration of, $T_{on}$.
21. The UV-C light projection unit of any of Examples 1-18, further comprising electronics configured to cause said array of UV-C light emitters to output a plurality of pulses of UV-C light having pulse durations of $T_{on}$.
22. The UV-C light projection unit of any of Examples 19-21, wherein a pulse of UV-C light output by said array of UV-C light emitters has a duration is in a range from 100 microseconds to 10 seconds.

23. The UV-C light projection unit of any of Examples 19-21, wherein a pulse of UV-C light output by said array of UV-C light emitters has a duration is in a range from 0.1 microseconds to 100 microseconds.
24. The UV-C light projection unit of any of Examples 19-23, wherein said electronics are configured to vary the duration of the pulse of UV-C light output by said array of UV-C light emitters.
25. The UV-C light projection unit of any of Examples 19-24, wherein a pulse of UV-C light output by said array of UV-C light emitters have a temporal spacing between consecutive pulses and said electronics is variable such that said temporal spacing between consecutive pulses can be varied.
26. The UV-C light projection unit of any of Examples 19-25, further comprising a button, switch, pedal, or touchscreen configured to cause a pulse of UV-C light to be emitted.
27. The UV-C light projection unit of any of Examples 26, wherein the duration over which the button, switch, pedal, or touchscreen is activated controls the duration of the pulse.
28. The UV-C light projection unit of any of Examples 19-25, further comprising a button, switch, pedal, or touchscreen configured to cause a plurality of pulses to be emitted.
29. The UV-C light projection unit of any of Examples 28, wherein the duration over which the button, switch, pedal, or touchscreen is activated controls the number of pulses emitted.
30. The UV-C light projection unit of any of Examples 1-18, further comprising electronics configured to cause said array of UV-C light emitters to output a group of pulses of UV-C light over a duration, $T_{on}$.
31. The UV-C light projection unit of Example 30, wherein said electronics is configured to cause said array of UV-C light emitters to output a plurality of groups of pulses of UV-C light having durations of $T_{on}$.
32. The UV-C light projection unit of Example 30 or 31, wherein said electronics is configured to cause said array of UV-C light emitters to output a plurality of groups of pulses of UV-C light and to not output said plurality of pulses of UV-C light for a time period $T_{off}$ between consecutive time periods $T_{on}$ during which said array of UV-C light emitters outputs respective ones of said groups of pulses of UV-C light.
33. The UV-C light projection unit of any of Examples 30-32, wherein a group of pulses of UV-C light output by said array of UV-C light emitters has a duration in a range from 100 microseconds to 10 seconds.
34. The UV-C light projection unit of any of Examples 30-32, wherein a pulse of UV-C light output by said array of UV-C light emitters has a duration in a range from 0.1 microseconds to 100 microseconds.
35. The UV-C light projection unit of any of Examples 30-34, wherein said electronics are configured to vary the duration of the group of pulses of UV-C light output by said array of UV-C light emitters.
36. The UV-C light projection unit of any of Examples 30-35, wherein groups of pulses of UV-C light output by said array of UV-C light emitters have a temporal spacing between consecutive groups of pulses and said electronics is variable such that said temporal spacing between consecutive groups of pulses can be varied.
37. The UV-C light projection unit of any of Examples 30-36, further comprising a button, switch, pedal, or touchscreen configured to cause a group of pulses of UV-C light to be emitted.
38. The UV-C light projection unit of any of Examples 37, wherein the duration over which the button, switch, pedal, or touchscreen is activated controls the duration of the group of pulses.
39. The UV-C light projection unit of any of Examples 30-36, further comprising a button, switch, pedal, or touchscreen configured to cause a plurality of groups of pulses to be emitted.
40. The UV-C light projection unit of any of Examples 39, wherein the duration over which the button, switch, or touchscreen is activated controls the number of groups of pulses emitted.
41. The UV-C light projection unit of any of Example 19-29, wherein said pulses of UV-C light output by said array of UV-C light emitters have a repetition rate and said electronics is variable such that said repetition rate can be varied.
42. The UV-C light projection unit of any of Examples 19 to 41, wherein said electronics comprises a pulsed power source.
43. The UV-C light projection unit of any of Examples 19-42, wherein said electronics comprises a variable pulsed power source configured to vary the repetition rate of pulses output by said array of UV-C light emitters.
44. The UV-C light projection unit of any of Examples 19-43, wherein said electronics comprises a variable pulsed power source configured to vary the duration of pulses output by said array of UV-C light emitters.
45. The UV-C light projection unit of any of Examples 19-44, wherein said electronics comprises a variable pulsed power source configured to vary the temporal spacing between consecutive pulses output by said array of UV-C light emitters.
46. The UV-C light projection unit of any of the examples above, further comprising UV-C focusing optics positioned to receive light from said array of UV-C emitters and to focus said light.
47. The UV-C light projection unit of Example 46, wherein said UV-C focusing optics are positioned to receive light from said array of UV-C emitters transmitted through said UV-C collecting optic.
48. The UV-C light projection unit of Example 46 or 47, wherein said UV-C collecting optics are disposed in an optical path between said array of UV-C emitters and said UV-C focusing optics.
49. The UV-C light projection unit of any of Examples 46-48, wherein said UV-C focusing optics comprises one or more UV-C lenses.
50. The UV-C light projection unit of any of Examples 46-49, wherein said UV-C focusing optics has positive optical power.
51. The UV-C light projection unit of any of Examples 46-50, wherein said UV-C focusing optics comprises an aspheric lens comprising at least one aspheric surface configured to refract UVC light.
52. The UV-C light projection unit of any of Examples 46-51, wherein said UV-C focusing optics comprises a lens doublet.
53. The UV-C light projection unit of any of Examples 46-51, wherein said UV-C focusing optics comprises a single lens.

54. The UV-C light projection unit of any of Examples 46-53, further comprising a fiber optic, said UV-C focusing optics configured to focus UV-C light from said array of UV-C emitters into said fiber optic.
55. The UV-C light projection unit of Example 54, further comprising a fiber coupling lens configured to receive light from said focusing optics and to decrease the divergence or increase convergence of said light coupled into the fiber optic.
56. The UV-C light projection unit of Example 54, further comprising a fiber coupling lens configured to receive light from said focusing optics and increase collimation of said light coupled into the fiber optic.
57. The UV-C light projection unit of any of Examples 1-53, further comprising a fiber optic, said array of UV-C emitters configured to couple UV-C light into said fiber optic.
58. The UV-C light projection unit of any of Examples 54-57, wherein said fiber optic comprises fused silica.
59. The UV-C light projection unit of any of Examples 54-58, wherein said fiber optic comprises an optical fiber.
60. The UV-C light projection unit of any of Examples 54-59, wherein said fiber optic comprises a single core optical fiber.
61. The UV-C light projection unit of any of Examples 54-60, wherein said fiber optic comprises a multi-mode optical fiber.
62. The UV-C light projection unit of any of Examples 54-61, wherein said fiber optic comprises an optical fiber having an optical core of at least 100 micrometers wide in cross-section.
63. The UV-C light projection unit of any of Examples 54-61, wherein said fiber optic comprises an optical fiber having an optical core of at least 250 micrometers wide in cross-section.
64. The UV-C light projection unit of any of Examples 54-61, wherein said fiber optic comprises an optical fiber having an optical core at least 600 micrometers wide in cross-section.
65. The UV-C light projection unit of any of Examples 54-61, wherein said fiber optic comprises an optical fiber having an optical core in the range of from 200 micrometers to 2500 micrometers wide in cross-section.
66. The UV-C light projection unit of any of Examples 54-61, wherein said fiber optic comprises an optical fiber having an optical core in the range of from 500 micrometers to 2500 micrometers wide in cross-section.
67. The UV-C light projection unit of any of Examples 54-61, wherein said fiber optic comprises an optical fiber having an optical core in the range of from 650 micrometers to 2500 micrometers wide in cross-section.
68. The UV-C light projection unit of any of Examples 54-61, wherein said fiber optic comprises an optical fiber having an optical core in the range from 700 micrometers to 2000 micrometers wide in cross-section.
69. The UV-C light projection unit of any of Examples 54-61, wherein said fiber optic comprises an optical fiber having an optical core in the range from 700 micrometers to 1500 micrometers wide in cross-section.
70. The UV-C light projection unit of any of Examples 54-61, wherein said fiber optic comprises an optical fiber having an optical core in the range from 800 micrometers to 1200 micrometers wide in cross-section.
71. The UV-C light projection unit of any of Examples 54-70, wherein said fiber optic has a length in a range from 6 inches to 2 feet long.
72. The UV-C light projection unit of any of Examples 54-70, wherein said fiber optic has a length in a range from 1 to 8 feet long.
73. The UV-C light projection unit of any of Examples 54-70, wherein said fiber optic has a length in a range from 4 to 12 feet long.
74. The UV-C light projection unit of any of Examples 54-70, wherein said fiber optic has a length in a range from 10 to 25 feet long.
75. The UV-C light projection unit of any of Examples 54-70, wherein said fiber optic has a length in a range from 1 to 30 feet long.
76. The UV-C light projection unit of any of Examples 54-70, wherein said fiber optic has a length in a range from 1.5 to 4 feet long.
77. The UV-C light projection unit of any of Examples 54-76, further comprising an output lens at the distal end of said optical fiber to receive light exiting the end of said fiber.
78. The UV-C light projection unit of any of Examples 54-76, further comprising an output lens at the distal end of said optical fiber to reduce divergence of light exiting the end of said fiber.
79. The UV-C light projection unit of any of Examples 54-76, further comprising an output lens at the distal end of said optical fiber to focus light exiting the end of said fiber.
80. The UV-C light projection unit of any of Examples 54-76, further comprising a lens at the distal end of said optical fiber to increase collimation of light exiting the end of said fiber.
81. The UV-C light projection unit of any of Examples 54-80, wherein said fiber optic has a core comprising silica.
82. The UV-C light projection unit of Example 81, wherein said silica includes a sufficiently high concentration of hydroxyl (OH) concentration such that said optical fiber transmits 250 nm.
83. The UV-C light projection unit of any of Examples 54-82, wherein said optical fiber further comprises a glass cladding.
84. The UV-C light projection unit of Example 83, wherein said glass cladding comprises doped glass.
85. The UV-C light projection unit of Example 83 or 84, wherein said glass cladding is fluorine doped.
86. The UV-C light projection unit of any of Examples 54-85, wherein said fiber optic has a core comprising fused silica.
87. The UV-C light projection unit of any of Examples 54-86, wherein said fiber optic comprises an optical fiber bundle.
88. The UV-C light projection unit of any of Examples 54-87, wherein said fiber optic forms part of or is optically coupled to an endoscope.
89. The UV-C light projection unit of Example 88, wherein said endoscope has a cross-sectional width or diameter at the distal end thereof of from 1 to 20 mm.
90. The UV-C light projection unit of Example 88, wherein said endoscope has a cross-sectional width or diameter at the distal end thereof of from 2 to 12 mm.

91. The UV-C light projection unit of any of Examples 88-90, wherein said endoscope comprises at least one relay lens or a least one fiber bundle to convey an image from the distal end of the endoscope to the proximal end of the endoscope.
92. The UV-C light projection unit of any of Examples 88-91, wherein said endoscope comprises a visible light emitters at the distal end thereof that provide illumination.
93. The UV-C light projection unit of any of Examples 88-92, wherein said endoscope comprises a camera at the distal end thereof to capture images.
94. The UV-C light projection unit of any of Examples 88-92, wherein said endoscope comprises a camera at the proximal end thereof to capture images or an ocular at the proximal end of the endoscope for viewing objects at the distal end of the endoscope.
95. The UV-C light projection unit of any of Examples 54-87, wherein said fiber optic forms part of or is optically coupled to a handheld output tool.
96. The UV-C light projection unit of Example 95, wherein said handheld output tool comprises a button or switch to activate output of UV-C light from said handheld output tool.
97. The UV-C light projection unit of any of Examples 95-96, wherein said handheld output tool has a cross-sectional width or diameter of from 10 to 60 mm.
98. The UV-C light projection unit of any of Examples 95-96, wherein said handheld output tool has a cross-sectional width or diameter of from 20 to 50 mm.
99. The UV-C light projection unit of any of Examples 95-98, wherein said handheld output tool has a tube at the distal end thereof.
100. The UV-C light projection unit of Example 99, wherein said tube has a cross-sectional width or diameter at the distal end thereof of from 1 to 12 mm.
101. The UV-C light projection unit of Example 99, wherein said tube has a cross-sectional width or diameter at the distal end thereof of from 2 to 15 mm.
102. The UV-C light projection unit of any of Examples 95-101, wherein said handheld output tool has a body that is contoured to ergonomically fit a hand.
103. The UV-C light projection unit of any of Examples 95-102, wherein said handheld output tool has a pistol grip.
104. The UV-C light projection unit of any of Examples 54-87, wherein said fiber optic is supported on an articulated arm or a robotic arm.
105. The UV-C light projection unit of Example 104, wherein said articulated or robotic arm further comprises a head at the distal end thereof wherein UV-C light is output.
106. The UV-C light projection unit of Examples 104 or 105, wherein said articulated or arm further comprises tube at the distal end thereof wherein UV-C light is output.
107. The UV-C light projection unit of Example 106, wherein said tube has a cross-sectional width or diameter at the distal end thereof of from 1 to 12 mm.
108. The UV-C light projection unit of Example 106, wherein said tube has a cross-sectional width or diameter at the distal end thereof of from 2 to 15 mm.
109. The UV-C light projection unit of any of Examples 54-87, wherein said fiber optic forms part of or is optically coupled to a translation stage.
110. The UV-C light projection unit of any of the examples above, wherein said UV-C light projection unit comprises a robotic system.
111. The UV-C light projection unit of any of the examples above, wherein said UV-C light projection unit comprises a robotic surgical system controllable by a surgeon.
112. The UV-C light projection unit of any of the examples above, wherein said array of UV-C light emitters outputs radiant flux in the range from 50 mW to 4000 mW.
113. The UV-C light projection unit of any of the examples above, wherein said array of UV-C light emitters outputs radiant flux in the range from 1 mW to 500 mW.
114. The UV-C light projection unit of any of the examples above, wherein said array of UV-C light emitters outputs radiant flux in the range from 1 μW to 5000 μW.
115. The UV-C light projection unit of any of the examples above, wherein said UVC light emitting diodes (LEDs) are configured to emit brightest in a wavelength in the range of 260 to 280 nm.
116. The UV-C light projection unit of any of the examples above, wherein said UVC light emitting diodes (LEDs) are configured to emit brightest in a wavelength in the range of 260 to 270 nm.
117. The UV-C light projection unit of any of the examples above, wherein said UVC light emitting diodes (LEDs) are configured to emit brightest at 265 nm.
118. The UV-C light projection unit of any of the examples above, wherein said array is configured to emit most UV-C light in the range of between 250 nm and 280 nm.
119. The UV-C light projection unit of any of the examples above, wherein said array is configured to emit most UV-C light in the range of between 260 nm and 270 nm.
120. The UV-C light projection unit of any of the examples above, wherein said array is configured to emit most UV light in the range of between 250 nm and 280 nm.
121. The UV-C light projection unit of any of the examples above, wherein said array is configured to emit most UV light in the range of between 260 nm and 270 nm.
122. The UV-C light projection unit of any of the examples above, wherein said array is configured to emit most light in the range of between 250 nm and 280 nm.
123. The UV-C light projection unit of any of the examples above, wherein said array is configured to emit most light in the range of between 260 nm and 270 nm.
124. The UV-C light projection unit of any of the examples above, wherein said array is configured to emit at least 70% of the UV-C light in the range of between 250 nm and 280 nm.
125. The UV-C light projection unit of any of the examples above, wherein said array is configured to emit at least 70% of the UV-C light in the range of between 260 nm and 270 nm.
126. The UV-C light projection unit of any of the examples above, wherein said array is configured to emit at least 70% of the UV light emitted therefrom in the range of between 250 nm and 280 nm.

127. The UV-C light projection unit of any of the examples above, wherein said array is configured to emit at least 70% of the UV light emitted therefrom in the range of between 260 nm and 270 nm.

128. The UV-C light projection unit of any of the examples above, wherein said array is configured to emit at least 70% of the light emitted therefrom in the range of between 250 nm and 280 nm.

129. The UV-C light projection unit of any of the examples above, wherein said array is configured to emit at least 70% of the light emitted therefrom in the range of between 260 nm and 270 nm.

130. The UV-C light projection unit of any of the Examples 54-91, wherein most of the UV-C light output from the fiber optic is in the range of between 250 nm and 280 nm.

131. The UV-C light projection unit of any of the Examples 54-91, wherein most of the UV-C light output from the fiber optic in the range of between 260 nm and 270 nm.

132. The UV-C light projection unit of any of the Examples 54-91, wherein most of the UV light output from the fiber optic in the range of between 250 nm and 280 nm.

133. The UV-C light projection unit of any of the Examples 54-91, wherein most of the UV light output from the fiber optic in the range of between 260 nm and 270 nm.

134. The UV-C light projection unit of any of the Examples 54-91, wherein most of the light output from the fiber optic in the range of between 250 nm and 280 nm.

135. The UV-C light projection unit of any of the Examples 54-91, wherein most of the light output from the fiber optic in the range of between 260 nm and 270 nm.

136. The UV-C light projection unit of any of the Examples 54-91, wherein at least 70% of the UV-C light output from the fiber optic is in the range of between 250 nm and 280 nm.

137. The UV-C light projection unit of any of the Examples 54-91, wherein at least 70% of the UV-C light output from the fiber optic in the range of between 260 nm and 270 nm.

138. The UV-C light projection unit of any of the Examples 54-91, wherein at least 70% of the UV light output from the fiber optic in the range of between 250 nm and 280 nm.

139. The UV-C light projection unit of any of the Examples 54-91, wherein at least 70% of the UV light output from the fiber optic in the range of between 260 nm and 270 nm.

140. The UV-C light projection unit of any of the Examples 54-91, wherein at least 70% of the light output from the fiber optic in the range of between 250 nm and 280 nm.

141. The UV-C light projection unit of any of the Examples 54-91, wherein at least 70% of the light output from the fiber optic in the range of between 260 nm and 270 nm.

142. The UV-C light projection unit of any of the examples above, wherein said UV-C collecting optics comprise at least one fused silica lens.

143. The UV-C light projection unit of any of the examples above, wherein said UV-C collecting optics comprise a single lens, and said single lens comprises fused silica lens.

144. The UV-C light projection unit of any of the examples above, wherein said UV-C focusing optics comprise at least one fused silica lens.

145. The UV-C light projection unit of any of the examples above, wherein said UV-C focusing optics comprise a single lens and said single lens comprises a fused silica lens.

146. The UV-C light projection unit of any of Examples 122-125, wherein said fused silica lens comprises fused silica having an internal transmittance corrected to eliminate the effects of scattering and surface reflection of UV-C light with 245-280 nm wavelength of at least 50% for fused silica glass having a thickness of 10 mm.

147. The UV-C light projection unit of any of Examples 122-125, wherein said fused silica lens comprises fused silica having an internal transmittance corrected to eliminate the effects of scattering and surface reflection of UV-C light with 245-280 nm wavelength of at least 95% for fused silica glass having a thickness of 10 mm.

148. The UV-C light projection unit of Example 126 or 127, wherein said fused silica lens has thickness in a range of from 0.1 mm to 10 mm.

149. The UV-C light projection unit of Example 126 or 127, wherein said fused silica lens has thickness in a range of from 0.1 mm to 9 mm.

150. The UV-C light projection unit of Example 126 or 127, wherein said fused silica lens has thickness in a range of from 0.1 mm to 5 mm.

151. The UV-C light projection unit of any of Examples 122-130, wherein said fused silica lens comprises fused silica wherein the OH content is not larger than 5 ppm.

152. The UV-C light projection unit of any of Examples 122-131, wherein said fused silica lens comprises fused silica wherein the content of each of Li, Na, K, Mg, Ca and Cu are smaller than 0.1 ppm.

153. The UV-C light projection unit of any of Examples 122-132, wherein said fused silica lens comprises fused silica fabricated by crystobalitizing powdery silica raw material and fusing the crystobalitized silica material in a non-reducing atmosphere.

154. The UV-C light projection unit of any of the examples above, wherein said UV-C light projection unit comprises at least part of an endoscope.

155. The UV-C light projection unit of any of the example above, wherein said UV-C light projection unit is optically coupled to an endoscope.

156. The UV-C light projection unit of any of the examples above, wherein said array of UV-C light emitters has a dimension along a side of between 8 mm to 50 mm.

157. The UV-C light projection unit of any of the examples above, wherein said array of UV-C light emitters has a dimension along one side of from 5 mm to 60 mm and a dimension along another side of from 5 to 60 mm.

158. The UV-C light projection unit of any of the examples above, wherein said array of UV-C light emitters has a dimension along a side of between 0.5 mm to 50 mm.

159. The UV-C light projection unit of any of the examples above, wherein said array of UV-C light emitters has a dimension along one side of from 0.5 mm to 50 mm and a dimension along another side of from 0.5 to 50 mm.

160. The UV-C light projection unit of any of the examples above, wherein the number of UV-C emitters in the array comprises from 2 to 6.

161. The UV-C light projection unit of any of the examples above, wherein the number of UV-C emitters in the array comprises from 3 to 5.

162. The UV-C light projection unit of any of the examples above, wherein the number of UV-C emitters in the array is 4.

163. The UV-C light projection unit of any of the examples above, wherein the number of UV-C emitters in the array comprises from 3 to 6.

164. The UV-C light projection unit of any of the examples above, wherein the number of UV-C emitters in the array comprises from 4 to 8.

165. The UV-C light projection unit of any of the examples above, wherein the number of UV-C emitters in the array comprises from 8 to 20.

166. The UV-C light projection unit of any of the examples above, wherein the number of UV-C emitters in the array comprises from 10 to 36.

167. The UV-C light projection unit of any of the examples above, wherein the UV-C collecting optics is disposed with respect to said array of UV-C light emitters to receive light emitted by said array of UV-C light emitters and to transmit said light and reduce said divergence.

168. The UV-C light projection unit of any of the examples above, wherein the UV-C collecting optics is configured to reduce said divergence thereby forming a UV-C light beam.

169. The UV-C light projection unit of Example 168, wherein said UV-C light beam comprises a collimated light beam.

170. The UV-C light projection unit of any of the examples above, wherein at least one of said UV-C light emitting diodes (LEDs) is configured to emit visible light.

171. The UV-C light projection unit of Example 170, further comprising a visible light emitter configured to emit visible light.

172. The UV-C light projection unit of Example 171, wherein said visible light emitter comprises a color LED.

173. The UV-C light projection unit of any of Examples 170-172, wherein said visible light can be used as a guide as to where UV-C light is directed at the target.

174. The UV-C light projection unit of any of Examples 170-173, wherein said visible light is color light.

175. The UV-C light projection unit of any of Examples 170-174, wherein said visible light is red, green, blue, or violet color light.

176. The UV-C light projection unit of any of Examples 170-175, wherein a UV-C light beam having a perimeter is formed at a target location by said UV-C light projection unit and said visible light forms a beam having a perimeter at said target location that matches the perimeter of the UV-C light beam to within 10% of the size of the UV-C light beam at said target location.

177. The UV-C light projection unit of any of Examples 170-175, wherein a UV-C light beam having a perimeter is formed at a target location by said UV-C light projection unit and said visible light forms a beam having a perimeter at said target location that matches the perimeter of the UV-C light beam to within 5% of the size of the UV-C light beam at said target location.

178. The UV-C light projection unit of any of the examples above, wherein said UV-C light projection unit outputs a UV-C light beam having a beamwidth (FWHM) of 20 mm or smaller at a target location.

179. The UV-C light projection unit of any of the examples above, wherein said UV-C light projection unit outputs a UV-C light beam having a beamwidth (FWHM) of 10 mm or smaller at a target location.

180. The UV-C light projection unit of any of the examples above, wherein said UV-C light projection unit outputs a UV-C light beam having a beamwidth (FWHM) of 5 mm or smaller at a target location.

181. The UV-C light projection unit of any of the examples above, wherein said UV-C light projection unit outputs a UV-C light beam having a beamwidth (FWHM) of 2 mm or smaller at a target location.

182. A kit comprising the UV-C light projection unit of any of the examples above, further comprising a plurality of output lenses configured to alter the size of the beam at a target location.

183. A kit comprising the UV-C light projection unit of Example 182, wherein said plurality of output lenses can be positioned at the output said UV-C projection unit to alter the size of the UV-C light beam at a target location.

184. A kit comprising the UV-C light projection unit of Example 182 or 183, wherein different output lenses of said plurality of output lenses can be positioned at the output said UV-C projection unit to provide a different respective size of the UV-C light beam at a target location.

185. The UV-C light projection unit of any of the examples above, wherein said an array of UV-C light emitting diodes (LEDs) are configured to emit light having a peak wavelength in the range of 260 to 270.

186. The UV-C light projection unit of any of the examples above, wherein said an array of UV-C light emitting diodes (LEDs) are configured to emit light having a peak wavelength in the range of 265 to 275.

187. The UV-C light projection unit of any of the examples above, wherein said an array of UV-C light emitting diodes (LEDs) are configured to emit light having a peak wavelength in the range of 263 to 267.

188. A UV-C light projection unit of any of the examples above, wherein the unit weighs from 15 lbs. to 80 lbs.

189. A UV-C light projection unit of any of the examples above, wherein the unit has a volume of from 200,000 $cm^3$ to 50,000 $cm^3$.

190. A UV-C light projection unit of any of the examples above, wherein the unit has a volume of from 100,000 $cm^3$ to 20,000 $cm^3$.

191. A UV-C light projection unit of any of the examples above, wherein the unit has a volume of from 30,000 $cm^3$ to 10,000 $cm^3$.

192. The UV-C light projection unit of any of the examples above, wherein said an array of UV-C light emitting diodes (LEDs) are configured to emit light having a peak wavelength with a bandwidth of 15 nm or less (FWHM).

193. The UV-C light projection unit of any of the examples above, wherein said an array of UV-C light emitting diodes (LEDs) are configured to emit light having a peak wavelength with a bandwidth of 12 nm or less (FWHM).

194. A method of treating cancer comprising exposing cancerous tissue or cell to UV-C provided by the UV-C light projection unit of any of the examples above.

195. The method of Example 194, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.

196. The method of Example 194, wherein said method is employed to treat leukemia.

197. The method of Example 194 or 196, wherein directing UV-C light onto said cancerous tissue or cells comprises directing UV-C light onto blood.

198. The method of any of Examples 194 or 196, wherein directing UV-C light onto said cancerous tissue or cells comprises directing UV-C light onto blood that has been extracted from the body of a patient.

199. The method of any of Examples 194-198, wherein said direction UV-C light onto said cancerous tissue or cell is performed ex vivo.

200. The UV-C light projection unit of any of the examples above, wherein said UV-C light projection unit is configured for medical use.

201. The UV-C light projection unit of any of the examples above, wherein said UV-C light projection unit includes an outer surface on at least a portion thereof that is sterile.

202. The UV-C light projection unit of any of the examples above, wherein said UV-C light projection unit includes an outer surface on at least a distal portion thereof that is sterile.

203. The UV-C light projection unit of any of the examples above, wherein said UV-C light projection unit includes an outer surface on portion thereof that is configured to contact a patient that is sterile.

204. The UV-C light projection unit of any of the examples above, wherein said UV-C light projection unit is include in sterile packaging.

205. The UV-C light projection unit of any of the examples above, wherein said UV-C light projection unit includes an outer surface on at least a portion thereof that is sterilizable.

206. The UV-C light projection unit of any of the examples above, wherein said UV-C light projection unit includes an outer surface on at least a distal portion thereof that is sterilizable.

207. The UV-C light projection unit of any of the examples above, wherein said UV-C light projection unit includes an outer surface on portion thereof that is configured to contact a patient that is sterilizable.

208. The UV-C light projection unit of any of the examples above, wherein said UV-C light projection unit comprises a cover configured to be positioned in front of an output of UV-C light.

209. The UV-C light projection unit of Example 208, wherein said cover is movable or switchable between first and second states without removing the cover from the body, the first state wherein said cover is positioned in front of said output of UV-C light and the second state wherein said cover provides less coverage in front of the output of UV-C light.

210. The UV-C light projection unit of Example 208 or 209, wherein said cover comprises a plurality of segments or sections that are movable so as to be positioned in first and second states without removing said cover from the body, said first state wherein said segments are in front of the output of UV-C light and said second state wherein said segments are moved to a position so as to provide less coverage in front of the output of UV-C light.

211. The UV-C light projection unit of any of Examples 208-210, further comprising a motor or actuator configured to move said cover or portions thereof.

212. The UV-C light projection unit of any of Examples 208-210, wherein the cover or portions thereof are configured to moved hydraulically.

213. The UV-C light projection unit of any of Examples 208-212, wherein said cover can be moved using a control located outside the body when the distal end of the UV-C light projection unit is in the body.

214. The UV-C light projection unit of of any of Examples 208-213, wherein said cover comprises an iris.

215. The UV-C light projection unit of any of Examples 208-214, wherein said cover is configured to be disposed in front of output optics and/or an optical fiber transmissive of UV-C light.

216. The UV-C light projection unit of any of Examples 208-215, wherein said cover UV-C light projection unit comprises or is part of an endoscope, said cover at the distal end of said endoscope.

217. The UV-C light projection unit of any of the examples above, wherein said cover UV-C light projection unit comprises or is part of a surgical tool having a tube for insertion into a body, said cover at the distal end of said tube.

218. The UV-C light projection unit of any of the examples above, further comprising shielding disposed with respect to said array of UV-C light emitters such that excluding UV-C light emission from the distal end of the optical fiber, UV-C light emissions 10 mm from said shielding is less than 1 $mJ/cm^2$ when said UV-C light emission from said distal end of said fiber optic cable is from 10 $mJ/cm^2$ to 100 $mJ/cm^2$.

219. The UV-C light projection unit of Example 218 above, wherein said UV-C light emissions, excluding UV-C light emission output from the distal end of said optical fiber, is 12 inches from said array is less than 1 $mJ/cm^2$ over an angular extent that is 180° in one direction and 70° in another orthogonal direction.

220. The UV-C light projection unit of Example 219, wherein said angular extent is 270° in one direction and 90° in another orthogonal direction.

221. The UV-C light projection unit of Example 219, wherein said angular extent of 360° in one direction and 90° in another orthogonal direction.

222. The UV-C light projection unit of any of Examples 218-221, said UV-C light emissions 12 inches from said array is less than 0.1 $mJ/cm^2$.

223. The UV-C light projection unit of any of Examples 218-221, said UV-C light emissions 12 inches from said array is less than 0.05 $mJ/cm^2$.

224. The UV-C light projection unit of any of Examples 218-221, said UV-C light emissions 12 inches from said array is less than 0.01 $mJ/cm^2$.

225. The UV-C light projection unit any of Examples 218-224, wherein said shielding comprises plastic.

226. The UV-C light projection unit of any of Examples 218-225, wherein said shielding comprises acrylic or polycarbonate.
227. The UV-C light projection unit of any of Examples 218-226, wherein said shielding is at least 3 mm thick.
228. The UV-C light projection unit of any of Examples 218-227, wherein said shielding is disposed about said array of UV-C light emitters on at least four sides.
229. The UV-C light projection unit of any of Examples 218-228, wherein said shielding is disposed about said array of UV-C light emitters on at least five sides.
230. The UV-C light projection unit of any of Examples 218-229, further comprising an optical fiber and shielding with respect to said distal end of said optical fiber that UV-C light emissions 12 inches from said distal end of said optical fiber is less than 1 $mJ/cm^2$ when UV-C light emission from said distal end of said fiber optic cable is from 10 $mJ/cm^2$ to 100 $mJ/cm^2$.
231. The UV-C light projection unit of Example 230, wherein said UV-C light emissions 12 inches from said distal end of said optical fiber is less than 1 $mJ/cm^2$ over an angular extent that is 180° in one direction and 70° in another orthogonal direction when said UV-C light emission from said distal end of said fiber optic cable is from 10 $mJ/cm^2$ to 100 $mJ/cm^2$.
232. The UV-C light projection unit of Example 231, wherein said angular extent is 270° in one direction and 90° in another orthogonal direction.
233. The UV-C light projection unit of Example 231, wherein said angular extent of 360° in one direction and 90° in another orthogonal direction.
234. The UV-C light projection unit of any of Examples 230-233, said UV-C light emissions 12 inches from said distal end of said optical fiber is less than 0.1 $mJ/cm^2$.
235. The UV-C light projection unit of any of Examples 230-234, said UV-C light emissions 12 inches from said distal end of said optical fiber is less than 0.05 $mJ/cm^2$.
236. The UV-C light projection unit of any of Examples 230-235, said UV-C light emissions 12 inches from said distal end of said optical fiber is less than 0.01 $mJ/cm^2$.
237. The UV-C light projection unit any of Examples 230-236, wherein said shielding comprises plastic.
238. The UV-C light projection unit of any of Examples 230-237, wherein said shielding comprises acrylic or polycarbonate.
239. The UV-C light projection unit of any of Examples 230-238, wherein said shielding is at least 3 mm thick.
240. The UV-C light projection unit of any of Examples 230-239, wherein said shielding is disposed about said distal end of said optical fiber of UV-C light emitters on at least four sides.
241. The UV-C light projection unit of any of Examples 230-240, wherein said shielding is disposed about said distal end of said optical fiber of UV-C light emitters on at least five sides.
242. The UV-C light projection unit of any of above, further comprising a mount for positioning said distal end of said optical fiber configured to receive UV-C light from said array of UV-C emitter with respect to a sample to direct UV-C light out of said distal end of said optical fiber and to said sample.
243. The UV-C light projection unit of any of above, configured for a sample on a microscope slide, in a petri dish or in a sample container.
244. The UV-C light projection unit of any of the examples above, wherein said optical fiber is included in, integrated with, or optically coupled to an endoscope or a hand held delivery device.
245. The UV-C light projection unit of any of the examples above, wherein said mount is configured to hold a distal end of said endoscope.
246. The UV-C light projection unit of any of the examples above, wherein said mount is configured to hold said hand held delivery device.
247. The UV-C light projection unit of any of the examples above, further comprising at least one fused silica lens configured to receive light emitted by said at least one light emitter having a wavelength in the UV wavelength range, said at least one fused silica lens comprising fused silica wherein the OH content is not larger than 5 ppm or wherein one or more of Li, Na, K, Mg, Ca and Cu are smaller than 0.1 ppm.
248. The UV-C light projection unit of any of the examples above, wherein the UV wavelength range in which said at least one UV light emitter emits light comprises the UV-C range.
249. The UV-C light projection unit of any of the examples above, wherein the UV wavelength range in which said at least one UV light emitter emits light comprises wavelengths in the range of from 200 to 280 nm.
250. The UV-C light projection unit of any of the examples above, wherein the UV wavelength range in which said at least one UV light emitter emits light comprises wavelengths in the range of from 280 to 325 nm.
251. The UV-C light projection unit of any of the examples above, wherein said optical fiber has a length of at least 7 feet.
252. The UV-C light projection unit of any of the examples above, wherein said optical fiber forms part of or is optically coupled to an endoscope.
253. The UV-C light projection unit of any of the examples above, further comprising shielding disposed with respect to said at least one UV light emitter such that, excluding output from a distal end of an optical fiber, light emission in said UV wavelength range at a location 10 mm from said shielding is less than 1 $mJ/cm^2$ when said UV light emission from said optical fiber is from 10 $mJ/cm^2$ to 100 $mJ/cm^2$.
254. The UV-C light projection unit of any of the examples above, further comprising shielding disposed with respect to said at least one UV light emitter such that, excluding output from a distal end of an optical fiber, said light in said UV wavelength range is less than 1 $mJ/cm^2$ over an angular extent that is 100° in one direction and 30° in another orthogonal direction 36 inches from said at least one UV light emitter when said UV light emission from said optical fiber is from 10 $mJ/cm^2$ to 100 $mJ/cm^2$.
255. The UV-C light projection unit of any of the examples above, further comprising a support on which a sample can be positioned to receive said light in said UV wavelength range from said distal end of said optical fiber.
256. The UV-C light projection unit of any of the examples above, further comprising a mount for positioning a distal end of an optical fiber configured to receive light in said UV wavelength range from said at least one UV light emitter with respect to a sample to direct light in said UV wavelength range out of said distal end of said optical fiber and to said sample.

257. The UV-C light projection unit of any of examples above, further comprising shielding disposed with respect to said distal end of said optical fiber to block light in said UV wavelength range output from said distal end of said optical fiber.

258. The UV-C light projection unit of Example 257, wherein said shielding is configured to block at least 50% of the light in said UV wavelength range output from said distal end of said optical fiber that is scattered or reflected from the sample in a direction above a support on which said sample is supported.

259. The UV-C light projection unit of Examples 257 or 258, wherein said UV light emission from said optical fiber at a location 10 mm from said shielding is less than 1 $mJ/cm^2$ when said UV light emission from said optical fiber is from 10 $mJ/cm^2$ to 100 $mJ/cm^2$.

260. The UV-C light projection unit of any of Examples 257-259, wherein said shielding is disposed with respect to said distal end of said optical fiber such that light emission in said UV wavelength range at a location 36 inches from said distal end of said optical fiber is less than 1 $mJ/cm^2$ when said UV light emission from said optical fiber is from 10 $mJ/cm^2$ to 100 $mJ/cm^2$.

261. The UV-C light projection unit of Example 260, wherein light emission in said UV wavelength range is less than 1 $mJ/cm^2$ over an angular extent that is 180° in one direction and 70° in another orthogonal direction 36 inches from said distal end of said optical fiber when said UV light emission from said optical fiber is from 10 $mJ/cm^2$ to 100 $mJ/cm^2$.

262. The UV-C light projection unit of any of the examples above, further comprising a plurality of output lenses configured to alter the size of a UV light beam at a target location when different ones of said output lenses are disposed at said distal end of said optical fiber at different times.

263. The UV-C light projection unit of Example 262, wherein said plurality of output lenses are configured to be attached at the output said UV light system to alter the size of the UV light beam at a target location.

264. A method comprising exposing cancerous tissue or cells to UV light provided by the system of any of the examples above.

265. The UV-C light projection unit of any of the examples above, wherein said optical fiber comprises separate fiber strands optically coupled together.

266. The UV-C light projection unit of any of the examples above, wherein said optical fiber comprises separate fiber strands butt coupled together.

267. The UV-C light projection unit of any Examples 1-264, wherein said optical fiber comprises a single fiber strand.

268. The system of any of the examples above, wherein excluding output from a distal end of said optical fiber, light emission from the system in said UV wavelength range is less than 1 $mJ/cm^2$ over a solid angle of $0.1\pi$ steradian at a distance of 36 inches from said distal end of said optical fiber when said light emission in said UV wavelength range from said optical fiber is from 10 $mJ/cm^2$ to 100 $mJ/cm^2$.

269. The system of any of the examples above, wherein excluding output from a distal end of said optical fiber, light emission from said system in said UV wavelength range is less than 1 $mJ/cm^2$ over a solid angle of $0.2\pi$ steradian at a distance of 36 inches from said distal end of said optical fiber when said light emission in said UV wavelength range from said optical fiber is from 10 $mJ/cm^2$ to 100 $mJ/cm^2$.

270. The system of any of the examples above, wherein excluding output from a distal end of said optical fiber, light emission from said system in said UV wavelength range is less than 1 $mJ/cm^2$ over a solid angle of $0.3\pi$ steradian at a distance of 36 inches from said distal end of said optical fiber when said light emission in said UV wavelength range from said optical fiber is from 10 $mJ/cm^2$ to 100 $mJ/cm^2$.

271. The system of any of the examples above, wherein excluding output from a distal end of said optical fiber, light emission from said system in said UV wavelength range is less than 1 $mJ/cm^2$ over a solid angle of $0.5\pi$ steradian at a distance of 36 inches from said distal end of said optical fiber when said light emission in said UV wavelength range from said optical fiber is from 10 $mJ/cm^2$ to 100 $mJ/cm^2$.

272. The system of any of the examples above, wherein a person applying light in said UV wavelength range to a patient is exposed to light emission from said system in said UV wavelength range of less than 1 $mJ/cm^2$ when said light emission in said UV wavelength range from said distal end of said fiber is from 10 $mJ/cm^2$ to 100 $mJ/cm^2$.

273. The system of Example 1, wherein a person applying light in said UV wavelength range to a patient is exposed to light emission from said system in said UV wavelength range of less than 0.05 $mJ/cm^2$ when said light emission in said UV wavelength range from said distal end of said fiber is from 10 $mJ/cm^2$ to 100 $mJ/cm^2$.

274. The system of Example 1, wherein a person applying light in said UV wavelength range to a patient is exposed to light emission from said system in said UV wavelength range of less than 0.01 $mJ/cm^2$ when said light emission in said UV wavelength range from said distal end of said fiber is from 10 $mJ/cm^2$ to 100 $mJ/cm^2$.

275. The system of any of the examples above, wherein excluding output from said distal end of said optical fiber, light emission from said system in said UV wavelength range is less than 1 $mJ/cm^2$ over the body of an operator holding the distal end of the fiber when said light emission in said UV wavelength range is from 10 $mJ/cm^2$ to 100 $mJ/cm^2$.

276. The system of any of the examples above, wherein, excluding possible output from said distal end of said optical fiber, an operator operating the system is exposed to light emission from said system of less than 1 $mJ/cm^2$ in said UV wavelength range when said light emission in said UV wavelength range from said distal end of said optical fiber is from 10 $mJ/cm^2$ to 100 $mJ/cm^2$.

Part II

1. A method of exposing cancerous tissue to UV-C light, said method comprising:
producing UV-C light from an array of UV-C light emitters, said UV-C light emitters comprising UV-C light emitting diodes (LEDs), said light having a wavelength in the range of 250 to 280 nm;
collecting light emitted by said array of UV-C light emitters with a UV-C collecting optics; and
directing UV-C light collected by said UV-C collecting optics onto said cancerous tissue.

2. The method of Example 1, further comprising directing said UV-C light onto said cancerous tissue using an endoscope.
3. The method of Example 1 or 2, further comprising coupling said UV-C light from said array of UV-C emitters into a fiber optic.
4. The method of Example 3, further comprising directing UV-C light collected by said UV-C collecting optics onto said cancerous tissue using said fiber optic.
5. The method of Example 3 or 4, further comprising focusing UV-C light from said collecting optics with focusing optics onto said into a fiber optic.
6. The method of any of Examples 3-5, wherein said fiber optic is part of or optically coupled to an endoscope.
7. The method of Example 1, further comprising focusing UV-C light from said collecting optic onto said cancerous tissue.
8. The method of Example 1, further comprising focusing UV-C light from said collecting optic with focusing optics onto said cancerous tissue.
9. The method of Examples 7, further comprising positioning said focusing optics to receive light from said collecting optic.
10. The method of any of Examples 7 or 8, wherein said focusing optics has a focal length and focusing UV-C light onto said cancerous tissue comprises positioning said cancerous tissue at a distance from said focusing optics about equal to said focal length.
11. The method of any of Examples 1-10, wherein said collecting optics comprises at least one fused silica lens.
12. The method of any of Examples 1-10, wherein said collecting optics comprises a single lens comprising a single fused silica lens.
13. The method of any of Examples 5, 8, 9, or 10, wherein said focusing optics comprises at least one fused silica lens.
14. The method of any of Examples 5, 8, 9, or 10, wherein said focusing optics comprises a single lens comprising a fused silica lens.
15. The method of any of Examples 11-14, wherein said fused silica lens comprises fused silica having an internal transmittance corrected to eliminate the effects of scattering and surface reflection of UV-C light with 245-280 nm wavelength of at least 90% for fused silica glass having a thickness of 10 mm.
16. The method of any of Examples 11-14, wherein said fused silica lens comprises fused silica having an internal transmittance corrected to eliminate the effects of scattering and surface reflection of UV-C light with 245-280 nm wavelength of at least 95% for fused silica glass having a thickness of 10 mm.
17. The method of any of Examples 15 or 16, wherein said fused silica lens has a thickness of 3-9 mm.
18. The method of any of Examples 11-17, wherein said fused silica lens comprises fused silica wherein the OH content is not larger than 5 ppm.
19. The method of any of Examples 11-18, wherein said fused silica lens comprises fused silica wherein the content of each of Li, Na, K, Mg, Ca and Cu are smaller than 0.1 ppm.
20. The method of any of Examples 11-19, wherein said fused silica lens comprises fused silica fabricated by crystobalitizing powdery silica raw material and fusing the crystobalitized silica material in a non-reducing atmosphere.
21. The method of any of the examples above, wherein said UV-C light emitters of said array of UV-C light emitters are formed on a single semiconductor substrate.
22. The method of any of Examples 1-21, wherein said UV-C light emitters of said array of UV-C light emitters are included in a single semiconductor chip.
23. The method of any of the examples above, wherein said UV-C collecting optics has a clear aperture of from 16 mm to 32 mm.
24. The method of any of the examples above, wherein said UV-C collecting optics has thickness of from 6 mm to 15 mm.
25. The method of any of the examples above, wherein said light having a wavelength in the range of 250 to 280 nm that diverges from said array of UV-C light emitters, further comprising reducing said divergence.
26. The method of any of the examples above, further comprising reducing the divergence of said UV-C light with said UV-C collecting optics.
27. The method of any of the examples above, further comprising forming a beam of UV-C light by reducing the divergence of said UV-C light.
28. The method of any of the examples above, wherein said UV-C light emitters of said array of UV-C light emitters are included in a single semiconductor chip.

Part III

1. A method of exposing cancerous tissue or cells to UV-C light, said method comprising:
   producing UV-C light;
   coupling said UV-C light into an optical fiber; and
   directing UV-C light onto said cancerous tissue or cells using said optical fiber,
   wherein most of said UV-C light directed onto said cancerous cells has a wavelength in the range of 250 to 280 nm.
2. The method of Example 1, wherein said most of the UV light output from said optical fiber and directed onto said cancerous tissue or cells is in the range of 250 to 280 nm.
3. The method of Example 1 or 2, wherein said most of the light output from said optical fiber and directed onto said cancerous tissue or cells is in the range of 250 to 280 nm.
4. The method of any of the examples above, wherein said most of the UV-C light output from said optical fiber and directed onto said cancerous tissue or cells is in the range of 260 to 270 nm.
5. The method of any of the examples above, wherein said most of the UV light output from said optical fiber and directed onto said cancerous tissue or cells is in the range of 260 to 270 nm.
6. The method of any of the examples above, wherein said most of the light output from said optical fiber and directed onto said cancerous tissue or cells is in the range of 260 to 270 nm.
7. The method of any of the examples above, wherein said fiber optic comprises an optical fiber having an optical core of at least 100 micrometers wide in cross-section.
8. The method of any of the examples above, wherein said fiber optic comprises an optical fiber having an optical core of at least 600 micrometers wide in cross-section.
9. The method of any of the examples above, wherein said fiber optic comprises fused silica.
10. The method of any of the examples above, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.

11. The method of any of the examples above, wherein said method is employed to treat leukemia.

12. The method of any of the examples above, wherein directing UV-C light onto said cancerous tissue or cells comprises directing UV-C light onto blood.

13. The method of any of the examples above, wherein directing UV-C light onto said cancerous tissue or cells comprises directing UV-C light onto blood that has been extracted from the body of a patient.

14. The method of any of the examples above, wherein said direction UV-C light onto said cancerous tissue or cell is performed ex vivo.

15. The method of any of the examples above, wherein producing said UV-C light comprises using at least one solid state UV-C light emitter.

16. The method of any of the examples above, wherein producing said UV-C light comprises using at least one UV-C light emitting diode (LED).

17. The method of any of the examples above, wherein producing said UV-C light comprises using an array of solid state UV-C light emitters.

18. The method of any of the examples above, wherein producing said UV-C light comprises using an array of UV-C light emitting diodes (LEDs).

29. The method of Example 17, wherein said UV-C light emitters of said array of UV-C light emitters are formed on a single semiconductor substrate.

30. The method of example 18, wherein said UV-C light emitting diodes (LEDs) of said array of UV-C light emitters are included in a single semiconductor chip.

19. The method of any of the examples above, wherein said optical fiber is part of or optically coupled to an endoscope.

20. The method of any of the examples above, wherein said optical fiber is supported by an articulated or robotic arm.

21. The method of any of the examples above, wherein said optical fiber comprises separate fiber strands butt coupled together.

22. The method of any Examples 1-267, wherein said optical fiber comprises single fiber strand.

Part IV

1. A UV-C light projection unit comprising:

at least one UV-C light emitter configured to emit light having a wavelength in the range of 250 to 280 nm; and an optical fiber configured to receive light from said at least one UV-C light emitter in the wavelength range of 250 to 280 nm and to transmit and output a portion of said light in the wavelength range of 250 to 280 nm.

2. The UV-C light projection unit of Example 1, wherein said at least one UV-C light emitter comprises a plurality of UV-C light emitters.

3. The UV-C light projection unit of Example 1 or 2, wherein said at least one UV-C light emitter comprises an array of UV-C light emitters.

4. The UV-C light projection unit of Example 3, wherein said UV-C light emitters of said array of UV-C light emitters extend across an area of 0.01 $mm^2$ to 125 $mm^2$.

5. The UV-C light projection unit of Examples 3 or 4, wherein said UV-C light emitters of said array have a center-to-center spacing of from 0.1 mm to 8 mm.

6. The UV-C light projection unit of any of Examples 3-5, wherein said UV-C light emitters of said array of UV-C light emitters are formed on a single semiconductor substrate.

7. The UV-C light projection unit of any of the examples above, wherein said unit can fit in a suitcase.

8. The UV-C light projection unit of any of the examples above, further comprising electronics configured to pulse said at least one UV-C light emitter such that said at least one UV-C light emitter emits pulses of UV-C light.

9. The UV-C light projection unit of Example 8, wherein said electronics comprises a pulsed power source.

10. The UV-C light projection unit of Example 8 or 9, wherein said electronics comprises a variable pulsed power source configured to vary the repetition rate of pulses output by said at least one UV-C light emitter.

11. The UV-C light projection unit of any of Examples 8-10, wherein said electronics comprises a variable pulsed power source configured to vary the duration of pulses output by said at least one UV-C light emitter.

12. The UV-C light projection unit of any of Examples 8-11, wherein said electronics comprises a variable pulsed power source configured to vary the temporal spacing between consecutive pulses output by said UV-C light emitters.

13. The UV-C light projection unit of any of the examples above, wherein said optical fiber comprises fused silica.

14. The UV-C light projection unit of any of the examples above, wherein said optical fiber has an optical core of at least 100 micrometers wide in cross-section.

15. The UV-C light projection unit of any of the examples above, wherein said optical fiber has an optical core of at least 250 micrometers wide in cross-section.

16. The UV-C light projection unit of any of the examples above, wherein said optical fiber has an optical core of at least 600 micrometers wide in cross-section.

17. The UV-C light projection unit of any of the examples above, wherein said optical fiber has an optical core in the range of from 200 micrometers to 2500 micrometers wide in cross-section.

18. The UV-C light projection unit of any of the examples above, wherein said optical fiber has an optical core in the range of from 500 micrometers to 2500 micrometers wide in cross-section.

19. The UV-C light projection unit of any of the examples above, wherein said optical fiber has an optical core in the range of from 650 micrometers to 2500 micrometers wide in cross-section.

20. The UV-C light projection unit of any of the examples above, wherein said optical fiber has an optical core in the range of from 700 micrometers to 2000 micrometers wide in cross-section.

21. The UV-C light projection unit of any of the examples above, wherein said optical fiber has an optical core in the range of from 200 micrometers to 1500 micrometers wide in cross-section.

22. The UV-C light projection unit of any of the examples above, wherein said optical fiber has an optical core in the range of from 800 micrometers to 1200 micrometers wide in cross-section.

23. The UV-C light projection unit of any of the examples above, wherein said optical fiber has a length in a range from 6 inches to 2 feet long.

24. The UV-C light projection unit of any of the examples above, wherein said optical has a length in a range from 1 to 8 feet long.

25. The UV-C light projection unit of any of the examples above, wherein said optical fiber has a length in a range from 4 to 12 feet long.

26. The UV-C light projection unit of any of the examples above, wherein said optical fiber has a length in a range from 10 to 25 feet long.

27. The UV-C light projection unit of any of the examples above, wherein said optical fiber has a length in a range from 1 to 30 feet long.

28. The UV-C light projection unit of any of the examples above, wherein said optical fiber has a length in a range from 1.5 to 4 feet long.

29. The UV-C light projection unit of any of the examples above, further comprising an output lens at the distal end of said optical fiber to receive light exiting the end of said fiber.

30. The UV-C light projection unit of any of examples above, further comprising an output lens at the distal end of said optical fiber to reduce divergence of light exiting the end of said fiber.

31. The UV-C light projection unit of any of the examples above, further comprising an output lens at the distal end of said optical fiber to focus light exiting the end of said fiber.

32. The UV-C light projection unit of any of the examples above, further comprising a lens at the distal end of said optical fiber to increase collimation of light exiting the end of said fiber.

33. The UV-C light projection unit of any of the examples above, wherein said optical fiber has a core comprising silica.

34. The UV-C light projection unit of Example 33, wherein said silica includes a sufficiently high concentration of hydroxyl (OH) concentration such that said optical fiber transmits 250 nm.

35. The UV-C light projection unit of any of the examples above, wherein said optical fiber further comprises a glass cladding.

36. The UV-C light projection unit of Example 35, wherein said glass cladding comprises doped glass.

37. The UV-C light projection unit of Example 35 or 36, wherein said glass cladding is fluorine doped.

38. The UV-C light projection unit of any of the examples above, wherein said optical fiber has a core comprising fused silica.

39. The UV-C light projection unit of any of the examples above, wherein said fiber optic forms part of or is optically coupled to an endoscope.

40. The UV-C light projection unit of Example 39, wherein said endoscope has a cross-sectional width or diameter at the distal end thereof of from 1 to 20 mm.

41. The UV-C light projection unit of Example 39, wherein said endoscope has a cross-sectional width or diameter at the distal end thereof of from 2 to 12 mm.

42. The UV-C light projection unit of any of Examples 39-41, wherein said endoscope comprises at least one relay lens or a least one fiber bundle to convey an image from the distal end of the endoscope to the proximal end of the endoscope.

43. The UV-C light projection unit of any of Examples 39-42, wherein said endoscope comprises a visible light emitter at the distal end thereof that provide illumination.

44. The UV-C light projection unit of any of Examples 39-43, wherein said endoscope comprises a camera at the distal end thereof to capture images.

45. The UV-C light projection unit of any of Examples 38-43, wherein said endoscope comprises a camera at the proximal end thereof to capture images or an ocular at the proximal end of the endoscope for viewing objects at the distal end of the endoscope.

46. The UV-C light projection unit of any of the examples above, wherein said fiber optic forms part of or is optically coupled to a handheld output tool.

47. The UV-C light projection unit of Example 46, wherein said handheld output tool comprises a button or switch to activate output of UV-C light from said handheld output tool.

48. The UV-C light projection unit of any of Examples 46-47, wherein said handheld output tool has a cross-sectional width or diameter of from 10 to 60 mm.

49. The UV-C light projection unit of any of Examples 46-47, wherein said handheld output tool has a cross-sectional width or diameter of from 20 to 50 mm.

50. The UV-C light projection unit of any of Examples 46-49, wherein said handheld output tool has a tube at the distal end thereof.

51. The UV-C light projection unit of Example 50, wherein said tube has a cross-sectional width or diameter at the distal end thereof of from 1 to 12 mm.

52. The UV-C light projection unit of Example 50, wherein said tube has a cross-sectional width or diameter at the distal end thereof of from 2 to 15 mm.

53. The UV-C light projection unit of any of Examples 46-52, wherein said handheld output tool has a body that is contoured to ergonomically fit a hand.

54. The UV-C light projection unit of any of Examples 46-53, wherein said handheld output tool has a pistol grip.

55. The UV-C light projection unit of any of the examples above, wherein said fiber optic is supported on an articulated arm or a robotic arm.

56. The UV-C light projection unit of Example 55, wherein said articulated or robotic arm further comprises a head at the distal end thereof wherein UV-C light is output.

57. The UV-C light projection unit of Examples 55 or 56, wherein said articulated or arm further comprises tube at the distal end thereof wherein UV-C light is output.

58. The UV-C light projection unit of Example 57, wherein said tube has a cross-sectional width or diameter at the distal end thereof of from 1 to 12 mm.

59. The UV-C light projection unit of Example 57, wherein said tube has a cross-sectional width or diameter at the distal end thereof of from 2 to 15 mm.

60. The UV-C light projection unit of any of the examples above, wherein said fiber optic forms part of or is optically coupled to a translation stage.

61. The UV-C light projection unit of any of the examples above, wherein said UV-C light projection unit comprises a robotic system.

62. The UV-C light projection unit of any of the examples above, wherein said UV-C light projection unit comprises a robotic surgical system controllable by a surgeon.
63. The UV-C light projection unit of any of the examples above, wherein at least one UV-C light emitter outputs radiant flux in the range from 50 mW to 4000 mW.
64. The UV-C light projection unit of any of the examples above, wherein said at least one UV-C light emitter outputs radiant flux in the range from 1 mW to 500 mW.
65. The UV-C light projection unit of any of the examples above, wherein said at least one UV-C light emitter outputs radiant flux in the range from 1 μW to 5000 μW.
66. The UV-C light projection unit of any of the examples above, wherein said at least one UV-C light emitter is configured to emit brightest in a wavelength in the range of 260 to 280 nm.
67. The UV-C light projection unit of any of the examples above, wherein said at least one UV-C light emitter is configured to emit brightest in a wavelength in the range of 260 to 270 nm.
68. The UV-C light projection unit of any of the examples above, wherein at least one UV-C light emitter is configured to emit brightest at 265 nm.
69. The UV-C light projection unit of any of the examples above, wherein said at least one UV-C light emitter is configured to emit most UV-C light in the range of between 250 nm and 280 nm.
70. The UV-C light projection unit of any of the examples above, wherein said at least one UV-C light emitter is configured to emit most UV-C light in the range of between 260 nm and 270 nm.
71. The UV-C light projection unit of any of the examples above, wherein said at least one UV-C light emitter is configured to emit most UV light in the range of between 250 nm and 280 nm.
72. The UV-C light projection unit of any of the examples above, wherein said at least one UV-C light emitter is configured to emit most UV light in the range of between 260 nm and 270 nm.
73. The UV-C light projection unit of any of the examples above, wherein said at least one UV-C light emitter is configured to emit most light in the range of between 250 nm and 280 nm.
74. The UV-C light projection unit of any of the examples above, wherein said at least one UV-C light emitter is configured to emit most light in the range of between 260 nm and 270 nm.
75. The UV-C light projection unit of any of the examples above, wherein said at least one UV-C light emitter is configured to emit at least 70% of the UV-C light in the range of between 250 nm and 280 nm.
76. The UV-C light projection unit of any of the examples above, wherein said at least one UV-C light emitter is configured to emit at least 70% of the UV-C light in the range of between 260 nm and 270 nm.
77. The UV-C light projection unit of any of the examples above, wherein said at least one UV-C light emitter is configured to emit at least 70% of the UV light emitted therefrom in the range of between 250 nm and 280 nm.
78. The UV-C light projection unit of any of the examples above, wherein said at least one UV-C light emitter is configured to emit at least 70% of the UV light emitted therefrom in the range of between 260 nm and 270 nm.
79. The UV-C light projection unit of any of the examples above, wherein said at least one UV-C light emitter is configured to emit at least 70% of the light emitted therefrom in the range of between 250 nm and 280 nm.
80. The UV-C light projection unit of any of the examples above, wherein said at least one UV-C light emitter is configured to emit at least 70% of the light emitted therefrom in the range of between 260 nm and 270 nm.
81. The UV-C light projection unit of any of the examples above, wherein most of the UV-C light output from the fiber optic is in the range of between 250 nm and 280 nm.
82. The UV-C light projection unit of any of the examples above, wherein most of the UV-C light output from the fiber optic in the range of between 260 nm and 270 nm.
83. The UV-C light projection unit of any of the examples above, wherein most of the UV light output from the fiber optic in the range of between 250 nm and 280 nm.
84. The UV-C light projection unit of any of the examples above, wherein most of the UV light output from the fiber optic in the range of between 260 nm and 270 nm.
85. The UV-C light projection unit of any of the examples above, wherein most of the light output from the fiber optic in the range of between 250 nm and 280 nm.
86. The UV-C light projection unit of any of the examples above, wherein most of the light output from the fiber optic in the range of between 260 nm and 270 nm.
87. The UV-C light projection unit of any of the examples above, wherein at least 70% of the UV-C light output from the fiber optic is in the range of between 250 nm and 280 nm.
88. The UV-C light projection unit of any of the examples above, wherein at least 70% of the UV-C light output from the fiber optic in the range of between 260 nm and 270 nm.
89. The UV-C light projection unit of any of the examples above, wherein at least 70% of the UV light output from the fiber optic in the range of between 250 nm and 280 nm.
90. The UV-C light projection unit of any of the examples above, wherein at least 70% of the UV light output from the fiber optic in the range of between 260 nm and 270 nm.
91. The UV-C light projection unit of any of the examples above, wherein at least 70% of the light output from the fiber optic in the range of between 250 nm and 280 nm.
92. The UV-C light projection unit of any of the examples above, wherein at least 70% of the light output from the fiber optic in the range of between 260 nm and 270 nm.
93. The UV-C light projection unit of any of the examples above, wherein said UV-C light projection unit comprises at least part of an endoscope.
94. The UV-C light projection unit of any of the examples above, wherein said UV-C light projection unit is optically coupled to an endoscope.
95. The UV-C light projection unit of any of the examples above, wherein said at least one light emitter comprises an array of UV-C light emitters that has a dimension along a side of between 8 mm to 50 mm.
96. The UV-C light projection unit of any of the examples above, wherein said at least one light emitter comprises an array of UV-C light emitters that has a dimension along one side of from 5 mm to 60 mm and a dimension along another side of from 5 to 60 mm.
97. The UV-C light projection unit of any of the examples above, wherein said at least one light emitter comprises an array of UV-C light emitters that has a dimension along a side of between 0.5 mm to 50 mm.

98. The UV-C light projection unit of any of the examples above, wherein said at least one light emitter comprises an array of UV-C light emitters that has a dimension along one side of from 0.5 mm to 50 mm and a dimension along another side of from 0.5 to 50 mm.
99. The UV-C light projection unit of any of the examples above, wherein said at least one light emitter comprises an array of UV-C emitters and the number of UV-C emitters in the array comprises from 2 to 6.
100. The UV-C light projection unit of any of the examples above, wherein said at least one light emitter comprises an array of UV-C emitters and the number of UV-C emitters in the array comprises from 3 to 5.
101. The UV-C light projection unit of any of the examples above, wherein said at least one light emitter comprises an array of UV-C emitters and the number of UV-C emitters in the array is 4.
102. The UV-C light projection unit of any of the examples above, wherein at least one UV-C light emitters is configured to emit visible light.
103. The UV-C light projection unit of any of Examples 1-101, further comprising a visible light emitter configured to emit visible light.
104. The UV-C light projection unit of Example 103, wherein said visible light emitter comprises a color LED.
105. The UV-C light projection unit of any of Examples 103-104, wherein said visible light can be used as a guide as to where UV-C light is directed at the target.
106. The UV-C light projection unit of any of Examples 103-105, wherein said visible light is color light.
107. The UV-C light projection unit of any of Examples 103-106, wherein said visible light is red, green, blue, or violet color light.
108. The UV-C light projection unit of any of Examples 103-107, wherein a UV-C light beam having a perimeter is formed at a target location by said UV-C light projection unit and said visible light forms a beam having a perimeter at said target location that matches the perimeter of the UV-C light beam to within 10% of the size of the UV-C light beam at said target location.
109. The UV-C light projection unit of any of Examples 103-108, wherein a UV-C light beam having a perimeter is formed at a target location by said UV-C light projection unit and said visible light forms a beam having a perimeter at said target location that matches the perimeter of the UV-C light beam to within 5% of the size of the UV-C light beam at said target location.
110. The UV-C light projection unit of any of the examples above, wherein said UV-C light projection unit outputs a UV-C light beam having a beamwidth (FWHM) of 20 mm or smaller at a target location.
111. The UV-C light projection unit of any of the examples above, wherein said UV-C light projection unit outputs a UV-C light beam having a beamwidth (FWHM) of 10 mm or smaller at a target location.
112. The UV-C light projection unit of any of the examples above, wherein said UV-C light projection unit outputs a UV-C light beam having a beamwidth (FWHM) of 5 mm or smaller at a target location.
113. The UV-C light projection unit of any of the examples above, wherein said UV-C light projection unit outputs a UV-C light beam having a beamwidth (FWHM) of 2 mm or smaller at a target location.
114. A kit comprising the UV-C light projection unit of any of the examples above, further comprising a plurality of output lenses configured to alter the size of the UV-C beam at a target location.
115. A kit comprising the UV-C light projection unit of Example 114, wherein said plurality of output lenses can be positioned at the output said UV-C projection unit to alter the size of the UV-C light beam at a target location.
116. A kit comprising the UV-C light projection unit of Example 114 or 115, wherein different output lenses of said plurality of output lenses can be positioned at the output of said UV-C projection unit to provide a different respective sizes of the UV-C light beam at a target location.
117. The UV-C light projection unit of any of the examples above, wherein said a least one light emitter is configured to emit light having a peak wavelength in the range of 260 to 270.
118. The UV-C light projection unit of any of the examples above, wherein said at least one UV-C light emitter is configured to emit light having a peak wavelength in the range of 265 to 275.
119. The UV-C light projection unit of any of the examples above, wherein said at least one UV-C light emitter is configured to emit light having a peak wavelength in the range of 263 to 267.
120. A UV-C light projection unit of any of the examples above, wherein the unit weighs from 15 lbs. to 80 lbs.
121. A UV-C light projection unit of any of the examples above, wherein the unit has a volume of from 200,000 $cm^3$ to 50,000 $cm^3$.
122. A UV-C light projection unit of any of the examples above, wherein the unit has a volume of from 100,000 $cm^3$ to 20,000 $cm^3$.
123. A UV-C light projection unit of any of the examples above, wherein the unit has a volume of from 30,000 $cm^3$ to 10,000 $cm^3$.
124. The UV-C light projection unit of any of the examples above, wherein said at least one UV-C light emitter is configured to emit light having a peak wavelength with a bandwidth of 15 nm or less (FWHM).
125. The UV-C light projection unit of any of the examples above, wherein said at least one UV-C light emitter is configured to emit light having a peak wavelength with a bandwidth of 12 nm or less (FWHM).
126. A method of treating cancer comprising exposing cancerous tissue or cells to UV-C light provided by the UV-C light projection unit of any of the examples above.
127. The method of Example 126, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.

128. The method of Example 126, wherein said method is employed to treat leukemia.

129. The method of Example 126 or 128, wherein directing UV-C light onto said cancerous tissue or cells comprises directing UV-C light onto blood.

130. The method of any of Examples 126 or 128, wherein directing UV-C light onto said cancerous tissue or cells comprises directing UV-C light onto blood that has been extracted from the body of a patient.

131. The method of any of Examples 127-130, wherein said direction UV-C light onto said cancerous tissue or cell is performed ex vivo.

132. The method of any of the examples above, wherein said at least one UV-C light emitter comprises a UV-C light emitting diode (LED).

133. The method of any of the examples above, wherein said at least one UV-C light emitter comprises a plurality of UV-C light emitting diodes (LEDs).

134. The method of any of the examples above, wherein said at least one UV-C light emitter comprises an array of UV-C light emitting diodes (LEDs).

135. The UV-C light projection unit of any of the examples above, wherein said UV-C light projection unit is configured for medical use.

136. The UV-C light projection unit of any of the examples above, wherein said UV-C light projection unit includes an outer surface on at least a portion thereof that is sterile.

137. The UV-C light projection unit of any of the examples above, wherein said UV-C light projection unit includes an outer surface on at least a distal portion thereof that is sterile.

138. The UV-C light projection unit of any of the examples above, wherein said UV-C light projection unit includes an outer surface on portion thereof that is configured to contact a patient that is sterile.

139. The UV-C light projection unit of any of the examples above, wherein said UV-C light projection unit is included in sterile packaging.

140. The UV-C light projection unit of any of the examples above, wherein said UV-C light projection unit includes an outer surface on at least a portion thereof that is sterilizable.

141. The UV-C light projection unit of any of the examples above, wherein said UV-C light projection unit includes an outer surface on at least a distal portion thereof that is sterilizable.

142. The UV-C light projection unit of any of the examples above, wherein said UV-C light projection unit includes an outer surface on portion thereof that is configured to contact a patient that is sterilizable.

143. The UV-C light projection unit of any of the examples above, wherein said UV-C light projection unit comprises a cover configured to be positioned in front of an output of UV-C light.

144. The UV-C light projection unit of Example 143, wherein said cover is movable or switchable between first and second states without removing the cover from the body, the first state wherein said cover is positioned in front of said output of UV-C light and the second state wherein said cover provides less coverage in front of the output of UV-C light.

145. The UV-C light projection unit of Example 143 or 144, wherein said cover comprises a plurality of segments or sections that are movable so as to be positioned in first and second states without removing said cover from the body, said first state wherein said segments are in front of the output of UV-C light and said second state wherein said segments are moved to a position so as to provide less coverage in front of the output of UV-C light.

146. The UV-C light projection unit of any of Examples 143-145, further comprising a motor or actuator configured to move said cover or portions thereof.

147. The UV-C light projection unit of any of Examples 143-146, wherein the cover or portions thereof are configured to moved hydraulically.

148. The UV-C light projection unit of any of Examples 143-147, wherein said cover can be moved using a control located outside the body when the distal end of the UV-C light projection unit is in the body.

149. The UV-C light projection unit of any of Examples 143-148, wherein said cover comprises an iris.

150. The UV-C light projection unit of any of Examples 143-149, wherein said cover is configured to be disposed in front of output optics and/or said optical fiber transmissive of UV-C light.

151. The UV-C light projection unit of any of Examples 143-150, wherein said cover UV-C light projection unit comprises or is part of an endoscope, said cover at the distal end of said endoscope.

152. The UV-C light projection unit of any of Examples 143-151, wherein said cover UV-C light projection unit comprises or is part of a surgical tool having a tube for insertion into a body, said cover at the distal end of said tube.

153. The UV-C light projection unit of any of the examples above, further comprising shielding disposed with respect to said array of UV-C light emitters such that excluding output from said distal end of said optical fiber, UV-C light emissions 10 mm from said shielding is less than 1 mJ/cm$^2$ when said UV-C light emission in said UV wavelength range from said distal end of said fiber is from 10 mJ/cm$^2$ to 100 mJ/cm$^2$.

154. The UV-C light projection unit of Example 153 above, wherein said UV-C light emissions 12 inches from said array is less than 1 mJ/cm$^2$ over an angular extent that is 180° in one direction and 70° in another orthogonal direction.

155. The UV-C light projection unit of Example 154, wherein said angular extent is 270° in one direction and 90° in another orthogonal direction.

156. The UV-C light projection unit of Example 154, wherein said angular extent of 360° in one direction and 90° in another orthogonal direction.

157. The UV-C light projection unit of any of Examples 153-156, said UV-C light emissions 12 inches from said array is less than 0.1 mJ/cm$^2$.

158. The UV-C light projection unit of any of Examples 153-156, said UV-C light emissions 12 inches from said array is less than 0.05 mJ/cm$^2$.

159. The UV-C light projection unit of any of Examples 153-156, said UV-C light emissions 12 inches from said array is less than 0.01 mJ/cm$^2$.

160. The UV-C light projection unit any of Examples 153-159, wherein said shielding comprises plastic.

161. The UV-C light projection unit of any of Examples 153-160, wherein said shielding comprises acrylic or polycarbonate.

162. The UV-C light projection unit of any of Examples 153-161, wherein said shielding is at least 3 mm thick.

163. The UV-C light projection unit of any of Examples 153-162, wherein said shielding is disposed about said array of UV-C light emitters on at least four sides.

164. The UV-C light projection unit of any of Examples 153-163, wherein said shielding is disposed about said array of UV-C light emitters on at least five sides.

165. The UV-C light projection unit of any of Examples 153-164, further comprising additional shielding with respect to said distal end of said optical fiber such that UV-C light emissions 12 inches from said distal end of said optical fiber is less than 1 $mJ/cm^2$ when said light emission in said UV wavelength range from said distal end of said fiber is from 10 $mJ/cm^2$ to 100 $mJ/cm^2$.

166. The UV-C light projection unit of Example 165, wherein said UV-C light emissions 12 inches from said distal end of said optical fiber is less than 1 $mJ/cm^2$ over an angular extent that is 180° in one direction and 70° in another orthogonal direction.

167. The UV-C light projection unit of Example 166, wherein said angular extent is 270° in one direction and 90° in another orthogonal direction.

168. The UV-C light projection unit of Example 167, wherein said angular extent of 360° in one direction and 90° in another orthogonal direction.

169. The UV-C light projection unit of any of Examples 165-168, said UV-C light emissions 12 inches from said distal end of said optical fiber is less than 0.1 $mJ/cm^2$.

170. The UV-C light projection unit of any of Examples 165-169, said UV-C light emissions 12 inches from said distal end of said optical fiber is less than 0.05 $mJ/cm^2$.

171. The UV-C light projection unit of any of Examples 165-170, said UV-C light emissions 12 inches from said distal end of said optical fiber is less than 0.01 $mJ/cm^2$.

172. The UV-C light projection unit any of Examples 165-171, wherein said shielding comprises plastic.

173. The UV-C light projection unit of any of Examples 165-172, wherein said shielding comprises acrylic or polycarbonate.

174. The UV-C light projection unit of any of Examples 165-173, wherein said shielding is at least 3 mm thick.

175. The UV-C light projection unit of any of Examples 165-174, wherein said shielding is disposed about said distal end of said optical fiber of UV-C light emitters on at least four sides.

176. The UV-C light projection unit of any of Examples 165-174, wherein said shielding is disposed about said distal end of said optical fiber of UV-C light emitters on at least five sides.

177. The UV-C light projection unit of any of above, further comprising a mount for positioning the distal end of said optical fiber configured to receive UV-C light from said array of UV-C emitter with respect to a sample to direct UV-C light out of said distal end of said optical fiber and to said sample.

178. The UV-C light projection unit of any of above, configured for a sample on a microscope slide, in a petri dish or in a sample container.

179. The UV-C light projection unit of any of above, further comprising shielding disposed with respect to said distal end of said optical fiber that UV-C light emissions 12 inches from said distal end of said optical fiber is less than 1 $mJ/cm^2$.

180. The UV-C light projection unit of any of the examples above, wherein said optical fiber is included in or integrated with an endoscope or a hand held delivery device.

181. The UV-C light projection unit of any of the examples above, wherein said mount is configured to hold a distal end of said endoscope.

182. The UV-C light projection unit of any of the examples above, wherein said mount is configured to hold said hand held delivery device.

183. The UV-C light projection unit of any of the examples above, further comprising at least one fused silica lens configured to receive light emitted by said at least one light emitter having a wavelength in the UV wavelength range, said at least one fused silica lens comprising fused silica wherein the OH content is not larger than 5 ppm or wherein one or more of Li, Na, K, Mg, Ca and Cu are smaller than 0.1 ppm.

184. The UV-C light projection unit of any of the examples above, wherein the UV wavelength range in which said at least one UV light emitter emits light comprises the UV-C range.

185. The UV-C light projection unit of any of the examples above, wherein the UV wavelength range in which said at least one UV light emitter emits light comprises wavelengths in the range of from 200 to 280 nm.

186. The UV-C light projection unit of any of the examples above, wherein the UV wavelength range in which said at least one UV light emitter emits light comprises wavelengths in the range of from 280 to 325 nm.

187. The UV-C light projection unit of any of the examples above, wherein said optical fiber has a length of at least 7 feet.

188. The UV-C light projection unit of any of the examples above, wherein said optical fiber forms part of or is optically coupled to an endoscope.

189. The UV-C light projection unit of any of the examples above, further comprising shielding disposed with respect to said at least one UV light emitter such that, excluding output from a distal end of said optical fiber, light emission in said UV wavelength range at a location 10 mm from said shielding is less than 1 $mJ/cm^2$ when said UV light emission from said optical fiber is from 10 $mJ/cm^2$ to 100 $mJ/cm^2$.

190. The UV-C light projection unit of any of the examples above, further comprising shielding disposed with respect to said at least one UV light emitter such that, excluding output from a distal end of said optical fiber, said light in said UV wavelength range is less than 1 $mJ/cm^2$ over an angular extent that is 120° in one direction and 40° in another orthogonal direction 36 inches from said at least one UV light emitter when said UV light emission from said distal end of said optical fiber is from 10 $mJ/cm^2$ to 100 $mJ/cm^2$.

191. The UV-C light projection unit of any of the examples above, further comprising a support on which a sample can be positioned to receive said light in said UV-C wavelength range from said distal end of said optical fiber.

192. The UV-C light projection unit of any of the examples above, further comprising a mount for positioning a distal end of said optical fiber configured to receive light in said UV-C wavelength range from said at least one UV-C light emitter with respect to a sample to direct light in said UV wavelength range out of said distal end of said optical fiber and to said sample.

193. The UV-C light projection unit of any of examples above, further comprising shielding disposed with respect to said distal end of said optical fiber to block light in said UV wavelength range output from said distal end of said optical fiber.

194. The UV-C light projection unit of Example 193, wherein said shielding is configured to block at least 50% of the light in said UV-C wavelength range output from said distal end of said optical fiber that is scattered or reflected from the sample in a direction above a support on which said sample is supported.

195. The UV-C light projection unit of Examples 193 or 194, wherein said UV light emission from said optical fiber at a location 10 mm from said shielding is less than 1 $mJ/cm^2$ when said UV light emission from said distal end of said optical fiber is from 10 $mJ/cm^2$ to 100 $mJ/cm^2$.

196. The UV-C light projection unit of any of Examples 193-195, wherein said shielding is disposed with respect to said distal end of said optical fiber such that light emission in said UV-C wavelength range at a location 36 inches from said distal end of said optical fiber is less than 1 $mJ/cm^2$ when said UV light emission from said distal end of said optical fiber is from 10 $mJ/cm^2$ to 100 $mJ/cm^2$.

197. The UV-C light projection unit of Example 196, wherein light emission in said UV wavelength range is less than 1 $mJ/cm^2$ over an angular extent that is 180° in one direction and 70° in another orthogonal direction 36 inches from said distal end of said optical fiber when said UV light emission from said distal end of said optical fiber is from 10 $mJ/cm^2$ to 100 $mJ/cm^2$.

198. The UV-C light projection unit of any of the examples above, further comprising a cover configured to be positioned in front of light in said UV wavelength range output by said optical fiber at the distal end thereof, said cover configured to provide protection against liquid or debris from blocking light in said wavelength range from being output from said optical fiber when said optical fiber is inserted into a body of a person or animal.

199. The UV-C light projection unit of any of the examples above, wherein said cover is movable or switchable between first and second states without removing the cover from the body, the first state wherein said cover is positioned in front of said optical output of optical fiber and the second state wherein said cover provides less coverage in front of the optical output of said optical fiber.

200. The UV-C light projection unit of any of the examples above, further comprising a plurality of output lenses configured to alter the size of a UV light beam at a target location when different ones of said output lenses are disposed at said distal end of said optical fiber at different times.

201. The UV-C light projection unit of Example 200, wherein said plurality of output lenses are configured to be attached at the output said UV light system to alter the size of the UV light beam at a target location.

202. A method comprising exposing cancerous tissue or cells to UV light provided by the system of any of the examples above.

203. The UV-C light projection unit of any of the examples above, wherein excluding output from a distal end of said optical fiber, light emission from the system in said UV wavelength range is less than 1 $mJ/cm^2$ over a solid angle of $0.1\pi$ steradian at a distance of 36 inches from said distal end of said optical fiber when said light emission in said UV wavelength range from said optical fiber is from 10 $mJ/cm^2$ to 100 $mJ/cm^2$.

204. The UV-C light projection unit of any of the examples above, wherein excluding output from a distal end of said optical fiber, light emission from said system in said UV wavelength range is less than 1 $mJ/cm^2$ over a solid angle of $0.2\pi$ steradian at a distance of 36 inches from said distal end of said optical fiber when said light emission in said UV wavelength range from said optical fiber is from 10 $mJ/cm^2$ to 100 $mJ/cm^2$.

205. The UV-C light projection unit of any of the examples above, wherein excluding output from a distal end of said optical fiber, light emission from said system in said UV wavelength range is less than 1 $mJ/cm^2$ over a solid angle of $0.3\pi$ steradian at a distance of 36 inches from said distal end of said optical fiber when said light emission in said UV wavelength range from said optical fiber is from 10 $mJ/cm^2$ to 100 $mJ/cm^2$.

206. The UV-C light projection unit of any of the examples above, wherein excluding output from a distal end of said optical fiber, light emission from said system in said UV wavelength range is less than 1 $mJ/cm^2$ over a solid angle of 0.5 steradian at a distance of 36 inches from said distal end of said optical fiber when said light emission in said UV wavelength range from said optical fiber is from 10 $mJ/cm^2$ to 100 $mJ/cm^2$.

207. The UV-C light projection unit of any of the examples above, wherein a person applying light in said UV wavelength range to a patient is exposed to light emission from said system in said UV wavelength range of less than 1 $mJ/cm^2$ when said light emission in said UV wavelength range from said distal end of said fiber is from 10 $mJ/cm^2$ to 100 $mJ/cm^2$.

208. The UV-C light projection unit of Example 1, wherein a person applying light in said UV wavelength range to a patient is exposed to light emission from said system in said UV wavelength range of less than 0.05 $mJ/cm^2$ when said light emission in said UV wavelength range from said distal end of said fiber is from 10 $mJ/cm^2$ to 100 $mJ/cm^2$.

209. The UV-C light projection unit of Example 1, wherein a person applying light in said UV wavelength range to a patient is exposed to light emission from said system in said UV wavelength range of less than 0.01 $mJ/cm^2$ when said light emission in said UV wavelength range from said distal end of said fiber is from 10 $mJ/cm^2$ to 100 $mJ/cm^2$.

210. The UV-C light projection unit of any of the examples above, wherein excluding output from a distal end of said optical fiber, light emission from said system in said UV wavelength range is less than 1 $mJ/cm^2$ over the body of an operator holding the distal end of the optical fiber when said light emission in said UV wavelength range from said distal end of said optical fiber is from 10 $mJ/cm^2$ to 100 $mJ/cm^2$.

211. The UV-C light projection unit of any of the examples above, wherein, excluding possible output from a distal end of said optical fiber, an operator operating the system is exposed to light emission from said system of less than 1 $mJ/cm^2$ in said UV wavelength range when said light emission in said UV wavelength range from said distal end of said optical fiber is from 10 $mJ/cm^2$ to 100 $mJ/cm^2$.

212. The UV-C light projection unit of any of the examples above, wherein said optical fiber comprises separate fiber strands optically coupled together.

213. The UV-C light projection unit of any of the examples above, wherein said optical fiber comprises separate fiber strands butt coupled together.

214. The UV-C light projection unit of any Examples 1-211, wherein said optical fiber comprises a single fiber strand.

Part V

1. A method of exposing cancerous cells to UV-C light, said method comprising:
   extracting a medium from a body of a person or animal, said medium having cancerous cells therein;
   producing UV-C light;
   directing UV-C light onto said cancerous cells in said medium extracted from said body of said person or animal; and
   returning said medium back to said body of said person or animal after exposing said cancerous cells to UV-C light.
2. The method of Example 1, wherein said medium comprises blood.
3. The method of Example 1 or 2, wherein said method is employed to treat leukemia.
4. The method of any of the examples above, wherein said UV-C light directed onto said cancerous cells has a wavelength in the range of 200 to 280 nm.
5. The method of any of the examples above, wherein most of said UV-C light directed onto said cancerous cells has a wavelength in the range of 250 to 280 nm.
6. The method of any of the examples above, wherein said most of the UV light directed onto said cancerous cells is in the range of 250 to 280 nm.
7. The method of any of the examples above, wherein said most of the light directed onto said cancerous cells is in the range of 250 to 280 nm.
8. The method of any of the examples above, wherein said most of the UV-C light directed onto said cancerous cells is in the range of 260 to 270 nm.
9. The method of any of the examples above, wherein said most of the UV light directed onto said cancerous cells is in the range of 260 to 270 nm.
10. The method of any of the examples above, wherein said most of the light directed onto said cancerous cells is in the range of 260 to 270 nm.
11. The method of any of the examples above, wherein producing said UV-C light comprises using at least one solid state UV-C light emitter.
12. The method of any of the examples above, wherein producing said UV-C light comprises using at least one UV-C light emitting diode (LED).
13. The method of any of the examples above, wherein producing said UV-C light comprises using plurality of solid state UV-C light emitters.
14. The method of any of the examples above, wherein producing said UV-C light comprises using a plurality of UV-C light emitting diodes (LEDs).
15. The method of any of the examples above, wherein producing said UV-C light comprises using an array of solid state UV-C light emitters.
16. The method of any of the examples above, wherein producing said UV-C light comprises using an array of UV-C light emitting diodes (LEDs).
17. The method of any of the examples above, wherein said UV-C light directed onto said cancerous cells has a wavelength in the range of 200 to 250 nm.
18. The method of any of the examples above, wherein said UV-C light directed onto said cancerous cells has a wavelength in the range of 200 to 230 nm.
19. The method of any of the examples above, wherein said UV-C light directed onto said cancerous cells has a spectral peak with a peak wavelength in the range of 200-210 nm.
20. The method of any of the examples above, wherein said UV-C light directed onto said cancerous cells has a spectral peak with a peak wavelength of 207 nm.
21. The method of any of the examples above, wherein said UV-C light directed onto said cancerous cells has a spectral peak with a peak wavelength in the range of 220-230 nm.
22. The method of any of the examples above, wherein said UV-C light directed onto said cancerous cells has a spectral peak with a peak wavelength of 222 nm.
23. The method of any of the examples above, wherein said optical fiber comprises separate fiber strands optically coupled together.
24. The method of any of the examples above, wherein said optical fiber comprises separate fiber strands butt coupled together.
25. The method of any Examples 1-22, wherein said optical fiber comprises a single fiber strand.

Part VI

1. A method of exposing cancerous tissue to UV-C light, said method comprising:
   producing UV-C light from one or more UV-C light emitters, said one or more UV-C light emitters comprising one or more UV-C light emitting diodes (LEDs), said light having a wavelength in the UV-C range;
   collecting light emitted by said array of UV-C light emitters with a UV-C collecting optics; and
   directing UV-C light collected by said UV-C collecting optics onto said cancerous tissue.
2. The method of Example 1, further comprising directing said UV-C light onto said cancerous tissue using an endoscope.
3. The method of Example 1 or 2, further comprising coupling said UV-C light from said array of UV-C emitters into a fiber optic.
4. The method of Example 3, further comprising directing UV-C light collected by said UV-C collecting optics onto said cancerous tissue using said fiber optic.
5. The method of Example 3 or 4, further comprising focusing UV-C light from said collecting optics with focusing optics onto said into a fiber optic.
6. The method of any of Examples 3-5, wherein said fiber optic is part of or optically coupled to an endoscope.
7. The method of Example 1, further comprising focusing UV-C light from said collecting optic onto said cancerous tissue.
8. The method of Example 1, further comprising focusing UV-C light from said collecting optic with focusing optics onto said cancerous tissue.
9. The method of Examples 7, further comprising positioning said focusing optics to receive light from said collecting optic.
10. The method of any of Examples 7 or 8, wherein said focusing optics has a focal length and focusing UV-C light onto said cancerous tissue comprises positioning said cancerous tissue at a distance from said focusing optics about equal to said focal length.

11. The method of any of Examples 1-10, wherein said collecting optics comprises at least one fused silica lens.

12. The method of any of Examples 1-10, wherein said collecting optics comprises a single lens comprising a single fused silica lens.

13. The method of any of Examples 5, 8, 9, or 10, wherein said focusing optics comprises at least one fused silica lens.

14. The method of any of Examples 5, 8, 9, or 10, wherein said focusing optics comprises a single lens comprising a fused silica lens.

15. The method of any of Examples 11-14, wherein said fused silica lens comprises fused silica having an internal transmittance corrected to eliminate the effects of scattering and surface reflection of UV-C light with 245-280 nm wavelength of at least 90% for fused silica glass having a thickness of 10 mm.

16. The method of any of Examples 11-14, wherein said fused silica lens comprises fused silica having an internal transmittance corrected to eliminate the effects of scattering and surface reflection of UV-C light with 245-280 nm wavelength of at least 95% for fused silica glass having a thickness of 10 mm.

17. The method of any of Examples 15 or 16, wherein said fused silica lens has a thickness of 3-9 mm.

18. The method of any of Examples 11-17, wherein said fused silica lens comprises fused silica wherein the OH content is not larger than 5 ppm.

19. The method of any of Examples 11-18, wherein said fused silica lens comprises fused silica wherein the content of each of Li, Na, K, Mg, Ca and Cu are smaller than 0.1 ppm.

20. The method of any of Examples 11-19, wherein said fused silica lens comprises fused silica fabricated by crystobalitizing powdery silica raw material and fusing the crystobalitized silica material in a non-reducing atmosphere.

21. The method of any of the examples above, wherein said UV-C light emitters of said array of UV-C light emitters are formed on a single semiconductor substrate.

22. The method of any of Examples 1-21, wherein said UV-C light emitters of said array of UV-C light emitters are included in a single semiconductor chip.

23. The method of any of the examples above, wherein said UV-C collecting optics has a clear aperture of from 16 mm to 32 mm.

24. The method of any of the examples above, wherein said UV-C collecting optics has thickness of from 6 mm to 15 mm.

25. The method of any of the examples above, wherein said UV-C light produced by said one or more UV-C emitters has a wavelength in the range of 200 to 280 nm.

26. The method of any of the examples above, wherein said UV-C light produced by said one or more UV-C emitters has a wavelength in the range of 250 to 280 nm.

27. The method of any of the examples above, wherein said UV-C light produced by said one or more UV-C emitters has a spectral peak with a peak wavelength in the range of 260-267 nm.

28. The method of any of the examples above, wherein said UV-C light produced by said one or more UV-C emitters has a spectral peak with a peak wavelength in the range of 265 nm.

29. The method of any of the examples above, wherein said light produced by said one or more UV-C emitters diverges from said one or more UV-C light emitters, further comprising reducing said divergence.

30. The method of any of the examples above, further comprising reducing the divergence of said UV-C light with said UV-C collecting optics.

31. The method of any of the examples above, further comprising forming a beam of UV-C light by reducing the divergence of said UV-C light.

32. The method of any of the examples above, wherein said UV-C light emitters of said array of UV-C light emitters are included in a single semiconductor chip.

33. The method of any of the examples above, wherein said UV-C light produced by said one or more UV-C emitters has a wavelength in the range of 200 to 250 nm.

34. The method of any of the examples above, wherein said UV-C light produced by said one or more UV-C emitters has a wavelength in the range of 200 to 230 nm.

35. The method of any of the examples above, wherein said UV-C light produced by said one or more UV-C emitters has a spectral peak with a peak wavelength in the range of 200-210 nm.

36. The method of any of the examples above, wherein said UV-C light produced by said one or more UV-C emitters has a spectral peak with a peak wavelength of 207 nm.

37. The method of any of the examples above, wherein said UV-C light produced by said one or more UV-C emitters has a spectral peak with a peak wavelength in the range of 220-230 nm.

38. The method of any of the examples above, wherein said UV-C light produced by said one or more UV-C emitters has a spectral peak with a peak wavelength of 222 nm.

39. The method of any of the examples above, wherein said optical fiber comprises separate fiber strands butt coupled together.

40. The method of any of the examples above, wherein said optical fiber comprises separate fiber strands optically coupled together.

41. The method of any Examples 1-38, wherein said optical fiber comprises a single fiber strand.

Part VII

1. A method of exposing cancerous tissue or cells to UV-C light, said method comprising:
producing UV-C light;
coupling said UV-C light into an optical fiber; and
directing UV-C light onto said cancerous tissue or cells using said optical fiber.

2. The method of Example 1, wherein said UV-C light directed onto said cancerous tissue or cells has a wavelength in the UV-C range of 200 to 280 nm.

3. The method of Example 1 or 2, wherein said UV-C light directed onto said cancerous tissue or cells has a wavelength in the UV-C range of 250 to 280 nm.

4. The method of any of the examples above, wherein said UV-C light directed onto said cancerous tissue or cells has a wavelength in the UV-C range of 260 to 270 nm.

5. The method of any of the examples above, wherein said most of the UV light output from said optical fiber and directed onto said cancerous tissue or cells is in the range of 250 to 280 nm.
6. The method of any of the examples above, wherein said most of the light output from said optical fiber and directed onto said cancerous tissue or cells is in the range of 250 to 280 nm.
7. The method of any of the examples above, wherein said most of the UV-C light output from said optical fiber and directed onto said cancerous tissue or cells is in the range of 260 to 270 nm.
8. The method of any of the examples above, wherein said most of the UV light output from said optical fiber and directed onto said cancerous tissue or cells is in the range of 260 to 270 nm.
9. The method of any of the examples above, wherein said most of the light output from said optical fiber and directed onto said cancerous tissue or cells is in the range of 260 to 270 nm.
10. The method of any of the examples above, wherein said fiber optic comprises an optical fiber having an optical core of at least 100 micrometers wide in cross-section.
11. The method of any of the examples above, wherein said fiber optic comprises an optical fiber having an optical core of at least 600 micrometers wide in cross-section.
12. The method of any of the examples above, wherein said fiber optic comprises fused silica.
13. The method of any of the examples above, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.
14. The method of any of the examples above, wherein said method is employed to treat leukemia.
15. The method of any of the examples above, wherein directing UV-C light onto said cancerous tissue or cells comprises directing UV-C light onto blood.
16. The method of any of the examples above, wherein directing UV-C light onto said cancerous tissue or cells comprises directing UV-C light onto blood that has been extracted from the body of a patient.
17. The method of any of the examples above, wherein said direction UV-C light onto said cancerous tissue or cell is performed ex vivo.
18. The method of any of the examples above, wherein producing said UV-C light comprises using at least one solid state UV-C light emitter.
19. The method of any of the examples above, wherein producing said UV-C light comprises using at least one UV-C light emitting diode (LED).
20. The method of any of the examples above, wherein producing said UV-C light comprises using an array of solid state UV-C light emitters.
21. The method of any of the examples above, wherein producing said UV-C light comprises using an array of UV-C light emitting diodes (LEDs).
42. The method of Example 18, wherein said UV-C light emitters of said array of UV-C light emitters are formed on a single semiconductor substrate.
43. The method of example 19, wherein said UV-C light emitting diodes (LEDs) of said array of UV-C light emitters are included in a single semiconductor chip.
22. The method of any of the examples above, wherein said optical fiber is part of or optically coupled to an endoscope.
23. The method of any of the examples above, wherein said optical fiber is supported by an articulated or robotic arm.
44. The method of any of the examples above, wherein said UV-C light directed onto said cancerous tissue or cells has a wavelength in the range of 200 to 250 nm.
45. The method of any of the examples above, wherein said UV-C light directed onto said cancerous tissue or cells has a wavelength in the range of 200 to 230 nm.
46. The method of any of the examples above, wherein said UV-C light directed onto said cancerous tissue or cells has a spectral peak with a peak wavelength in the range of 200-210 nm.
47. The method of any of the examples above, wherein said UV-C light directed onto said cancerous tissue or cells has a spectral peak with a peak wavelength of 207 nm.
48. The method of any of the examples above, wherein said UV-C light directed onto said cancerous tissue or cells has a spectral peak with a peak wavelength in the range of 220-230 nm.
49. The method of any of the examples above, wherein said UV-C light directed onto said cancerous tissue or cells has a spectral peak with a peak wavelength of 222 nm.
50. The method of any of the examples above, wherein said optical fiber comprises separate fiber strands optically coupled together.
51. The method of any of the examples above, wherein said optical fiber comprises separate fiber strands butt coupled together.
52. The method of any Examples 1-46, wherein said optical fiber comprises a single fiber strand.

Part VIII

1. A UV-C light projection unit comprising:
   at least one UV-C light emitter configured to emit light having a wavelength in the UV-C range; and
   an optical fiber configured to receive light from said at least one UV-C light emitter in UV-C range and to transmit and output a portion of said light in the UV-C.
2. The UV-C light projection unit of Example 1, wherein said at least one UV-C light emitter comprises a plurality of UV-C light emitters.
3. The UV-C light projection unit of Example 1 or 2, wherein said at least one UV-C light emitter comprises an array of UV-C light emitters.

4. The UV-C light projection unit of Example 3, wherein said UV-C light emitters of said array of UV-C light emitters extend across an area of 0.01 $mm^2$ to 125 $mm^2$.

5. The UV-C light projection unit of Examples 3 or 4, wherein said UV-C light emitters of said array have a center-to-center spacing of from 0.1 mm to 8 mm.

6. The UV-C light projection unit of any of Examples 3-5, wherein said UV-C light emitters of said array of UV-C light emitters are formed on a single semiconductor substrate.

7. The UV-C light projection unit of any of the examples above, wherein said unit can fit in a suitcase.

8. The UV-C light projection unit of any of the examples above, further comprising electronics configured to pulse said at least one UV-C light emitter such that said at least one UV-C light emitter emits pulses of UV-C light.

9. The UV-C light projection unit of Example 8, wherein said electronics comprises a pulsed power source.

10. The UV-C light projection unit of Example 8 or 9, wherein said electronics comprises a variable pulsed power source configured to vary the repetition rate of pulses output by said at least one UV-C light emitter.

11. The UV-C light projection unit of any of Examples 8-10, wherein said electronics comprises a variable pulsed power source configured to vary the duration of pulses output by said at least one UV-C light emitter.

12. The UV-C light projection unit of any of Examples 8-11, wherein said electronics comprises a variable pulsed power source configured to vary the temporal spacing between consecutive pulses output by said UV-C light emitters.

13. The UV-C light projection unit of any of the examples above, wherein said optical fiber comprises fused silica.

14. The UV-C light projection unit of any of the examples above, wherein said optical fiber has an optical core of at least 100 micrometers wide in cross-section.

15. The UV-C light projection unit of any of the examples above, wherein said optical fiber has an optical core of at least 250 micrometers wide in cross-section.

16. The UV-C light projection unit of any of the examples above, wherein said optical fiber has an optical core of at least 600 micrometers wide in cross-section.

17. The UV-C light projection unit of any of the examples above, wherein said optical fiber has an optical core in the range of from 200 micrometers to 2500 micrometers wide in cross-section.

18. The UV-C light projection unit of any of the examples above, wherein said optical fiber has an optical core in the range of from 500 micrometers to 2500 micrometers wide in cross-section.

19. The UV-C light projection unit of any of the examples above, wherein said optical fiber has an optical core in the range of from 650 micrometers to 2500 micrometers wide in cross-section.

20. The UV-C light projection unit of any of the examples above, wherein said optical fiber has an optical core in the range of from 700 micrometers to 2000 micrometers wide in cross-section.

21. The UV-C light projection unit of any of the examples above, wherein said optical fiber has an optical core in the range of from 200 micrometers to 1500 micrometers wide in cross-section.

22. The UV-C light projection unit of any of the examples above, wherein said optical fiber has an optical core in the range of from 800 micrometers to 1200 micrometers wide in cross-section.

23. The UV-C light projection unit of any of the examples above, wherein said optical fiber has a length in a range from 6 inches to 2 feet long.

24. The UV-C light projection unit of any of the examples above, wherein said optical has a length in a range from 1 to 8 feet long.

25. The UV-C light projection unit of any of the examples above, wherein said optical has a length in a range from 4 to 12 feet long.

26. The UV-C light projection unit of any of the examples above, wherein said optical fiber has a length in a range from 10 to 25 feet long.

27. The UV-C light projection unit of any of the examples above, wherein said optical fiber has a length in a range from 1 to 30 feet long.

28. The UV-C light projection unit of any of the examples above, wherein said optical fiber has a length in a range from 1.5 to 4 feet long.

29. The UV-C light projection unit of any of the examples above, further comprising an output lens at the distal end of said optical fiber to receive light exiting the end of said optical fiber.

30. The UV-C light projection unit of any of examples above, further comprising an output lens at the distal end of said optical fiber to reduce divergence of light exiting the end of said fiber.

31. The UV-C light projection unit of any of the examples above, further comprising an output lens at the distal end of said optical fiber to focus light exiting the end of said fiber.

32. The UV-C light projection unit of any of the examples above, further comprising a lens at the distal end of said optical fiber to increase collimation of light exiting the end of said fiber.

33. The UV-C light projection unit of any of the examples above, wherein said optical fiber has a core comprising silica.

34. The UV-C light projection unit of Example 33, wherein said silica includes a sufficiently high concentration of hydroxyl (OH) concentration such that said optical fiber transmits 250 nm.

35. The UV-C light projection unit of any of the examples above, wherein said optical fiber further comprises a glass cladding.

36. The UV-C light projection unit of Example 35, wherein said glass cladding comprises doped glass.

37. The UV-C light projection unit of Example 35 or 36, wherein said glass cladding is fluorine doped.

38. The UV-C light projection unit of any of the examples above, wherein said optical fiber has a core comprising fused silica.

39. The UV-C light projection unit of any of the examples above, wherein said fiber optic forms part of or is optically coupled to an endoscope.

40. The UV-C light projection unit of Example 39, wherein said endoscope has a cross-sectional width or diameter at the distal end thereof of from 1 to 20 mm.

41. The UV-C light projection unit of Example 39, wherein said endoscope has a cross-sectional width or diameter at the distal end thereof of from 2 to 12 mm.

42. The UV-C light projection unit of any of Examples 39-41, wherein said endoscope comprises at least one relay lens or a least one fiber bundle to convey an image from the distal end of the endoscope to the proximal end of the endoscope.

43. The UV-C light projection unit of any of Examples 39-42, wherein said endoscope comprises a visible light emitter at the distal end thereof that provide illumination.

44. The UV-C light projection unit of any of Examples 39-43, wherein said endoscope comprises a camera at the distal end thereof to capture images.
45. The UV-C light projection unit of any of Examples 38-43, wherein said endoscope comprises a camera at the proximal end thereof to capture images or an ocular at the proximal end of the endoscope for viewing objects at the distal end of the endoscope.
46. The UV-C light projection unit of any of the examples above, wherein said fiber optic forms part of or is optically coupled to a handheld output tool.
47. The UV-C light projection unit of Example 46, wherein said handheld output tool comprises a button or switch to activate output of UV-C light from said handheld output tool.
48. The UV-C light projection unit of any of Examples 46-47, wherein said handheld output tool has a cross-sectional width or diameter of from 10 to 60 mm.
49. The UV-C light projection unit of any of Examples 46-47, wherein said handheld output tool has a cross-sectional width or diameter of from 20 to 50 mm.
50. The UV-C light projection unit of any of Examples 46-49, wherein said handheld output tool has a tube at the distal end thereof.
51. The UV-C light projection unit of Example 50, wherein said tube has a cross-sectional width or diameter at the distal end thereof of from 1 to 12 mm.
52. The UV-C light projection unit of Example 50, wherein said tube has a cross-sectional width or diameter at the distal end thereof of from 2 to 15 mm.
53. The UV-C light projection unit of any of Examples 46-52, wherein said handheld output tool has a body that is contoured to ergonomically fit a hand.
54. The UV-C light projection unit of any of Examples 46-53, wherein said handheld output tool has a pistol grip.
55. The UV-C light projection unit of any of the examples above, wherein said fiber optic is supported on an articulated arm or a robotic arm.
56. The UV-C light projection unit of Example 55, wherein said articulated or robotic arm further comprises a head at the distal end thereof wherein UV-C light is output.
57. The UV-C light projection unit of Examples 55 or 56, wherein said articulated or arm further comprises tube at the distal end thereof wherein UV-C light is output.
58. The UV-C light projection unit of Example 57, wherein said tube has a cross-sectional width or diameter at the distal end thereof of from 1 to 12 mm.
59. The UV-C light projection unit of Example 57, wherein said tube has a cross-sectional width or diameter at the distal end thereof of from 2 to 15 mm.
60. The UV-C light projection unit of any of the examples above, wherein said fiber optic forms part of or is optically coupled to a translation stage.
61. The UV-C light projection unit of any of the examples above, wherein said UV-C light projection unit comprises a robotic system.
62. The UV-C light projection unit of any of the examples above, wherein said UV-C light projection unit comprises a robotic surgical system controllable by a surgeon.
63. The UV-C light projection unit of any of the examples above, wherein at least one UV-C light emitter outputs radiant flux in the range from 50 mW to 4000 mW.
64. The UV-C light projection unit of any of the examples above, wherein said at least one UV-C light emitter outputs radiant flux in the range from 1 mW to 500 mW.
65. The UV-C light projection unit of any of the examples above, wherein said at least one UV-C light emitter outputs radiant flux in the range from 1 μW to 5000 μW.
66. The UV-C light projection unit of any of the examples above, wherein said at least one UV-C light emitter is configured to emit light in the UV-C range having a wavelength in the range of 200 to 280 nm.
67. The UV-C light projection unit of any of the examples above, wherein said at least one UV-C light emitter is configured to emit light having a wavelength in the range of 250 to 280 nm and said optical fiber is configured to receive light from said at least one UV-C light emitter in the wavelength range of 250 to 280 nm and to transmit and output a portion of said light in the wavelength range of 250 to 280 nm.
68. The UV-C light projection unit of any of the examples above, wherein said at least one UV-C light emitter is configured to emit brightest in a wavelength in the range of 250 to 280 nm.
69. The UV-C light projection unit of any of the examples above, wherein said at least one UV-C light emitter is configured to emit brightest in a wavelength in the range of 260 to 280 nm.
70. The UV-C light projection unit of any of the examples above, wherein said at least one UV-C light emitter is configured to emit brightest in a wavelength in the range of 260 to 270 nm.
71. The UV-C light projection unit of any of the examples above, wherein at least one UV-C light emitter is configured to emit brightest at 265 nm.
72. The UV-C light projection unit of any of the examples above, wherein said at least one UV-C light emitter is configured to emit most UV-C light in the range of between 250 nm and 280 nm.
73. The UV-C light projection unit of any of the examples above, wherein said at least one UV-C light emitter is configured to emit most UV-C light in the range of between 260 nm and 270 nm.
74. The UV-C light projection unit of any of the examples above, wherein said at least one UV-C light emitter is configured to emit most UV light in the range of between 250 nm and 280 nm.
75. The UV-C light projection unit of any of the examples above, wherein said at least one UV-C light emitter is configured to emit most UV light in the range of between 260 nm and 270 nm.
76. The UV-C light projection unit of any of the examples above, wherein said at least one UV-C light emitter is configured to emit most light in the range of between 250 nm and 280 nm.
77. The UV-C light projection unit of any of the examples above, wherein said at least one UV-C light emitter is configured to emit most light in the range of between 260 nm and 270 nm.
78. The UV-C light projection unit of any of the examples above, wherein said at least one UV-C light emitter is configured to emit at least 70% of the UV-C light in the range of between 250 nm and 280 nm.
79. The UV-C light projection unit of any of the examples above, wherein said at least one UV-C light emitter is configured to emit at least 70% of the UV-C light in the range of between 260 nm and 270 nm.
80. The UV-C light projection unit of any of the examples above, wherein said at least one UV-C light emitter is configured to emit at least 70% of the UV light emitted therefrom in the range of between 250 nm and 280 nm.

81. The UV-C light projection unit of any of the examples above, wherein said at least one UV-C light emitter is configured to emit at least 70% of the UV light emitted therefrom in the range of between 260 nm and 270 nm.

82. The UV-C light projection unit of any of the examples above, wherein said at least one UV-C light emitter is configured to emit at least 70% of the light emitted therefrom in the range of between 250 nm and 280 nm.

83. The UV-C light projection unit of any of the examples above, wherein said at least one UV-C light emitter is configured to emit at least 70% of the light emitted therefrom in the range of between 260 nm and 270 nm.

84. The UV-C light projection unit of any of the examples above, wherein most of the UV-C light output from the fiber optic is in the range of between 250 nm and 280 nm.

85. The UV-C light projection unit of any of the examples above, wherein most of the UV-C light output from the fiber optic in the range of between 260 nm and 270 nm.

86. The UV-C light projection unit of any of the examples above, wherein most of the UV light output from the fiber optic in the range of between 250 nm and 280 nm.

87. The UV-C light projection unit of any of the examples above, wherein most of the UV light output from the fiber optic in the range of between 260 nm and 270 nm.

88. The UV-C light projection unit of any of the examples above, wherein most of the light output from the fiber optic in the range of between 250 nm and 280 nm.

89. The UV-C light projection unit of any of the examples above, wherein most of the light output from the fiber optic in the range of between 260 nm and 270 nm.

90. The UV-C light projection unit of any of the examples above, wherein at least 70% of the UV-C light output from the fiber optic is in the range of between 250 nm and 280 nm.

91. The UV-C light projection unit of any of the examples above, wherein at least 70% of the UV-C light output from the fiber optic in the range of between 260 nm and 270 nm.

92. The UV-C light projection unit of any of the examples above, wherein at least 70% of the UV light output from the fiber optic in the range of between 250 nm and 280 nm.

93. The UV-C light projection unit of any of the examples above, wherein at least 70% of the UV light output from the fiber optic in the range of between 260 nm and 270 nm.

94. The UV-C light projection unit of any of the examples above, wherein at least 70% of the light output from the fiber optic in the range of between 250 nm and 280 nm.

95. The UV-C light projection unit of any of the examples above, wherein at least 70% of the light output from the fiber optic in the range of between 260 nm and 270 nm.

96. The UV-C light projection unit of any of the examples above, wherein said UV-C light projection unit comprises at least part of an endoscope.

97. The UV-C light projection unit of any of the examples above, wherein said UV-C light projection unit is optically coupled to an endoscope.

98. The UV-C light projection unit of any of the examples above, wherein said at least one light emitter comprises an array of UV-C light emitters that has a dimension along a side of between 8 mm to 50 mm.

99. The UV-C light projection unit of any of the examples above, wherein said at least one light emitter comprises an array of UV-C light emitters that has a dimension along one side of from 5 mm to 60 mm and a dimension along another side of from 5 to 60 mm.

100. The UV-C light projection unit of any of the examples above, wherein said at least one light emitter comprises an array of UV-C light emitters that has a dimension along a side of between 0.5 mm to 50 mm.

101. The UV-C light projection unit of any of the examples above, wherein said at least one light emitter comprises an array of UV-C light emitters that has a dimension along one side of from 0.5 mm to 50 mm and a dimension along another side of from 0.5 to 50 mm.

102. The UV-C light projection unit of any of the examples above, wherein said at least one light emitter comprises an array of UV-C emitters and the number of UV-C emitters in the array comprises from 2 to 6.

103. The UV-C light projection unit of any of the examples above, wherein said at least one light emitter comprises an array of UV-C emitters and the number of UV-C emitters in the array comprises from 3 to 5.

104. The UV-C light projection unit of any of the examples above, wherein said at least one light emitter comprises an array of UV-C emitters and the number of UV-C emitters in the array is 4.

105. The UV-C light projection unit of any of the examples above, wherein at least one UV-C light emitters is configured to emit visible light.

106. The UV-C light projection unit of any of Examples 1-104, further comprising a visible light emitter configured to emit visible light.

107. The UV-C light projection unit of Example 106, wherein said visible light emitter comprises a color LED.

108. The UV-C light projection unit of any of Examples 106-107, wherein said visible light can be used as a guide as to where UV-C light is directed at the target.

109. The UV-C light projection unit of any of Examples 106-108, wherein said visible light is color light.

110. The UV-C light projection unit of any of Examples 106-109, wherein said visible light is red, green, blue, or violet color light.

111. The UV-C light projection unit of any of Examples 106-110, wherein a UV-C light beam having a perimeter is formed at a target location by said UV-C light projection unit and said visible light forms a beam having a perimeter at said target location that matches the perimeter of the UV-C light beam to within 10% of the size of the UV-C light beam at said target location.

112. The UV-C light projection unit of any of Examples 106-111, wherein a UV-C light beam having a perimeter is formed at a target location by said UV-C light projection unit and said visible light forms a beam having a perimeter at said target location that matches the perimeter of the UV-C light beam to within 5% of the size of the UV-C light beam at said target location.

113. The UV-C light projection unit of any of the examples above, wherein said UV-C light projection unit outputs a UV-C light beam having a beamwidth (FWHM) of 20 mm or smaller at a target location.

114. The UV-C light projection unit of any of the examples above, wherein said UV-C light projection unit outputs a UV-C light beam having a beamwidth (FWHM) of 10 mm or smaller at a target location.

115. The UV-C light projection unit of any of the examples above, wherein said UV-C light projection unit outputs a UV-C light beam having a beamwidth (FWHM) of 5 mm or smaller at a target location.

116. The UV-C light projection unit of any of the examples above, wherein said UV-C light projection unit outputs a UV-C light beam having a beamwidth (FWHM) of 2 mm or smaller at a target location.

117. A kit comprising the UV-C light projection unit of any of the examples above, further comprising a plurality of output lenses configured to alter the size of the UV-C beam at a target location.

118. A kit comprising the UV-C light projection unit of Example 117, wherein said plurality of output lenses can be positioned at the output said UV-C projection unit to alter the size of the UV-C light beam at a target location.

119. A kit comprising the UV-C light projection unit of Example 117 or 118, wherein different output lenses of said plurality of output lenses can be positioned at the output of said UV-C projection unit to provide a different respective sizes of the UV-C light beam at a target location.

120. The UV-C light projection unit of any of the examples above, wherein said at least one light emitter is configured to emit light having a peak wavelength in the range of 250 to 280.

121. The UV-C light projection unit of any of the examples above, wherein said at least one light emitter is configured to emit light having a peak wavelength in the range of 260 to 270.

122. The UV-C light projection unit of any of the examples above, wherein said at least one UV-C light emitter is configured to emit light having a peak wavelength in the range of 265 to 275.

123. The UV-C light projection unit of any of the examples above, wherein said at least one UV-C light emitter is configured to emit light having a peak wavelength in the range of 263 to 267.

124. A UV-C light projection unit of any of the examples above, wherein the unit weighs from 15 lbs. to 80 lbs.

125. A UV-C light projection unit of any of the examples above, wherein the unit has a volume of from 200,000 $cm^3$ to 50,000 $cm^3$.

126. A UV-C light projection unit of any of the examples above, wherein the unit has a volume of from 100,000 $cm^3$ to 20,000 $cm^3$.

127. A UV-C light projection unit of any of the examples above, wherein the unit has a volume of from 30,000 $cm^3$ to 10,000 $cm^3$.

128. The UV-C light projection unit of any of the examples above, wherein said at least one UV-C light emitter is configured to emit light having a peak wavelength with a bandwidth of 15 nm or less (FWHM).

129. The UV-C light projection unit of any of the examples above, wherein said at least one UV-C light emitter is configured to emit light having a peak wavelength with a bandwidth of 12 nm or less (FWHM).

130. A method of treating cancer comprising exposing cancerous tissue or cells to UV-C light provided by the UV-C light projection unit of any of the examples above.

131. The method of Example 126, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.

132. The method of Example 130, wherein said method is employed to treat leukemia.

133. The method of Example 130 or 132, wherein directing UV-C light onto said cancerous tissue or cells comprises directing UV-C light onto blood.

134. The method of any of Examples 130 or 132, wherein directing UV-C light onto said cancerous tissue or cells comprises directing UV-C light onto blood that has been extracted from the body of a patient.

135. The method of any of Examples 130-134, wherein said direction UV-C light onto said cancerous tissue or cell is performed ex vivo.

136. The method of any of the examples above, wherein said at least one UV-C light emitter comprises a UV-C light emitting diode (LED).

137. The method of any of the examples above, wherein said at least one UV-C light emitter comprises a plurality of UV-C light emitting diodes (LEDs).

138. The method of any of the examples above, wherein said at least one UV-C light emitter comprises an array of UV-C light emitting diodes (LEDs).

139. The UV-C light projection unit of any of the examples above, wherein said UV-C light projection unit is configured for medical use.

140. The UV-C light projection unit of any of the examples above, wherein said UV-C light projection unit includes an outer surface on at least a portion thereof that is sterile.

141. The UV-C light projection unit of any of the examples above, wherein said UV-C light projection unit includes an outer surface on at least a distal portion thereof that is sterile.

142. The UV-C light projection unit of any of the examples above, wherein said UV-C light projection unit includes an outer surface on portion thereof that is configured to contact a patient that is sterile.

143. The UV-C light projection unit of any of the examples above, wherein said UV-C light projection unit is included in sterile packaging.

144. The UV-C light projection unit of any of the examples above, wherein said UV-C light projection unit includes an outer surface on at least a portion thereof that is sterilizable.

145. The UV-C light projection unit of any of the examples above, wherein said UV-C light projection unit includes an outer surface on at least a distal portion thereof that is sterilizable.

146. The UV-C light projection unit of any of the examples above, wherein said UV-C light projection unit includes an outer surface on portion thereof that is configured to contact a patient that is sterilizable.

147. The UV-C light projection unit of Examples 1-66 and 96-146, wherein said at least one UV-C light emitter is configured to emit brightest in a wavelength in the range of 200 to 250 nm.

148. The UV-C light projection unit of Examples 1-66 and 96-146, wherein said at least one UV-C light emitter is configured to emit brightest in a wavelength in the range of 200 to 230 nm.
149. The UV-C light projection unit of Examples 1-66 and 96-146, wherein said at least one UV-C light emitter is configured to emit brightest in a wavelength in the range of 200 to 210 nm.
150. The UV-C light projection unit of Examples 1-66 and 96-146, wherein at least one UV-C light emitter is configured to emit brightest at 207 nm.
151. The UV-C light projection unit of Examples 1-66 and 96-146, wherein said at least one UV-C light emitter is configured to emit brightest in a wavelength in the range of 220 to 230 nm.
152. The UV-C light projection unit of Examples 1-66 and 96-146, wherein at least one UV-C light emitter is configured to emit brightest at 222 nm.
153. The UV-C light projection unit of Examples 1-66 and 96-146, wherein said at least one UV-C light emitter is configured to emit most UV-C light in the range of between 200 nm and 250 nm.
154. The UV-C light projection unit of Examples 1-66 and 96-146, wherein said at least one UV-C light emitter is configured to emit most UV-C light in the range of between 200 nm and 230 nm.
155. The UV-C light projection unit of Examples 1-66 and 96-146, wherein said at least one UV-C light emitter is configured to emit most UV light in the range of between 200 nm and 250 nm.
156. The UV-C light projection unit of Examples 1-66 and 96-146, wherein said at least one UV-C light emitter is configured to emit most UV light in the range of between 200 nm and 230 nm.
157. The UV-C light projection unit of Examples 1-66 and 96-146, wherein said at least one UV-C light emitter is configured to emit most light in the range of between 200 nm and 250 nm.
158. The UV-C light projection unit of Examples 1-66 and 96-146, wherein said at least one UV-C light emitter is configured to emit most light in the range of between 200 nm and 230 nm.
159. The UV-C light projection unit of Examples 1-66 and 96-146, wherein said at least one UV-C light emitter is configured to emit at least 70% of the UV-C light in the range of between 200 nm and 250 nm.
160. The UV-C light projection unit of Examples 1-66 and 96-146, wherein said at least one UV-C light emitter is configured to emit at least 70% of the UV-C light in the range of between 200 nm and 230 nm.
161. The UV-C light projection unit of Examples 1-66 and 96-146, wherein said at least one UV-C light emitter is configured to emit at least 70% of the UV light emitted therefrom in the range of between 200 nm and 250 nm.
162. The UV-C light projection unit of Examples 1-66 and 96-146, wherein said at least one UV-C light emitter is configured to emit at least 70% of the UV light emitted therefrom in the range of between 200 nm and 230 nm.
163. The UV-C light projection unit of Examples 1-66 and 96-146, wherein said at least one UV-C light emitter is configured to emit at least 70% of the light emitted therefrom in the range of between 200 nm and 250 nm.
164. The UV-C light projection unit of Examples 1-66 and 96-146, wherein said at least one UV-C light emitter is configured to emit at least 70% of the light emitted therefrom in the range of between 200 nm and 230 nm.
165. The UV-C light projection unit of Examples 1-66 and 96-146, wherein most of the UV-C light output from the fiber optic is in the range of between 200 nm and 250 nm.
166. The UV-C light projection unit of Examples 1-66 and 96-146, wherein most of the UV-C light output from the fiber optic in the range of between 200 nm and 230 nm.
167. The UV-C light projection unit of Examples 1-66 and 96-146, wherein most of the UV light output from the fiber optic in the range of between 200 nm and 250 nm.
168. The UV-C light projection unit of Examples 1-66 and 96-146, wherein most of the UV light output from the fiber optic in the range of between 200 nm and 230 nm.
169. The UV-C light projection unit of Examples 1-66 and 96-146, wherein most of the light output from the fiber optic in the range of between 200 nm and 250 nm.
170. The UV-C light projection unit of Examples 1-66 and 96-146, wherein most of the light output from the fiber optic in the range of between 200 nm and 230 nm.
171. The UV-C light projection unit of Examples 1-66 and 96-146, wherein at least 70% of the UV-C light output from the fiber optic is in the range of between 200 nm and 250 nm.
172. The UV-C light projection unit of Examples 1-66 and 96-146, wherein at least 70% of the UV-C light output from the fiber optic in the range of between 200 nm and 230 nm.
173. The UV-C light projection unit of Examples 1-66 and 96-146, wherein at least 70% of the UV light output from the fiber optic in the range of between 200 nm and 250 nm.
174. The UV-C light projection unit of Examples 1-66 and 96-146, wherein at least 70% of the UV light output from the fiber optic in the range of between 200 nm and 230 nm.
175. The UV-C light projection unit of Examples 1-66 and 96-146, wherein at least 70% of the light output from the fiber optic in the range of between 200 nm and 250 nm.
176. The UV-C light projection unit of Examples 1-66 and 96-146, wherein at least 70% of the light output from the fiber optic in the range of between 200 nm and 230 nm.
177. The system of any of the examples above, wherein said optical fiber comprises separate fiber strands optically coupled together.
178. The system of any of the examples above, wherein said optical fiber comprises separate fiber strands butt coupled together.
179. The UV-C light projection unit of any Examples 1-176, wherein said optical fiber comprises single fiber strand.
180. The system of any of the examples above, wherein excluding output from a distal end of said optical fiber, light emission from the system in said UV wavelength range is less than 1 $mJ/cm^2$ over a solid angle of $0.1\pi$ steradian at a distance of 36 inches from said distal end of said optical fiber when said light emission in said UV wavelength range from said distal end of said optical fiber is from 10 $mJ/cm^2$ to 100 $mJ/cm^2$.
181. The system of any of the examples above, wherein excluding output from a distal end of said optical fiber, light emission from said system in said UV wavelength range is less than 1 $mJ/cm^2$ over a solid angle of $0.2\pi$ steradian at a distance of 36 inches from said distal end of said optical fiber when said light emission in said UV wavelength range from said distal end of said optical fiber is from 10 $mJ/cm^2$ to 100 $mJ/cm^2$.

182. The system of any of the examples above, wherein excluding output from a distal end of said optical fiber, light emission from said system in said UV wavelength range is less than 1 $mJ/cm^2$ over a solid angle of $0.3\pi$ steradian at a distance of 36 inches from said distal end of said optical fiber when said light emission in said UV wavelength range from said distal end of said optical fiber is from 10 $mJ/cm^2$ to 100 $mJ/cm^2$.

183. The system of any of the examples above, wherein excluding output from a distal end of said optical fiber, light emission from said system in said UV wavelength range is less than 1 $mJ/cm^2$ over a solid angle of $0.5\pi$ steradian at a distance of 36 inches from said distal end of said optical fiber when said light emission in said UV wavelength range from said distal end of said optical fiber is from 10 $mJ/cm^2$ to 100 $mJ/cm^2$.

184. The system of any of the examples above, wherein a person applying light in said UV wavelength range to a patient is exposed to light emission from said system in said UV wavelength range of less than 1 $mJ/cm^2$ when said light emission in said UV wavelength range from said distal end of said fiber is from 10 $mJ/cm^2$ to 100 $mJ/cm^2$.

185. The system of any of the examples above, wherein a person applying light in said UV wavelength range to a patient is exposed to light emission from said system in said UV wavelength range of less than 0.05 $mJ/cm^2$ when said light emission in said UV wavelength range from said distal end of said fiber is from 10 $mJ/cm^2$ to 100 $mJ/cm^2$.

186. The system of any of the examples above, wherein a person applying light in said UV wavelength range to a patient is exposed to light emission from said system in said UV wavelength range of less than 0.01 $mJ/cm^2$ when said light emission in said UV wavelength range from said distal end of said fiber is from 10 $mJ/cm^2$ to 100 $mJ/cm^2$.

187. The system of any of the examples above, wherein excluding output from a distal end of said optical fiber, light emission from said system in said UV wavelength range is less than 1 $mJ/cm^2$ over the body of an operator holding the distal end of the fiber when said light emission in said UV wavelength range from said distal end of said optical fiber is from 10 $mJ/cm^2$ to 100 $mJ/cm^2$.

188. The system of any of the examples above, wherein, excluding possible output from a distal end of said optical fiber, an operator operating the system is exposed to light emission from said system of less than 1 $mJ/cm^2$ in said UV wavelength range when said light emission in said UV wavelength range from said distal end of said optical fiber is from 10 $mJ/cm^2$ to 100 $mJ/cm^2$.

Part—IX Fiber Length

1. A system for outputting UV light, said system comprising:
   at least one UV light emitter configured to emit light having a wavelength in the UV range; and
   an optical fiber line configured to receive light from said at least one UV light emitter in said UV range and to transmit and output a portion of said light in said UV range, said optical fiber line having a length of at least 4 feet.
2. The system of Example 1, wherein said optical fiber line has a length in a range from 4 to 12 feet long.
3. The system of Example 1, wherein said optic fiber line has a length in a range from 10 to 25 feet long.
4. The system of Example 1, wherein said optical fiber line has a length of from 12 to 30 feet long.
5. The system of Example 1, wherein said optical fiber line has a length of from 8 to 50 feet long.
6. The system of any of the examples above, wherein said optical fiber line has an optical core of at least 500 micrometers wide in cross-section.
7. The system of any of the examples above, wherein said optical fiber line has an optical core of at least 1000 micrometers wide in cross-section.
8. The system of any of the examples above, wherein said optical fiber line has a core comprises silica and said silica includes a sufficiently high concentration of hydroxyl (OH) concentration such that said optical fiber line transmits light having a wavelength of 250 nm.
9. The system of any of the examples above, wherein said optical fiber line comprises fused silica.
10. The system of any of the examples above, wherein said optical fiber line has a hydroxyl (OH) content in the core material of at least 200 ppm.
11. The system of any of the examples above, wherein said optical fiber line has a hydroxyl (OH) content in the core material from 600 to 800 ppm.
12. The system of any of the examples above, further comprising an output lens at the distal end of said optical fiber line to receive light exiting the end of said optical fiber line.
13. The system of any of the examples above, wherein said optical fiber line further comprises a glass cladding.
14. The system of Example 13, wherein said glass cladding comprises doped glass.
15. The system of Example 13 or 14, wherein said glass cladding is fluorine doped.
16. The system of any of the examples above, wherein the UV wavelength range in which said at least one UV light emitter emits light and said optical fiber line transmits and outputs light comprises the UV-C range.
17. The system of any of the examples above, wherein the UV wavelength range in which said at least one UV light emitter emits light and said optical fiber line transmits and outputs light comprises wavelengths in the range of from 200 to 280 nm.
18. The system of any of the examples above, wherein the UV wavelength range in which said at least one UV light emitter emits light and said optical fiber line transmits and outputs light comprises wavelengths in the range of from 280 to 320 nm.
19. The system of any of the examples above, wherein said optical fiber line forms part of an endoscope.
20. The system of any of the examples above, wherein said optical fiber line is optically coupled to an endoscope.
21. The system of any of the examples above, wherein said optical fiber line is optically coupled to a handheld delivery device.
22. The system of any of the examples above, wherein said optical fiber line comprises separate fiber strands optically coupled together.
23. The system of any of the examples above, wherein said optical fiber line comprises separate fiber strands butt coupled together.
24. The system of any Examples 1-21, wherein said optical fiber line comprises a single fiber strand.

25. A method comprising exposing cancerous tissue or cells to UV light provided by the system of any of the examples above.

Part X—Shielding

1. A system for outputting UV light, said system comprising:
   at least one UV light emitter configured to emit light having a wavelength in the UV range;
   an optical fiber line configured to receive light from said at least one UV light emitter in said UV range and to transmit and output a portion of said light in said UV range, and
   shielding disposed with respect to said at least one UV light emitter such that, excluding output from said distal end of said optical fiber line, a person applying light in said UV wavelength range to a patient is exposed to light emission from said system in said UV wavelength range of less than 1 mJ/cm$^2$ when said light emission in said UV wavelength range from said distal end of said optical fiber line is from 10 mJ/cm$^2$ to 100 mJ/cm$^2$.
2. The system of Example 1, wherein a person applying light in said UV wavelength range to a patient is exposed to light emission from said system in said UV wavelength range of less than 0.1 mJ/cm$^2$ when said light emission in said UV wavelength range from said distal end of said optical fiber line is from 10 mJ/cm$^2$ to 100 mJ/cm$^2$.
3. The system of Example 1, wherein a person applying light in said UV wavelength range to a patient is exposed to light emission from said system in said UV wavelength range of less than 0.05 mJ/cm$^2$ when said light emission in said UV wavelength range from said distal end of said optical fiber line is from 10 mJ/cm$^2$ to 100 mJ/cm$^2$.
4. The system of Example 1, wherein a person applying light in said UV wavelength range to a patient is exposed to light emission from said system in said UV wavelength range of less than 0.01 mJ/cm$^2$ when said light emission in said UV wavelength range from said distal end of said optical fiber line is from 10 mJ/cm$^2$ to 100 mJ/cm$^2$.
5. The system of any of the examples above, wherein excluding output from said distal end of said optical fiber line, light emission from said system in said UV wavelength range is less than 1 mJ/cm$^2$ over the body of an operator holding the distal end of the optical fiber line when said light emission in said UV wavelength range from said distal end of said optical fiber line is from 10 mJ/cm$^2$ to 100 mJ/cm$^2$.
6. The system of any of the examples above, wherein, excluding possible output from said distal end of said optical fiber line, an operator operating the system is exposed to light emission from said system of less than 1 mJ/cm$^2$ in said UV wavelength range when said light emission in said UV wavelength range from said distal end of said optical fiber line is from 10 mJ/cm$^2$ to 100 mJ/cm$^2$.
7. The system of any of the examples above, wherein excluding output from a distal end of said optical fiber line, light emission from the system in said UV wavelength range is less than 1 mJ/cm$^2$ over a solid angle of 0.1π steradian at a distance of 36 inches from said distal end of said optical fiber line when said light emission in said UV wavelength range from said distal end of said optical fiber line is from 10 mJ/cm$^2$ to 100 mJ/cm$^2$.
8. The system of any of the examples above, wherein excluding output from a distal end of said optical fiber line, light emission from said system in said UV wavelength range is less than 1 mJ/cm$^2$ over a solid angle of 0.2π steradian at a distance of 36 inches from said distal end of said optical fiber line when said light emission in said UV wavelength range from said distal end of said optical fiber line is from 10 mJ/cm$^2$ to 100 mJ/cm$^2$.
9. The system of any of the examples above, wherein excluding output from a distal end of said optical fiber line, light emission from said system in said UV wavelength range is less than 1 mJ/cm$^2$ over a solid angle of 0.3π steradian at a distance of 36 inches from said distal end of said optical fiber line when said light emission in said UV wavelength range from said distal end of said optical fiber line is from 10 mJ/cm$^2$ to 100 mJ/cm$^2$.
10. The system of any of the examples above, wherein excluding output from a distal end of said optical fiber line, light emission from said system in said UV wavelength range is less than 1 mJ/cm$^2$ over a solid angle of 0.5 steradian at a distance of 36 inches from said distal end of said optical fiber line when said light emission in said UV wavelength range from said optical fiber line is from 10 mJ/cm$^2$ to 100 mJ/cm$^2$.
11. The system of any of the examples above, wherein excluding output from said distal end of said optical fiber line, light emission in said UV wavelength range from said at least one UV light emitter at a location 10 mm from said shielding is less than 1 mJ/cm$^2$ when said light emission in said UV wavelength range from said distal end of said optical fiber line is from 10 mJ/cm$^2$ to 100 mJ/cm$^2$.
12. The system of any of the examples above, wherein excluding output from said distal end of said optical fiber line, light emission in said UV wavelength range 10 mm from said shielding is less than 0.1 mJ/cm$^2$ when said light emission in said UV wavelength range from said distal end of said optical fiber line is from 10 mJ/cm$^2$ to 100 mJ/cm$^2$.
13. The system of any of the examples above, wherein excluding output from said distal end of said optical fiber line, light emission in said UV wavelength range 10 mm from said shielding is less than 0.05 mJ/cm$^2$ when said light emission in said UV wavelength range from said distal end of said optical fiber line is from 10 mJ/cm$^2$ to 100 mJ/cm$^2$.
14. The system of any of the examples above, wherein excluding output from said distal end of said optical fiber line, light emission in said UV wavelength range 10 mm from said shielding is less than 0.01 mJ/cm$^2$ when said light emission in said UV wavelength range from said distal end of said optical fiber line is from 10 mJ/cm$^2$ to 100 mJ/cm$^2$.
15. The system of any of the examples above, wherein excluding output from said distal end of said optical fiber line, light emission in said UV wavelength range is less than 1 mJ/cm$^2$ over an angular extent that is 100° in one direction and 30° in another orthogonal direction 36 inches from said at least one UV light emitter when said light emission in said UV wavelength range from said distal end of said optical fiber line is from 10 mJ/cm$^2$ to 100 mJ/cm$^2$.
16. The system of Example 15, wherein said angular extent is 270° in one direction and 90° in another orthogonal direction.

17. The system of Example 15, wherein said angular extent of 360° in one direction and 90° in another orthogonal direction.
18. The system of any of Examples 15-17, wherein excluding output from said distal end of said optical fiber line, light emission in said UV wavelength range is less than 0.1 mJ/$cm^2$ over said angular extents 36 inches from said at least one UV light emitter when said light emission in said UV wavelength range from said distal end of said optical fiber line is from 10 mJ/$cm^2$ to 100 mJ/$cm^2$.
19. The system of any of Examples 15-17, excluding output from said distal end of said optical fiber line, light emission in said UV wavelength range is less than 0.05 mJ/$cm^2$ over said angular extents 36 inches from said at least one UV light emitter when said light emission in said UV wavelength range from said distal end of said optical fiber line is from 10 mJ/$cm^2$ to 100 mJ/$cm^2$.
20. The system of any of Examples 15-17, excluding output from said distal end of said optical fiber line, light emission in said UV wavelength range is less than 0.01 mJ/$cm^2$ over said angular extents 36 inches from said at least one UV light emitter when said light emission in said UV wavelength range from said distal end of said optical fiber line is from 10 mJ/$cm^2$ to 100 mJ/$cm^2$.
21. The system of any of the examples above, wherein excluding output from said distal end of said optical fiber line, light emission from said system in said UV wavelength range is less than 1 mJ/$cm^2$ at most locations 1 foot away from one or more UV emitters when said light emission in said UV wavelength range from said distal end of said optical fiber line is from 10 mJ/$cm^2$ to 100 mJ/$cm^2$.
22. The system any of the examples above, wherein said shielding comprises plastic.
23. The system of any of the examples above, wherein said shielding comprises acrylic or polycarbonate.
24. A system of any of the examples above, wherein said shielding is transparent to visible light.
25. The system of any of the examples above, wherein said shielding is at least 3 mm thick.
26. The system of any of the examples above, wherein said shielding is at least 5 mm thick.
27. The system of any of the examples above, wherein said shielding is disposed about said at least one UV light emitter on at least three sides.
28. The system of any of the examples above, wherein said shielding is disposed about said at least one UV light emitter on at least four sides.
29. The system of any of Examples above, wherein said shielding is disposed about said at least one UV light emitter on at least five sides.
30. The system of any of Examples above, wherein said shielding is disposed about said at least one UV light emitter on at least six sides.
31. The system of any of the examples above, wherein the UV wavelength range in which said at least one UV light emitter emits light comprises the UV-C range.
32. The system of any of the examples above, wherein the UV wavelength range in which said at least one UV light emitter emits light comprises wavelengths in the range of from 200 to 280 nm.
33. The system of any of the examples above, wherein the UV wavelength range in which said at least one UV light emitter emits light comprises wavelengths in the range of from 280 to 320 nm.
34. The system of any of the examples above, wherein said optical fiber line has a length of at least 7 feet.
35. The system of any of the examples above, wherein said optical fiber line forms part of or is optically coupled to an endoscope.
36. The system of any of the examples above, further comprising additional shielding disposed with respect to the distal end of said optical fiber line such that light emission in said UV wavelength range 36 inches from said distal end of said optical fiber line is less than 1 mJ/$cm^2$ when said light emission in said UV wavelength range from said distal end of said optical fiber line is from 10 mJ/$cm^2$ to 100 mJ/$cm^2$.
37. The system of any of the examples above, further comprising additional shielding disposed with respect to the distal end of said optical fiber line such that UV light emissions over an angular extent that is 100° in one direction and 30° in another orthogonal direction 36 inches from said distal end of said optical fiber line is less than 1 mJ/$cm^2$ when said light emission in said UV wavelength range from said distal end of said optical fiber line is from 10 mJ/$cm^2$ to 100 mJ/$cm^2$.
38. The system of any of the examples above, further comprising additional shielding disposed with respect to the distal end of said optical fiber line such that an operator operating the system is exposed to light emission from said system of less than 1 mJ/$cm^2$ in said UV wavelength range when said light emission in said UV wavelength range from said distal end of said optical fiber line is from 10 mJ/$cm^2$ to 100 mJ/$cm^2$.
39. The system of any of the examples above, further comprising additional shielding disposed with respect to the distal end of said optical fiber line such that light from the system in said UV wavelength range is less than 1 mJ/$cm^2$ over a solid angle of 0.1$\pi$ steradian at a distance of 36 inches from said distal end of said optical fiber line when said light emission in said UV wavelength range from said distal end of said optical fiber line is from 10 mJ/$cm^2$ to 100 mJ/$cm^2$.
40. The system of any of the examples above, wherein said optical fiber line comprises separate fiber strands optically coupled together.
41. The system of any of the examples above, wherein said optical fiber line comprises separate fiber strands butt coupled together.
42. The system of any Examples 1-39, wherein said optical fiber line comprises a single fiber strand.
43. A method comprising exposing cancerous tissue or cells to UV light provided by the system of any of the examples above.

Part XI—Fused Silica Optics

1. A system for outputting ultraviolet (UV) light, said system comprising:
   at least one UV light emitter configured to emit light having a wavelength in the UV range; and
   at least one fused silica lens configured to receive light emitted by said UV light emitter having a wavelength in the range UV, said at least one fused silica lens comprising fused silica wherein the OH content is not larger than 5 ppm or wherein one or more of Li, Na, K, Mg, Ca and Cu are smaller than 0.1 ppm.
2. The system of Example 1, wherein the OH content in said fused silica is not larger than 5 ppm.

3. The system of Example 1 or 2, wherein said at least one fused silica lens comprises fused silica wherein the content of one or more of Li, Na, K, Mg, Ca and Cu are smaller than 0.1 ppm.
4. The system of any of the examples above, wherein said at least one fused silica lens comprises fused silica wherein the content of each of Li, Na, K, Mg, Ca and Cu are smaller than 0.1 ppm.
5. The system of any of the examples above, wherein said at least one fused silica lens comprises focusing optics positioned to receive light from said at least one UV light emitter and focus said light.
6. The system of any of the examples above, wherein said at least one fused silica lens comprises collecting optics disposed to receive light emitted by said at least one UV light emitter and to transmit said light in said UV wavelength range and reduce the divergence of said light.
7. The system of any of the examples above, wherein said at least one fused silica lens comprises focusing optics positioned to receive light from said at least one light emitter transmitted through said collecting optic.
8. The system of any of the examples above, wherein the OH content in said fused silica is not larger than 1 ppm.
9. The system of any of the examples above, wherein said at least one fused silica lens comprises fused silica wherein the content of one or more of Li, Na, K, Mg, Ca and Cu are smaller than 0.01 ppm.
10. The system of any of the examples above, wherein said at least one fused silica lens comprises fused silica wherein the content of each of Li, Na, K, Mg, Ca and Cu are smaller than 0.01 ppm.
11. The system of any of the examples above, wherein the UV wavelength range in which said at least one UV light emitter emits light comprises the UV-C range.
12. The system of any of the examples above, wherein the UV wavelength range in which said at least one UV light emitter emits light comprises wavelengths in the range of from 200 to 280 nm.
13. The system of Example 12, wherein said at least one fused silica lens comprises fused silica having an internal transmittance corrected to eliminate the effects of scattering and surface reflection of UV-C light with a wavelength of 245-280 nm of at least 50% for fused silica glass having a thickness of 10 mm.
14. The system of Example 12, wherein said at least one fused silica lens comprises fused silica having an internal transmittance corrected to eliminate the effects of scattering and surface reflection of UV-C light with a wavelength of 245-280 nm of at least 95% for fused silica glass having a thickness of 10 mm.
15. The system of Example 13 or 14, wherein said fused silica lens has thickness in a range of from 0.1 mm to 9 mm.
16. The system of any of the examples above, wherein the UV wavelength range in which said at least one UV light emitter emits light comprises wavelengths in the range of from 280 to 320 nm.
17. The system of any of the examples above, further comprising an optical fiber configured to receive light from said at least one UV light emitter in said UV wavelength range and to transmit and output a portion of said light in said UV wavelength range.
18. The system of Example 17, wherein said at least one fused silica lens comprises an output lens at the distal end of said optical fiber to receive light exiting the end of said fiber.
19. The system of Example 17 or 18, wherein said at least one fused silica lens comprises focusing optics configured to focus UV light from said at least one UV light emitter onto said optical fiber.
20. The system of any of Examples 17-19, wherein said optical fiber light has a length of at least 7 feet.
21. The system of any of Examples 17-20, wherein said optical fiber forms part of or is optically coupled to an endoscope.
22. The system of any of Examples 17-21, further comprising shielding disposed with respect to said at least one UV light emitter such that, excluding output from said distal end of said optical fiber, a person applying light in said UV wavelength range to a patient is exposed to light emission from said system in said UV wavelength range of less than 1 $mJ/cm^2$ when said light emission in said UV wavelength range from said distal end of said fiber is from 10 $mJ/cm^2$ to 100 $mJ/cm^2$.
23. The system of any of Examples 17-22, wherein excluding output from a distal end of said optical fiber, light emission from the system in said UV wavelength range is less than 1 $mJ/cm^2$ over a solid angle of $0.1\pi$ steradian at a distance of 36 inches from said distal end of said optical fiber when said light emission in said UV wavelength range from said optical fiber is from 10 $mJ/cm^2$ to 100 $mJ/cm^2$.
24. The system of any of Examples 17-23, further comprising shielding disposed with respect to the distal end of said optical fiber such that an operator operating the system is exposed to light emission from said system of less than 1 $mJ/cm^2$ in said UV wavelength range when said light emission in said UV wavelength range from said optical fiber is from 10 $mJ/cm^2$ to 100 $mJ/cm^2$.
25. The system of any of Examples 17-24, wherein said optical fiber comprises separate fiber strands optically coupled together.
26. The system of any of Examples 17-25, wherein said optical fiber comprises separate fiber strands butt coupled together.
27. The system of any Examples 1-24, wherein said optical fiber comprises a single fiber strand.
28. A method comprising exposing cancerous tissue or cells to UV light provided by the system of any of the examples above.

Part XII—Sample Platform at Distal End of Fiber

1. A system for outputting ultraviolet (UV) light, said system comprising:
   at least one UV light emitter configured to emit light having a wavelength in the UV range;
   a fiber optic cable configured to receive light from said at least one UV light emitter in said UV wavelength range and to transmit and output a portion of said light in said UV wavelength range onto a sample, said fiber optic cable having a proximal end positioned to receive light from said at least one UV light emitter and a distal end that outputs light in said UV wavelength range; and
   a support on which a sample can be positioned to receive said light in said UV wavelength range from said distal end of said fiber optic cable.
2. The system of any of the examples above, further comprising a mount for positioning a distal end of said fiber optic cable configured to receive light in said UV wavelength range from said at least one UV light emitter with respect to said sample on said support to direct light in said UV wavelength range out of said distal end of said fiber optic cable and to said sample.

3. The system of Example 2, wherein said mount is configured to laterally translate said distal end of said fiber optic cable.
4. The system of Example 2 or 3, wherein said mount is configured to longitudinally translate said distal end of said fiber optic cable with respect to said support.
5. The system of any of Examples 2-4, wherein said mount is configured to hold a distal end of an endoscope.
6. The system of any of the examples above, wherein said mount is configured to hold a hand held delivery device optically coupled to said fiber optic cable.
7. The system of any of the examples above, wherein said fiber optic cable is included in or integrated with an endoscope or a hand held delivery device.
8. The system of any of examples above, configured for positioning a sample on a microscope slide, in a petri dish or in a sample container.
9. The system of any of examples above, wherein said support is configured for translating and/or rotating the positioning said sample.
10. The system of any of examples above, further comprising shielding disposed with respect to said support and said distal end of said fiber optic cable to block light in said UV wavelength range output from said distal end of said fiber optic cable.
11. The system of Example 10, wherein said shielding is configured to block at least 25% of the light in said UV wavelength range output from said distal end of said fiber optic cable that is scattered or reflected in a direction above said support.
12. The system of Example 10 or 11, wherein said shielding is configured to block at least 50% of the light in said UV wavelength range output from said distal end of said fiber optic cable that is scattered or reflected in a direction above said support.
13. The system of any of Examples 10-12, wherein said shielding is configured to block at least 75% of the light in said UV wavelength range output from said distal end of said fiber optic cable that is scattered or reflected in a direction above said support.
14. The system of any of Examples 10-13, wherein said shielding is configured to block at least 90% of the light in said UV wavelength range output from said distal end of said fiber optic cable that is scattered or reflected in a direction above said support.
15. The system of any of Examples 10-14, wherein said light emission in said UV wavelength range from said fiber optic cable at a location 10 mm from said shielding is less than 1 mJ/cm$^2$ when said light emission in said UV wavelength range from said distal end of said fiber optic cable is from 10 mJ/cm$^2$ to 100 mJ/cm$^2$.
16. The system of any of Examples 10-15, wherein said shielding is disposed with respect to said support and said distal end of said fiber optic cable such that light emission in said UV wavelength range at a location 36 inches from said distal end of said fiber optic cable is less than 1 mJ/cm$^2$ when said light emission in said UV wavelength range from said distal end of said fiber optic cable is from 10 mJ/cm$^2$ to 100 mJ/cm$^2$.
17. The system of Example 16, wherein light emission in said UV wavelength range is less than 1 mJ/cm$^2$ over an angular extent that is 100° in one direction and 30° in another orthogonal direction at a location 36 inches from said distal end of said fiber optic cable when said light emission in said UV wavelength range from said distal end of said fiber optic cable is from 10 mJ/cm$^2$ to 100 mJ/cm$^2$.
18. The system of Example 17, wherein said angular extent is 270° in one direction and 90° in another orthogonal direction.
19. The system of Example 17, wherein said angular extent of 360° in one direction and 90° in another orthogonal direction.
20. The system any of Examples 17-19, wherein said light emission in said UV wavelength range over said angular extents at a location 36 inches from said distal end of said fiber optic cable is less than 0.1 mJ/cm$^2$ when said UV light emission from said distal end of said fiber optic cable is at least 10 mJ/cm$^2$ to 100 mJ/cm$^2$.
21. The system of any of Examples 10-20, wherein said shielding is such that, light emission from the system in said UV wavelength range is less than 1 mJ/cm$^2$ over a solid angle of 0.1$\pi$ steradian at a distance of 36 inches from said distal end of said fiber optic cable when said light emission in said UV wavelength range from said distal end of said fiber optic cable is from 10 mJ/cm$^2$ to 100 mJ/cm$^2$.
22. The system of any of Examples 10-20, wherein said shielding is such that, an operator operating the system is exposed to light emission from said system of less than 1 mJ/cm$^2$ in said UV wavelength range when said light emission in said UV wavelength range from said distal end of said fiber optic cable is from 10 mJ/cm$^2$ to 100 mJ/cm$^2$.
23. The system any of Examples 10-22, wherein said shielding comprises plastic.
24. The system of any of Examples 10-23, wherein said shielding comprises acrylic or polycarbonate.
25. The system of any of Examples 10-24, wherein said shielding is at least 5 mm thick.
26. The system of any of Examples 10-25, wherein said shielding is disposed about said distal end of said fiber optic cable and said at least one light emitter on at least three sides.
27. The system of any of Examples 10-25, wherein said shielding is disposed about said distal end of said fiber optic cable and said at least one light emitter on at least four sides.
28. The system of any of Examples 10-25, wherein said shielding is disposed about said distal end of said fiber optic cable and said at least one light emitter on at least five sides.
29. The system of any of the examples above, further comprising at least one fused silica lens configured to receive light emitted by said at least one light emitter having a wavelength the range UV, said at least one fused silica lens comprising fused silica wherein the OH content is not larger than 5 ppm or wherein one or more of Li, Na, K, Mg, Ca and Cu are smaller than 0.1 ppm.
30. The system of any of the examples above, wherein the UV wavelength range in which said at least one UV light emitter emits light comprises the UV-C range.
31. The system of any of the examples above, wherein the UV wavelength range in which said at least one UV light emitter emits light comprises wavelengths in the range of from 200 to 280 nm.
32. The system of any of the examples above, wherein the UV wavelength range in which said at least one UV light emitter emits light comprises wavelengths in the range of from 280 to 320 nm.

33. The system of any of the examples above, wherein said fiber optic cable has a length of at least 7 feet.
34. The system of any of the examples above wherein said fiber optic cable forms part of or is optically coupled to an endoscope.
35. The system of any of the examples above, further comprising shielding disposed with respect to said at least one UV light emitter such that an operator operating the system is exposed to light emission from said system of less than 1 mJ/cm$^2$ in said UV wavelength range when said light emission in said UV wavelength range from said distal end of said fiber optic cable is from 10 mJ/cm$^2$ to 100 mJ/cm$^2$.
36. The system of any of the examples above, further comprising shielding disposed with respect to said at least one UV light emitter such that light emission from the system in said UV wavelength range is less than 1 mJ/cm$^2$ over a solid angle of 0.1π steradian at a distance of 36 inches from said distal end of said fiber optic cable when said light emission in said UV wavelength range from distal end of said fiber optic cable is from 10 mJ/cm$^2$ to 100 mJ/cm$^2$.
37. The system of any of the examples above, further comprising shielding disposed with respect to said at least one UV light emitter such that light emission from said system in said UV wavelength range is less than 1 mJ/cm$^2$ at most locations 1 foot away from one or more UV emitters when said light emission in said UV wavelength range from said distal end of said fiber optic cable is from 10 mJ/cm$^2$ to 100 mJ/cm$^2$.
38. A method comprising exposing cancerous tissue or cells to UV light provided by the system of any of the examples above.
39. The system of any of the examples above, wherein said fiber optic cable comprises separate fiber strands optically coupled together.
40. The system of any of the examples above, wherein said fiber optic cable comprises separate fiber strands butt coupled together.
41. The system of any Examples 1-38, wherein said fiber optic cable comprises a single fiber strand.

Part XIII—Shielding at Distal End of Fiber

1. A system for outputting ultraviolet (UV) light, said system comprising:
   at least one UV light emitter configured to emit light having a wavelength in the UV range;
   a fiber optic cable configured to receive light from said at least one UV light emitter in said UV wavelength range and to transmit and output a portion of said light in said UV wavelength range onto a sample, said fiber optic cable having a proximal end positioned to receive light from said at least one UV light emitter and a distal end that outputs light in said UV wavelength range;
   a support on which a sample can be positioned to receive said light in said UV wavelength range from said distal end of said optical fiber cable; and
   shielding disposed with respect to said support and said distal end of said fiber optic cable to block light in said UV wavelength range output from said distal end of said fiber optic cable.
2. The system of Example 1, wherein said shielding is configured to block at least 25% of the light in said UV wavelength range output from said distal end of said fiber optic cable that is scattered or reflected in a direction above said support.
3. The system of Example 1, wherein said shielding is configured to block at least 50% of the light in said UV wavelength range output from said distal end of said fiber optic cable that is scattered or reflected in a direction above said support.
4. The system of Example 1, wherein said shielding is configured to block at least 75% of the light in said UV wavelength range output from said distal end of said fiber optic cable that is scattered or reflected in a direction above said support.
5. The system of Example 1, wherein said shielding is configured to block at least 90% of the light in said UV wavelength range output from said distal end of said fiber optic cable that is scattered or reflected in a direction above said support.
6. The system of the examples above, wherein said light emission in said UV wavelength range from said fiber optic cable at a location 10 mm from said shielding is less than 1 mJ/cm$^2$ when said light emission in said wavelength range from said fiber optic cable is from 10 mJ/cm$^2$ to 100 mJ/cm$^2$.
7. The system of Example 1, wherein said light emission in said UV wavelength range 10 mm from said shielding is less than 0.1 mJ/cm$^2$ when said light emission in said UV wavelength range from said fiber optic cable is from 10 mJ/cm$^2$ to 100 mJ/cm$^2$.
8. The system of Example 1, wherein said light emission in said UV wavelength range 10 mm from said shielding is less than 0.05 mJ/cm$^2$ when said light emission in said UV wavelength range from said fiber optic cable is from 10 mJ/cm$^2$ to 100 mJ/cm$^2$.
9. The system of Example 1, wherein said light emission in said UV wavelength range 10 mm from said shielding is less than 0.01 mJ/cm$^2$ when said light emission in said UV wavelength range from said fiber optic cable is from 10 mJ/cm$^2$ to 100 mJ/cm$^2$.
10. The system any of the examples above, wherein said shielding is disposed with respect to said support and said distal end of said fiber optic cable such that light emission in said UV wavelength range at a location 36 inches from said distal end of said fiber optic cable is less than 1 mJ/cm$^2$ when said light emission in said UV wavelength from said optical fiber cable is from 10 mJ/cm$^2$ to 100 mJ/cm$^2$.
11. The system of Example 10, wherein light emission in said UV wavelength range is less than 1 mJ/cm$^2$ over an angular extent that is 120° in one direction and 30° in another orthogonal direction 36 inches from said distal end of said optical fiber cable when said light emission in said UV wavelength range from said fiber optic cable is from 10 mJ/cm$^2$ to 100 mJ/cm$^2$.
12. The system of Example 11, wherein said angular extent is 270° in one direction and 90° in another orthogonal direction.
13. The system of Example 11, wherein said angular extent of 360° in one direction and 90° in another orthogonal direction.
14. The system any of Examples 11-13, wherein said light emission in said UV wavelength range is less than 0.1 mJ/cm$^2$ when said light emission in said UV wavelength range from said fiber optic cable is at least 10 mJ/cm$^2$ to 100 mJ/cm$^2$ over said angular extents 36 inches from said distal end of said fiber optic cable.
15. The system of any of Examples 11-14, said UV light emission is less than 0.05 mJ/cm$^2$ when said light emission in said UV wavelength range from said fiber optic cable is at least 10 mJ/cm$^2$ to 100 mJ/cm$^2$ over said angular extents 36 inches from said distal end of said fiber optic cable.

16. The system of any of Examples 10-15, said UV light emission is less than 0.01 mJ/cm$^2$ when said light emission in said UV wavelength range from said fiber optic cable is at least 10 mJ/cm$^2$ to 100 mJ/cm$^2$ over said angular extents 36 inches from said distal end of said fiber optic cable.
17. The system any of the examples above, wherein said shielding comprises plastic.
18. The system of any of the examples above, wherein said shielding comprises acrylic or polycarbonate.
19. The system of any of the examples above, wherein said shielding is transparent to visible light.
20. The system of any of the examples above, wherein said shielding is at least 3 mm thick.
21. The system of any of the examples above, wherein said shielding is at least 5 mm thick.
22. The system of any of the examples above, wherein said shielding is disposed about said distal end of said fiber optic cable and said at least one light emitter on at least three sides.
23. The system of any of the examples above, wherein said shielding is disposed about said distal end of said fiber optic cable and said at least one light emitter on at least four sides.
24. The system of any of the examples above, wherein said shielding is disposed about said distal end of said fiber optic cable and said at least one light emitter on at least five sides.
25. The system of any of the examples above, further comprising at least one fused silica lens configured to receive light emitted by said at least one light emitter having a wavelength in the UV range, said at least one fused silica lens comprising fused silica wherein the OH content is not larger than 5 ppm or wherein one or more of Li, Na, K, Mg, Ca and Cu are smaller than 0.1 ppm.
26. The system of any of the examples above, wherein the UV wavelength range in which said at least one UV light emitter emits light comprises the UV-C range.
27. The system of any of the examples above, wherein the UV wavelength range in which said at least one UV light emitter emits light comprises wavelengths in the range of from 200 to 280 nm.
28. The system of any of the examples above, wherein the UV wavelength range in which said at least one UV light emitter emits light comprises wavelengths in the range of from 280 to 320 nm.
29. The system of any of the examples above, wherein said fiber optic cable has a length of at least 7 feet.
30. The system of any of the examples above wherein said fiber optic cable forms part of or is optically coupled to an endoscope.
31. The system of any of the examples above, further comprising shielding disposed with respect to said at least one UV light emitter such that an operator operating the system is exposed to light emission from said system of less than 1 mJ/cm$^2$ in said UV wavelength range when said light emission in said UV wavelength range from said distal end of said fiber optic cable is from 10 mJ/cm$^2$ to 100 mJ/cm$^2$.
32. The system of any of the examples above, further comprising shielding disposed with respect to said at least one UV light emitter such that light emission from the system in said UV wavelength range is less than 1 mJ/cm$^2$ over a solid angle of 0.1$\pi$ steradian at a distance of 36 inches from said distal end of said optical fiber cable when said light emission in said UV wavelength range from said fiber optic cable is from 10 mJ/cm$^2$ to 100 mJ/cm$^2$.
33. The system of any of the examples above, further comprising shielding disposed with respect to said at least one UV light emitter such that light emission from said system in said UV wavelength range is less than 1 mJ/cm$^2$ at most locations 1 foot away from one or more UV emitters when said light emission in said UV wavelength range is from 10 mJ/cm$^2$ to 100 mJ/cm$^2$.
34. The system of any of the examples above, further comprising shielding disposed with respect to said at least one UV light emitter such that, excluding output from a distal end said optical fiber cable, light emission in said UV wavelength range at a location 10 mm from said shielding is less than 1 mJ/cm$^2$ when said light emission in said UV wavelength range from said fiber optic cable is from 10 mJ/cm$^2$ to 100 mJ/cm$^2$.
35. The system of any of the examples above, further comprising shielding disposed with respect to said at least one UV light emitter such that, excluding output from a distal end of said fiber optic cable, said light in said UV wavelength range is less than 1 mJ/cm$^2$ over an angular extent that is 120° in one direction and 30° in another orthogonal direction when said light emission in said UV wavelength range from said fiber optic cable is from 10 mJ/cm$^2$ to 100 mJ/cm$^2$ 36 inches from said at least one UV light emitter.
36. A system of any of the examples above, wherein said shielding is transparent to visible light.
37. The system of any of the examples above, wherein said shielding is such that an operator operating the system is exposed to light emission from said system of less than 1 mJ/cm$^2$ in said UV wavelength range when said light emission in said UV wavelength range from said distal end of said fiber optic cable is from 10 mJ/cm$^2$ to 100 mJ/cm$^2$.
38. The system of any of the examples above, wherein said shielding is such that light emission in said UV wavelength range is less than 1 mJ/cm$^2$ over a solid angle of 0.1$\pi$ steradian at a distance of 36 inches from said distal end of said fiber optic cable when light emission in said UV wavelength range from said fiber optic cable is from 10 mJ/cm$^2$ to 100 mJ/cm$^2$
39. The system of any of the examples above, wherein said shielding is such that light emission in said UV wavelength range is less than 1 mJ/cm$^2$ over a solid angle of 0.2$\pi$ steradian at a distance of 36 inches from said distal end of said fiber optic cable when said light emission in said UV wavelength range from said fiber optic cable is from 10 mJ/cm$^2$ to 100 mJ/cm$^2$.
40. The system of any of the examples above, wherein said shielding is such that light emission in said UV wavelength range is less than 1 mJ/cm$^2$ over a solid angle of 0.3$\pi$ steradian at a distance of 36 inches from said distal end of said fiber optic cable when said light emission in said UV wavelength range from said fiber optic cable is from 10 mJ/cm$^2$ to 100 mJ/cm$^2$.
41. The system of any of the examples above, wherein said shielding is such that light emission in said UV wavelength range is less than 1 mJ/cm$^2$ over a solid angle of 0.5$\pi$ steradian at a distance of 36 inches from said distal end of said fiber optic cable when said light emission in said UV wavelength range from said fiber optic cable is from 10 mJ/cm$^2$ to 100 mJ/cm$^2$.

42. The system of any of the examples above, wherein light emission in said UV wavelength range is less than 1 $mJ/cm^2$ over for an operator within 1 foot of the distal end of the fiber cable system when said light emission in said UV wavelength range from said distal end of said fiber optic cable is from 10 $mJ/cm^2$ to 100 $mJ/cm^2$.
43. A method comprising exposing cancerous tissue or cells to UV light provided by the system of any of the examples above.
44. The system of any of the examples above, wherein said fiber optic cable comprises separate fiber strands optically coupled together.
45. The system of any of the examples above, wherein said fiber optic cable comprises separate fiber strands butt coupled together.
46. The system of any Examples 1-43, wherein said fiber optic cable comprises a single fiber strand.

Part XIV—Cover on Output of Fiber

1. A system for outputting ultraviolet (UV) light, said system comprising:
   at least one UV light emitter configured to emit light having a wavelength in the UV range;
   an optical fiber line configured to receive light from said at least one UV light emitter in said UV wavelength range and to transmit and output a portion of said light in said UV wavelength range, said optical fiber line having a proximal end positioned to receive light from said at least one UV light emitter and a distal end that outputs light in said UV wavelength range; and
   a cover configured to be positioned in front of light in said UV wavelength range output by said optical fiber line at the distal end thereof, said cover configured to provide protection against liquid or debris from blocking light in said wavelength range from being output from said optical fiber line when said optical fiber line is inserted into a body of a person or animal.
2. The system of Example 1, wherein said cover is movable or switchable between first and second states without removing the cover from the body, the first state wherein said cover is positioned in front of said optical output of optical fiber line and the second state wherein said cover provides less coverage in front of the optical output of said optical fiber line.
3. The system of Example 1 or 2, wherein said cover comprises a plurality of segments or sections that are movable so as to be positioned in first and second states without removing said cover from the body, said first state wherein said segments are in front of the output of light in said UV wavelength range and said second state wherein said segments are moved to a position so as to provide less coverage in front of the output of light in said UV wavelength of range.
4. The system of any of the examples above, further comprising a motor or actuator configured to move said cover or portions thereof.
5. The system of any of the examples above, wherein the cover or portions thereof are configured to moved hydraulically.
6. The system of any of the examples above, wherein said cover can be moved using a control located outside the body when the distal end of the UV light system is in the body.
7. The system of any of the examples above, wherein said cover comprises an iris.
8. The system of any of the examples above, wherein said cover is configured to be disposed in front of output optics and/or said optical fiber line transmissive of light in said UV wavelength range.
9. The system of any of the examples above, wherein said system comprises, is integrated with, and/or optically coupled to an endoscope, said cover at the distal end of said endoscope.
10. The system of any of the examples above, wherein said system comprises, is integrated with, and/or optically coupled to a surgical tool having a tube for insertion into a body, said cover at the distal end of said tube.
11. The system of any of the examples above, further comprising at least one fused silica lens configured to receive light emitted by said at least one light emitter having a wavelength the range UV, said at least one fused silica lens comprising fused silica wherein the OH content is not larger than 5 ppm or wherein one or more of Li, Na, K, Mg, Ca and Cu are smaller than 0.1 ppm.
12. The system of any of the examples above, wherein the UV wavelength range in which said at least one UV light emitter emits light comprises the UV-C range.
13. The system of any of the examples above, wherein the UV wavelength range in which said at least one UV light emitter emits light comprises wavelengths in the range of from 200 to 280 nm.
14. The system of any of the examples above, wherein the UV wavelength range in which said at least one UV light emitter emits light comprises wavelengths in the range of from 280 to 320 nm.
15. The system of any of the examples above, wherein said optical fiber line has a length of at least 7 feet.
16. The system of any of the examples above, wherein said optical fiber line forms part of or is optically coupled to an endoscope.
17. The system of any of examples above, further comprising shielding disposed with respect to said distal end of said optical fiber line to block light in said UV wavelength range output from said distal end of said optical fiber line.
18. The system of Example 17, wherein said shielding is configured to block at least 50% of the light in said UV wavelength range output from said distal end of said optical fiber line that is scattered or reflected from the sample in a direction above said support.
19. The system of Examples 17 or 18, wherein said UV light emission from said optical fiber line at a location 10 mm from said shielding is less than 1 $mJ/cm^2$ when said UV light emission from said optical fiber line is from 10 $mJ/cm^2$ to 100 $mJ/cm^2$.
20. The system of any of Examples 17-19, wherein said shielding is disposed with respect to said distal end of said optical fiber line such that light emission in said UV wavelength range at a location 36 inches from said distal end of said optical fiber line is less than 1 $mJ/cm^2$ when said UV light emission from said optical fiber line is from 10 $mJ/cm^2$ to 100 $mJ/cm^2$.
21. The system of Example 20, wherein light emission in said UV wavelength range at a location 36 inches from said distal end of said optical fiber line is less than 1 $mJ/cm^2$ over an angular extent that is 180° in one direction and 30° in another orthogonal direction when said UV light emission from said optical fiber line is from 10 $mJ/cm^2$ to 100 $mJ/cm^2$.

22. The system of any of examples above, further comprising shielding disposed with respect to said at least one UV light emitter such that, excluding output from said distal end of said optical fiber line, a person applying light in said UV wavelength range to a patient is exposed to light emission from said system in said UV wavelength range of less than 1 $mJ/cm^2$ when said light emission in said UV wavelength range from said distal end of said fiber line is from 10 $mJ/cm^2$ to 100 $mJ/cm^2$.
23. The system of any of the examples above, further comprising shielding disposed with respect to said at least one UV light emitter such that, excluding output from a distal end of said optical fiber line, light emission from the system in said UV wavelength range is less than 1 $mJ/cm^2$ over a solid angle of 0.1π steradian at a distance of 36 inches from said distal end of said optical fiber line when said light emission in said UV wavelength range from said optical fiber line is from 10 $mJ/cm^2$ to 100 $mJ/cm^2$.
24. The system of any of the examples above, further comprising shielding disposed with respect to the distal end of said optical fiber line such that an operator operating the system is exposed to light emission from said system of less than 1 $mJ/cm^2$ in said UV wavelength range when said light emission in said UV wavelength range from said distal end of said fiber optic cable is from 10 $mJ/cm^2$ to 100 $mJ/cm^2$.
25. The system of any of the examples above, further comprising shielding disposed with respect to said at least one UV light emitter such that, excluding output from a distal end of said optical fiber line, light emission in said UV wavelength range at a location 10 mm from said shielding is less than 1 $mJ/cm^2$ when said UV light emission from said optical fiber line is from 10 $mJ/cm^2$ to 100 $mJ/cm^2$.
26. The system of any of the examples above, further comprising shielding disposed with respect to said at least one UV light emitter such that, excluding output from a distal end of said optical fiber line, said light in said UV wavelength range 36 inches from said at least one UV light emitter is less than 1 $mJ/cm^2$ over an angular extent that is 180° in one direction and 70° in another orthogonal direction when said UV light emission from said optical fiber line is from 10 $mJ/cm^2$ to 100 $mJ/cm^2$.
27. The system of any of the examples above, further comprising a mount for positioning a distal end of said optical fiber line configured to receive light in said UV wavelength range from said at least one UV light emitter with respect to a sample to direct light in said UV wavelength range out of said distal end of said optical fiber line and to said sample.
28. The system of any of the examples above, further comprising a support on which a sample can be positioned to receive said light in said UV wavelength range from said distal end of said optical fiber line.
29. A method comprising exposing cancerous tissue or cells to UV light provided by the system of any of the examples above.
30. The system of any of the examples above, wherein said optical fiber line comprises separate fiber strands optically coupled together.
31. The system of any of the examples above, wherein said optical fiber line comprises separate fiber strands butt coupled together.
32. The system of any Examples 1-29, wherein said optical fiber line comprises single fiber strand.

Part XV—Lenses to Alter Beam Width

1. A system for outputting ultraviolet (UV) light, said system comprising:
   at least one UV light emitter configured to emit light having a wavelength in the UV range;
   an optical fiber configured to receive light from said at least one UV light emitter in said UV wavelength range and to transmit and output a portion of said light in said UV wavelength range, said optical fiber has a proximal end positioned to receive light from said at least one UV light emitter and a distal end that outputs light in said UV wavelength range; and a plurality of output lenses configured to alter the size of a UV light beam at a target location when different ones of said output lenses are positioned to receive light from said optical fiber at different times.
2. The system of Example 1, wherein said output lenses are configured to be attached at the output said system to alter the size of the UV light beam at a target location.
3. The system of Example 1 or 2, wherein system comprises, is integrated with, or optically coupled to an endoscope having proximal and distal ends and said optical lenses are configured to be attached to a distal end of said endoscope.
4. The system of any of the examples above, wherein said system comprises, is integrated with, or optically coupled to a surgical tool having a tube for insertion into a body, and said optical lenses are configured to be attached to a distal end of said tube through which light in said UV wavelength range is output.
5. The system of any of the examples above, wherein said output lenses are configured to alter the size of a UV light beam at a target location when different ones of said output lenses are disposed at said distal end of said optical fiber at different times.
6. The system of any of the examples above, further comprising a cover configured to be positioned in front of light in said UV wavelength range output by said optical fiber at the distal end thereof, said cover configured to provide protection against liquid or debris from blocking light in said wavelength range from being output from said optical fiber when said optical fiber is inserted into a body of a person or animal.
7. The system of any of the examples above, wherein said cover is movable or switchable between first and second states without removing the cover from the body, the first state wherein said cover is positioned in front of said optical output of optical fiber and the second state wherein said cover provides less coverage in front of the optical output of said optical fiber.
8. The system of any of the examples above, further comprising a mount for positioning a distal end of said optical fiber configured to receive light in said UV wavelength range from said at least one UV light emitter with respect to a sample on said support to direct light in said UV wavelength range out of said distal end of said optical fiber and to said sample.
9. The system of any of the examples above, further comprising a support on which a sample can be positioned to receive said light in said UV wavelength range from said distal end of said optical fiber.
10. The system of any of examples above, further comprising shielding disposed with respect to said distal end of said optical fiber to block light in said UV wavelength range output from said distal end of said optical fiber.

11. The system of Example 10, wherein said shielding is configured to block at least 50% of the light in said UV wavelength range output from said distal end of said optical fiber that is scattered or reflected from the sample in a direction above said support.

12. The system of Examples 10 or 11, wherein said UV light emission from said optical fiber at a location 10 mm from said shielding is less than 1 mJ/cm$^2$ when said UV light emission from said optical fiber is from 10 mJ/cm$^2$ to 100 mJ/cm$^2$.

13. The system of any of Examples 10-12, wherein said shielding is disposed with respect to said distal end of said optical fiber such that light emission in said UV wavelength range at a location 36 inches from said distal end of said optical fiber is less than 1 mJ/cm$^2$ when said UV light emission from said optical fiber is from 10 mJ/cm$^2$ to 100 mJ/cm$^2$.

14. The system of Example 13, wherein light emission in said UV wavelength range at a location 36 inches from said distal end of said optical fiber is less than 1 mJ/cm$^2$ over an angular extent that is 180° in one direction and 40° in another orthogonal direction when said UV light emission from said optical fiber is from 10 mJ/cm$^2$ to 100 mJ/cm$^2$.

15. The system of any of the examples above, further comprising at least one fused silica lens configured to receive light emitted by said at least one light emitter having a wavelength the range UV, said at least one fused silica lens comprising fused silica wherein the OH content is not larger than 5 ppm or wherein one or more of Li, Na, K, Mg, Ca and Cu are smaller than 0.1 ppm.

16. The system of any of the examples above, wherein the UV wavelength range in which said at least one UV light emitter emits light comprises the UV-C range.

17. The system of any of the examples above, wherein the UV wavelength range in which said at least one UV light emitter emits light comprises wavelengths in the range of from 200 to 280 nm.

18. The system of any of the examples above, wherein the UV wavelength range in which said at least one UV light emitter emits light comprises wavelengths in the range of from 280 to 320 nm.

19. The system of any of the examples above, wherein said optical fiber has a length of at least 7 feet.

20. The system of any of the examples above wherein said optical fiber forms part of or is optically coupled to an endoscope.

21. The system of any of the examples above, further comprising shielding disposed with respect to said at least one UV light emitter such that, excluding output from a distal end of said optical fiber, light emission in said UV wavelength range at a location 10 mm from said shielding is less than 1 mJ/cm$^2$ when said UV light emission from said optical fiber is from 10 mJ/cm$^2$ to 100 mJ/cm$^2$.

22. The system of any of the examples above, further comprising shielding disposed with respect to said at least one UV light emitter such that, excluding output from a distal end of said optical fiber, said light in said UV wavelength range 36 inches from said at least one UV light emitter is less than 1 mJ/cm$^2$ over an angular extent that is 180° in one direction and 40° in another orthogonal direction when said UV light emission from said optical fiber is from 10 mJ/cm$^2$ to 100 mJ/cm$^2$.

23. The system of any of examples above, further comprising shielding disposed with respect to said at least one UV light emitter such that, excluding output from said distal end of said optical fiber, a person applying light in said UV wavelength range to a patient is exposed to light emission from said system in said UV wavelength range of less than 1 mJ/cm$^2$ when said light emission in said UV wavelength range from said distal end of said fiber is from 10 mJ/cm$^2$ to 100 mJ/cm$^2$.

24. The system of any of the examples above, further comprising shielding disposed with respect to said at least one UV light emitter such that, excluding output from a distal end of said optical fiber, light emission from the system in said UV wavelength range is less than 1 mJ/cm$^2$ over a solid angle of 0.1$\pi$ steradian at a distance of 36 inches from said distal end of said optical fiber when said light emission in said UV wavelength range from said optical fiber is from 10 mJ/cm$^2$ to 100 mJ/cm$^2$.

25. The system of any of the examples above, further comprising shielding disposed with respect to the distal end of said optical fiber such that an operator operating the system is exposed to light emission from said system of less than 1 mJ/cm$^2$ in said UV wavelength range when said light emission in said UV wavelength range from said distal end of said fiber optic cable is from 10 mJ/cm$^2$ to 100 mJ/cm$^2$.

26. A method comprising exposing cancerous tissue or cells to UV light provided by the system of any of the examples above.

27. The system of any of the examples above, wherein said optical fiber comprises separate fiber strands optically coupled together.

28. The system of any of the examples above, wherein said optical fiber comprises separate fiber strands butt coupled together.

29. The system of any Examples 1-26, wherein said optical fiber comprises a single fiber strand.

Part XVI—Robotic Surgery

1. A system for outputting ultraviolet (UV) light, said system comprising:
   at least one UV light emitter configured to emit light having a wavelength in the UV range; and
   an optical fiber configured to receive light from said at least one UV light emitter in said UV wavelength range and to transmit and output a portion of said light in said UV wavelength range, said optical fiber having a proximal end positioned to receive light from said at least one UV light emitter and a distal end that outputs light in said UV wavelength range,
   wherein UV light system comprises a robotic system.

2. The system of any of the examples above, wherein said UV light system comprises a robotic surgical system controllable by a surgeon so as to provide robotically assisted surgery.

3. The system of Example 1 or 2, wherein said fiber optic is supported on an articulated arm or a robotic arm.

4. The system of Example 3, wherein said articulated or robotic arm further comprises a head at the distal end thereof where light in said UV wavelength range is output.

5. The system of Examples 3 or 4, wherein said articulated or arm further comprises tube at the distal end thereof wherein light in said UV wavelength range is output.

6. The system of Example 1 or 2, wherein said optical fiber forms part of or is optically coupled to a translation stage.
7. The system of any of the examples above, further comprising at least one fused silica lens configured to receive light emitted by said at least one light emitter having a wavelength in the UV wavelength range, said at least one fused silica lens comprising fused silica wherein the OH content is not larger than 5 ppm or wherein one or more of Li, Na, K, Mg, Ca and Cu are smaller than 0.1 ppm.
8. The system of any of the examples above, wherein the UV wavelength range in which said at least one UV light emitter emits light comprises the UV-C range.
9. The system of any of the examples above, wherein the UV wavelength range in which said at least one UV light emitter emits light comprises wavelengths in the range of from 200 to 280 nm.
10. The system of any of the examples above, wherein the UV wavelength range in which said at least one UV light emitter emits light comprises wavelengths in the range of from 280 to 325 nm.
11. The system of any of the examples above, wherein said optical fiber has a length of at least 7 feet.
12. The system of any of the examples above, wherein said optical fiber forms part of or is optically coupled to an endoscope.
13. The system of any of the examples above, further comprising shielding disposed with respect to said at least one UV light emitter such that, excluding output from a distal end of said optical fiber, light emission in said UV wavelength range at a location 10 mm from said shielding is less than 1 $mJ/cm^2$ when said UV light emission from said optical fiber is from 10 $mJ/cm^2$ to 100 $mJ/cm^2$.
14. The system of any of the examples above, further comprising shielding disposed with respect to said at least one UV light emitter such that, excluding output from a distal end of said optical fiber, said light in said UV wavelength range is less than 1 $mJ/cm^2$ over an angular extent that is 180° in one direction and 30° in another orthogonal direction 36 inches from said at least one UV light emitter when said UV light emission from said optical fiber is from 10 $mJ/cm^2$ to 100 $mJ/cm^2$.
15. The system of any of the examples above, further comprising a support on which a sample can be positioned to receive said light in said UV wavelength range from said distal end of said optical fiber.
16. The system of any of the examples above, further comprising a mount for positioning a distal end of said optical fiber configured to receive light in said UV wavelength range from said at least one UV light emitter with respect to a sample to direct light in said UV wavelength range out of said distal end of said optical fiber and to said sample.
17. The system of any of examples above, further comprising shielding disposed with respect to said distal end of said optical fiber to block light in said UV wavelength range output from said distal end of said optical fiber.
18. The system of Example 17, wherein said shielding is configured to block at least 50% of the light in said UV wavelength range output from said distal end of said optical fiber that is scattered or reflected from the sample in a direction above a support on which said sample is supported.
19. The system of Examples 17 or 18, wherein said UV light emission from said optical fiber at a location 10 mm from said shielding is less than 1 $mJ/cm^2$ when said UV light emission from said optical fiber is from 10 $mJ/cm^2$ to 100 $mJ/cm^2$.
20. The system of any of Examples 17-19, wherein said shielding is disposed with respect to said distal end of said optical fiber such that light emission in said UV wavelength range at a location 36 inches from said distal end of said optical fiber is less than 1 $mJ/cm^2$ when said UV light emission from said optical fiber is from 10 $mJ/cm^2$ to 100 $mJ/cm^2$.
21. The system of Example 20, wherein light emission in said UV wavelength range is less than 1 $mJ/cm^2$ over an angular extent that is 180° in one direction and 30° in another orthogonal direction 36 inches from said distal end of said optical fiber when said UV light emission from said optical fiber is from 10 $mJ/cm^2$ to 100 $mJ/cm^2$.
22. The system of any of the examples above, further comprising a cover configured to be positioned in front of light in said UV wavelength range output by said optical fiber at the distal end thereof, said cover configured to provide protection against liquid or debris from blocking light in said wavelength range from being output from said optical fiber when said optical fiber is inserted into a body of a person or animal.
23. The system of any of the examples above, wherein said cover is movable or switchable between first and second states without removing the cover from the body, the first state wherein said cover is positioned in front of said optical output of optical fiber and the second state wherein said cover provides less coverage in front of the optical output of said optical fiber.
24. The system of any of the examples above, further comprising a plurality of output lenses configured to alter the size of a UV light beam at a target location when different ones of said output lenses are disposed at said distal end of said optical fiber at different times.
25. The system of Example 24, wherein said plurality of output lenses are configured to be attached at the output said UV light system to alter the size of the UV light beam at a target location.
26. A method comprising exposing cancerous tissue or cells to UV light provided by the system of any of the examples above.
27. The system of any of the examples above, wherein said optical fiber comprises separate fiber strands optically coupled together.
28. The system of any of the examples above, wherein said optical fiber comprises separate fiber strands butt coupled together.
29. The system of any Examples 1-26, wherein said optical fiber comprises a single strand.

Part XVII—Method of Determining Parameter Values

1. A method of determining a value of at least one parameter of an ultraviolet (UV) light system, said method comprising:
   producing output from at least one UV light emitter configured to emit light having a wavelength in a UV range;
   coupling light from said at least one UV light emitter in said UV wavelength range into a proximal end of an optical fiber such that a least a portion of said light is transmitted through and output from a distal end of said optical fiber;

directing light in said UV wavelength range output from said optical fiber onto a sample;

adjusting at least one parameter of said at least one UV light emitter; and selecting a value of said at least one parameter of said UV light system for directing light onto the body of a living human or animal based on information obtained by said directing light in said UV wavelength range onto said sample.

2. The method of Example 1, wherein said at least one parameter includes one or more of the following: a rate of pulses or groups of pulses, a duration of said pulses or groups of pulses, a temporal spacing between said pulses or groups of pulses, or a duty cycle of said pulses or said group of pulses.

3. The method of Example 1 or 2, wherein said a least one parameter includes one or more of the following: the radiant flux, the brightness, power, intensity, or exitance of said at least one UV light emitter.

4. The method of any of the examples above, wherein said sample comprises cancer cells.

5. The method of any of Examples 1-4, wherein one or more values for one or more respective parameters are selected that provide increased effectiveness in disabling, deactivating, or destroying cancer cells.

6. The method of any of Examples 1-4, wherein one or more values for one or more respective parameters are selected that provide increased effectiveness in disabling, deactivating, or destroying cancer cells and providing reduced damage to non-cancerous cells.

7. The method of any of the examples above, wherein said sample comprises the same type of cancer as in said body of said living human or animal.

8. The method of any of the examples above, wherein said sample comprises the same cancer cell line as in said body of said living human or animal.

9. The method of any of the examples above, wherein said sample comprise a biopsy of said living human or animal.

10. The method of any of the examples above, wherein the same UV light system is used to both direct light in said UV wavelength range output from said optical fiber onto a sample and is used at a future time to direct light in said UV wavelength range that is output from said optical fiber on said body of said living human or animal.

11. The method of any of the examples above, further comprising setting said at least one parameter of said UV light system based on the value selected.

12. The method of Example 11, further comprising exposing cancerous tissue or cells of said living human or animal to UV light provided by said UV light system.

13. The method of any of Examples 1-9, wherein a first UV light system is used to direct light in said UV wavelength range output from said optical fiber onto a sample and a second UV light system is used at a future time to direct light in said UV wavelength range that is output from said optical fiber on said body of said living human or animal.

14. The method of Example 13, further comprising setting said at least one parameter of said second UV light system based on the value selected.

15. The method of Example 14, further comprising exposing cancerous tissue or cells of said living human or animal to UV light provided by said second UV light system.

16. The method of any of Examples 1-9, further comprising setting said at least one parameter of another UV light system based on the value selected.

17. The method of any of the examples above, wherein said sample is positioned to receive said light in said UV wavelength range from said distal end of said optical fiber.

18. The method of any of the examples above, further comprising positioning a distal end of said optical fiber with respect to a sample to direct light in said UV wavelength range out of said distal end of said optical fiber and to said sample.

19. The method of any of the examples above, wherein said optical fiber is included in or optically coupled to an endoscope and said distal end of said endoscope is positioned with respect to a sample to direct light in said UV wavelength range out onto said sample.

20. The method of any of the examples above, wherein said optical fiber is included in or optically coupled to hand held delivery device and the distal end of said hand held delivery device is positioned with respect to a sample to direct light in said UV wavelength range out onto said sample.

21. The method of any of examples above, wherein said sample is on a microscope slide, in a petri dish or in a sample container.

22. The method of any of examples above, wherein said value is used in directing light in said UV wavelength range that is output from said optical fiber on said body of said living human or animal within 14 days of directing light in said UV wavelength range that was output from said optical fiber onto said sample.

23. The method of any of examples above, wherein said value is used in directing light in said UV wavelength range that is output from said optical fiber on said body of said living human or animal within 7 days of directing light in said UV wavelength range that was output from said optical fiber onto said sample.

24. The method of any of examples above, wherein said value is used in directing light in said UV wavelength range that is output from said optical fiber on said body of said living human or animal within 5 days of directing light in said UV wavelength range that was output from said optical fiber onto said sample.

25. The method of any of examples above, wherein said value is used in directing light in said UV wavelength range that is output from said optical fiber on said body of said living human or animal within 3 days of directing light in said UV wavelength range that was output from said optical fiber onto said sample.

26. The method of any of examples above, further comprising blocking light in said UV wavelength range output from at least one UV light emitter with shielding proximal said at least one UV light emitter.

27. The method of any of examples above, further comprising blocking light in said UV wavelength range output from said distal end of said optical fiber with shielding proximal said distal end of said optical fiber.

28. The method of any of the examples above, comprising shielding said distal end of said optical fiber on at least three sides.

29. The method of any of the examples above, comprising shielding said distal end of said optical fiber on at least four sides.

30. The method of any of the examples above, comprising shielding said distal end of said optical fiber on at least five sides.

31. The method of any of the examples above, comprising shielding said at least one light emitter on at least three sides.
32. The method of any of the examples above, comprising shielding said at least one light emitter on at least four sides.
33. The method of any of the examples above, comprising shielding said at least one light emitter on at least five sides.
34. The method of any of the examples above, wherein the UV wavelength range in which said at least one UV light emitter emits light comprises the UV-C range.
35. The method of any of the examples above, wherein the UV wavelength range in which said at least one UV light emitter emits light comprises wavelengths in the range of from 200 to 280 nm.
36. The method of any of the examples above, wherein the UV wavelength range in which said at least one UV light emitter emits light comprises wavelengths in the range of from 280 to 320 nm.
37. The method of any of the examples above, wherein said optical fiber has a length of at least 7 feet.
38. The method of any of the examples above, wherein said optical fiber forms part of or is optically coupled to an endoscope.
39. The method of any of the examples above wherein said optical fiber is optically coupled to and/or integrate with a handheld delivery device.
40. The system of any of the examples above, wherein said optical fiber comprises separate fiber strands optically coupled together.
41. The system of any of the examples above, wherein said optical fiber comprises separate fiber strands butt coupled together.
42. The system of any Examples 1-39, wherein said optical fiber comprises a single fiber strand.

Part XVIII

1. A system for output ultraviolet (UV) light, said system comprising:
   at least one UV light emitter configured to emit light having a wavelength in the UV wavelength range; and
   an optical fiber line configured to receive light from said at least one UV light emitter in UV range and to transmit and output a portion of said light in the UV.
2. The system of Example 1, wherein said at least one UV light emitter comprises a plurality of UV light emitters.
3. The system of Example 1 or 2, wherein said at least one UV light emitter comprises an array of UV light emitters.
4. The system of Example 3, wherein said UV light emitters of said array of UV light emitters extend across an area of 0.01 $mm^2$ to 125 $mm^2$.
5. The system of Examples 3 or 4, wherein said UV light emitters of said array have a center-to-center spacing of from 0.1 mm to 8 mm.
6. The system of any of Examples 3-5, wherein said UV light emitters of said array of UV light emitters are formed on a single semiconductor substrate.
7. The system of any of the examples above, wherein said unit can fit in a suitcase.
8. The system of any of the examples above, further comprising electronics configured to pulse said at least one UV light emitter such that said at least one UV light emitter emits pulses of UV light.
9. The system of Example 8, wherein said electronics comprises a pulsed power source.
10. The system of Example 8 or 9, wherein said electronics comprises a variable pulsed power source configured to vary the repetition rate of pulses output by said at least one UV light emitter.
11. The system of any of Examples 8-10, wherein said electronics comprises a variable pulsed power source configured to vary the duration of pulses output by said at least one UV light emitter.
12. The system of any of Examples 8-11, wherein said electronics comprises a variable pulsed power source configured to vary the temporal spacing between consecutive pulses output by said UV-C light emitters.
13. The system of any of the examples above, wherein said optical fiber line comprises fused silica.
14. The system of any of the examples above, wherein said optical fiber line has an optical core of at least 100 micrometers wide in cross-section.
15. The system of any of the examples above, wherein said optical fiber line has an optical core of at least 250 micrometers wide in cross-section.
16. The system of any of the examples above, wherein said optical fiber line has an optical core of at least 600 micrometers wide in cross-section.
17. The system of any of the examples above, wherein said optical fiber line has an optical core in the range of from 200 micrometers to 2500 micrometers wide in cross-section.
18. The system of any of the examples above, wherein said optical fiber line has an optical core in the range of from 500 micrometers to 2500 micrometers wide in cross-section.
19. The system of any of the examples above, wherein said optical fiber line has an optical core in the range of from 650 micrometers to 2500 micrometers wide in cross-section.
20. The system of any of the examples above, wherein said optical fiber line has an optical core in the range of from 700 micrometers to 2000 micrometers wide in cross-section.
21. The system of any of the examples above, wherein said optical fiber line has an optical core in the range of from 200 micrometers to 1500 micrometers wide in cross-section.
22. The system of any of the examples above, wherein said optical fiber line has an optical core in the range of from 800 micrometers to 1200 micrometers wide in cross-section.
23. The system of any of the examples above, wherein said optical fiber line has a length in a range from 6 inches to 2 feet long.
24. The system of any of the examples above, wherein said optical fiber line has a length in a range from 1 to 8 feet long.
25. The system of any of the examples above, wherein said optical fiber line has a length in a range from 4 to 12 feet long.
26. The system of any of the examples above, wherein said optical fiber line has a length in a range from 10 to 25 feet long.
27. The system of any of the examples above, wherein said optical fiber line has a length in a range from 1 to 30 feet long.
28. The system of any of the examples above, wherein said optical fiber line has a length in a range from 1.5 to 4 feet long.

29. The system of any of the examples above, further comprising an output lens at the distal end of said optical fiber to receive light exiting the end of said optical fiber line.

30. The system of any of examples above, further comprising an output lens at the distal end of said optical fiber to reduce divergence of light exiting the end of said optical fiber line.

31. The system of any of the examples above, further comprising an output lens at the distal end of said optical fiber to focus light exiting the end of said optical fiber line.

32. The system of any of the examples above, further comprising a lens at the distal end of said optical fiber to increase collimation of light exiting the end of said optical fiber line.

33. The system of any of the examples above, wherein said optical fiber has a core comprising silica.

34. The system of Example 33, wherein said silica includes a sufficiently high concentration of hydroxyl (OH) concentration such that said optical fiber transmits 250 nm.

35. The system of any of the examples above, wherein said optical fiber further comprises a glass cladding.

36. The system of Example 35, wherein said glass cladding comprises doped glass.

37. The system of Example 35 or 36, wherein said glass cladding is fluorine doped.

38. The system of any of the examples above, wherein said optical fiber has a core comprising fused silica.

39. The system of any of the examples above, wherein said fiber optic forms part of or is optically coupled to an endoscope.

40. The system of Example 39, wherein said endoscope has a cross-sectional width or diameter at the distal end thereof of from 1 to 20 mm.

41. The system of Example 39, wherein said endoscope has a cross-sectional width or diameter at the distal end thereof of from 2 to 12 mm.

42. The system of any of Examples 39-41, wherein said endoscope comprises at least one relay lens or a least one fiber bundle to convey an image from the distal end of the endoscope to the proximal end of the endoscope.

43. The system of any of Examples 39-42, wherein said endoscope comprises a visible light emitter at the distal end thereof that provide illumination.

44. The system of any of Examples 39-43, wherein said endoscope comprises a camera at the distal end thereof to capture images.

45. The system of any of Examples 38-43, wherein said endoscope comprises a camera at the proximal end thereof to capture images or an ocular at the proximal end of the endoscope for viewing objects at the distal end of the endoscope.

46. The system of any of the examples above, wherein said optical fiber line forms part of or is optically coupled to a handheld output tool.

47. The system of Example 46, wherein said handheld output tool comprises a button or switch to activate output of UV-C light from said handheld output tool.

48. The system of any of Examples 46-47, wherein said handheld output tool has a cross-sectional width or diameter of from 10 to 60 mm.

49. The system of any of Examples 46-47, wherein said handheld output tool has a cross-sectional width or diameter of from 20 to 50 mm.

50. The system of any of Examples 46-49, wherein said handheld output tool has a tube at the distal end thereof.

51. The system of Example 50, wherein said tube has a cross-sectional width or diameter at the distal end thereof of from 1 to 12 mm.

52. The system of Example 50, wherein said tube has a cross-sectional width or diameter at the distal end thereof of from 2 to 15 mm.

53. The system of any of Examples 46-52, wherein said handheld output tool has a body that is contoured to ergonomically fit a hand.

54. The system of any of Examples 46-53, wherein said handheld output tool has a pistol grip.

55. The system of any of the examples above, wherein said optical fiber line is supported on an articulated arm or a robotic arm.

56. The system of Example 55, wherein said articulated or robotic arm further comprises a head at the distal end thereof wherein UV-C light is output.

57. The system of Examples 55 or 56, wherein said articulated or arm further comprises tube at the distal end thereof wherein UV-C light is output.

58. The system of Example 57, wherein said tube has a cross-sectional width or diameter at the distal end thereof of from 1 to 12 mm.

59. The system of Example 57, wherein said tube has a cross-sectional width or diameter at the distal end thereof of from 2 to 15 mm.

60. The system of any of the examples above, wherein said fiber optic forms part of or is optically coupled to a translation stage.

61. The system of any of the examples above, wherein said system comprises a robotic system.

62. The system of any of the examples above, wherein said system comprises a robotic surgical system controllable by a surgeon.

63. The system of any of the examples above, wherein at least one UV light emitter outputs radiant flux in the range from 50 mW to 4000 mW.

64. The system of any of the examples above, wherein said at least one UV light emitter outputs radiant flux in the range from 1 mW to 500 mW.

65. The system of any of the examples above, wherein said at least one UV light emitter outputs radiant flux in the range from 1 μW to 5000 μW.

66. The system of any of the examples above, wherein said at least one UV light emitter is configured to emit light in the UV range having a wavelength in the range of 280 to 320 nm.

67. The system of any of the examples above, wherein said at least one UV light emitter is configured to emit light having a wavelength in the range of 280 to 320 nm and said optical fiber is configured to receive light from said at least one UV light emitter in the wavelength range of 280 to 320 nm and to transmit and output a portion of said light in the wavelength range of 280 to 320 nm.

68. The system of any of the examples above, wherein said at least one UV light emitter is configured to emit brightest in a wavelength in the range of 280 to 320 nm.

69. The system of any of the examples above, wherein said at least one UV light emitter is configured to emit brightest in a wavelength in the range of 280 to 290 nm.

70. The system of any of the examples above, wherein said at least one UV-C light emitter is configured to emit brightest in a wavelength in the range of 290 to 300 nm.

71. The system of any of the examples above, wherein said at least one UV-C light emitter is configured to emit brightest in a wavelength in the range of 300 to 315 nm.
72. The system of any of the examples above, wherein said at least one UV light emitter is configured to emit most UV light in the range of between 280 nm and 320 nm.
73. The system of any of the examples above, wherein said at least one UV-C light emitter is configured to emit most UV light in the range of between 280 nm and 290 nm.
74. The system of any of the examples above, wherein said at least one UV light emitter is configured to emit most UV light in the range of between 290 nm and 300 nm.
75. The system of any of the examples above, wherein said at least one UV light emitter is configured to emit most UV light in the range of between 300 nm and 320 nm.
76. The system of any of the examples above, wherein said at least one UV-C light emitter is configured to emit most light in the range of between 280 nm and 320 nm.
77. The system of any of the examples above, wherein said at least one UV-C light emitter is configured to emit most light in the range of between 280 nm and 300 nm.
78. The system of any of the examples above, wherein said at least one UV light emitter is configured to emit at least 70% of the UV light in the range of between 280 nm and 320 nm.
79. The system of any of the examples above, wherein said at least one UV light emitter is configured to emit at least 70% of the UV light in the range of between 280 nm and 290 nm.
80. The system of any of the examples above, wherein said at least one UV light emitter is configured to emit at least 70% of the UV light emitted therefrom in the range of between 290 nm and 300 nm.
81. The system of any of the examples above, wherein said at least one UV light emitter is configured to emit at least 70% of the UV light emitted therefrom in the range of between 300 nm and 310 nm.
82. The system of any of the examples above, wherein said at least one UV light emitter is configured to emit at least 70% of the light emitted therefrom in the range of between 280 nm and 320 nm.
83. The system of any of the examples above, wherein said at least one UV light emitter is configured to emit at least 70% of the light emitted therefrom in the range of between 280 nm and 290 nm.
84. The system of any of the examples above, wherein most of the UV light output from the fiber optic is in the range of between 280 nm and 320 nm.
85. The system of any of the examples above, wherein most of the UV light output from the fiber optic in the range of between 280 nm and 290 nm.
86. The system of any of the examples above, wherein most of the UV light output from the fiber optic in the range of between 290 nm and 300 nm.
87. The system of any of the examples above, wherein most of the UV light output from the fiber optic in the range of between 300 nm and 320 nm.
88. The system of any of the examples above, wherein most of the light output from the fiber optic in the range of between 280 nm and 320 nm.
89. The system of any of the examples above, wherein most of the light output from the fiber optic in the range of between 280 nm and 300 nm.
90. The system of any of the examples above, wherein at least 70% of the UV light output from the fiber optic is in the range of between 280 nm and 320 nm.
91. The system of any of the examples above, wherein at least 70% of the UV light output from the fiber optic in the range of between 280 nm and 290 nm.
92. The system of any of the examples above, wherein at least 70% of the UV light output from the fiber optic in the range of between 290 nm and 300 nm.
93. The system of any of the examples above, wherein at least 70% of the UV light output from the fiber optic in the range of between 300 nm and 320 nm.
94. The system of any of the examples above, wherein at least 70% of the light output from the fiber optic in the range of between 280 nm and 320 nm.
95. The system of any of the examples above, wherein at least 70% of the light output from the fiber optic in the range of between 280 nm and 300 nm.
96. The system of any of the examples above, wherein said system comprises at least part of an endoscope.
97. The system of any of the examples above, wherein said system is optically coupled to an endoscope.
98. The system of any of the examples above, wherein said at least one light emitter comprises an array of UV light emitters that has a dimension along a side of between 8 mm to 50 mm.
99. The system of any of the examples above, wherein said at least one light emitter comprises an array of UV light emitters that has a dimension along one side of from 5 mm to 60 mm and a dimension along another side of from 5 to 60 mm.
100. The system of any of the examples above, wherein said at least one light emitter comprises an array of UV light emitters that has a dimension along a side of between 0.5 mm to 50 mm.
101. The system of any of the examples above, wherein said at least one light emitter comprises an array of UV light emitters that has a dimension along one side of from 0.5 mm to 50 mm and a dimension along another side of from 0.5 to 50 mm.
102. The system of any of the examples above, wherein said at least one light emitter comprises an array of UV emitters and the number of UV emitters in the array comprises from 2 to 6.
103. The system of any of the examples above, wherein said at least one light emitter comprises an array of UV emitters and the number of UV emitters in the array comprises from 3 to 5.
104. The system of any of the examples above, wherein said at least one light emitter comprises an array of UV emitters and the number of UV emitters in the array is 4.
105. The system of any of the examples above, wherein at least one UV light emitters is configured to emit visible light.
106. The system of any of Examples 1-104, further comprising a visible light emitter configured to emit visible light.
107. The system of Example 106, wherein said visible light emitter comprises a color LED.
108. The system of any of Examples 106-107, wherein said visible light can be used as a guide as to where UV light is directed at the target.

109. The system of any of Examples 106-108, wherein said visible light is color light.
110. The system of any of Examples 106-109, wherein said visible light is red, green, blue, or violet color light.
111. The system of any of Examples 106-110, wherein a UV light beam having a perimeter is formed at a target location by said system and said visible light forms a beam having a perimeter at said target location that matches the perimeter of the UV light beam to within 10% of the size of the UV light beam at said target location.
112. The system of any of Examples 106-111, wherein a UV light beam having a perimeter is formed at a target location by said System and said visible light forms a beam having a perimeter at said target location that matches the perimeter of the UV light beam to within 5% of the size of the UV light beam at said target location.
113. The system of any of the examples above, wherein said system outputs a UV light beam having a beamwidth (FWHM) of 20 mm or smaller at a target location.
114. The system of any of the examples above, wherein said system outputs a UV light beam having a beamwidth (FWHM) of 10 mm or smaller at a target location.
115. The system of any of the examples above, wherein said system outputs a UV light beam having a beamwidth (FWHM) of 5 mm or smaller at a target location.
116. The system of any of the examples above, wherein said system outputs a UV light beam having a beamwidth (FWHM) of 2 mm or smaller at a target location.
117. A kit comprising the system of any of the examples above, further comprising a plurality of output lenses configured to alter the size of the UV beam at a target location.
118. A kit comprising the system of Example 117, wherein said plurality of output lenses can be positioned at the output said UV projection unit to alter the size of the UV light beam at a target location.
119. A kit comprising the system of Example 117 or 118, wherein different output lenses of said plurality of output lenses can be positioned at the output of said system to provide a different respective sizes of the UV light beam at a target location.
120. The system of any of the examples above, wherein said at least one light emitter is configured to emit light having a peak wavelength in the range of 280 to 320.
121. The system of any of the examples above, wherein said at least one light emitter is configured to emit light having a peak wavelength in the range of 280 to 290.
122. The system of any of the examples above, wherein said at least one UV-C light emitter is configured to emit light having a peak wavelength in the range of 290 to 300.
123. The system of any of the examples above, wherein said at least one UV-C light emitter is configured to emit light having a peak wavelength in the range of 300 to 320.
124. A system of any of the examples above, wherein the unit weighs from 15 lbs.
125. A system of any of the examples above, wherein the unit has a volume of from 200,000 $cm^3$ to 50,000 $cm^3$.
126. A system of any of the examples above, wherein the unit has a volume of from 100,000 $cm^3$ to 20,000 $cm^3$.
127. A system of any of the examples above, wherein the unit has a volume of from 30,000 $cm^3$ to 10,000 $cm^3$.
128. The system of any of the examples above, wherein said at least one UV light emitter is configured to emit light having a peak wavelength with a bandwidth of 15 nm or less (FWHM).
129. The system of any of the examples above, wherein said at least one UV light emitter is configured to emit light having a peak wavelength with a bandwidth of 12 nm or less (FWHM).
130. A method of treating cancer comprising exposing cancerous tissue or cells to UV light provided by the system of any of the examples above.
131. The method of Example 130, wherein said cancerous tissue or cells comprises or is caused by brain tumors or brain cancer, breast cancer, brain metastases, bone cancer, bladder cancer, basal cell carcinoma, bile duct cancer, cervical cancer, colon cancer, colorectal cancer, esophageal cancer, gallbladder cancer, gastrointestinal tumors, lung cancer, anal cancer, genitourinary cancer, kidney cancer, renal cancer, renal carcinoma, adrenal tumors, prostate cancer, testicular cancer, liver cancer, liver metastases, lymphoma, melanoma, male breast cancer, oral cancer, ovarian cancer, pancreatic cancer, pancreatic cysts, pituitary gland tumors or adenomas, rectal cancer, salivary gland cancer, skin cancer, skull base tumors, soft tissue sarcoma, fibrosarcoma, choriocarcinoma, spine tumors or spinal cancer, squamous cell carcinoma, stomach (gastric) cancer, throat cancer, thryroid cancer, glioma, uterine cancer or uterine sarcoma.
132. The method of Example 130, wherein said method is employed to treat leukemia.
133. The method of Example 130 or 132, wherein directing UV light onto said cancerous tissue or cells comprises directing UV light onto blood.
134. The method of any of Examples 130 or 132, wherein directing UV light onto said cancerous tissue or cells comprises directing UV light onto blood that has been extracted from the body of a patient.
135. The method of any of Examples 130-134, wherein said direction UV light onto said cancerous tissue or cell is performed ex vivo.
136. The method of any of the examples above, wherein said at least one UV light emitter comprises a UV light emitting diode (LED).
137. The method of any of the examples above, wherein said at least one UV light emitter comprises a plurality of UV light emitting diodes (LEDs).
138. The method of any of the examples above, wherein said at least one UV light emitter comprises an array of UV light emitting diodes (LEDs).
139. The system of any of the examples above, wherein said system is configured for medical use.
140. The system of any of the examples above, wherein said system includes an outer surface on at least a portion thereof that is sterile.
141. The system of any of the examples above, wherein said system includes an outer surface on at least a distal portion thereof that is sterile.
142. The system of any of the examples above, wherein said system includes an outer surface on portion thereof that is configured to contact a patient that is sterile.
143. The system of any of the examples above, wherein said system is included in sterile packaging.

144. The system of any of the examples above, wherein said system includes an outer surface on at least a portion thereof that is sterilizable.
145. The system of any of the examples above, wherein said system includes an outer surface on at least a distal portion thereof that is sterilizable.
146. The system of any of the examples above, wherein said system includes an outer surface on portion thereof that is configured to contact a patient that is sterilizable.
147. The system of any of the examples above, wherein said optical fiber comprises separate fiber strands optically coupled together.
148. The system of any of the examples above, wherein said optical fiber line comprises separate fiber strands butt coupled together.
149. The system of any Examples 1-146, wherein said optical fiber comprises a single fiber strand.
150. The system of any of the examples above, wherein said system comprises a cover configured to be positioned in front of an output of light in said UV wavelength range.
151. The system of Example 150, wherein said cover is movable or switchable between first and second states without removing the cover from the body, the first state wherein said cover is positioned in front of said output of UV light and the second state wherein said cover provides less coverage in front of the output of light in said UV wavelength range.
152. The system of Example 150 or 151, wherein said cover comprises a plurality of segments or sections that are movable so as to be positioned in first and second states without removing said cover from the body, said first state wherein said segments are in front of the output of light in said UV wavelength range and said second state wherein said segments are moved to a position so as to provide less coverage in front of the output of light in said UV wavelength range.
153. The system of any of Examples 150-152, further comprising a motor or actuator configured to move said cover or portions thereof.
154. The system of any of Examples 150-153, wherein the cover or portions thereof are configured to moved hydraulically.
155. The system of any of Examples 150-154, wherein said cover can be moved using a control located outside the body when the distal end of the UV-C light projection unit is in the body.
156. The system of any of Examples 150-155, wherein said cover comprises an iris.
157. The system of any of Examples 150-156, wherein said cover is configured to be disposed in front of output optics and/or said optical fiber transmissive of light in said UV wavelength range.
158. The system of any of Examples 150-157, wherein said cover comprises or is part of an endoscope, said cover at the distal end of said endoscope.
159. The system of any of Examples 150-158, wherein said cover comprises or is part of a surgical tool having a tube for insertion into a body, said cover at the distal end of said tube.
160. The system of any of the examples above, further comprising shielding disposed with respect to said at least on UV light emitter such that excluding output from said distal end of said optical fiber, light in said UV wavelength range 10 mm from said shielding is less than 1 $mJ/cm^2$ when said light in said UV wavelength range in said UV wavelength range from said distal end of said fiber is from 10 $mJ/cm^2$ to 100 $mJ/cm^2$.
161. The system of Example 160 above, wherein said light in said UV wavelength range 12 inches from said at least on UV light emitter is less than 1 $mJ/cm^2$ over an angular extent that is 180° in one direction and 70° in another orthogonal direction.
162. The system of Example 161, wherein said angular extent is 270° in one direction and 90° in another orthogonal direction.
163. The system of Example 161, wherein said angular extent of 360° in one direction and 90° in another orthogonal direction.
164. The system of any of Examples 160-163, said light in said UV wavelength range 12 inches from said array is less than 0.1 $mJ/cm^2$.
165. The system of any of Examples 160-163, said light in said UV wavelength range 12 inches from said array is less than 0.05 $mJ/cm^2$.
166. The system of any of Examples 160-163, said light in said UV wavelength range 12 inches from said array is less than 0.01 $mJ/cm^2$.
167. The system any of Examples 160-166, wherein said shielding comprises plastic.
168. The system unit of any of Examples 160-167, wherein said shielding comprises acrylic or polycarbonate.
169. The system of any of Examples 160-168, wherein said shielding is at least 3 mm thick.
170. The system of any of Examples 160-169, wherein said shielding is disposed about said at least one UV light emitter on at least four sides.
171. The system of any of Examples 160-170, wherein said shielding is disposed about said array of said at least one UV light emitter on at least five sides.
172. The system of any of Examples 160-171, further comprising additional shielding with respect to said distal end of said optical fiber such that light in said UV wavelength range 12 inches from said distal end of said optical fiber is less than 1 $mJ/cm^2$ when said light in said UV wavelength range from said distal end of said fiber is from 10 $mJ/cm^2$ to 100 $mJ/cm^2$.
173. The system of Example 171, wherein said UV-C light emissions 12 inches from said distal end of said optical fiber is less than 1 $mJ/cm^2$ over an angular extent that is 100° in one direction and 30° in another orthogonal direction.
174. The system of Example 172, wherein said angular extent is 270° in one direction and 90° in another orthogonal direction.
175. The system of Example 172, wherein said angular extent of 360° in one direction and 90° in another orthogonal direction.
176. The system of any of Examples 172-175, said light in said UV wavelength range 12 inches from said distal end of said optical fiber is less than 0.1 $mJ/cm^2$.
177. The system of any of Examples 172-175, said light in said UV wavelength range 12 inches from said distal end of said optical fiber is less than 0.05 $mJ/cm^2$.
178. The system of any of Examples 172-175, said light in said UV wavelength range 12 inches from said distal end of said optical fiber is less than 0.01 $mJ/cm^2$.
179. The system any of Examples 172-175, wherein said shielding comprises plastic.
180. The system of any of Examples 172-179, wherein said shielding comprises acrylic or polycarbonate.

181. The system of any of Examples 172-180, wherein said shielding is at least 3 mm thick.

182. The system of any of Examples 172-181, wherein said shielding is disposed about said distal end of said optical fiber on at least four sides.

183. The system of any of Examples 172-181, wherein said shielding is disposed about said distal end of said optical fiber on at least five sides.

184. The system of any of above, further comprising a mount for positioning the distal end of said optical fiber configured to receive light in said UV wavelength range from said at least one UV light emitter with respect to a sample to direct light in said UV wavelength range out of said distal end of said optical fiber and to said sample.

185. The system of any of above, configured for a sample on a microscope slide, in a petri dish or in a sample container.

186. The system of any of above, further comprising shielding disposed with respect to said distal end of said optical fiber that light in said UV wavelength range 12 inches from said distal end of said optical fiber is less than 1 mJ/cm$^2$.

187. The system of any of the examples above, wherein said optical fiber is included in or integrated with an endoscope or a hand held delivery device.

188. The system of any of the examples above, wherein said mount is configured to hold a distal end of said endoscope.

189. The system of any of the examples above, wherein said mount is configured to hold said hand held delivery device.

190. The system of any of the examples above, further comprising at least one fused silica lens configured to receive light emitted by said at least one light emitter having a wavelength in the UV wavelength range, said at least one fused silica lens comprising fused silica wherein the OH content is not larger than 5 ppm or wherein one or more of Li, Na, K, Mg, Ca and Cu are smaller than 0.1 ppm.

191. The system of any of the examples above, wherein the UV wavelength range in which said at least one UV light emitter emits light comprises the UV-C range.

192. The system of any of the examples above, wherein the UV wavelength range in which said at least one UV light emitter emits light comprises wavelengths in the range of from 200 to 280 nm.

193. The system of any of the examples above, wherein the UV wavelength range in which said at least one UV light emitter emits light comprises wavelengths in the range of from 200 to 280 nm.

194. The system of any of the examples above, wherein the UV wavelength range in which said at least one UV light emitter emits light comprises wavelengths in the range of from 280 to 325 nm.

195. The system of any of the examples above, wherein said optical fiber has a length of at least 7 feet.

196. The system of any of the examples above, wherein said optical fiber forms part of or is optically coupled to an endoscope.

197. The system of any of the examples above, further comprising shielding disposed with respect to said at least one UV light emitter such that, excluding output from a distal end of said optical fiber, light emission in said UV wavelength range at a location 10 mm from said shielding is less than 1 mJ/cm$^2$ when said UV light emission from said optical fiber is from 10 mJ/cm$^2$ to 100 mJ/cm$^2$.

198. The system of any of the examples above, further comprising shielding disposed with respect to said at least one UV light emitter such that, excluding output from a distal end of said optical fiber, said light in said UV wavelength range is less than 1 mJ/cm$^2$ over an angular extent that is 120° in one direction and 40° in another orthogonal direction 36 inches from said at least one UV light emitter when said UV light emission from said distal end of said optical fiber is from 10 mJ/cm$^2$ to 100 mJ/cm$^2$.

199. The system of any of the examples above, further comprising a support on which a sample can be positioned to receive said light in said UV wavelength range from said distal end of said optical fiber.

200. The system of any of the examples above, further comprising a mount for positioning a distal end of said optical fiber configured to receive light in said UV wavelength range from said at least one UV light emitter with respect to a sample to direct light in said UV wavelength range out of said distal end of said optical fiber and to said sample.

201. The system of any of examples above, further comprising shielding disposed with respect to said distal end of said optical fiber to block light in said UV wavelength range output from said distal end of said optical fiber.

202. The system of Example 201, wherein said shielding is configured to block at least 50% of the light in said UV wavelength range output from said distal end of said optical fiber that is scattered or reflected from the sample in a direction above a support on which said sample is supported.

203. The system of Examples 201 or 202, wherein said UV light emission from said optical fiber at a location 10 mm from said shielding is less than 1 mJ/cm$^2$ when said UV light emission from said distal end of said optical fiber is from 10 mJ/cm$^2$ to 100 mJ/cm$^2$.

204. The system of any of Examples 201-203, wherein said shielding is disposed with respect to said distal end of said optical fiber such that light in said UV wavelength range at a location 36 inches from said distal end of said optical fiber is less than 1 mJ/cm$^2$ when said light in said UV wavelength range from said distal end of said optical fiber is from 10 mJ/cm$^2$ to 100 mJ/cm$^2$.

205. The system of Example 204, wherein light emission in said light in said UV wavelength range is less than 1 mJ/cm$^2$ over an angular extent that is 100° in one direction and 30° in another orthogonal direction 36 inches from said distal end of said optical fiber when said UV light emission from said distal end of said optical fiber is from 10 mJ/cm$^2$ to 100 mJ/cm$^2$.

206. The system of any of the examples above, wherein excluding output from a distal end of said optical fiber, light emission from the system in said UV wavelength range is less than 1 mJ/cm$^2$ over a solid angle of 0.1$\pi$ steradian at a distance of 36 inches from said distal end of said optical fiber when said light emission in said UV wavelength range from said distal end of said optical fiber is from 10 mJ/cm$^2$ to 100 mJ/cm$^2$.

207. The system of any of the examples above, wherein excluding output from a distal end of said optical fiber, light emission from said system in said UV wavelength range is less than 1 mJ/cm$^2$ over a solid angle of 0.2$\pi$ steradian at a distance of 36 inches from said distal end of said optical fiber when said light emission in said UV wavelength range from said distal end of said optical fiber is from 10 mJ/cm$^2$ to 100 mJ/cm$^2$.

208. The system of any of the examples above, wherein excluding output from a distal end of said optical fiber, light emission from said system in said UV wavelength range is less than 1 mJ/cm$^2$ over a solid angle of 0.3π steradian at a distance of 36 inches from said distal end of said optical fiber when said light emission in said UV wavelength range from said distal end of said optical fiber is from 10 mJ/cm$^2$ to 100 mJ/cm$^2$.

209. The system of any of the examples above, wherein excluding output from a distal end of said optical fiber, light emission from said system in said UV wavelength range is less than 1 mJ/cm$^2$ over a solid angle of 0.5π steradian at a distance of 36 inches from said distal end of said optical fiber when said light emission in said UV wavelength range from said distal end of said optical fiber is from 10 mJ/cm$^2$ to 100 mJ/cm$^2$.

210. The system of any of the examples above, wherein a person applying light in said UV wavelength range to a patient is exposed to light emission from said system in said UV wavelength range of less than 1 mJ/cm$^2$ when said light emission in said UV wavelength range from said distal end of said fiber is from 10 mJ/cm$^2$ to 100 mJ/cm$^2$.

211. The system of any of the examples above, wherein a person applying light in said UV wavelength range to a patient is exposed to light emission from said system in said UV wavelength range of less than 0.05 mJ/cm$^2$ when said light emission in said UV wavelength range from said distal end of said fiber is from 10 mJ/cm$^2$ to 100 mJ/cm$^2$.

212. The system of any of the examples above, wherein a person applying light in said UV wavelength range to a patient is exposed to light emission from said system in said UV wavelength range of less than 0.01 mJ/cm$^2$ when said light emission in said UV wavelength range from said distal end of said fiber is from 10 mJ/cm$^2$ to 100 mJ/cm$^2$.

213. The system of any of the examples above, wherein excluding output from a distal end of said optical fiber, light emission from said system in said UV wavelength range is less than 1 mJ/cm$^2$ over the body of an operator holding the distal end of the fiber when said light emission in said UV wavelength range from said distal end of said optical fiber is from 10 mJ/cm$^2$ to 100 mJ/cm$^2$.

214. The system of any of the examples above, wherein, excluding possible output from a distal end of said optical fiber, an operator operating the system is exposed to light emission from said system of less than 1 mJ/cm$^2$ in said UV wavelength range when said light emission in said UV wavelength range from said distal end of said optical fiber is from 10 mJ/cm$^2$ to 100 mJ/cm$^2$.

Part XIX

1. A UV-C light projection unit comprising:
   an array of UV-C light emitters, said UV-C light emitters comprising UV-C light emitting diodes (LEDs) configured to emit light having a wavelength in the range of 250 to 280 nm that diverges; and
   UV-C optics disposed to receive light emitted by said array of UV-C light emitters and to transmit said light and reduce divergence of said UV-C light.
2. The UV-C light projection unit of Example 1, further comprising a fiber optic, said array of UV-C emitters configured to couple UV-C light into said fiber optic.
3. The UV-C light projection unit of Example 2, wherein said fiber optic comprises an optical fiber having an optical core of at least 100 micrometers wide in cross-section.
4. The UV-C light projection unit of Example 3, wherein said fiber optic comprises fused silica.
5. The UV-C light projection unit of Example 1, wherein said array of UV-C light emitters has dimensions from 2 mm×2 mm to 5 mm×5 mm.
6. The UV-C light projection unit of Example 1, wherein said UV-C light emitters of said array of UV-C light emitters extend across an area of 1 mm$^2$ to 125 mm$^2$.
7. The UV-C light projection unit of Example 1, wherein said UV-C light emitters of said array have a center-to-center spacing of from 0.1 mm to 8 mm.
8. The UV-C light projection unit of Example 1, wherein said UV-C light emitters of said array of UV-C light emitters are formed on a single semiconductor substrate.
9. A method of exposing cancerous tissue to UV-C light, said method comprising:
   producing UV-C light from an array of UV-C light emitters, said UV-C light emitters comprising UV-C light emitting diodes (LEDs), said light having a wavelength in the range of 250 to 280 nm that diverges from said array of UV-C light emitters;
   collecting light emitted by said array of UV-C light emitters with a UV-C collecting optics reducing said divergence; and
   directing UV-C light collected by said UV-C collecting optics onto said cancerous tissue.
10. The method of Example 9, further comprising directing said UV-C light onto said cancerous tissue using an endoscope.
11. The method of Example 9, further comprising coupling said UV-C light from said array of UV-C emitters into a fiber optic.
12. The method of Example 11, wherein said fiber optic comprises an optical fiber having an optical core of at least 100 micrometers wide in cross-section.
13. The method of Example 11, wherein said fiber optic comprises fused silica.
14. The method of Example 11, wherein said fiber optic is part of or optically coupled to an endoscope.
15. The method of Example 9, further comprising focusing UV-C light from said collecting optic onto said cancerous tissue.
16. The method of Example 9, wherein said collecting optics comprises at least one fused silica lens.
17. The UV method of Examples 10-14, wherein said fiber optic comprises separate fiber strands butt coupled together.
18. The method of any of Examples 10-14, wherein said fiber optic comprises a single fiber strand.
19. The system of any of Examples 1-3, wherein said optical fiber comprises separate fiber strands optically coupled together.
20. The UV-C light projection unit of Examples 1-3, wherein said fiber optic comprises separate fiber strands butt coupled together.
21. The UV-C light projection unit of any of Examples 1-3, wherein said fiber optic comprises a single fiber strand.

ADDITIONAL INFORMATION

A wide variety of other variations, for example, to any of the embodiments or implementation disclosed herein, are possible. Components can be added, removed, and/or rearranged. Similarly, in any method or process disclosed herein, steps or operations can be added, removed, and/or rearranged. Other configurations are possible.

Configurations other than those described herein are possible. The structures, devices, systems, and methods may include additional components, features, and steps and any of these components, features, and steps may be excluded and may or may not be replaced with others. The arrangements may be different. Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Some examples of some of certain embodiments disclosed and/or described herein are listed below. These examples of various embodiments are not meant to be limiting, but rather illustrate some of the embodiments of systems and methods that that are disclosed by this description and accompanying figures. Such embodiments can include:

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. A UV-C light projection unit comprising:

an array of UV-C light emitters, said UV-C light emitters comprising UV-C light emitting diodes (LEDs) configured to emit UV-C light having a wavelength in the range of 250 to 280 nm that diverges; and UV-C optics disposed to receive UV-C light emitted by said array of UV-C light emitters and to transmit said UV-C light and reduce divergence of said UV-C light; and a fiber optic, said array of UV-C emitters configured to couple UV-C light into said fiber optic, said fiber optic comprising an optical fiber optically transmissive to UV-C light having a length of at least 12 feet, wherein said fiber optic forms part of or is optically coupled to an endoscope.

2. The UV-C light projection unit of claim 1, wherein said optical fiber has a length in the range of from 12 to 30 feet long.

3. The UV-C light projection unit of claim 1, wherein said fiber optic comprises an optical fiber having an optical core of at least 100 micrometers wide in cross-section.

4. The UV-C light projection unit of claim 1, wherein said fiber optic comprises fused silica.

5. The UV-C light projection unit of claim 1, wherein said array of UV-C light emitters has dimensions in the range from 2 mm×2 mm to 5 mm×5 mm.

6. The UV-C light projection unit of claim 1, wherein said UV-C optics comprises UV-C collimating optics configured to form a collimated beam from UV-C light from said array of UV-C light emitters.

7. The UV-C light projection unit of claim 6, further comprising UV-C focusing optics positioned to receive UV-C light from said array of UV-C emitters and to focus UV-C light from said array of UV-C emitters into said fiber optic.

8. The UV-C light projection unit of claim 7, further comprising a fiber coupling lens configured to receive light from said focusing optics and to decrease the divergence or increase convergence of said light coupled into the fiber optic.

9. The UV-C light projection unit of claim 1, wherein said optical fiber has a hydroxyl (OH) content in the core material of at least 200 ppm.

10. The UV-C light projection unit of claim 1, wherein said optical fiber has a hydroxyl (OH) content in the core material in the range from 600 to 800 ppm.

11. The UV-C light projection unit of claim 1, wherein said UV-C light emitters of said array of UV-C light emitters are formed on a single semiconductor substrate.

12. The UV-C light projection unit of claim 1, wherein the length of said optical fiber is in the range from 15 feet to 28 feet long.

13. The UV-C light projection unit of claim 1, wherein the length of said optical fiber is in the range from 18 feet to 35 feet long.

14. The UV-C light projection unit of claim 1, wherein said UV-C light projection unit comprises a robotic system.

15. A method of exposing cancerous tissue to UV-C light, said method comprising:

producing UV-C light from an array of UV-C light emitters, said UV-C light emitters comprising UV-C light emitting diodes (LEDs), said UV-C light having a wavelength in the range of 250 to 280 nm that diverges from said array of UV-C light emitters;

collecting UV-C light emitted by said array of UV-C light emitters with UV-C collecting optics reducing said divergence;

coupling said UV-C light from said array of UV-C emitters into a fiber optic, said fiber optic comprising an optical fiber optically transmissive to UV-C light having a length of at least 12 feet; and directing UV-C light collected by said UV-C collecting optics onto said cancerous tissue, wherein said fiber optic is part of or optically coupled to an endoscope and said UV-C light is directed onto said cancerous tissue using said endoscope.

16. The method of claim 15, wherein said optical fiber has a length of from 12 to 30 feet long.

17. The method of claim 15, wherein said fiber optic comprises an optical fiber having an optical core of at least 100 micrometers wide in cross-section.

18. The method of claim 15, wherein said optical fiber has a hydroxyl (OH) content in the core material in the range from 600 to 800 ppm.

19. The method of claim 15, wherein the length of said optical fiber is in the range from 16 feet to 30 feet long.

20. The method of claim 15, wherein the length of said optical fiber is in the range from 20 feet to 40 feet long.

* * * * *